United States Patent
Ninkovic et al.

(10) Patent No.: US 10,544,095 B2
(45) Date of Patent: Jan. 28, 2020

(54) 3-INDOL SUBSTITUTED DERIVATIVES, PHARMACEUTICAL COMPOSITIONS AND METHODS FOR USE

(71) Applicants: Pfizer Inc., New York, NY (US); iTeos Therapeutics, Charleroi (BE)

(72) Inventors: Sacha Ninkovic, La Jolla, CA (US); Michael Raymond Collins, San Diego, CA (US); Stefano Crosignani, Nivelles (BE); Andreas Maderna, San Diego, CA (US); Indrawan James McAlpine, San Diego, CA (US); Stephanie Anne Scales, San Diego, CA (US); Martin Wythes, Solana Beach, CA (US)

(73) Assignees: Pfizer Inc., New York, NY (US); iTeos Therapeutics, Charleroi (BE)

( * ) Notice: Subject to any disclaimer, the term of this patent is extended or adjusted under 35 U.S.C. 154(b) by 0 days.

(21) Appl. No.: 15/749,963

(22) PCT Filed: Aug. 4, 2016

(86) PCT No.: PCT/IB2016/054701
§ 371 (c)(1),
(2) Date: Feb. 2, 2018

(87) PCT Pub. No.: WO2017/025868
PCT Pub. Date: Feb. 16, 2017

(65) Prior Publication Data
US 2018/0222862 A1    Aug. 9, 2018

Related U.S. Application Data

(60) Provisional application No. 62/203,032, filed on Aug. 10, 2015, provisional application No. 62/309,530, filed on Mar. 17, 2016.

(51) Int. Cl.
| | | |
|---|---|---|
| *A61K 31/404* | (2006.01) | |
| *C07D 209/10* | (2006.01) | |
| *C07D 209/18* | (2006.01) | |
| *C07D 403/12* | (2006.01) | |
| *C07D 403/14* | (2006.01) | |
| *C07D 409/12* | (2006.01) | |
| *C07D 413/12* | (2006.01) | |
| *A61P 25/28* | (2006.01) | |
| *A61P 35/02* | (2006.01) | |
| *A61P 25/24* | (2006.01) | |
| *A61P 25/16* | (2006.01) | |
| *C07D 401/12* | (2006.01) | |
| *C07D 401/14* | (2006.01) | |
| *C07D 403/10* | (2006.01) | |
| *C07D 405/12* | (2006.01) | |

(52) U.S. Cl.
CPC ............ *C07D 209/18* (2013.01); *A61P 25/16* (2018.01); *A61P 25/24* (2018.01); *A61P 25/28* (2018.01); *A61P 35/02* (2018.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 409/12* (2013.01); *C07D 413/12* (2013.01)

(58) Field of Classification Search
CPC ... C07D 209/10; C07D 209/18; A61K 31/404
See application file for complete search history.

(56) References Cited

U.S. PATENT DOCUMENTS

| 7,151,108 B2 | 12/2006 | Prudhomme et al. |
| 8,008,481 B2 | 8/2011 | Ericsson et al. |
| 9,126,984 B2 | 9/2015 | Crosignani et al. |
| 2003/0109550 A1 | 6/2003 | Clare et al. |
| 2005/0165005 A1 | 7/2005 | Genevois et al. |

(Continued)

FOREIGN PATENT DOCUMENTS

| CA | 2668905 | * 12/2010 |
| CN | 101265259 A | 9/2008 |

(Continued)

OTHER PUBLICATIONS

CAS Reg No. 1309271-49-5, entered into STN Jun. 13, 2011 (Year: 2011).*

(Continued)

*Primary Examiner* — Karen Cheng
(74) *Attorney, Agent, or Firm* — Howson and Howson LLP; Cathy Kodroff; David Rubin

(57) ABSTRACT

A compound of Formula I is provided:

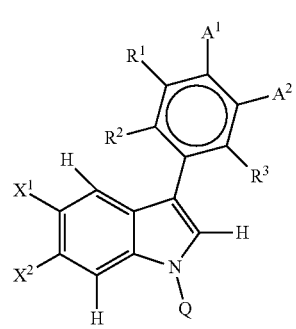

or pharmaceutically acceptable enantiomers, salts or solvates thereof. The invention further relates to the use of the compounds of Formula I as TDO2 inhibitors. The invention also relates to the use of the compounds of Formula I for the treatment and/or prevention of cancer, neurodegenerative disorders such as Parkinson's disease, Alzheimer's disease and Huntington's disease, chronic viral infections such as HCV and HIV, depression, and obesity. The invention also relates to a process for manufacturing compounds of Formula I.

7 Claims, No Drawings

(56) References Cited

U.S. PATENT DOCUMENTS

| | | |
|---|---|---|
| 2009/0118292 A1 | 5/2009 | Deng et al. |
| 2010/0305133 A1 | 12/2010 | Colon et al. |
| 2010/0317863 A1 | 12/2010 | Kuzmich et al. |
| 2011/0046370 A1 | 2/2011 | Sim et al. |
| 2011/0166143 A1 | 7/2011 | Bretschneider et al. |
| 2012/0053345 A1 | 3/2012 | Ericson et al. |
| 2015/0266857 A1 | 3/2015 | Crosignani et al. |
| 2015/0225367 A1 | 8/2015 | Crosignani et al. |
| 2015/0328228 A1 | 11/2015 | Crosignani et al. |
| 2015/0329525 A1 | 11/2015 | Crosignani et al. |
| 2016/0263087 A1 | 9/2016 | Crosignani et al. |

FOREIGN PATENT DOCUMENTS

| | | |
|---|---|---|
| EP | 1411057 A1 | 4/2004 |
| JP | 2000-095759 A | 4/2000 |
| WO | WO-1997/043230 A1 | 11/1997 |
| WO | WO-2000/043393 A1 | 7/2000 |
| WO | WO-2003/082869 | 10/2003 |
| WO | WO-2003/101981 A1 | 12/2003 |
| WO | WO-2005/058035 A1 | 6/2005 |
| WO | WO-2006/005608 A1 | 1/2006 |
| WO | WO-2006/086484 A1 | 8/2006 |
| WO | WO-2007/039580 A1 | 4/2007 |
| WO | WO-2007/045622 A1 | 4/2007 |
| WO | WO-2007/050963 A1 | 5/2007 |
| WO | WO-2007/087488 A2 | 8/2007 |
| WO | WO-2007/117465 A2 | 10/2007 |
| WO | WO-2007/124252 | 11/2007 |
| WO | WO-2008/068621 | 6/2008 |
| WO | WO-2008/073306 A1 | 6/2008 |
| WO | WO-2008/094992 A2 | 8/2008 |
| WO | WO-2008/115804 A1 | 9/2008 |
| WO | WO-2009/015067 A2 | 1/2009 |
| WO | WO-2009/073497 A2 | 6/2009 |
| WO | 2009/118292 A1 | 10/2009 |
| WO | WO-2009/118292 A1 | 10/2009 |
| WO | WO-2010/008427 A1 | 1/2010 |
| WO | WO-2010/046013 A1 | 4/2010 |
| WO | WO 2010/096389 A1 | 8/2010 |
| WO | WO-2010/136491 A1 | 12/2010 |
| WO | WO-2011/038163 A1 | 3/2011 |
| WO | WO-2011/046954 A1 | 4/2011 |
| WO | WO-2012/068406 A2 | 5/2012 |
| WO | WO-2012/129338 A1 | 9/2012 |
| WO | WO-2012/161877 A1 | 11/2012 |
| WO | WO-2013/025883 A1 | 2/2013 |
| WO | 2015/121812 A1 | 8/2015 |
| WO | WO2015121812 * | 8/2015 |
| WO | WO-2015/140717 A1 | 9/2015 |
| WO | WO-2015/173764 | 11/2015 |
| WO | PCT/IB2016/054701 | 9/2016 |

OTHER PUBLICATIONS

Chittimalla et al, Eur. J. Org. Chem, 2014, p. 2565-2575 (Year: 2014).*

Baroni et al., Synthesis of 3-Heteroaryloxindoles through t-BuOCl-Mediated Oxidation of 3-Heteroarylindoles, Synthesis, vol. 2010(23):4075-4081, Oct. 2010.

Beevers, Low molecular weight indole fragments as IMPDH inhibitors, Bioorganic & Medicinal Chemistry Letters, vol. 16(9):2535-2538, May 2006.

Bennett & Plum (EDS), Cecil Textbook of Medicine (20$^{th}$ Ed., vol. 2), W.B. Saunders Company, Philadelphia, pp. 1992-1996 and 2050-2057, Jan. 1996.

Cancer [Online], [Retrieved on Jul. 6, 2007], Retrieved from the internet, URL http://en.wikipedia.org/wiki/Cancer.

Cancer [Online], [Retrieved on Jul. 6, 2007], Retrieved from the internet, URL http://www.nlm.nih.gov/medlineplus/cancer.html.

Cavallo et al., 2011: The Immune Hallmarks of Cancer, Cancer Immunology Immunotherapy, vol. 60(3):319-326, Nov. 26, 2011. (Epub Jan. 26, 2011).

Chemical Abstract Service, Database Registry Accession No. 1309341-94-3 RN, Jun. 14, 2011.

Chemical Abstracts Service, Database Registry Accession No. 1125444-69-0, Mar. 23, 2009.

Chemical Abstracts Service, Database Registry Accession No. 859666-30-1, Aug. 11, 2005.

Chen et al. Synthesis and antiproliferative activity of novel 2-aryl-4-benzoyl-imidazole derivatives targeting tubulin polymerization. Bioorganic & Medicinal Chemistry. vol. 19(16):4782-4795. Aug. 2011.

Comings et al., Exon and intron variants in the human tryptophan 2,3-dioxygenase gene: potential association with Tourette syndrome, substance abuse and other disorders, Pharmacogenetics, vol. 6(4):307-318, Aug. 1996.

Davies et al., Tryptophan, Neurodegeneration and HIV-Associated Neurocognitive Disorder, Int J Tryptophan Res, vol. 3: 121-140, Jun. 2010.

Dolusic et al., Indoleamine 2,3-dioxygenase inhibitors: a patent review (2008-2012), Expert Opin Ter Pat., vol. 23(10):1367-1381, Oct. 2013 (ePub Aug. 2013).

Dolusic et al., Tryptophan 2,3-dioxygenase (TDO) inhibitors. 3-(2-(pyridyl)ethenyl)indoles as potential anticancer immunomodulators, J Med Chem., vol. 54(15):5320-5334, Aug. 2011 (ePub Jul. 2011).

Fallarino et al., T cell apoptosis by tryptophan catabolism, Cell Death Differ, vol. 9(10):1069-1077, Oct. 2002.

FDA mulls drug to slow late-stage Alzheimer's [online], [retrieved on Sep. 23, 2003]. Retrieved form the Internet, URL: Http://www.cnn.com/2003/HEALTH/conditions/09/24/alzheimers.drug.ap/index.html.

Forrest et al., Blood levels of kynurenines, interleukin-23 and soluble human leucocyte antigen-G at different stages of Huntington's disease, J Neurochem, vol. 112(1):112-122, Jan. 2010.

Fuvesi et al., The role of kynurenines in the pathomechanism of amyotrophic lateral sclerosis and multiple sclerosis: therapeutic implications, J Neural Transm (Vienna), vol. 119(2):225-234, Feb. 2012 (ePub Jan. 2012).

Galon et al. Cancer classification using the immunoscore: a worldwide task force, J Transl Med, vol. 10(205):Oct. 1-9, 2012.

Godin-Ethier et al., Indoleamine 2, 3-dioxygenase expression in human cancers: clinical and immunologic perspectives, Clin Cancer Res, vol. 17:6985-6991, Nov. 2011.

Golub et al., Molecular classification of cancer: class discovery and class prediction by gene expression monitoring, Science, 286(5439): 531-7, Oct. 15, 1999.

Guo et al. Solubility-Driven Optimization of (Pyridin-3-yl) Benzoxazinyl-oxazolidinones Leading to a Promising Antibacterial Agent. Journal of Medicinal Chemistry. vol. 56(6):2642-2650. Feb. 2013.

Gupton et al., Preparation of indole containing building blocks for the regiospecific construction of indole appended pyrazoles and pyrroles, Tetrahedron, vol. 69(69):5829-5840, May 2013.

Hanahan et al., The hallmarks of cancer, Cell, vol. 100(1):57-70, Jan. 2000.

Hanahan, et al., Hallmarks of Cancer: The Next Generation, Cell, vol. 144:646-674, Mar. 4, 2011.

Henon et al., Expedited Synthesis of Substituted Dipyrrolo [3,4-a:3,4-c] carbazole-1,3,4,6-tetraones Structrually Related to Granulatimide, Synthesis, vol. 2006(4):711-715, Jan. 1, 2006.

Henon et al., Synthesis and biological evaluation of new dipyrrolo [3,4-a:3,4-c] carbazole-1,3,4,6-tetraones, substituted with various saturated and unsaturated side chains via palladium catalyzed cross-coupling reactions, Bioorganic & Medicinal Chemistry, vol. 14(11):3825-3834, Jun. 1, 2006.

Holmgaard et al., Indoleamine 2,3-dioxygenase is a critical resistance mechanism in antitumor T cell immunotherapy targeting CTLA-4, J Exp Med., vol. 210(7):1389-1402, Jul. 2013 (ePub Jun. 2013).

Jakse et al., Application of alkyl 3-dimethylamino-2-(1H-indol-3-yl)propenoates in the synthesis of 3-heteroarylindoles, Tetrahedron, vol. 60:4601-4608, Mar. 2004.

(56) References Cited

OTHER PUBLICATIONS

Jimenez et al., "4-(1-Phenyl-1H-pyrazol-4-yl)quinolones as novel, selective and brain penetrant metabotropic glutamate receptor 4 positive allosteric modulators", Bioorg. Med. Chem. Let., vol. 22(9):3235-3239, Mar. 7, 2012.
Kyrgidia et al., "Melanoma: Stem cells, sun exposure and hallmarks for carcinogenesis, molecular concepts and future clinical implications", Journal of Carcinogenesis, vol. 9(1):1-16, Feb. 16, 2010.
Lahdou et al., Increased serum levels of quinolinic acid indicate enhanced severity of hepatic dysfunction in patients with liver cirrhosis, Hum Immunol, vol. 74(1):60-66, Jan. 2013.
Lala, et al., Role of nitric oxide in tumor progression: lessons from experimental tumors, Cancer and Metastasis Reviews 17.1 (1998): 91-106.
Macor, A Direct Synthesis of 3-(Pyrrolidin-3-y1) Indoles for Use as Conformationally Restricted Analogs of Tryptamines, Synthesis, 1997(4):443-449, Apr. 4, 1007.
Mahboobi, 3-Bromo-4-(1H-3-indolyl)-2, 5-dihydro-1H-2, 5-pyrroledione derivatives as new lead compounds for antibacterially active substances, European Journal of Medicinal Chemistry, vol. 41(2):176-191, Feb. 1, 2006.
Manna et al., UPLC-MS-based urine metabolomics reveals indole-3-lactic acid and phenyllactic acid as conserved biomarkers for alcohol-induced liver disease in the Ppara-null mouse model, J Proteome Res, vol. 10(9):4120-4133, Sep. 2011.
Martin et al. Synthesis of Novel Analogs of Acetyl Coenzyme A: Mimics of Enzyme Reaction Intermediates. Journal of the American Chemical Society. vol. 116(11):4660-4668. Jun. 1994.
Mellor et al., Creating immune privilege: active local suppression that benefits friends, but protects foes, Nat Rev Immunol, vol. 8(1):74-80, Jan. 2008.
Miller et al., Expression of the kynurenine pathway enzyme tryptophan 2,3-dioxygenase is increased in the frontal cortex of individuals with schizophrenia, Neurobiol Dis., vol. 15(3):618-629, Apr. 2004.
Motz et al., Deciphering and Reversing Tumor Immune Suppression, Immunity, vol. 39(1):61-73. Jul. 25, 2013.
Muller et al., Chronic inflammation that facilitates tumor progression creates local immune suppression by inducing indoleamine 2,3-dioxygenase, PNAS, vol. 105(44):17073-17078, Nov. 2008.
Munn et al., Indoleamine 2, 3-dioxygenase and metabolic control of immune responses, Trends Immunol, vol. 34(3):137-143, Mar. 2013.
Munn et al., Inhibition of T cell proliferation by macrophage tryptophan catabolism, J Exp Med, vol. 189(9):1363-1372, May 1999.
Munn et al., Prevention of allogeneic fetal rejection by tryptophan catabolism, Science, vol. 281(5380):1191-1193, Aug. 1998.
Munn, Blocking IDO activity to enhance anti-tumor immunity, Front Biosci Elite, vol. 4:734-745, Jan. 2012.
Ohta et al., Relationship between the level of serum L-tryptophan and its hepatic uptake and metabolism in rats with carbon tetrachloride-induced liver cirrhosis, Amino Acids, vol. 10(4):369-378, Dec. 1996.
Opitz et al., An endogenous tumour-promoting ligand of the human aryl hydrocarbon receptor, Nature, vol. 478(7368):197-203, Oct. 2011.
Pilotte et al., Reversal of tumoral immune resistance by inhibition of tryptophan 2,3-dioxygenase, PNAS, vol. 109(7):2497-2502, Feb. 2012.

Sahm et al., The endogenous tryptophan metabolite and NAD+ precursor quinolinic acid confers resistance of gliomas to oxidative stress, Cancer Res, vol. 73(11):3225-3234, Jun. 2013 (ePub Apr. 2013).
Shigemitsu, Synthesis of 3-Methylthio-4-aryl-3-pyrroline-2, 5-diones and 3-Arylpyrrolidine-2, 5-diones by Reaction of Nitroketene Dithioacetal with Arylacetonitriles, Heterocycles, vol. 55(12):2257-2260, Feb. 1, 2001.
Sperner-Unterweger et al., Enhanced tryptophan degradation in patients with ovarian carcinoma correlates with several serum soluble immune activation markers, Immunobiology, vol. 216(3):296-301, Mar. 2011.
Stone et al., The kynurenine pathway as a therapeutic target in cognitive and neurodegenerative disorders, Br J Pharmacol, vol. 169(6):1211-1227, Jul. 2013.
Tilman et al., Human periostin gene expression in normal tissues, tumors and melanoma: evidences for periostin production by both stromal and melanoma cells, Mol Cancer, vol. 6:80, pp. 1-13, Dec. 2007.
Tominaga et al., Synthesis of Methylthiomaleimides for the Preparation of Pyridazines and Related Compounds, J Heterocyclic Chem, vol. 39(3):571-591, May 2002.
Turiso et al. Discovery and in Vivo Evaluation of Dual PI3Kβ/δ Inhibitors. Journal of Medicinal Chemistry. vol. 55(17):7667-7685. Aug. 2012.
Uyttenhove et al., Evidence for a tumoral immune resistance mechanism based on tryptophan degradation by indoleamine 2,3-dioxygenase, Nat Med., vol. 9(10):1269-1274, Oct. 2003 (ePub Sep. 2003).
Vippagunta, et al. Crystalline solids, Advanced drug delivery reviews 48(1): May 3-26, 2001.
Widner et al., Increased neopterin production and tryptophan degradation in advanced Parkinson's disease, J Neural Transm (Vienna), vol. 109(2):191-189, Feb. 2002.
Wu et al., Expression of Tryptophan 2,3-Dioxygenase and Production of Kynurenine Pathway Metabolites in Triple Transgenic Mice and Human Alzheimer's Disease Brain, PLOS One, vol. 8(4):e59749, Apr. 2013.
International Search Report and Written Opinion in International Patent Application No. PCT/IB2016/051509, dated Apr. 21, 2016.
International Search Report and Written Opinion in International Patent Application No. PCT/IB2016/054701, dated Sep. 30, 2016.
International Search Report and Written Opinion issued in International Patent Application No. PCT/IB2016/052748, dated Jul. 12, 2016.
International Search Report and Written Opinion issued in International Patent Application No. PCT/IB2015/051957, dated Apr. 30, 2015.
Office Action in U.S. Appl. No. 15/072,534 dated May 8, 2017 and Response filed Aug. 25, 2017.
Office Action in U.S. Appl. No. 15/072,534 dated Dec. 27, 2016 and Response filed Mar. 27, 2017.
Notice of Allowance issued in U.S. Appl. No. 15/072,534, dated Sep. 7, 2017.
Office Action dated Oct. 14, 2016 in U.S. Appl. No. 14/660,082 and Responses filed Mar. 27, 2017 and Apr. 14, 2017.
Office Action dated May 17, 2017 in U.S. Appl. No. 14/660,082.
European Search Report in European Application No. EP14 16 0578, dated May 20, 2015.
Dolusic, Journal of Medicinal Chemistry, Tryptophan 2, 3-Dioxygenase (TDO) Inhibitors. 3-(2-(Pyridyl)ethenyl) indoles as Potential Anticancer Immunomodulators, vol. 54(15):5320-5334, Aug. 11, 2011.

* cited by examiner

3-INDOL SUBSTITUTED DERIVATIVES, PHARMACEUTICAL COMPOSITIONS AND METHODS FOR USE

FIELD OF INVENTION

The present invention relates to novel 3-(indol-3-yl)-pyridine derivatives, including pharmaceutically acceptable enantiomers, salts and solvates thereof. Compounds of the invention are inhibitors of TDO2 (tryptophan 2,3-dioxygenase) and are useful as therapeutic compounds, particularly in the treatment and/or prevention of cancers.

BACKGROUND OF INVENTION

Two decades after the importance of tryptophan catabolism for maintaining the immune privilege of the placenta was discovered (Munn, D. H. et al., Science, 1998, 281, 1191-1193), increasing evidence is extending its biological relevance beyond immune tolerance to non-self. According to the generally accepted concept, tryptophan, an essential amino acid, is catabolized in the local microenvironment of tumors, immune-privileged sites, or sites of inflammation (Mellor A L and Munn D H., Nat Rev Immunol, 2008, 8, 74-80). In these tissues, cancer cells, immune cells, or specialized epithelial cells (e.g., syncytiotrophoblasts in the placenta) create an immunosuppressive environment in tumors that shuts down antitumor immune responses in tumors and in tumor-draining lymph nodes by inducing T-cell anergy and apoptosis through depletion of tryptophan and accumulation of immunosuppressive tryptophan catabolites (Munn D H et al., J Exp Med., 1999, 189, 1363-1372; Fallarino F et al., Cell Death Differ., 2002, 9, 1069-1077).

It has recently been discovered that a key enzyme in tryptophan catabolism, tryptophan 2,3-dioxygenase (TDO2), which is considered responsible for regulating systemic tryptophan levels in the liver, is constitutively expressed in a wide variety of cancers, such as for example in bladder carcinoma, hepatocarcinoma, melanoma, mesothelioma, neuroblastoma, sarcoma, breast carcinoma, leukemia, renal cell carcinoma, colorectal carcinoma, head and neck carcinoma, lung carcinoma, brain tumor, glioblastoma, astrocytoma, myeloma, and pancreatic carcinoma (Pilotte L et al., Proc Natl Acad Sci USA, 2012, 109(7), 2497-502). TDO2 expression in tumor cells prevents tumor surveillance by the immune system and thus prevents tumor rejection by locally degrading tryptophan (Opitz C A et al., Nature, 2011, 478(7368), 197-203). The first evidence for this was provided through inhibition of TDO2 by a small molecule which inhibited tumor growth in a P815 mastocytoma tumor model with a prophylactic vaccination approach (Pilotte L et al., Proc Natl Acad Sci USA, 2012, 109(7), 2497-502). P815mTDO2 expressing tumors were rejected less in comparison to P815 tumors transfected with an empty vector, clearly demonstrating a growth benefit for TDO2 expressing tumors. Inhibition with a TDO2 inhibitor strongly decreased tumor growth in P815mTDO2 implanted tumors. Anti-tumor activity with the TDO2 inhibitor was equally observed in the P815 control implanted tumors negative for TDO2, thus providing evidence for an effect of TDO2 expressed in the immune system of the animal. These experiments for the first time provided clear evidence for a role of TDO2 in regulating tumor growth through expression in the cancer cell as well as immune compartment.

In line with its expression profile in liver, TDO2 was found predominantly in hepatocellular carcinoma (HCC) (Pilotte L et al., Proc Natl Acad Sci USA, 2012, 109(7), 2497-502). Inhibition of tryptophan catabolism and thus restoration of tryptophan concentration and decreased production of downstream metabolites could prove beneficial in the context of liver disease progressing to the stage of liver carcinoma. More particularly: (i) several reports have shown evidence that increased availability of tryptophan through supplementation is beneficial for example, cirrhotic livers, allowing the direct use of tryptophan for protein synthesis (Ohta et al., Amino Acids, 1996, 10(4), 369-78); (ii) there is a correlation between increased downstream serum tryptophan metabolites, such as quinolinic acid, and hepatic dysfunction in patients with liver cirrhosis (Lahdou et al., Hum Immunol, 2013, 74(1), 60-6) and (iii) increased secretion of another tryptophan metabolite, indole-3-lactic acid, has been associated with alcohol-induced liver disease in mice (Manna et al., J Proteome Res, 2011, 10(9), 4120-33). In the context of liver carcinoma itself, very high RNA expression is a good indication for therapeutic evaluation of TDO2 inhibitors (Pilotte L et al., Proc Natl Acad Sci USA, 2012, 109(7), 2497-502). The above thus provides a clear rationale for TDO2 activity modulation in the control of liver tumor development.

In addition to expression in liver, TDO2 is expressed in neurons, microglia and astrocytes and the potential benefit of TDO2 inhibition in the context of glioma was shown in another animal model. Platten and collaborators demonstrated that the tryptophan catabolite kynurenine produced by TDO expressed in the tumor cells suppresses antitumour immune responses and promotes tumor-cell survival and motility through the AHR in an autocrine/paracrine fashion (Opitz C A et al., Nature, 2011, 478(7368), 197-203). The TDO-AHR pathway is active in human brain tumors and is associated with malignant progression and poor survival. Further evidence came from the accumulation of a downstream metabolite, quinolinic acid which accumulates in human gliomas and was associated with a malignant phenotype (Sahm et al., Cancer Res, 2013, 73(11), 3225-34). Here tryptophan catabolism was shown to occur in microglia cells as well. The above data thus provides evidence for TDO2 targeting in glioma with brain-penetrant small molecules.

Other tumor types in which TDO2 mRNA was found are breast carcinoma, bladder, renal cell, pancreatic, colorectal, head & neck carcinoma and lung carcinoma as well as melanoma thus broadening the scope of TDO2 targeting beyond HCC and glioma (Pilotte L et al., Proc Natl Acad Sci USA, 2012, 109(7), 2497-502).

The enhanced Tryptophan degradation observed in patients with gynecological cancers (ovarian carcinoma, cervical cancer, endometrial cancer) provides additional rationale for TDO2 targeting in those cancers (Sperner-Unterweger B et al, Immunology, 2011, 216 (3); 296-301).

The tryptophan catabolism in some cancers might be also increased by the expression of indoleamine 2,3-dioxygenase (IDO1) by tumor cells (Uyttenhove, C. et al., Nat. Med., 2003, 9, 1269-1274).

Because tryptophan catabolism is induced by inflammatory mediators, notably IFN-gamma, it is thought to represent an endogenous mechanism that restricts excessive immune responses, thereby preventing immunopathology. However in the context of cancer, there is strong evidence that suppression of antitumor immune responses in precancerous lesions and established cancers by tryptophan catabolism promotes tumor growth, which would make such catabolism an attractive target for therapeutic intervention (Dolušić E and Frédérick R., Expert Opin Ther Pat., 2013, 23(10), 1367-81). Hence, a considerable effort is being made to identify selective and efficient inhibitors of tryptophan catabolism to enhance the efficacy of conventional chemotherapy, immune checkpoints (Holmgaard R B et al., J Exp Med., 2013, 210(7), 1389-402) or therapeutic vaccines.

In the context of neurological brain disorders, TDO2 expression has been demonstrated in neurons, brain vasculature and additionally in the case of schizophrenia in astroglial cells (Miller C et al., 2004, Neurobiology Dis, 15(3):618-29). The kynurenine pathway is now considered as a therapeutic target in cognitive diseases like bipolar disorder or Tourette syndrome and neurodegenerative disorders like Alzheimer, motor neuron disease like Amyotrophic lateral sclerosis, Multiple sclerosis, Huntington or Parkinson's disease (Stone T W, 2013, Br J of Pharmacol, 169(6): 1211-27; Wu et al, 2013, Plos One, 8(4):e59749; Füvesi et al, 2012, J Neural Transm, 119(2):225-34; Widner et al, 2002, J Neural Transm, 109(2):181-9; Comings et al, 1996, Pharmacogenetics, 6(4):307-18; Forrest 2010, J Neurochem, 112(1):112-22).

Cognitive changes related to Tryptophan catabolism have also been shown in patients infected with human immunodeficiency virus type-1 (HIV), called HIV-associated neurocognitive disorder (HAND) (Davies et al, 2010, Int J of Tryptophan Res, 3:121-40). In addition, T cell hyporesponsiveness has been recently associated with the Tryptophan catabolic pathway in HIV-infected patients with possibly extension to other chronic infectious diseases like e.g. Hepatitis C.

Some TDO2 inhibitors were proposed in WO2010/008427 and by Dolusic, E. et al. (Dolusic et al., J. Med. Chem., 2011, 54, 5320-5334), however either their affinity for the target is limited, or their pharmacokinetic properties are not suitable for development as a drug for human use.

Therefore, there is a need for new TDO2 inhibitors with improved efficacy for cancer treatment and/or prevention.

SUMMARY OF THE INVENTION

The present invention provides new TDO2 inhibitors which may be administered to a mammalian subject having a condition or disease where it is desirable to modulate, and in particular decrease, activity of TDO2, including, without limitation, patients diagnosed with cancer, or any subject being at risk of developing a cancer. Also provided are compositions containing these compounds and uses thereof.

In one aspect, a compound of Formula I is provided or a pharmaceutically acceptable salt, solvent or solvate thereof, where $A^1$, $A^2$, Q, $R^1$, $R^2$, $R^3$, $X^1$ and $X^2$ are as defined herein.

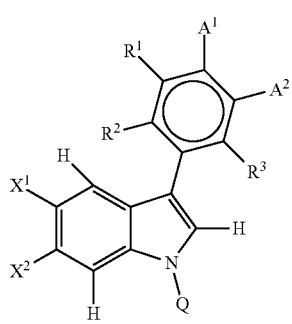

I

In a further aspect, a pharmaceutical composition is provided which comprises a compound according to Formula I is provided, or a pharmaceutically acceptable enantiomer, salt or solvate thereof, and at least one pharmaceutically acceptable carrier, diluent, excipient and/or adjuvant.

In yet another aspect, a medicament is provided which comprises a compound according to Formula I, or a pharmaceutically acceptable enantiomer, salt or solvate thereof.

In yet a further aspect, a compound of Formula I, or a pharmaceutically acceptable enantiomer, salt or solvate thereof is provided, for use in the treatment and/or prevention of cancer, neurodegenerative disorders such as Parkinson's disease, Alzheimer's disease and Huntington's disease, chronic viral infections such as HCV and HIV, depression, and obesity, or for use as TDO2 inhibitor.

In still another aspect, a method of treating and/or preventing of cancer, neurodegenerative disorders such as Parkinson's disease, Alzheimer's disease and Huntington's disease, chronic viral infections such as HCV and HIV, depression, and obesity, or inhibiting TD02 is provide. The method comprises administering a compound of Formula I, or a pharmaceutically acceptable salt thereof.

In a further aspect, a process for manufacturing a compound of Formula I or a pharmaceutically acceptable enantiomer, salt or solvate thereof is provide. The process comprises:

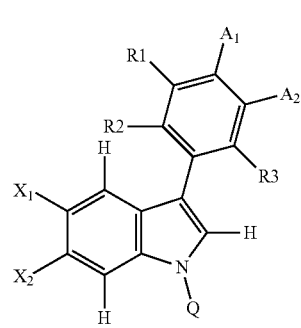

I and pharmaceutically acceptable enantiomers, salts and solvates thereof, wherein $X^1$, $X^2$, $R^1$, $R^2$, $R^3$, $A^1$, $A^2$ and Q are as defined in Formula I;

comprising:

(a1) reacting a compound of Formula (i)

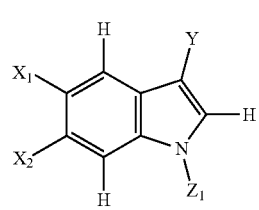

(i)

wherein $X^1$ and $X^2$ are as defined in Formula I;

$Z^1$ represents Q or an amino protecting group such as for example an arylsulphonyl, a tert-butoxy carbonyl, a methoxymethyl, a para-methoxy benzyl, a benzyl or any other suitable protecting group known to those skilled in the art Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art with a compound of Formula (ii)

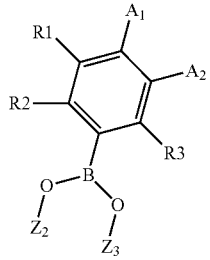

(ii)

wherein $R^1$, $R^2$, $R^3$, $A^1$, $A^2$ and $A^3$ are as defined in Formula I;

$Z^2$ and $Z^3$ represent H or alkyl groups, with the possibility for $Z^2$ and $Z^3$ to form a ring;

so as to obtain a compound of Formula (iii),

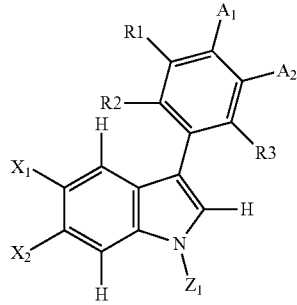

(iii)

wherein $X^1$, $X^2$, $R^1$, $R^2$, $R^3$, $A^1$, $A^2$ and $Z^1$ are as defined above;

and (b1) in the case wherein $Z^1$ is not Q, deprotecting the indole amine of compound of Formula (iii), to afford compound of Formula I.

Still other aspects and advantages of the invention will be apparent from the following detailed description of the invention.

DETAILED DESCRIPTION OF THE INVENTION

Compounds

Provided herein are Compounds of Formula I, or a pharmaceutically acceptable enantiomer, salt, or solvate therein. Unless otherwise specified, while reference is made to Formula I and its uses and methods of production for convenience, it will be understood that its subformula: Formula Ia, Ib, and II are encompassed within these descriptions. Formula I has the structure:

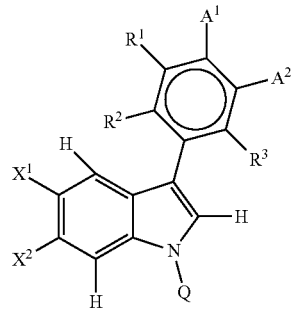

I or a pharmaceutically acceptable enantiomer, salt, or solvate thereof, wherein:

$X^1$ and $X^2$ represent each independently H, halogen, OH, OR7; or C1-C4 alkyl;

$R^1$, $R^2$, and $R^3$ are independently: H, halogen, cyano, $R^7$, OH, $OR^7$, $NR^7R^8$, $CONR^7$, $N(R^7)COR^8$, $SO_2R^7$, or alkyl$NR^7R^8$;

Q is H or $COR^7$ or $CONR^7R^8$;

$R^7$ and $R^8$ are independently (i) H, (ii) $NH_2$, (iii) C1 to C6 branched or unbranched alkyl, optionally substituted with one to three substituents selected from oxo, amino, OH, halogen, C1 to C4 alkyl, (iv) a C1-C3 alkyl-heterocycle or a heterocycle, an optionally substituted five or six-membered heterocycle in which the substituent is oxo, OH, NH2, or a C1 to C3 alkyl, which is optionally substituted;

$A^1$ is (i) H, (ii) halogen, (iii) OH, (iv) $SO_2R^5$, (v) $SO_2NR^5R^6$, (vi) an optionally substituted C1-C4 alkyl, wherein the substituent is selected from one or more of a halogen, alkyl, OH, or amino, or (vii) $CONR^5R^6$, or $A^2$ is (i) H, (ii) halogen, (iii) OH, (iv) $SO_2R^5$, (v)$SO_2NR^5R^6$, (vi) an optionally substituted C1-C4 alkyl, wherein the substituent is selected from one or more of a halogen, alkyl, OH, or amino, or (vii) $CONR^5R^6$, or $A^1$ and $A^2$ together form a 5-membered fused ring structure comprising $SO_2NR^5CR^9$, wherein $R^9$ is a hydrogen atom or a group, optionally substituted, selected from C1-C6 alkyl, aryl, arylalkyl, alkylaryl, heteroaryl, heteroarylalkyl, alkylheteroaryl, or amino;

$R^5$ and $R^6$ are independently: (i') H, (ii') oxo, (iii') amino, (iv') halogen or a group, optionally substituted, selected from:

(v') C1-C6 alkyl, linear or branched; optionally substituted with up to three substituents selected from halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SOR^9$, aryl, or CO-alkyl, wherein $R^9$ and $R^{10}$ represent each independently a hydrogen atom or a group, optionally substituted, selected from C1-C6 alkyl, heterocyclyl, aryl, arylalkyl, alkylaryl, heteroaryl, heteroarylalkyl, alkylheteroaryl, or amino;

(vi') heterocyclyl or C1-C2 alkyl-heterocyclyl. the heterocyclyl being optionally substituted with up to three substituents which are independently halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, or alkyl, the alkyl group being optionally substituted by one or more groups selected from halogen, hydroxyl, amino or COOH; wherein $R^9$ and $R^{10}$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

(vii') cycloalkyl, optionally substituted with up to three substituents selected from halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO2R^{10}$, $SO_2R^9$, aryl, CO-alkyl, or C1-C6 alkyl which is optionally substituted by one or more groups selected from halogen, hydroxyl, amino or COOH; wherein $R^9$ and $R^{10}$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

provided that:
if one of $A^1$ or $A^2$ is H, halogen, OH, or the optionally substituted C1 to C4 alkyl, then the other is not H, halogen, OH, or the optionally substituted C1 to C4 alkyl;
if $A^1$, $X^1$, $X^2$, $R^1$, $R^2$, $R^3$ are each H, then $A^2$ is not $COONH_2$;
if $A^2$ is H, $X^1$ is $CH_3$, $R^1$ and $R^2$ are each H, and $R^2$ is halogen, then $A^1$ is not $SO_2NH_2$. In certain embodiments of Formula I, Q is H. In certain embodiments of Formula I, $X^1$ and $X^2$ are independently H, F or Cl, preferably F. In certain embodiments, in a compound of Formula I, $A^2$ is H, halogen, or OH, preferably H.

In certain embodiments of Formula I, in $R^5$ and/or $R^6$, the heterocycle is an optionally substituted 4, 5 or 6-membered heterocycle ring, or $NR^5R^6$ together form a heterocycle ring of 4, 5 or 6 members having 1, 2 or 3 heteroatoms, said heterocycle being optionally substituted with 1, 2 or 3 substituents independently selected from C1 to C6 alkyl, OH, halogen, amino, $SO_2$, or oxo.

In certain embodiments of Formula I, wherein $X^1$ is H and $X^2$ is F.

In certain embodiments of Formula I, $A^1$ is $SO_2NR^5R^6$.

In certain embodiments of Formula I, in certain embodiments, $A^1$ and $A^2$ together form a 5-membered fused ring structure comprising $SO_2NR^5CR^9$, wherein $R^9$ is a hydrogen atom or a group, optionally substituted, selected from C1-C6 alkyl, aryl, arylalkyl, alkylaryl, heteroaryl, heteroarylalkyl, alkylheteroaryl, or amino. In a further embodiment, $A^1$ and $A^2$ together form a 5-membered fused ring structure comprising $SO_2NR^5CR^{9'}$, wherein $R^{9'}$ is a $C_1$-$C_4$ alkyl, OH, or halogen.

In another embodiment, $X^1$ and $X^2$ represent each independently H, halogen, OH, $OR^7$; or C1-C4 alkyl; $R^1$, $R^2$, and $R^3$ are independently: H, halogen, cyano, $R^7$, $OR^7$, $NR^7R^8$, $CONR^7$, $N(R^7)COR^8$, $SO_2R^7$, or $alkylNR^7R^8$; Q is H or $COR^7$ or $CONR^7R^8$; $R^7$ and $R^8$ are independently (i) H, (ii) $NH_2$, (iii) C1 to C6 branched or unbranched alkyl, optionally substituted with one to three substituents selected from one or more of oxo, amino, OH, halogen, or C1 to C4 alkyl, (iv) a C1-C3 alkyl-heterocycle or (v) a heterocycle, wherein the heterocycle of (iv) or (v) is an optionally substituted five or six-membered heterocycle in which the substituent is oxo, OH, $NH_2$, or a C1 to C3 alkyl which is optionally substituted with one to three substituents selected from one or more of a halogen, alkyl, OH, oxo, or amino.

In certain embodiments, $A^1$ or $A^2$ are independently (i) H, (ii) halogen, (iii) OH, (iv) $SO_2R^5$, (v)$SO_2NR^5R^6$, wherein $R^5$ and $R^6$ are as defined below in (v')-(vii') or $NR^5R^6$ optionally together form a heterocycle ring of 4, 5 or 6 members having 1, 2 or 3 heteroatoms, said heterocycle being optionally substituted with 1, 2 or 3 substituents selected from one or more of $C_1$ to $C_6$ alkyl, OH, halogen, amino, $SO_2$, or oxo, (vi) a C1-C4 alkyl optionally substituted with one to three substituents selected from one or more of a halogen, alkyl, OH, oxo, or amino, or (vii)(C1-C2) $ONR^5R^6$.

In certain embodiments, $A^1$ and $A^2$ together form a 5-membered fused ring structure comprising $SO_2NR^5CR^9R^{9'}$, wherein $R^{9'}$ is H, or $R^{9'}$ and $R^9$ are each methyl, wherein when $R^{9'}$ is H, $R^9$ is a hydrogen atom, cyclopropyl, or a group, optionally substituted, selected from C1-C6 alkyl, aryl, arylalkyl, alkylaryl, heteroaryl, heteroarylalkyl, or alkylheteroaryl, wherein the optionally substituted group has one, two or three substituents selected from one or more of a halogen, C1-C4 alkyl, OH, oxo, or amino.

In certain embodiments, $R^5$ and $R^6$ are independently: (I') H, (ii') oxo, (iii') amino, (iv') halogen or a group, optionally substituted, selected from:
(v') C1-C6 alkyl, linear or branched, optionally substituted with up to three substituents selected from one or more of halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SOR^9$, aryl, or CO-alkyl,
(vi') heterocyclyl or C1-C3 alkyl-heterocyclyl, the heterocyclyl being optionally substituted with up to three substituents which are selected from one or more of halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, a five or six membered heterocycle having 2 N atoms in its backbone; a piperidine substituted with F and three OH, or alkyl, the alkyl group being optionally substituted by one to three groups selected from one or more of halogen, hydroxyl, oxo, amino or COOH;
(vii') cycloalkyl, optionally substituted with up to three substituents selected from halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, or C1-C6 alkyl which is optionally substituted by one or more groups selected from halogen, hydroxyl, amino or COOH;

$R^9$ and $R^{10}$ represent each independently a hydrogen atom or a group, optionally substituted, selected from C1-C6 alkyl, wherein when substituted, the C1-C6 alkyl has one, two or three groups selected from one or more halogen, hydroxyl, oxo, amino or COOH, heterocyclyl, aryl, arylalkyl, alkylaryl, heteroaryl, heteroarylalkyl, or alkylheteroaryl, wherein when substituted, the aryl, arylalkyl, alkylaryl, heteroaryl, heteroarylalkyl, alkylheteroaryl has up to three substituents which are one or more of halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, CO-alkyl, or amino;

and provided that: if one of $A^1$ or $A^2$ is H, halogen, OH, or the optionally substituted C1 to C4 alkyl, then the other is not H, halogen, OH, or the optionally substituted C1 to C4 alkyl; if $A^1$, $X^1$, $X^2$, $R^1$, $R^2$, $R^3$ are each H, then $A^2$ is not $COONH_2$; if A2 is H, $X^1$ is $CH_3$, $R^1$ and $R^2$ are each H, and $R^2$ is halogen, then A1 is not $SO_2NH_2$.

In certain embodiments, A1 is $SO_2NR^5R^6$. In other embodiments, the heterocycle of $R^5$ and/or $R^6$, is an optionally substituted 4, 5 or 6-membered heterocycle ring, or $NR^5R^6$ together form a heterocycle ring of 4, 5 or 6 members having 1, 2 or 3 heteroatoms, said heterocycle being optionally substituted with 1, 2 or 3 substituents independently selected from $C_1$ to $C_6$ alkyl, OH, halogen, amino, $SO_2$, or oxo. In certain embodiments, the 1, 2, or 3 heteroatom of the 4, 5 or 6-membered heterocycle ring comprise at least one N atom.

In other embodiments, when $SO_2NR^5CR^9$, $R^9$ is a $C_1$-$C_4$ alkyl which is optionally substituted with OH or halogen.

In certain embodiments, a compound of Formula I is in a salt form. In another embodiment, the free base (non-salt) form of a compound of Formula I is provided.

Provided herein is a compound of Formula Ia:

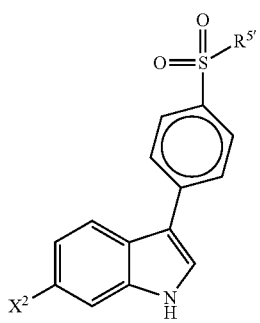

Ia or a pharmaceutically acceptable enantiomer, salt or solvate thereof, wherein:

$X^2$ is H, halogen, OH, $OR^7$; or C1-C4 alkyl;

$R^{5'}$ is a heterocyclyl or C1-C2 alkyl-heterocyclyl. the heterocyclyl being optionally substituted with up to three substituents which are independently halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, or alkyl, the alkyl group being optionally substituted by one or more groups selected from halogen, hydroxyl, amino or COOH; wherein $R^9$ and $R^{10}$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

In certain embodiments in Formula Ia, $X^2$ is F. In certain embodiments in Formula Ia, in $X^1$, wherein $R^5$ is the heterocycle or C1-C2 alkyl-heterocycle, the heterocycle is a 5 or 6-membered ring having a one, two or three heteroatoms selected from N and O. In certain embodiments in Formula Ia, the heterocycle is a six membered ring having at least one N. In certain embodiments in Formula Ia, the heterocycle has a second N heteroatom. In certain embodiments, a compound of Formula Ia is in a salt form. In another embodiment, the free base (non-salt) form of a compound of Formula Ia is provided.

Provided herein is a compound of Formula Ia':

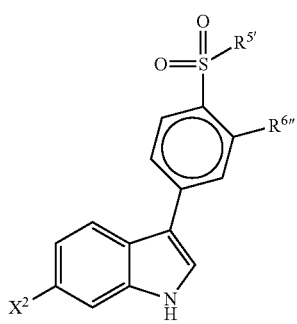

Ia' or a pharmaceutically acceptable enantiomer, salt or solvate thereof, wherein:

$X^2$ is H, halogen, OH, $OR^7$; or C1-C4 alkyl;

$R^{5'}$ is heterocyclyl or C1-C3 alkyl-heterocyclyl, the heterocyclyl being optionally substituted with up to three substituents which are selected from one or more of halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, a five or six membered heterocycle having 2 N atoms in its backbone; a piperidine substituted with F and three OH, or alkyl, the alkyl group being optionally substituted by one to three groups selected from one or more of halogen, hydroxyl, oxo, amino or COOH.

In certain embodiments, $R^{6''}$ is a H or C1-C4 alkyl, optionally substituted with one, two or three OH, oxo or amino.

In certain embodiments in Formula Ia, $X^2$ is F. In certain embodiments in Formula Ia, in $X^1$, wherein $R^5$ is the heterocycle or C1-C2 alkyl-heterocycle, the heterocycle is a 5 or 6-membered ring having a one, two or three heteroatoms selected from N and O. In certain embodiments in Formula Ia, the heterocycle is a six membered ring having at least one N. In certain embodiments in Formula Ia, the heterocycle has a second N heteroatom. In other embodiments in Formula Ia, the heterocycle has three N heteroatoms. In certain embodiments, a compound of Formula Ia is in a salt form. In another embodiment, the free base (non-salt) form of a compound of Formula Ia is provided.

Further provided herein is a compound of formula Ib or Ib' is provided:

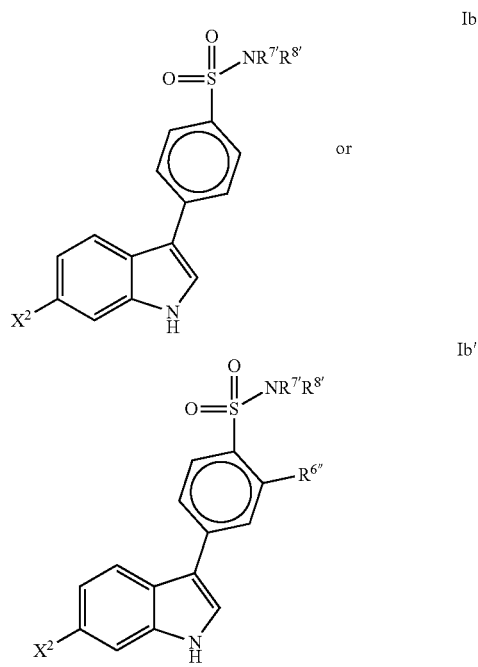

or a pharmaceutically acceptable enantiomer, salt or solvate thereof, wherein:

$X^2$ is H, halogen, OH, $OR^7$; or C1-C4 alkyl;

$R^{7'}$ and $R^{8'}$ are independently: H; $NH_2$; C1 to C6 branched or unbranched alkyl, optionally substituted with one to three substituents selected from oxo, amino, OH, halogen, C1 to C4 alkyl; a C1-C3 alkyl-heterocycle or a heterocycle, an optionally substituted five or six-membered heterocycle in which the substituent is a C1 to C3 alkyl, which is itself optionally substituted with a group selected from oxo, OH, or NH2;

provided that when $X^2$ is $CH_3$, $R^7$ and $R^8$ are not both H.

In certain embodiments, $NR^{7'}R^{8'}$ optionally together form a heterocycle ring of 4, 5 or 6 members having 1, 2 or 3 heteroatoms, said heterocycle being optionally substituted with 1, 2 or 3 substituents selected from one or more of $C_1$ to $C_6$ alkyl, OH, halogen, amino, $SO_2$, or oxo.

In certain embodiments, $R^{6''}$ is a H or C1-C4 alkyl, optionally substituted with one, two or three OH, oxo or amino.

In certain embodiments of Formula Ib, one of $R^{7'}$ and $R^{8'}$ is C1 to C6 branched or unbranched alkyl, optionally substituted with one to three substituents selected from oxo, amino, OH, halogen, or a heterocycle.

In certain embodiments, the heterocycle is optionally substituted with 1, 2 or 3 substituents selected from one or more of $C_1$ to $C_6$ alkyl, OH, halogen, amino, $SO_2$, or oxo. In other embodiments of Formula Ib, the alkyl is an optionally substituted C2 to C4 alkyl.

In certain embodiments of Formula Ib, the optionally substituted C2 to C4 alkyl is substituted with one or more of an oxo, OH, methyl, or an amino group. In certain embodiments, a compound of Formula Ib is in a salt form. In another embodiment, the free base (non-salt) form of a compound of Formula Ib is provided.

Illustrative compounds of Formula I are those listed in Table 1 hereafter.

| Compound-IUPAC name | Structure |
|---|---|
| 6-Fluoro-3-(4-methanesulfonyl-phenyl)-1H-indole | 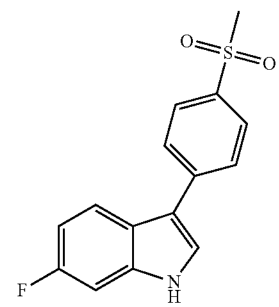 [SMILES: CS(=O)(=O)c1ccc(-c2c[nH]c3cc(F)ccc23)cc1] |
| N-(2-aminoethyl)-4-(6-fluoro-1H-indol-3-yl)benzamide | 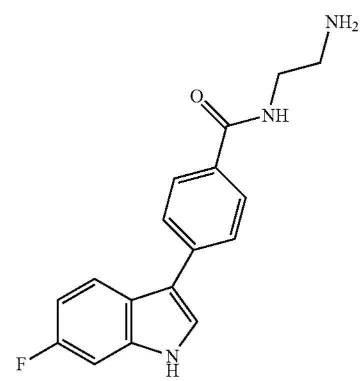 [SMILES: NCCNC(=O)c1ccc(-c2c[nH]c3cc(F)ccc23)cc1] |
| (4-(6-fluoro-1H-indol-3-yl)phenyl)(piperazin-1-yl)methanone | 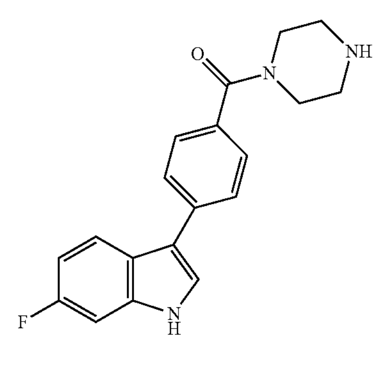 [SMILES: O=C(c1ccc(-c2c[nH]c3cc(F)ccc23)cc1)N1CCNCC1] |

-continued

| Compound-IUPAC name | Structure |
|---|---|
| 6-fluoro-3-(4-(piperazin-1-yl-sulfonyl)-phenyl)-7H-indole | 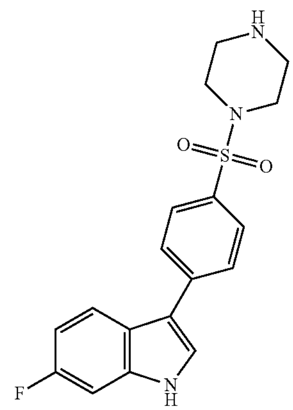 [SMILES: O=S(=O)(c1ccc(-c2c[nH]c3cc(F)ccc23)cc1)N1CCNCC1] |
| 4-((4-(6-fluoro-1H-indol-3-yl)-phenyl)sulfonyl)morpholine | 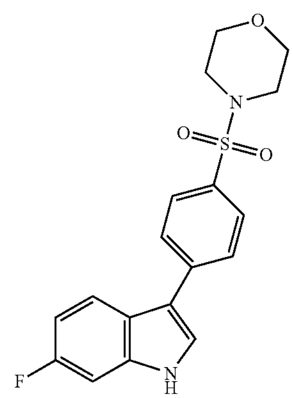 [SMILES: O=S(=O)(c1ccc(-c2c[nH]c3cc(F)ccc23)cc1)N1CCOCC1] |
| 4-(6-fluoro-1H-indol-3-yl)benzenesulfonamide | 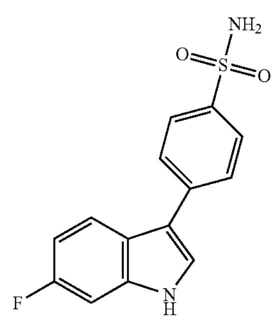 [SMILES: NS(=O)(=O)c1ccc(-c2c[nH]c3cc(F)ccc23)cc1] |
| 6-fluoro-3-(3-(piperazin-1-ylsulfonyl)phenyl)-1H-indole | 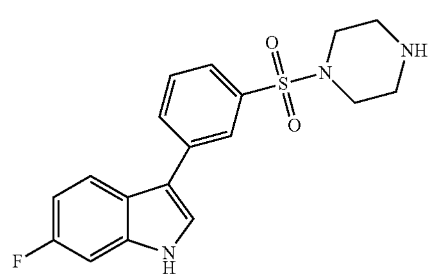 [SMILES: O=S(=O)(c1cccc(-c2c[nH]c3cc(F)ccc23)c1)N1CCNCC1] |

| Compound-IUPAC name | Structure |
|---|---|
| N-(2-aminoethyl)-4-(6-fluoro-1H-indol-3-yl)benzenesulfonamide | 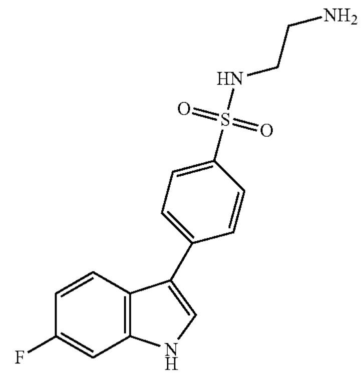 [SMILES: NCCNS(=O)(=O)c1ccc(-c2c[nH]c3cc(F)ccc23)cc1] |
| N-(2-aminoethyl)-3-(6-fluoro-1H-indol-3-yl)benzenesulfon-amide | 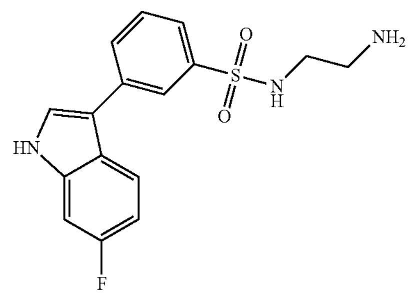 [SMILES: NCCNS(=O)(=O)c1cccc(-c2c[nH]c3cc(F)ccc23)c1] |
| 3-(6-fluoro-1H-indol-3-yl)benzene-sulfonamide | 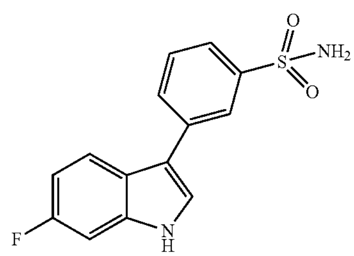 [SMILES: NS(=O)(=O)c1cccc(-c2c[nH]c3cc(F)ccc23)c1] |
| 3-(4-(((cis)-3,5-dimethylpiperazin-1-yl)sulfonyl)phenyl)-6-fluoro-1H-indole | 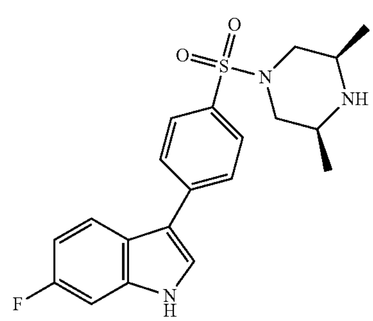 [SMILES: C[C@@H]1CN(S(=O)(=O)c2ccc(-c3c[nH]c4cc(F)ccc34)cc2)C[C@H](C)N1] |
| (4-((4-(6-fluoro-1H-indol-3-yl)phenyl)sulf-onyl)piperazin-2-yl)methanol | 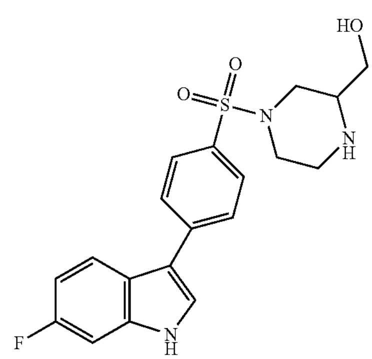 [SMILES: O=S(=O)(c1ccc(-c2c[nH]c3cc(F)ccc23)cc1)N1CCNC(CO)C1] |

| Compound-IUPAC name | Structure |
|---|---|
| (1-((4-(6-fluoro-1H-indol-3-yl)phenyl)sulfonyl) piperazin-2-yl)methanol | 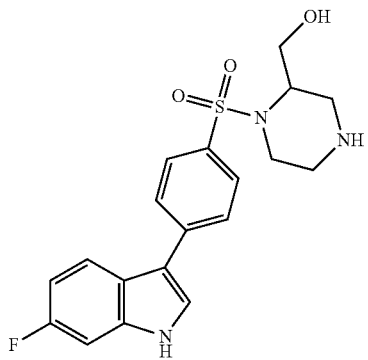 [SMILES: O=S(=O)(c1ccc(-c2c[nH]c3cc(F)ccc23)cc1)N1CCNCC1CO] |
| (3R,5R)-3-[4-(3,5-dimethyl-piperazine-1-sulfonyl)-phenyl]-6-fluoro-1H-indole | 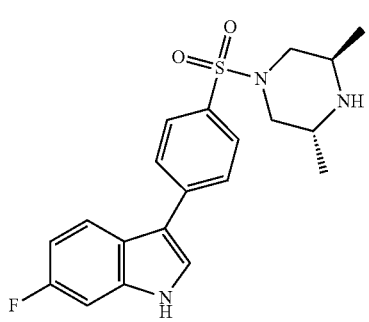 [SMILES: C[C@@H]1CN(S(=O)(=O)c2ccc(-c3c[nH]c4cc(F)ccc34)cc2)C[C@@H](C)N1] |
| 3-(4-(((3S,5S)-3,5-dimethylpiperazin-1-yl)sulfonyl) phenyl)-6-fluoro-1H-indole | 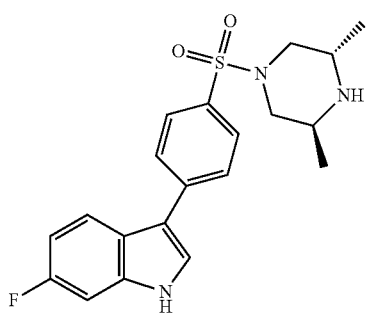 [SMILES: C[C@H]1CN(S(=O)(=O)c2ccc(-c3c[nH]c4cc(F)ccc34)cc2)C[C@H](C)N1] |
| N-(2-(4-(6-fluoro-1H-indol-3-yl)phenyl-sulfonamido)ethyl)acetamide | 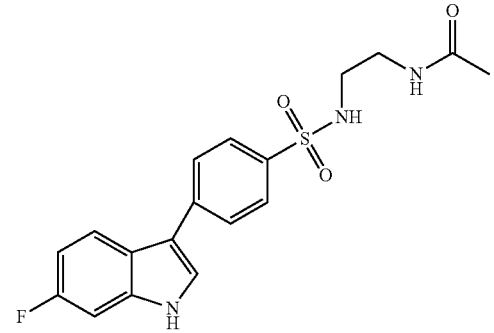 [SMILES: CC(=O)NCCNS(=O)(=O)c1ccc(-c2c[nH]c3cc(F)ccc23)cc1] |

| Compound-IUPAC name | Structure |
|---|---|
| (R)-(4-((4-(6-fluoro-1H-indol-3-yl)phenyl)sulfonyl)piperazin-2-yl)methanol | 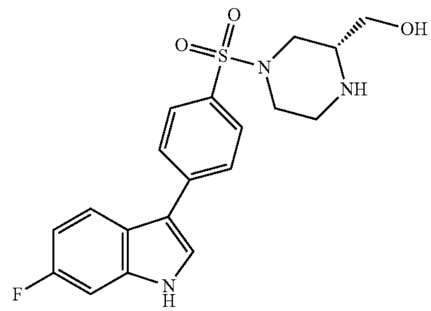 [SMILES: O=S(=O)(c1ccc(-c2c[nH]c3cc(F)ccc23)cc1)N1CCN[C@@H](CO)C1] |
| (S)-(4-((4-(6-fluoro-1H-indol-3-yl)phenyl)sulfonyl)piperazin-2-yl)methanol | 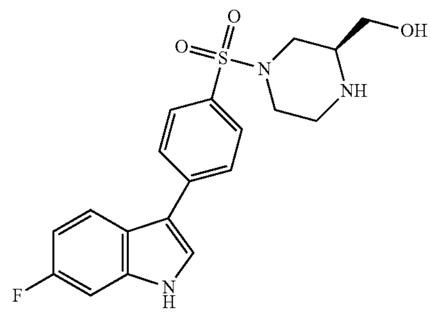 [SMILES: O=S(=O)(c1ccc(-c2c[nH]c3cc(F)ccc23)cc1)N1CCN[C@H](CO)C1] |
| 6-fluoro-3-(4-((4-(methylsulfonyl)-piperazin-1-yl)sulfonyl)phenyl)-1H-indole | 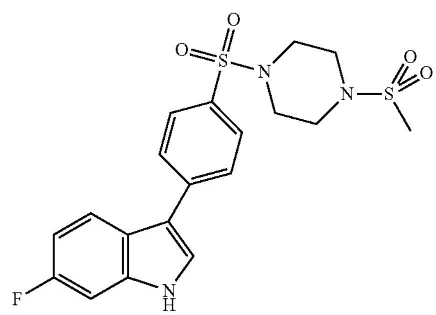 [SMILES: CS(=O)(=O)N1CCN(S(=O)(=O)c2ccc(-c3c[nH]c4cc(F)ccc34)cc2)CC1] |
| 3-(4-(piperazin-1-ylsulfonyl)phenyl)-1H-indole | 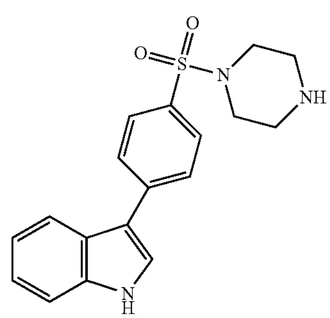 [SMILES: O=S(=O)(c1ccc(-c2c[nH]c3ccccc23)cc1)N1CCNCC1] |
| 4-(6-fluoro-1H-indol-3-yl)-N-(2-(methylsulfonamido)ethyl)benzenesulfonamide | 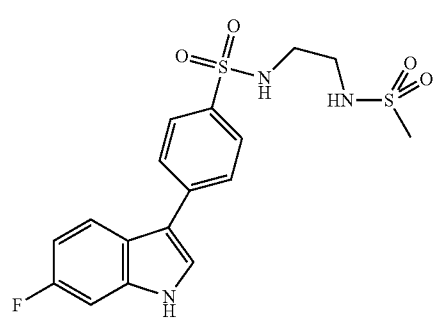 [SMILES: CS(=O)(=O)NCCNS(=O)(=O)c1ccc(-c2c[nH]c3cc(F)ccc23)cc1] |

| Compound-IUPAC name | Structure |
|---|---|
| 6-fluoro-3-(2-fluoro-4-(piperazin-1-yl-sulfonyl)phenyl)-1H-indole | 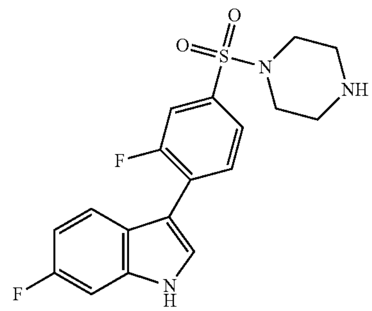 [SMILES: O=S(=O)(c1ccc(-c2c[nH]c3cc(F)ccc23)c(F)c1)N1CCNCC1] |
| 3-(4-chloro-3-(piperazin-1-ylsulfonyl)phenyl)-6-fluoro-1H-indole | 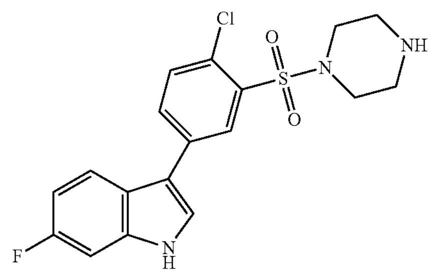 [SMILES: O=S(=O)(c1cc(-c2c[nH]c3cc(F)ccc23)ccc1Cl)N1CCNCC1] |
| 6-fluoro-3-(4-(piperazin-1-ylsulfonyl)-3-(trifluoromethyl)phenyl)-1H-indole | 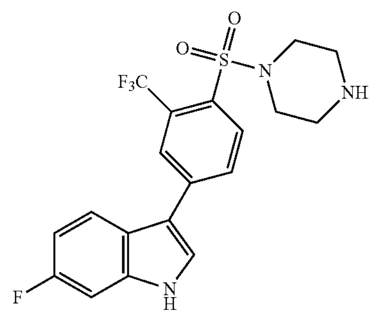 [SMILES: O=S(=O)(c1ccc(-c2c[nH]c3cc(F)ccc23)cc1C(F)(F)F)N1CCNCC1] |
| 6-fluoro-3-(2-methyl-4-(piperazin-1-ylsulfonyl)phenyl)-1H-indole | 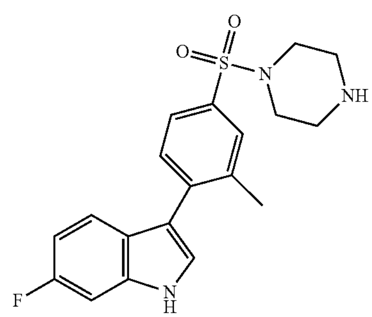 [SMILES: Cc1cc(S(=O)(=O)N2CCNCC2)ccc1-c1c[nH]c2cc(F)ccc12] |
| 3-(4-(6-fluoro-1H-indol-3-yl)phenylsulfonamido)propanamide | 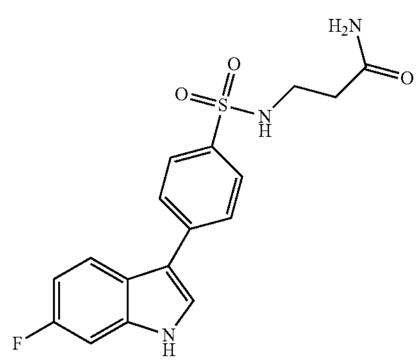 [SMILES: NC(=O)CCNS(=O)(=O)c1ccc(-c2c[nH]c3cc(F)ccc23)cc1] |

-continued

| Compound-IUPAC name | Structure |
|---|---|
| 3-(4-(6-fluoro-1H-indol-3-yl)-N-methylphenyl-sulfonamido)propanamide | 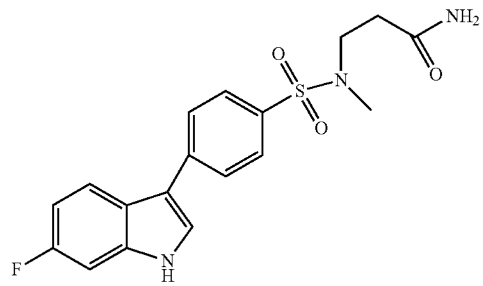 [SMILES: CN(CCC(N)=O)S(=O)(=O)c1ccc(-c2c[nH]c3cc(F)ccc23)cc1] |
| 6-fluoro-3-(3-fluoro-4-(piperazin-1-ylsulfonyl)phenyl)-1H-indole | 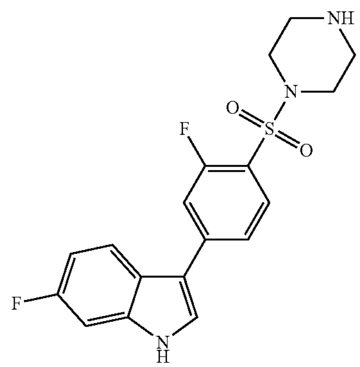 [SMILES: O=S(=O)(c1ccc(-c2c[nH]c3cc(F)ccc23)cc1F)N1CCNCC1] |
| 6-fluoro-3-(3-methoxy-4-(piperazin-1-yl-sulfonyl)phenyl)-1H-indole | 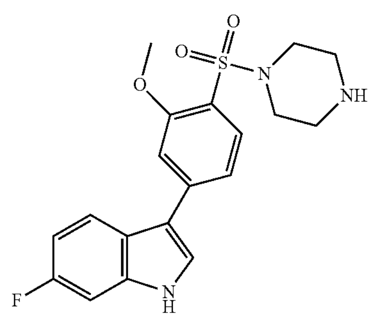 [SMILES: COc1cc(-c2c[nH]c3cc(F)ccc23)ccc1S(=O)(=O)N1CCNCC1] |
| N-(2-aminoethyl)-3-(6-fluoro-1H-indol-3-yl)-5-methylbenzenesulfonamide | 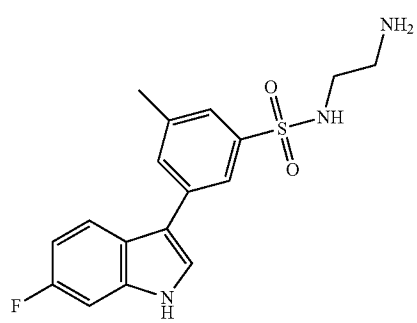 [SMILES: Cc1cc(-c2c[nH]c3cc(F)ccc23)cc(S(=O)(=O)NCCN)c1] |
| 6-fluoro-3-(3-(methylsulfonyl)phenyl)-1H-indole | 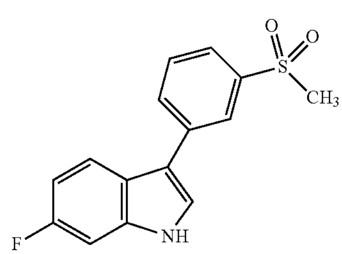 [SMILES: CS(=O)(=O)c1cccc(-c2c[nH]c3cc(F)ccc23)c1] |

-continued

| Compound-IUPAC name | Structure |
|---|---|
| 5-(6-Fluoro-1H-indol-3-yl)-2-(piperazine-1-sulfonyl)-benzonitrile | 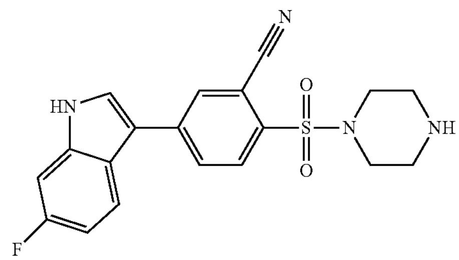 [SMILES: N#Cc1cc(-c2c[nH]c3cc(F)ccc23)ccc1S(=O)(=O)N1CCNCC1] |
| N-(2-Amino-ethyl)-5-(6-fluoro-1H-indol-3-yl)-2-methyl-benzenesulfonamide | 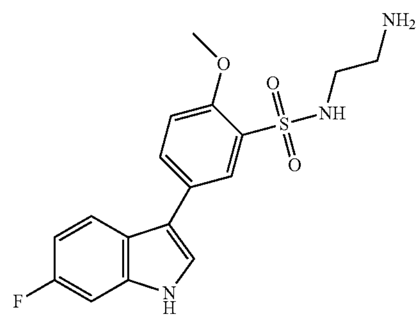 [SMILES: COc1ccc(-c2c[nH]c3cc(F)ccc23)cc1S(=O)(=O)NCCN] |
| 6-fluoro-3-(3-methyl-4-(piperazin-1-ylsulfonyl)phenyl)-7H-indole | 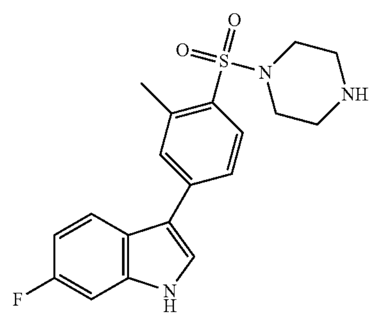 [SMILES: Cc1cc(-c2c[nH]c3cc(F)ccc23)ccc1S(=O)(=O)N1CCNCC1] |
| 5-(6-fluoro-1H-indol-3-yl)-2-(piperazin-1-ylsulfonyl)phenol | 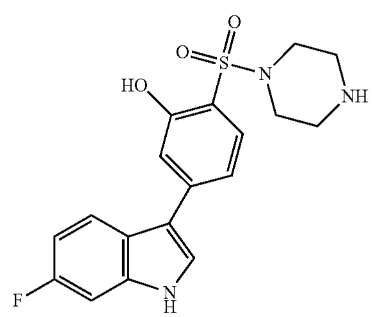 [SMILES: O=S(=O)(c1ccc(-c2c[nH]c3cc(F)ccc23)cc1O)N1CCNCC1] |
| N-(2-aminoethyl)-2-chloro-5-(6-fluoro-1H-indol-3-yl)benzenesulfonamide | 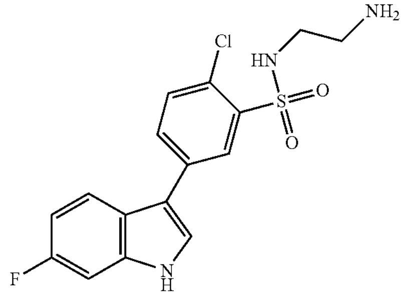 [SMILES: NCCNS(=O)(=O)c1cc(-c2c[nH]c3cc(F)ccc23)ccc1Cl] |

-continued

| Compound-IUPAC name | Structure |
|---|---|
| 2-(6-fluoro-1H-indol-3-yl)-5-(piperazin-1-ylsulfonyl)benzonitrile | 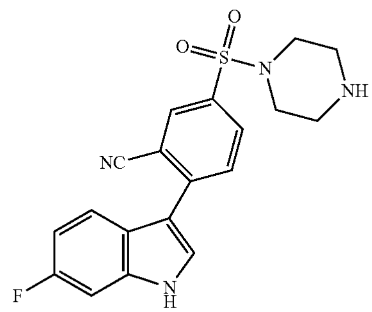 [SMILES: N#Cc1cc(S(=O)(=O)N2CCNCC2)ccc1-c1c[nH]c2cc(F)ccc12] |
| N-(2-aminoethyl)-3-chloro-5-(6-fluoro-1H-indol-3-yl)benzenesulfonamide | 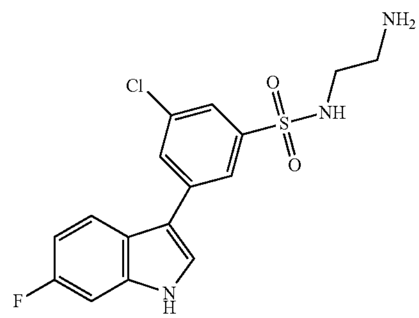 [SMILES: NCCNS(=O)(=O)c1cc(Cl)cc(-c2c[nH]c3cc(F)ccc23)c1] |
| N-(2-aminoethyl)-5-(6-fluoro-1H-indol-3-yl)-2-hydroxybenzenesulfonamide | 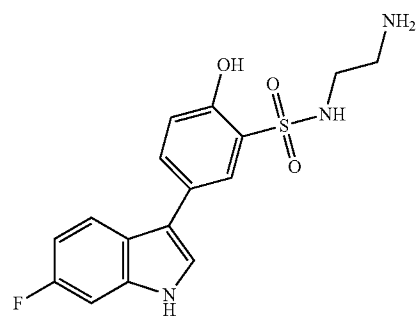 [SMILES: NCCNS(=O)(=O)c1cc(-c2c[nH]c3cc(F)ccc23)ccc1O] |
| 4-((4-(6-fluoro-1H-indol-3-yl)phenyl)sulfonyl)-piperazin-2-one | 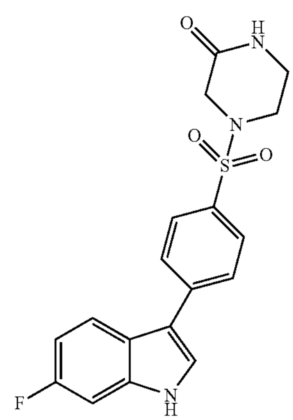 [SMILES: O=C1CN(S(=O)(=O)c2ccc(-c3c[nH]c4cc(F)ccc34)cc2)CCN1] |
| 5-(6-fluoro-1H-indol-3-yl)-2-(piperazin-1-ylsulfonyl)benzamide | 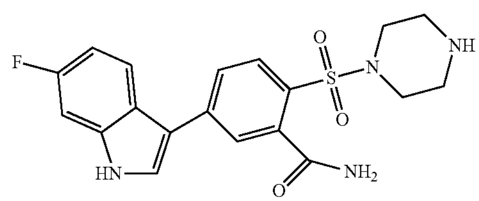 [SMILES: NC(=O)c1cc(-c2c[nH]c3cc(F)ccc23)ccc1S(=O)(=O)N1CCNCC1] |

| Compound-IUPAC name | Structure |
|---|---|
| 4-((4-(6-fluoro-1H-indol-3-yl)phenyl)sulfonyl)-1-methylpiperazin-2-one | 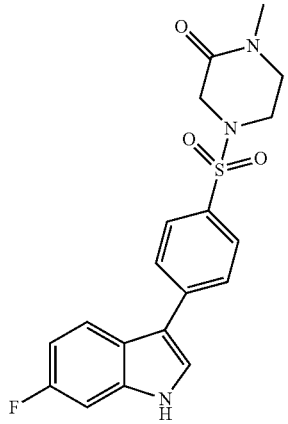 [SMILES: CN1CCN(S(=O)(=O)c2ccc(-c3c[nH]c4cc(F)ccc34)cc2)CC1=O] |
| N-(2-aminoethyl)-2-fluoro-5-(6-fluoro-1H-indol-3-yl)benzenesulfonamide | 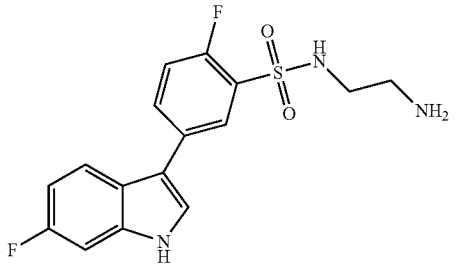 [SMILES: NCCNS(=O)(=O)c1cc(-c2c[nH]c3cc(F)ccc23)ccc1F] |
| N-(2-aminoethyl)-3-fluoro-5-(6-fluoro-1H-indol-3-yl)benzenesulfonamide | 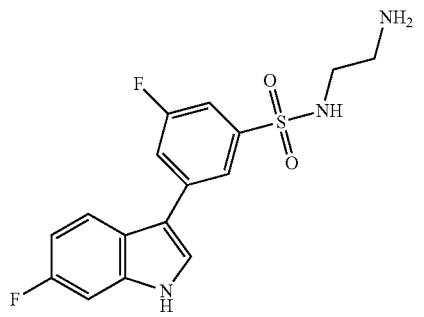 [SMILES: NCCNS(=O)(=O)c1cc(F)cc(-c2c[nH]c3cc(F)ccc23)c1] |
| 3-(3-chloro-4-(piperazin-1-ylsulfonyl)-phenyl)-6-fluoro-1H-indole | 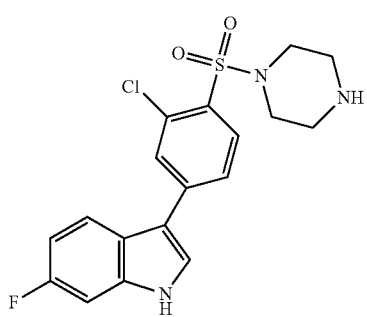 [SMILES: O=S(=O)(c1ccc(-c2c[nH]c3cc(F)ccc23)cc1Cl)N1CCNCC1] |

-continued

| Compound-IUPAC name | Structure |
| --- | --- |
| 4-(6-fluoro-1H-indol-3-yl)-N-(tetrahydro-pyran-4-yl)-benzenesulfonamide | 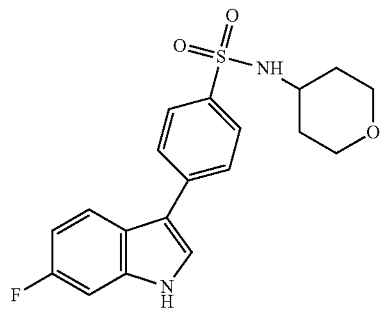 [SMILES: O=S(=O)(NC1CCOCC1)c1ccc(-c2c[nH]c3cc(F)ccc23)cc1] |
| 6-fluoro-N,N-dimethyl-3-(4-(piperazin-1-ylsulfonyl)phenyl)-1H-indole-1-carboxamide | 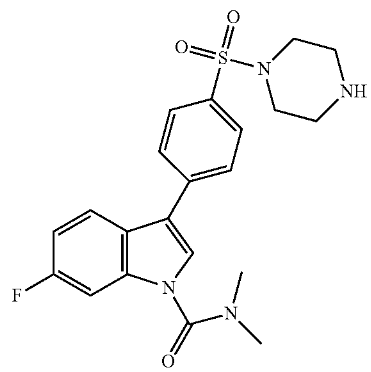 [SMILES: CN(C)C(=O)n1cc(-c2ccc(S(=O)(=O)N3CCNCC3)cc2)c2ccc(F)cc21] |
| 4-(6-fluoro-1H-indol-3-yl)-N-(2-(5-oxo-4,5-dihydro-1,3,4-oxadiazol-2-yl)ethyl)benz-enesulfonamide | 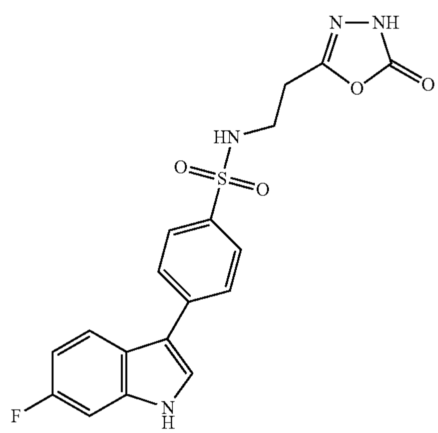 [SMILES: O=c1[nH]nc(CCNS(=O)(=O)c2ccc(-c3c[nH]c4cc(F)ccc34)cc2)o1] |
| 3-(4-(6-fluoro-1H-indol-3-yl)phenylsulfonamido)-N,N-dimethylpropanamide | 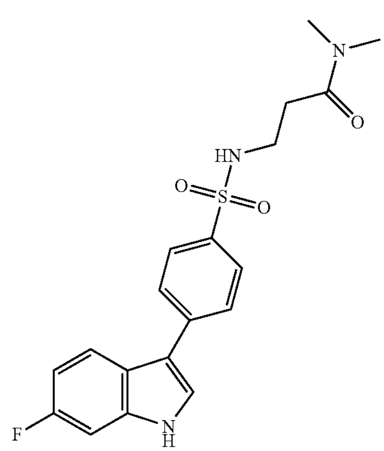 [SMILES: CN(C)C(=O)CCNS(=O)(=O)c1ccc(-c2c[nH]c3cc(F)ccc23)cc1] |

| Compound-IUPAC name | Structure |
|---|---|
| 3-(4-(6-fluoro-1H-indol-3-yl)phenylsulfonamido)-N-methylpropanamide | 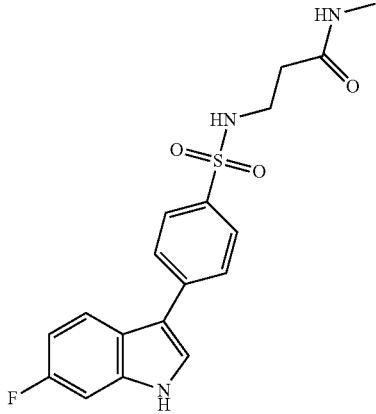 [SMILES: CNC(=O)CCNS(=O)(=O)c1ccc(-c2c[nH]c3cc(F)ccc23)cc1] |
| 1-(6-fluoro-3-(4-(piperazin-1-ylsulfonyl)phenyl)-1H-indol-1-yl)propan-1-one | 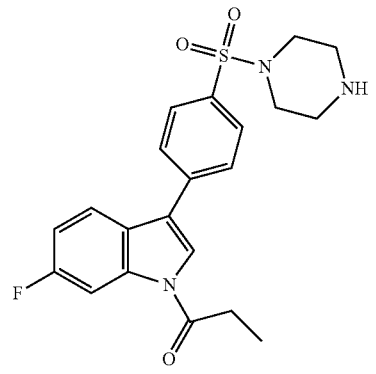 [SMILES: CCC(=O)n1cc(-c2ccc(S(=O)(=O)N3CCNCC3)cc2)c2ccc(F)cc21] |
| 1-(6-fluoro-3-(4-(piperazin-1-ylsulfonyl)phenyl)-1H-indol-1-yl)-3-methylbutan-1-one | 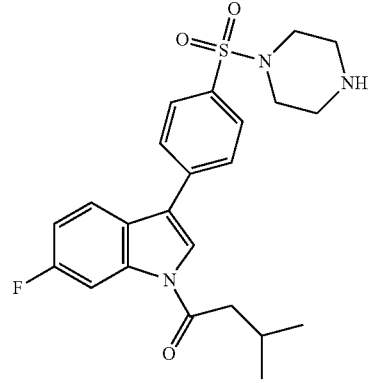 [SMILES: CC(C)CC(=O)n1cc(-c2ccc(S(=O)(=O)N3CCNCC3)cc2)c2ccc(F)cc21] |
| 4-(4-(6-fluoro-1H-indol-3-yl)phenylsulfonamido)butanamide | 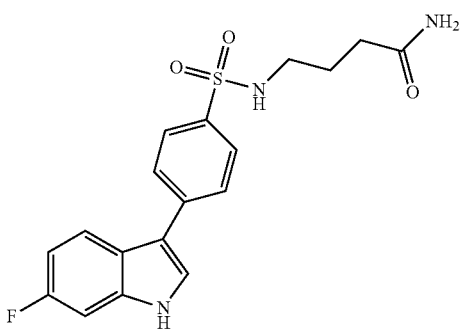 [SMILES: NC(=O)CCCNS(=O)(=O)c1ccc(-c2c[nH]c3cc(F)ccc23)cc1] |

| Compound-IUPAC name | Structure |
|---|---|
| 4-(4-(6-fluoro-1H-indol-3-yl)-N-methylphenyl-sulfonamido)butanamide | 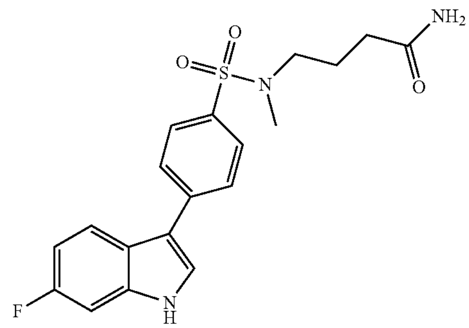 [SMILES: CN(CCCC(N)=O)S(=O)(=O)c1ccc(-c2c[nH]c3cc(F)ccc23)cc1] |
| (R)-4-(6-fluoro-1H-indol-3-yl)-N-(tetrahydrofuran-3-yl)benzenesulfonamide | 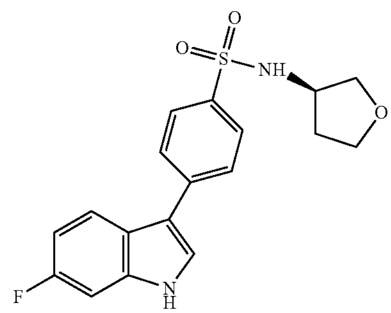 [SMILES: O=S(=O)(N[C@@H]1CCOC1)c1ccc(-c2c[nH]c3cc(F)ccc23)cc1] |
| N-(2-aminoethyl)-5-(6-fluoro-1H-indol-3-yl)-2-methylbenzenesulfonamide | 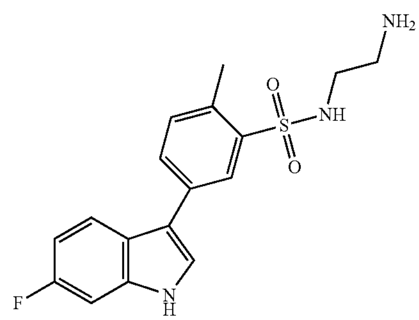 [SMILES: Cc1ccc(-c2c[nH]c3cc(F)ccc23)cc1S(=O)(=O)NCCN] |
| 5-(6-fluoro-1H-indol-3-yl)-N-methyl-2-(piperazin-1-ylsulfonyl)benzamide | 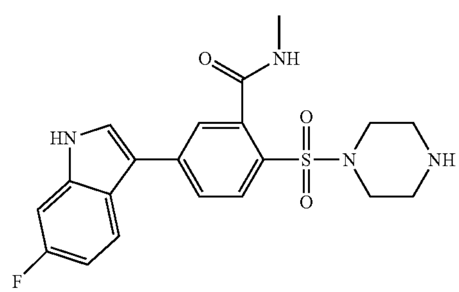 [SMILES: CNC(=O)c1cc(-c2c[nH]c3cc(F)ccc23)ccc1S(=O)(=O)N1CCNCC1] |
| (cis)-1-((4-(6-fluoro-1H-indol-3-yl)phenyl)sulfonyl)pyrrolidine-3,4-diol | 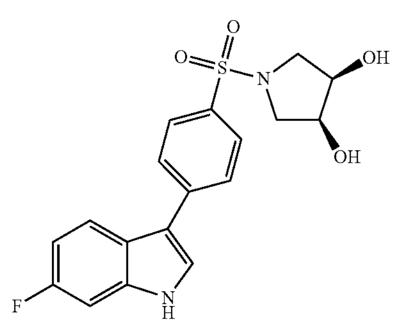 [SMILES: O=S(=O)(c1ccc(-c2c[nH]c3cc(F)ccc23)cc1)N1C[C@@H](O)[C@@H](O)C1] |

| Compound-IUPAC name | Structure |
|---|---|
| 4-(6-fluoro-1H-indol-3-yl)-N-(2-(3-methyl-1,2,4-oxadiazol-5-yl)ethyl)benzenesulfonamide | 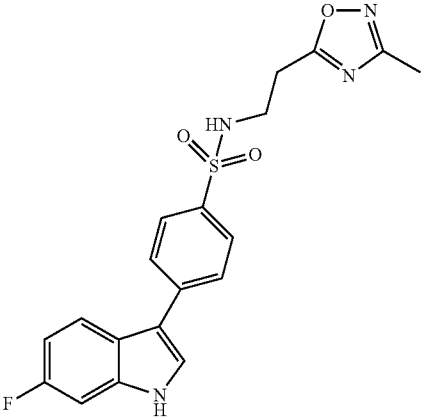 [SMILES: Cc1noc(CCNS(=O)(=O)c2ccc(-c3c[nH]c4cc(F)ccc34)cc2)n1] |
| 6-fluoro-N-methyl-3-(4-(piperazin-1-yl-sulfonyl)phenyl)-1H-indole-1-carboxamide | 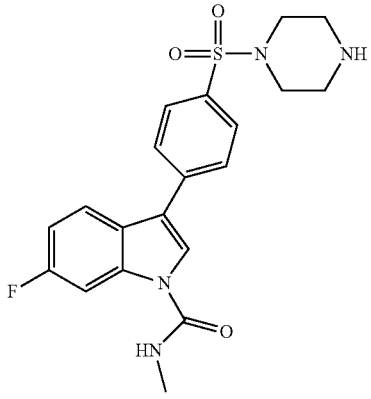 [SMILES: CNC(=O)n1cc(-c2ccc(S(=O)(=O)N3CCNCC3)cc2)c2ccc(F)cc21] |
| N-(2-aminoethyl)-3-(6-fluoro-1H-indol-3-yl)-5-methoxybenzenesulfonamide | 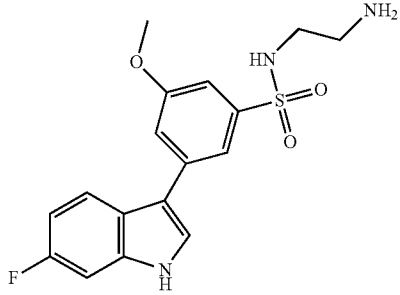 [SMILES: COc1cc(-c2c[nH]c3cc(F)ccc23)cc(S(=O)(=O)NCCN)c1] |
| N-(2-aminoethyl)-4-fluoro-3-(6-fluoro-1H-indol-3-yl)benzenesulfonamide | 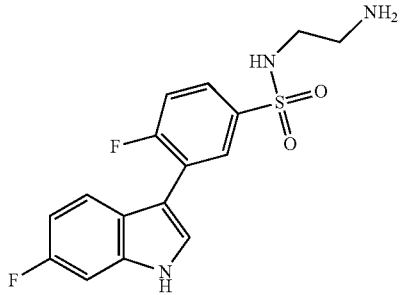 [SMILES: NCCNS(=O)(=O)c1ccc(F)c(-c2c[nH]c3cc(F)ccc23)c1] |

-continued
| Compound-IUPAC name | Structure |
|---|---|
| (1-((4-(6-fluoro-1H-indol-3-yl)phenyl)sulf-onyl)azetidin-3-yl)methanol | 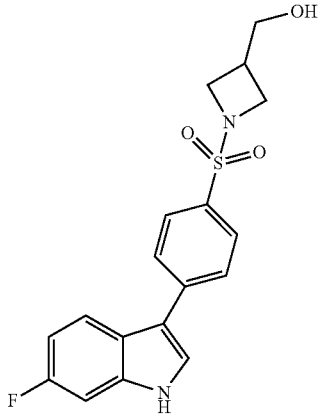 [SMILES: O=S(=O)(c1ccc(-c2c[nH]c3cc(F)ccc23)cc1)N1CC(CO)C1] |
| (S)-4-(6-fluoro-1H-indol-3-yl)-N-(tetrahydrofuran-3-yl)benzenesulfonamide | 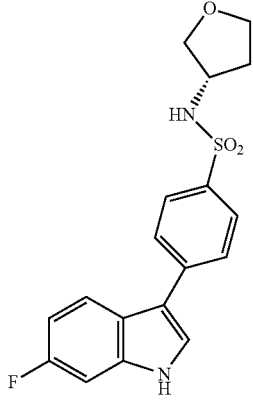 [SMILES: O=S(=O)(N[C@H]1CCOC1)c1ccc(-c2c[nH]c3cc(F)ccc23)cc1] |
| 1-((4-(6-fluoro-1H-indol-3-yl)phenyl)sulfonyl)azetidin-3-ol | 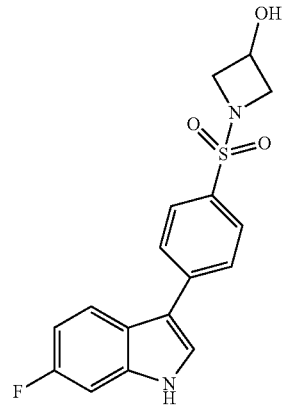 [SMILES: O=S(=O)(c1ccc(-c2c[nH]c3cc(F)ccc23)cc1)N1CC(O)C1] |
| (3S,4S)-1-[4-(6-Fluoro-1H-indol-3-yl)-benzenesulfonyl]-pyrrolidine-3,4-diol | 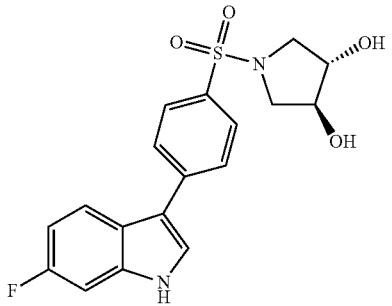 [SMILES: O=S(=O)(c1ccc(-c2c[nH]c3cc(F)ccc23)cc1)N1C[C@H](O)[C@@H](O)C1] |

-continued

| Compound-IUPAC name | Structure |
|---|---|
| 1-((4-(6-fluoro-1H-indol-3-yl)phenyl)-sulfonyl)azetidine-3-carboxamide | 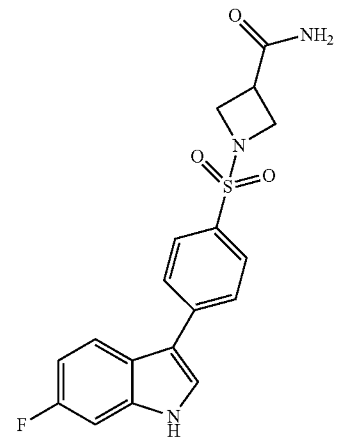 [SMILES: NC(=O)C1CN(S(=O)(=O)c2ccc(-c3c[nH]c4cc(F)ccc34)cc2)C1] |
| N-(azetidin-3-yl)-4-(6-fluoro-1H-indol-3-yl)benzenesulfonamide | 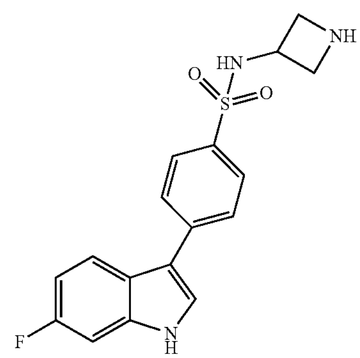 [SMILES: O=S(=O)(NC1CNC1)c1ccc(-c2c[nH]c3cc(F)ccc23)cc1] |
| N-(2-aminoethyl)-3-(6-fluoro-1H-indol-3-yl)-5-hydroxybenzenesulfonamide | 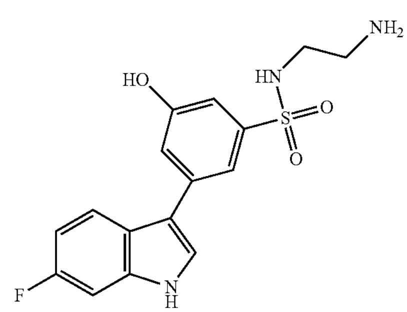 [SMILES: NCCNS(=O)(=O)c1cc(O)cc(-c2c[nH]c3cc(F)ccc23)c1] |
| 1-(6-fluoro-3-(4-(piperazin-1-ylsulfonyl)phenyl)-1H-indol-1-yl)ethanone | 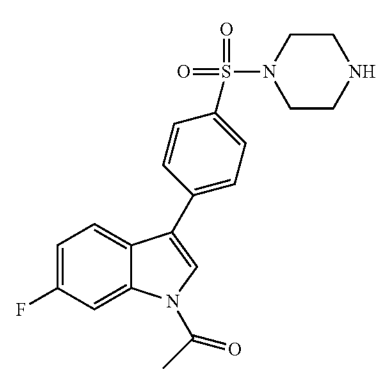 [SMILES: CC(=O)n1cc(-c2ccc(S(=O)(=O)N3CCNCC3)cc2)c2ccc(F)cc21] |

-continued

| Compound-IUPAC name | Structure |
|---|---|
| 3-(3,5-dimethyl-4-(piperazin-1-ylsulfonyl)phenyl)-6-fluoro-1H-indole | 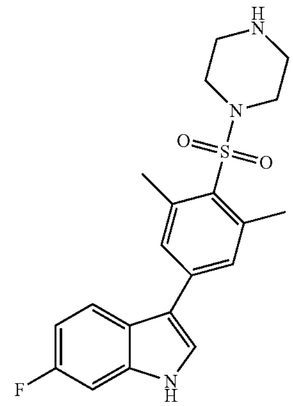 |
| N-(2-(1H-1,2,3-triazol-4-yl)ethyl)-4-(6-fluoro-1H-indol-3-yl)benzenesulfonamide | 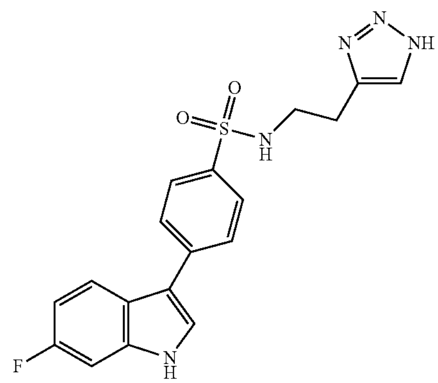 [SMILES: O=S(=O)(NCCc1c[nH]nn1)c1ccc(-c2c[nH]c3cc(F)ccc23)cc1] |
| N-(2-(1H-imidazol-2-yl)ethyl)-4-(6-fluoro-1H-indol-3-yl)benzenesulfonamide | 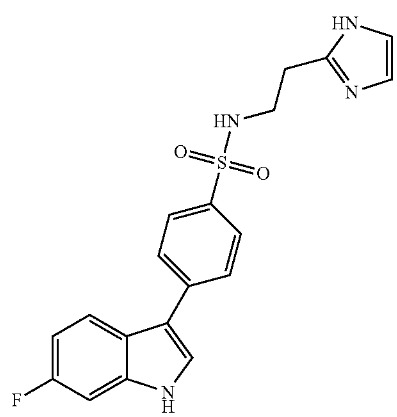 [SMILES: O=S(=O)(NCCc1ncc[nH]1)c1ccc(-c2c[nH]c3cc(F)ccc23)cc1] |
| (3R,4R)-1-((4-(6-fluoro-1H-indol-3-yl)phenyl)sulfonyl)pyrrolidine-3,4-diol | |

| Compound-IUPAC name | Structure |
|---|---|
| 3-(3,5-difluoro-4-(piperazin-1-ylsulfonyl)phenyl)-6-fluoro-1H-indole | 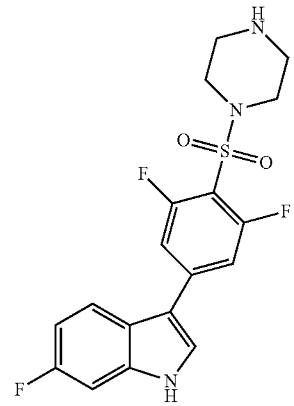 [SMILES: O=S(=O)(c1c(F)cc(-c2c[nH]c3cc(F)ccc23)cc1F)N1CCNCC1] |
| 3-(3,5-dichloro-4-(piperazin-1-ylsulfonyl)phenyl)-6-fluoro-1H-indole | 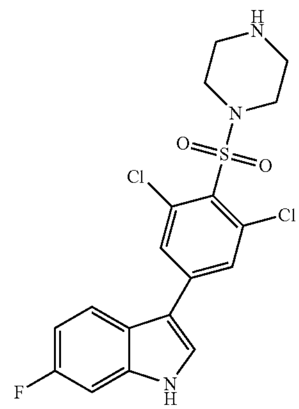 [SMILES: O=S(=O)(c1c(Cl)cc(-c2c[nH]c3cc(F)ccc23)cc1Cl)N1CCNCC1] |
| (R)-1-((4-(6-fluoro-1H-indol-3-yl)phenyl)sulfonyl)pyrrolidin-3-ol | 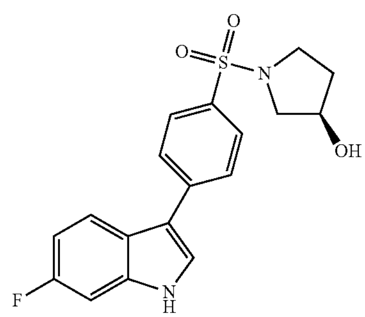 [SMILES: O=S(=O)(c1ccc(-c2c[nH]c3cc(F)ccc23)cc1)N1CC[C@@H](O)C1] |
| 6-fluoro-3-(4-(piperazin-1-ylsulfonyl)phenyl)-1H-indole-1-carboxamide | |

| Compound-IUPAC name | Structure |
|---|---|
| (S)-1-((4-(6-fluoro-1H-indol-3-yl)phenyl)sulfonyl)pyrrolidin-3-ol | 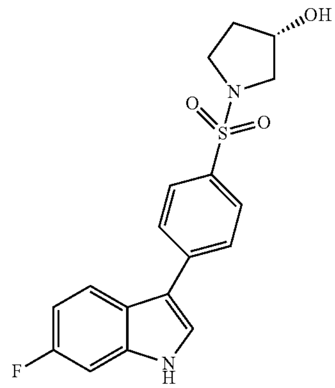 [SMILES: O=S(=O)(c1ccc(-c2c[nH]c3cc(F)ccc23)cc1)N1CC[C@H](O)C1] |
| (3S,4S)-4-fluoro-1-{[4-(6-fluoro-1H-indol-3-yl)phenyl]sulfonyl}pyrrolidin-3-amine | 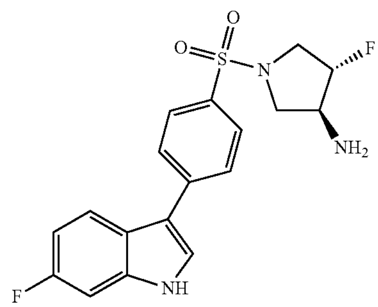 [SMILES: N[C@H]1CN(S(=O)(=O)c2ccc(-c3c[nH]c4cc(F)ccc34)cc2)C[C@@H]1F] |
| (+)-cis-4-fluoro-1-{[4-(6-fluoro-1H-indol-3-yl)phenyl]sulfonyl}pyrrolidin-3-amine | |
| (3R,4R)-4-fluoro-1-{[4-(6-fluoro-1H-indol-3-yl)phenyl]sulfonyl}pyrrolidin-3-amine | 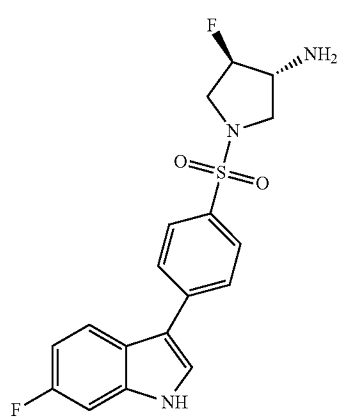 [SMILES: N[C@@H]1CN(S(=O)(=O)c2ccc(-c3c[nH]c4cc(F)ccc34)cc2)C[C@H]1F] |

| Compound-IUPAC name | Structure |
|---|---|
| (−)-(cis)-4-fluoro-1-((4-(6-fluoro-1H-indol-3-yl)phenyl)sulfonyl)pyrrolidin-3-amine | 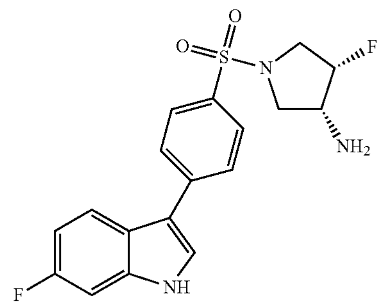 [SMILES: N[C@@H]1CN(S(=O)(=O)c2ccc(-c3c[nH]c4cc(F)ccc34)cc2)C[C@@H]1F] |
| 2-[(1-{[4-(6-fluoro-1H-indol-3-yl)phenyl]-sulfonyl}piperidin-4-yl)oxy]acetamide | 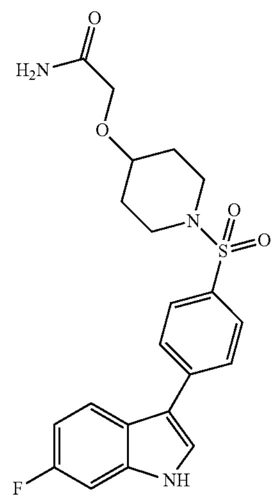 [SMILES: NC(=O)COC1CCN(S(=O)(=O)c2ccc(-c3c[nH]c4cc(F)ccc34)cc2)CC1] |
| 4-(6-fluoro-1H-indol-3-yl)-N-[1-(4-methyl-4H-1,2,4-triazol-3-yl)ethyl]benzenesulfonamide | 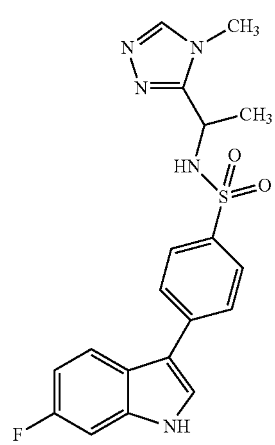 [SMILES: CC(NS(=O)(=O)c1ccc(-c2c[nH]c3cc(F)ccc23)cc1)c1nncn1C] |

| Compound-IUPAC name | Structure |
|---|---|
| 4-(6-fluoro-1H-indol-3-yl)-N-[(4-methyl-5-oxo-morpholin-2-yl)methyl]benzenesulfonamide | 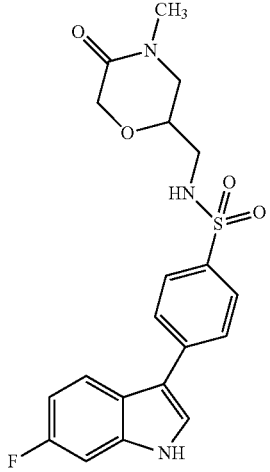 [SMILES: CN1CC(CNS(=O)(=O)c2ccc(-c3c[nH]c4cc(F)ccc34)cc2)OCC1=O] |
| N-(1,1-dioxidotetrahydrothiophen-3-yl)-4-(6-fluoro-1H-indol-3-yl)benzenesulfonamide | 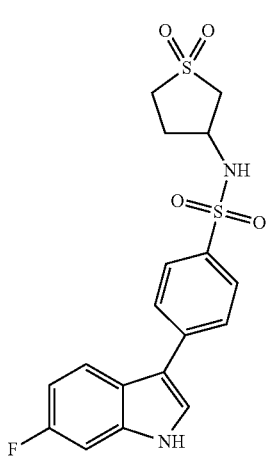 [SMILES: O=S1(=O)CCC(NS(=O)(=O)c2ccc(-c3c[nH]c4cc(F)ccc34)cc2)C1] |
| 4-(6-fluoro-1H-indol-3-yl)-N-[2-(methylsulfonyl)ethyl]benzenesulfonamide | 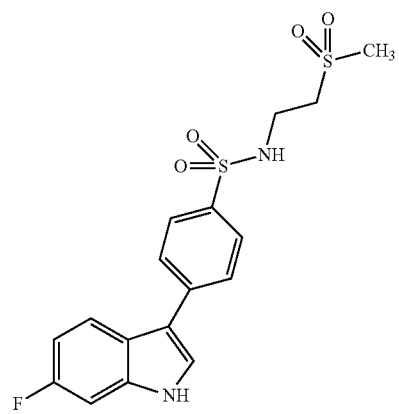 [SMILES: CS(=O)(=O)CCNS(=O)(=O)c1ccc(-c2c[nH]c3cc(F)ccc23)cc1] |

| Compound-IUPAC name | Structure |
|---|---|
| 4-(6-fluoro-1H-indol-3-yl)-N-((5-methyl-1,3,4-oxadiazol-2-yl)methyl)benzenesulfonamide | 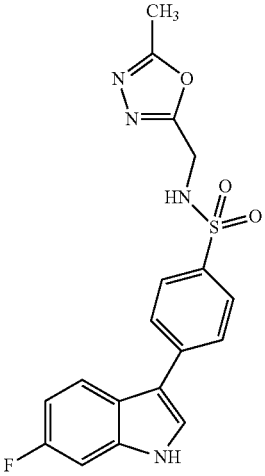 [SMILES: Cc1nnc(CNS(=O)(=O)c2ccc(-c3c[nH]c4cc(F)ccc34)cc2)o1] |
| 1-((4-(6-fluoro-1H-indol-3-yl)phenyl)sulfonyl)-1,4-diazepan-5-one | 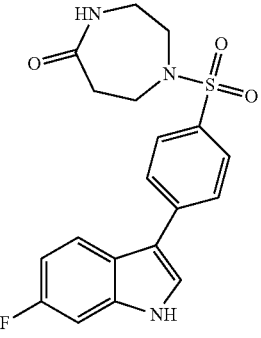 [SMILES: O=C1CCN(S(=O)(=O)c2ccc(-c3c[nH]c4cc(F)ccc34)cc2)CCN1] |
| 4-(6-fluoro-1H-indol-3-yl)-N-(1-methyl-1H-pyrazol-5-yl)benzenesulfonamide | 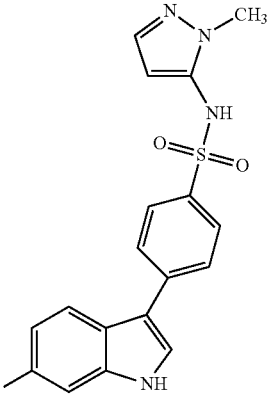 |

| Compound-IUPAC name | Structure |
|---|---|
| 4-(6-fluoro-1H-indol-3-yl)-N-[(4-methyl-4H-1,2,4-triazol-3-yl)methyl]benzenesulfonamide | 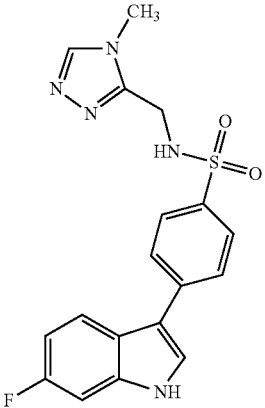 [SMILES: Cn1cnnc1CNS(=O)(=O)c1ccc(-c2c[nH]c3cc(F)ccc23)cc1] |
| (−)-(R)-4-(6-fluoro-1H-indol-3-yl)-N-(2-hydroxypropyl)benzenesulfonamide | 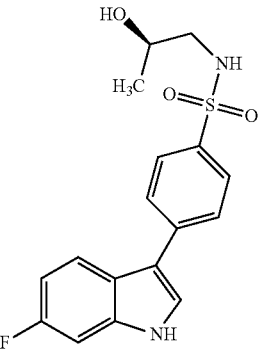 [SMILES: C[C@@H](O)CNS(=O)(=O)c1ccc(-c2c[nH]c3cc(F)ccc23)cc1] |
| (+)-(S)-4-(6-fluoro-1H-indol-3-yl)-N-(2-hydroxypropyl)benzenesulfonamide | 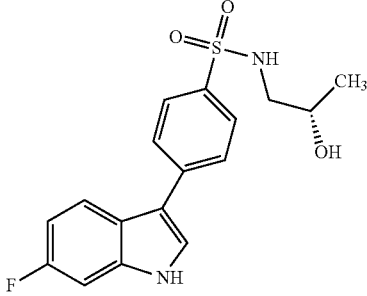 [SMILES: C[C@H](O)CNS(=O)(=O)c1ccc(-c2c[nH]c3cc(F)ccc23)cc1] |
| (cis)-3-(4-(6-fluoro-1H-indol-3-yl)phenylsulfonamido)cyclobutanecarboxamide | 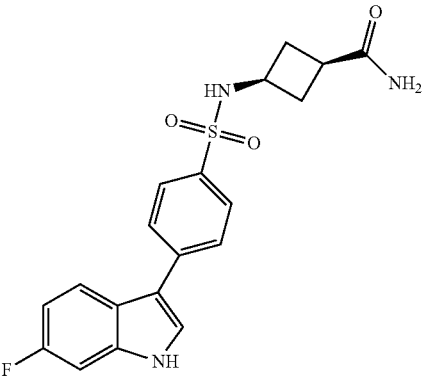 [SMILES: NC(=O)[C@H]1C[C@@H](NS(=O)(=O)c2ccc(-c3c[nH]c4cc(F)ccc34)cc2)C1] |

-continued

| Compound-IUPAC name | Structure |
| --- | --- |
| 4-(6-fluoro-1H-indol-3-yl)-N-[(2R)-1-hydroxypropan-2-yl]benzenesulfonamide | 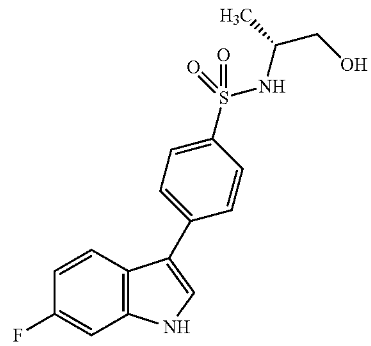 [SMILES: C[C@H](CO)NS(=O)(=O)c1ccc(-c2c[nH]c3cc(F)ccc23)cc1] |
| (Trans)-3-(4-(6-fluoro-1H-indol-3-yl)-phenylsulfonamido)cyclobutanecarboxamide | 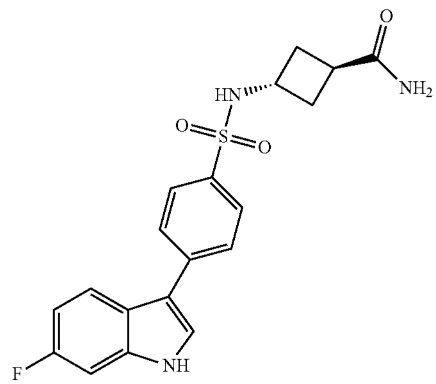 [SMILES: NC(=O)[C@H]1C[C@H](NS(=O)(=O)c2ccc(-c3c[nH]c4cc(F)ccc34)cc2)C1] |
| 4-(6-fluoro-1H-indol-3-yl)-N-methyl-N-(2-sulfamoylethyl)benzenesulfonamide | 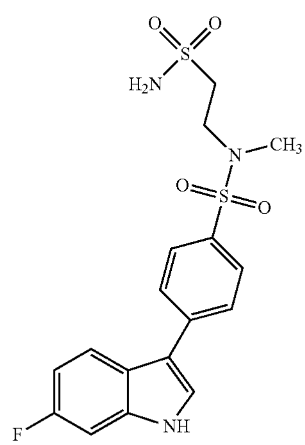 [SMILES: CN(CCS(N)(=O)=O)S(=O)(=O)c1ccc(-c2c[nH]c3cc(F)ccc23)cc1] |
| 4-(6-fluoro-1H-indol-3-yl)-N-[2-(1H-1,2,4-triazol-1-yl)ethyl]benzenesulfonamide | 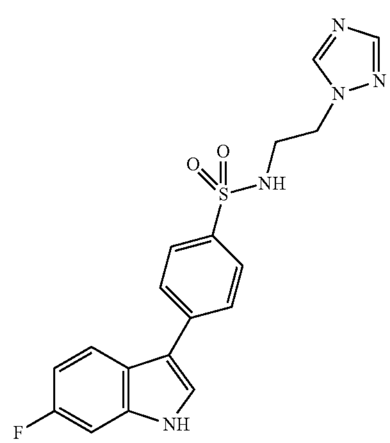 [SMILES: O=S(=O)(NCCn1cncn1)c1ccc(-c2c[nH]c3cc(F)ccc23)cc1] |

| Compound-IUPAC name | Structure |
| --- | --- |
| 4-(6-fluoro-1H-indol-3-yl)-N-methyl-N-[2-(methylsulfamoyl)ethyl] benzenesulfonamide | 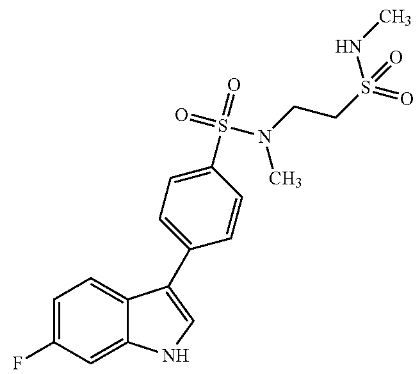 [SMILES: CNS(=O)(=O)CCN(C)S(=O)(=O)c1ccc(-c2c[nH]c3cc(F)ccc23)cc1] |
| (−)-(6-fluoro-1H-indol-3-yl)-N-[(2S)-1-hydroxy-propan-2-yl]benzenesulfonamide | 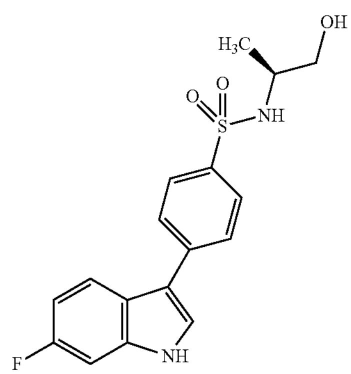 [SMILES: C[C@@H](CO)NS(=O)(=O)c1ccc(-c2c[nH]c3cc(F)ccc23)cc1] |
| 4-(6-fluoro-1H-indol-3-yl)-N-(3-oxo-3-(piperazin-1-yl)propyl) benzenesulfonamide | 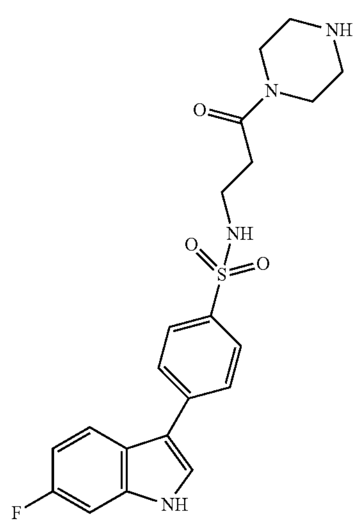 [SMILES: O=C(CCNS(=O)(=O)c1ccc(-c2c[nH]c3cc(F)ccc23)cc1)N1CCNCC1] |

| Compound-IUPAC name | Structure |
|---|---|
| 4-(6-fluoro-1H-indol-3-yl)-N-(3-(4-methyl-piperazin-1-yl)-3-oxopropyl)- benzenesulfonamide | 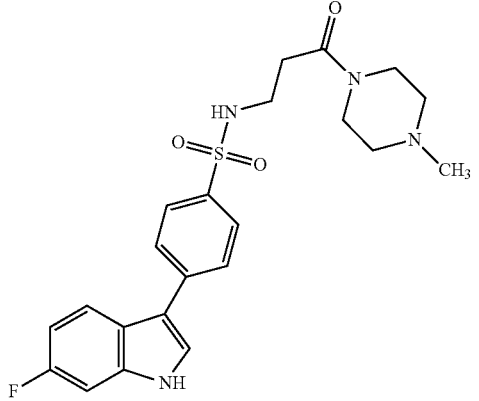 [SMILES: CN1CCN(C(=O)CCNS(=O)(=O)c2ccc(-c3c[nH]c4cc(F)ccc34)cc2)CC1] |
| (−)-(S)-3-(4-(6-fluoro-1H-indol-3-yl)phenylsulfon-amido)-N-(tetrahydrofuran-3-yl)propanamide | 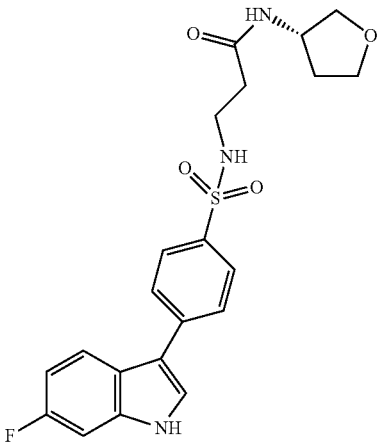 [SMILES: O=C(CCNS(=O)(=O)c1ccc(-c2c[nH]c3cc(F)ccc23)cc1)N[C@H]1CCOC1] |
| (−)-N-(3-((3S,4S)-3-amino-4-fluoropyrrol-idin-1-yl)-3-oxopropyl)-4-(6-fluoro-1H-indol-3-yl)benzenesulfonamide | 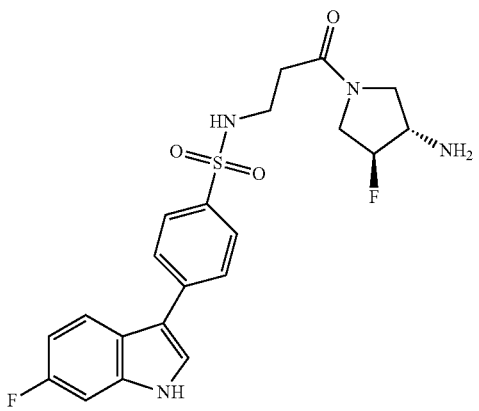 [SMILES: N[C@H]1CN(C(=O)CCNS(=O)(=O)c2ccc(-c3c[nH]c4cc(F)ccc34)cc2)C[C@@H]1F] |

| Compound-IUPAC name | Structure |
|---|---|
| 4-(6-fluoro-1H-indol-3-yl)-N-(3-morpholino-3-oxopropyl)benzenesulfonamide | 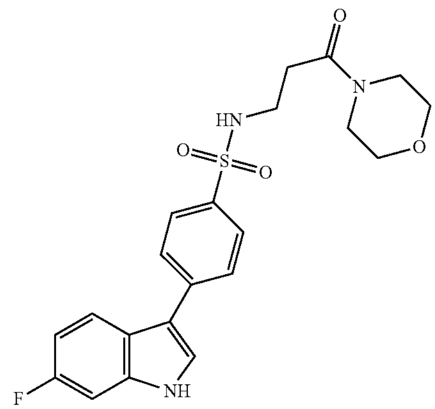 [SMILES: O=C(CCNS(=O)(=O)c1ccc(-c2c[nH]c3cc(F)ccc23)cc1)N1CCOCC1] |
| (+)-(R)-3-(4-(6-fluoro-1H-indol-3-yl)phenylsulfonamido)-N-(tetrahydrofuran-3-yl)propanamide | 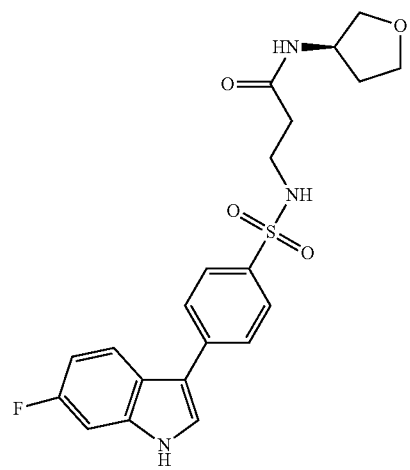 [SMILES: O=C(CCNS(=O)(=O)c1ccc(-c2c[nH]c3cc(F)ccc23)cc1)N[C@@H]1CCOC1] |
| N-(2-(4-(6-fluoro-1H-indol-3-yl)phenylsulfonamido)ethyl)morpholine-4-carbox-amide | 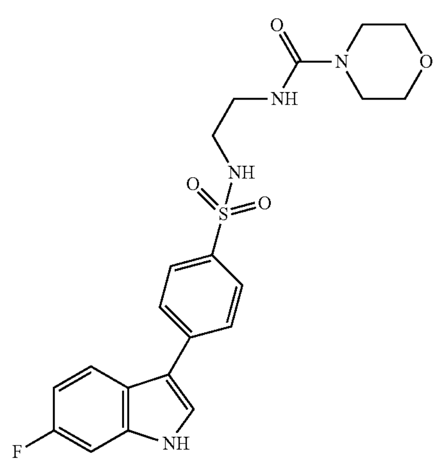 [SMILES: O=C(NCCNS(=O)(=O)c1ccc(-c2c[nH]c3cc(F)ccc23)cc1)N1CCOCC1] |

| Compound-IUPAC name | Structure |
|---|---|
| N-(2-(4-(6-fluoro-1H-indol-3-yl)phenyl-sulfonamido)ethyl)piperazine-1-carbox-amide | 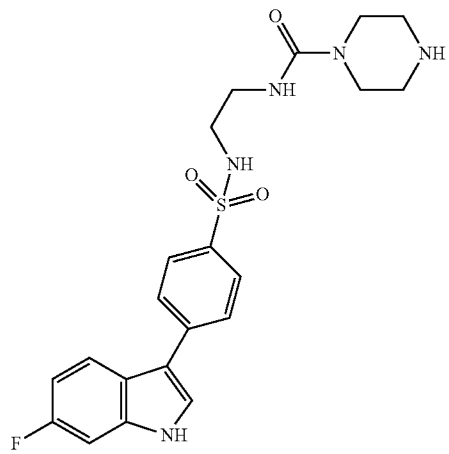 [SMILES: O=C(NCCNS(=O)(=O)c1ccc(-c2c[nH]c3cc(F)ccc23)cc1)N1CCNCC1] |
| N-(2-(4-(6-fluoro-1H-indol-3-yl)phenylsulfonamido)ethyl)-4-methylpiperazine-1-carboxamide | 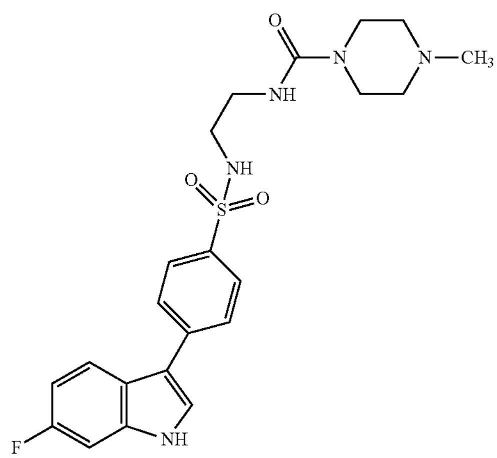 [SMILES: CN1CCN(C(=O)NCCNS(=O)(=O)c2ccc(-c3c[nH]c4cc(F)ccc34)cc2)CC1] |
| 4-(6-fluoro-1H-indol-3-yl)-N-((2S,3R)-3-hydroxy-butan-2-yl)-N-(2-hydroxyethyl)benzenesulfonamide | 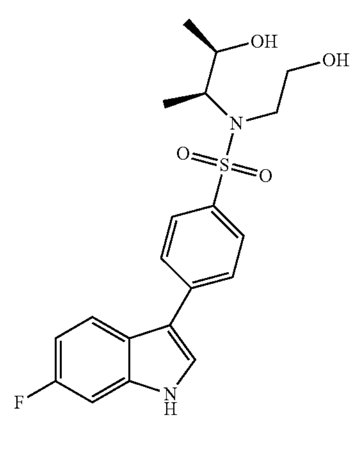 [SMILES: C[C@@H](O)[C@H](C)N(CCO)S(=O)(=O)c1ccc(-c2c[nH]c3cc(F)ccc23)cc1] |

| Compound-IUPAC name | Structure |
|---|---|
| (S)-(4-((4-(6-fluoro-1H-indol-3-yl)phenyl)sulfonyl)morpholin-3-yl)methanol | 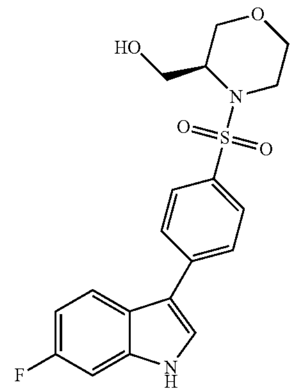 [SMILES: O=S(=O)(c1ccc(-c2c[nH]c3cc(F)ccc23)cc1)N1CCOC[C@@H]1CO] |
| 1-((4-(6-fluoro-1H-indol-3-yl)phenyl)sulfonyl)-3-(1-methyl-1H-pyrazol-5-yl)pyrrolidin-3-ol | 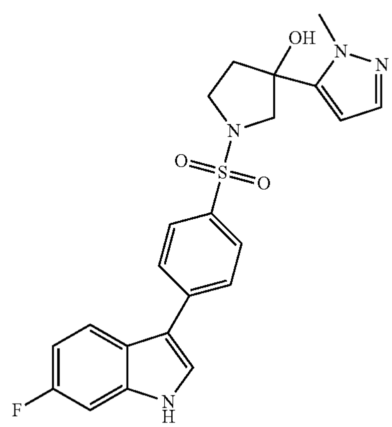 [SMILES: Cn1nccc1C1(O)CCN(S(=O)(=O)c2ccc(-c3c[nH]c4cc(F)ccc34)cc2)C1] |
| 4-(6-fluoro-1H-indol-3-yl)-N-(2-hydroxyethyl)-N-((1-methyl-1H-pyrazol-4-yl)methyl)benzenesulfonamide | 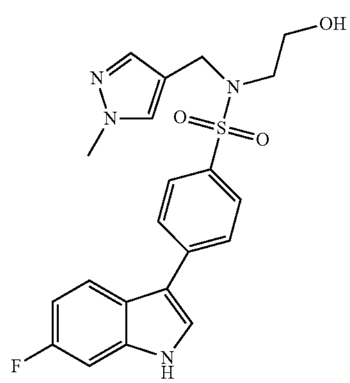 [SMILES: Cn1cc(CN(CCO)S(=O)(=O)c2ccc(-c3c[nH]c4cc(F)ccc34)cc2)cn1] |
| (R)-(4-((4-(6-fluoro-1H-indol-3-yl)phenyl)sulfonyl)morpholin-3-yl)methanol | 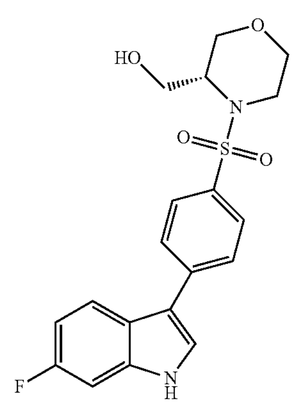 [SMILES: O=S(=O)(c1ccc(-c2c[nH]c3cc(F)ccc23)cc1)N1CCOC[C@H]1CO] |

-continued

| Compound-IUPAC name | Structure |
| --- | --- |
| (S)-1-((4-(6-fluoro-1H-indol-3-yl)phenyl)sulfonyl)-3-methylpyrrolidin-3-ol | 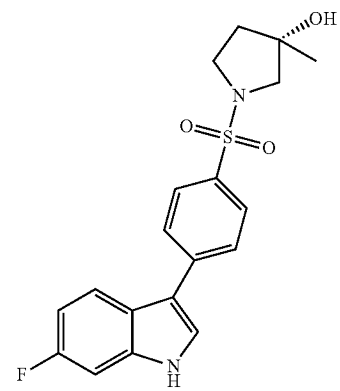 [SMILES: C[C@]1(O)CCN(S(=O)(=O)c2ccc(-c3c[nH]c4cc(F)ccc34)cc2)C1] |
| 4-(6-fluoro-1H-indol-3-yl)-N-(2-hydroxyethyl)-N-(3-hydroxypropyl)benzenesulfonamide | 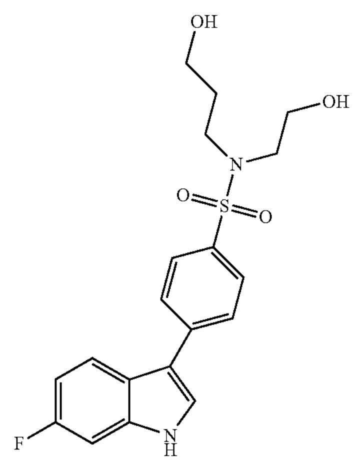 [SMILES: O=S(=O)(c1ccc(-c2c[nH]c3cc(F)ccc23)cc1)N(CCO)CCCO] |
| 4-((4-(6-fluoro-1H-indol-3-yl)phenyl)sulfonyl)-1,4-oxazepan-6-ol | 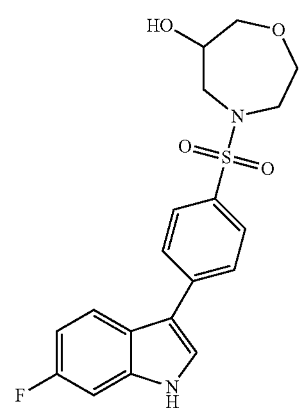 [SMILES: O=S(=O)(c1ccc(-c2c[nH]c3cc(F)ccc23)cc1)N1CCOCC(O)C1] |

-continued

| Compound-IUPAC name | Structure |
|---|---|
| 1-((4-(6-fluoro-1H-indol-3-yl)phenyl)sulfonyl)-3-(pyrimidin-4-yl)pyrrolidin-3-ol | 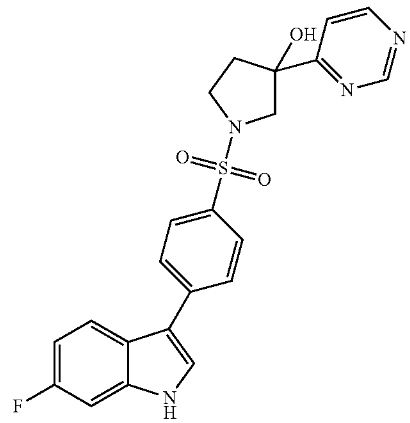 [SMILES: O=S(=O)(c1ccc(-c2c[nH]c3cc(F)ccc23)cc1)N1CCC(O)(c2ccncn2)C1] |
| 1-((4-(6-fluoro-1H-indol-3-yl)phenyl)sulfonyl)-3-(pyrimidin-5-yl)pyrrolidin-3-ol | 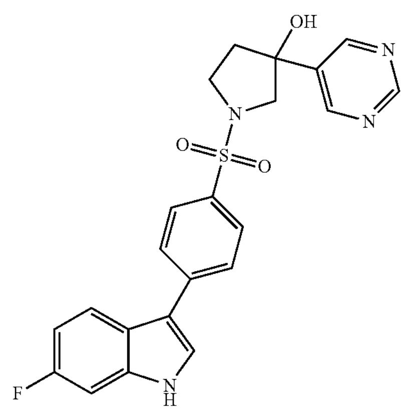 [SMILES: O=S(=O)(c1ccc(-c2c[nH]c3cc(F)ccc23)cc1)N1CCC(O)(c2cncnc2)C1] |
| 4-(6-fluoro-1H-indol-3-yl)-N-(2-hydroxy-2-(pyridazin-3-yl)ethyl)-N-methylbenzenesulfonamide | 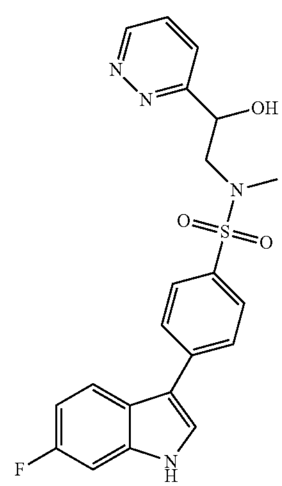 [SMILES: CN(CC(O)c1cccnn1)S(=O)(=O)c1ccc(-c2c[nH]c3cc(F)ccc23)cc1] |

-continued

| Compound-IUPAC name | Structure |
|---|---|
| 1-((4-(6-fluoro-1H-indol-3-yl)phenyl)sulfonyl)-3-((2-methyl-1H-imidazol-1-yl)methyl)piperidin-3-ol | |
| ((2S,4S)-4-fluoro-1-((4-(6-fluoro-1H-indol-3-yl)phenyl)sulfonyl)pyrrolidin-2-yl)methanol | 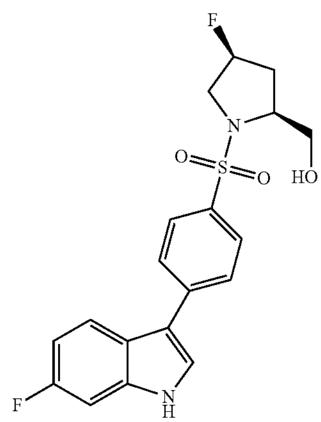 [SMILES: O=S(=O)(c1ccc(-c2c[nH]c3cc(F)ccc23)cc1)N1C[C@@H](F)C[C@H]1CO] |
| 1-((4-(6-fluoro-1H-indol-3-yl)phenyl)sulfonyl)pyrrolidin-3-ol | 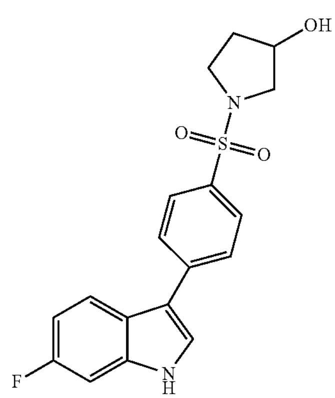 [SMILES: O=S(=O)(c1ccc(-c2c[nH]c3cc(F)ccc23)cc1)N1CCC(O)C1] |

-continued

| Compound-IUPAC name | Structure |
|---|---|
| ((2R,4R)-4-fluoro-1-((4-(6-fluoro-1H-indol-3-yl)phenyl)sulfonyl)pyrrolidin-2-yl)methanol | 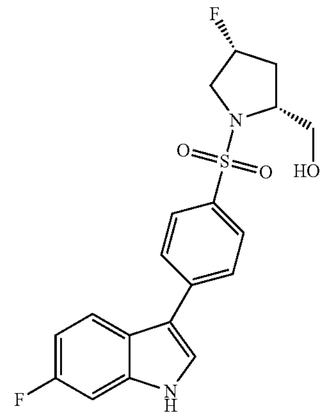 [SMILES: O=S(=O)(c1ccc(-c2c[nH]c3cc(F)ccc23)cc1)N1C[C@H](F)C[C@@H]1CO] |
| ((2R,4S)-4-fluoro-1-((4-(6-fluoro-1H-indol-3-yl)phenyl)sulfonyl)pyrrolidin-2-yl)methanol | 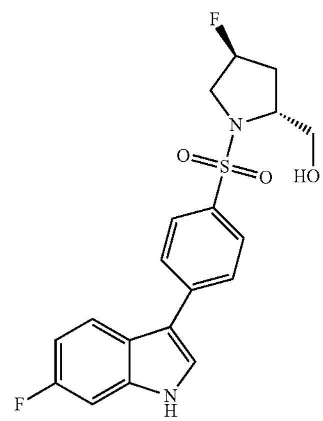 [SMILES: O=S(=O)(c1ccc(-c2c[nH]c3cc(F)ccc23)cc1)N1C[C@@H](F)C[C@@H]1CO] |
| 1-((1-((4-(6-fluoro-1H-indol-3-yl)phenyl)sulfonyl)-3-hydroxypyrrolidin-3-yl)methyl)pyrrolidin-2-one | 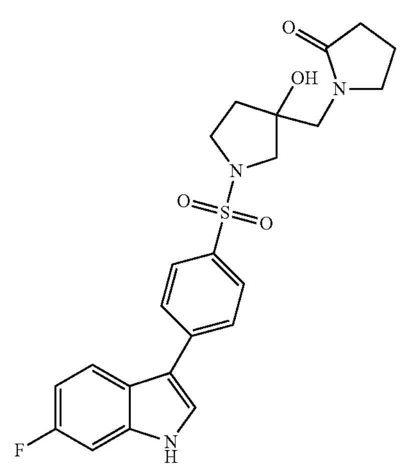 [SMILES: O=C1CCCN1CC1(O)CCN(S(=O)(=O)c2ccc(-c3c[nH]c4cc(F)ccc34)cc2)C1] |

-continued

| Compound-IUPAC name | Structure |
|---|---|
| (3S,4R)-1-((4-(6-fluoro-1H-indol-3-yl)phenyl)sulfonyl)piperidine-3,4-diol | 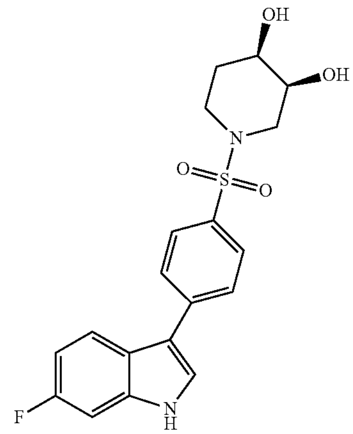 [SMILES: O=S(=O)(c1ccc(-c2c[nH]c3cc(F)ccc23)cc1)N1CC[C@@H](O)[C@@H](O)C1] |
| (2R,3R,4S,5S)-5-fluoro-1-((4-(6-fluoro-1H-indol-3-yl)phenyl)sulfonyl)-2-(hydroxymethyl)piperidine-3,4-diol | 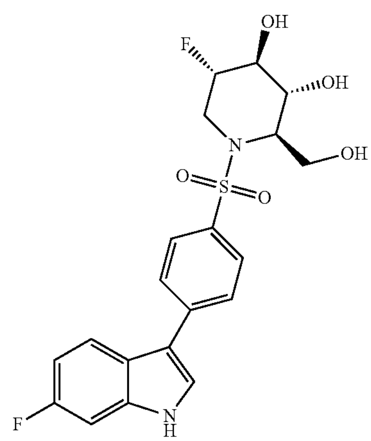 [SMILES: O=S(=O)(c1ccc(-c2c[nH]c3cc(F)ccc23)cc1)N1C[C@H](F)[C@@H](O)[C@H](O)[C@H]1CO] |
| (3R,4R)-1-((4-(6-fluoro-1H-indol-3-yl)phenyl)sulfonyl)piperidine-3,4-diol | 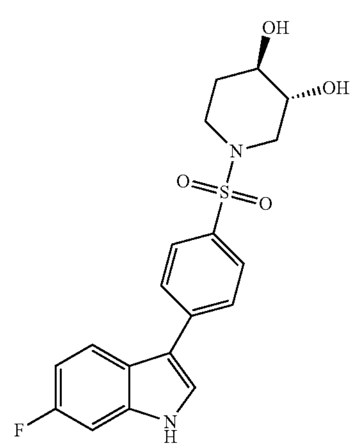 [SMILES: O=S(=O)(c1ccc(-c2c[nH]c3cc(F)ccc23)cc1)N1CC[C@@H](O)[C@H](O)C1] |

| Compound-IUPAC name | Structure |
|---|---|
| 1-((4-(6-fluoro-1H-indol-3-yl)phenyl)sulfonyl)-3-((2-methyl-1H-imidazol-1-yl)methyl) pyrrolidin-3-ol | 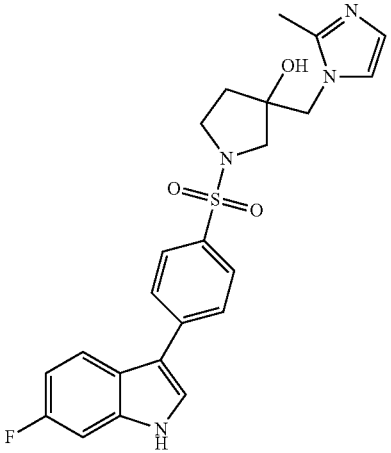 [SMILES: Cc1nccn1CC1(O)CCN(S(=O)(=O)c2ccc(-c3c[nH]c4cc(F)ccc34)cc2)C1] |
| 1-((1-((4-(6-fluoro-1H-indol-3-yl)phenyl)sulfonyl)-3-hydroxypiperidin-3-yl)methyl) pyrrolidin-2-one | 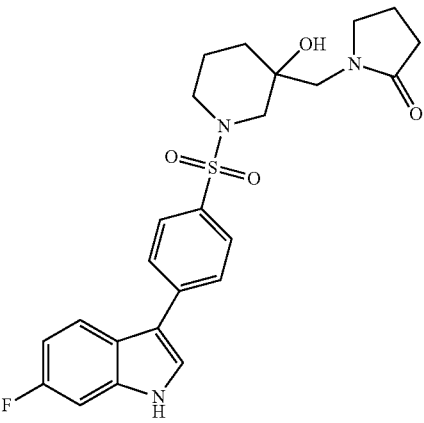 [SMILES: O=C1CCCN1CC1(O)CCCN(S(=O)(=O)c2ccc(-c3c[nH]c4cc(F)ccc34)cc2)C1] |
| 4-(6-fluoro-1H-indol-3-yl)-N-(2-hydroxy-2-(1H-imidazol-2-yl)ethyl)-N-methylbenzenesulfonamide | 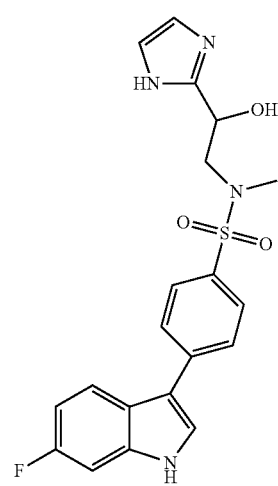 [SMILES: CN(CC(O)c1ncc[nH]1)S(=O)(=O)c1ccc(-c2c[nH]c3cc(F)ccc23)cc1] |

| Compound-IUPAC name | Structure |
|---|---|
| (2S,3S,4S)-1-((4-(6-fluoro-1H-indol-3-yl)phenyl)sulfonyl)-2-(hydroxymethyl)pyrrolidine-3,4-diol | 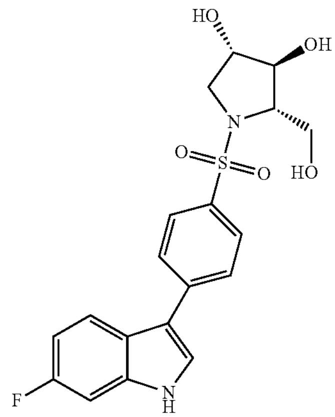 [SMILES: O=S(=O)(c1ccc(-c2c[nH]c3cc(F)ccc23)cc1)N1C[C@H](O)[C@@H](O)[C@@H]1CO] |
| 4-(6-fluoro-1H-indol-3-yl)-N-(2-hydroxy-2-(pyrazin-2-yl)ethyl)-N-methylbenzenesulfonamide | 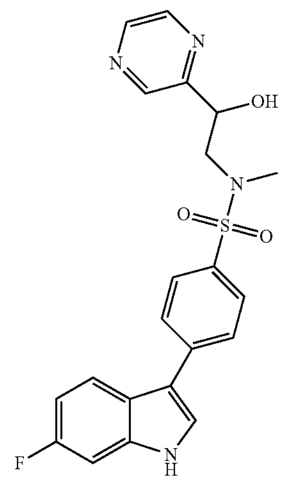 [SMILES: CN(CC(O)c1cnccn1)S(=O)(=O)c1ccc(-c2c[nH]c3cc(F)ccc23)cc1] |
| 3-chloro-4-(6-fluoro-1H-indol-3-yl)benzenesulfonamide | 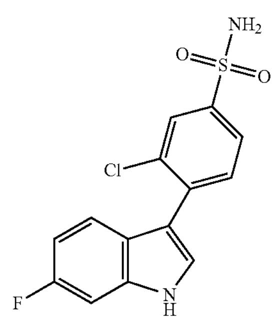 [SMILES: NS(=O)(=O)c1ccc(-c2c[nH]c3cc(F)ccc23)c(Cl)c1] |
| 3,5-dichloro-4-(6-fluoro-1H-indol-3-yl)benzenesulfonamide | 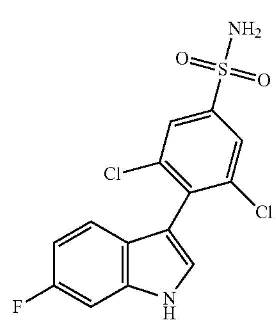 [SMILES: NS(=O)(=O)c1cc(Cl)c(-c2c[nH]c3cc(F)ccc23)c(Cl)c1] |

-continued
| Compound-IUPAC name | Structure |
|---|---|
| 2-(5-(6-fluoro-1H-indol-3-yl)-2-sulfamoylphenyl)-N,N-dimethylacetamide | 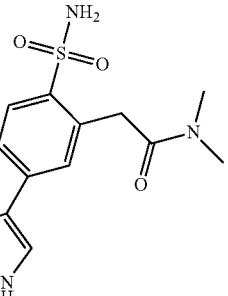 |
| 4-(6-fluoro-1H-indol-3-yl)-2-(2-hydroxyethyl)benzenesulfonamide | 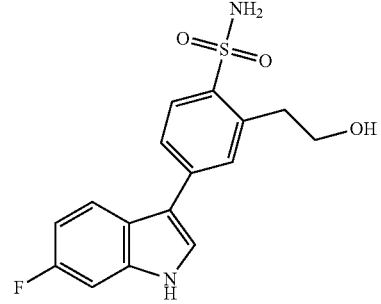 [SMILES: NS(=O)(=O)c1ccc(-c2c[nH]c3cc(F)ccc23)cc1CCO] |
| 4-(6-fluoro-1H-indol-3-yl)-2-(2-(methylamino)ethyl)benzenesulfonamide | 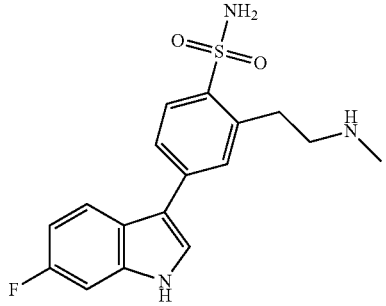 [SMILES: CNCCc1cc(-c2c[nH]c3cc(F)ccc23)ccc1S(N)(=O)=O] |
| 2-(2-(dimethylamino)ethyl)-4-(6-fluoro-1H-indol-3-yl)benzenesulfonamide | 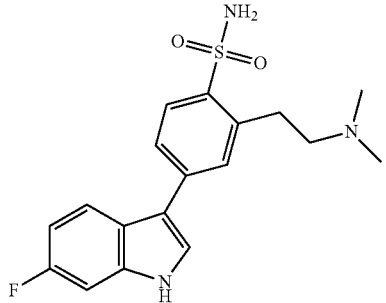 [SMILES: CN(C)CCc1cc(-c2c[nH]c3cc(F)ccc23)ccc1S(N)(=O)=O] |
| 4-(6-fluoro-1H-indol-3-yl)-2-(2,2,2-trifluoroethyl)benzenesulfonamide | 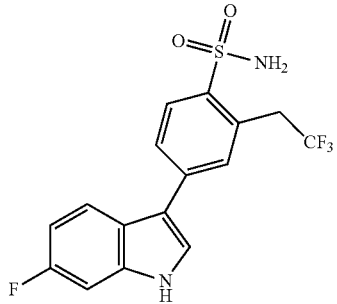 [SMILES: NS(=O)(=O)c1ccc(-c2c[nH]c3cc(F)ccc23)cc1CC(F)(F)F] |

| Compound-IUPAC name | Structure |
|---|---|
| 2-(5-(6-fluoro-1H-indol-3-yl)-2-sulfamoylphenyl)-N-methylacetamide | 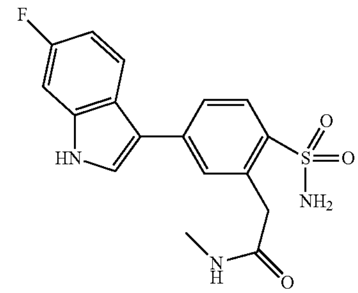 [SMILES: CNC(=O)Cc1cc(-c2c[nH]c3cc(F)ccc23)ccc1S(N)(=O)=O] |
| 2-(5-(6-fluoro-1H-indol-3-yl)-2-sulfamoylphenyl)acetamide | 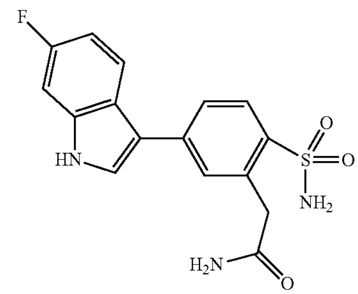 [SMILES: NC(=O)Cc1cc(-c2c[nH]c3cc(F)ccc23)ccc1S(N)(=O)=O] |
| 4-((4-(6-fluoro-1H-indol-3-yl)phenyl)sulfonyl)-1-methylpiperazine-2,6-dione | 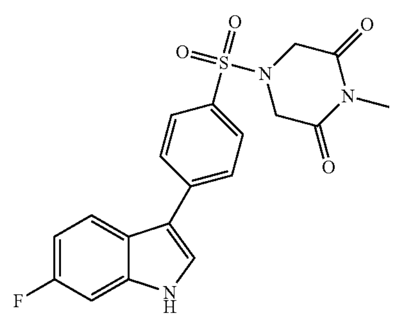 [SMILES: CN1C(=O)CN(S(=O)(=O)c2ccc(-c3c[nH]c4cc(F)ccc34)cc2)CC1=O] |
| (R)-1-(2,3-dihydroxypropyl)-4-((4-(6-fluoro-1H-indol-3-yl)phenyl)sulfonyl)piperazin-2-one | 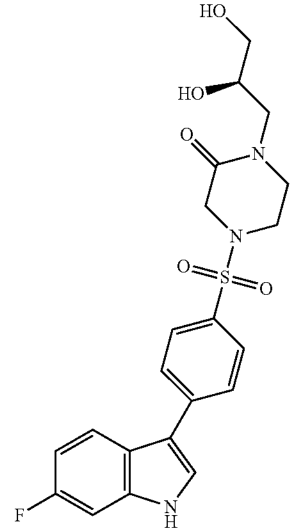 [SMILES: O=C1CN(S(=O)(=O)c2ccc(-c3c[nH]c4cc(F)ccc34)cc2)CCN1C[C@@H](O)CO] |

| Compound-IUPAC name | Structure |
|---|---|
| (S)-1-(2,3-dihydroxypropyl)-4-((4-(6-fluoro-1H-indol-3-yl)phenyl)sulfonyl)piperazin-2-one | 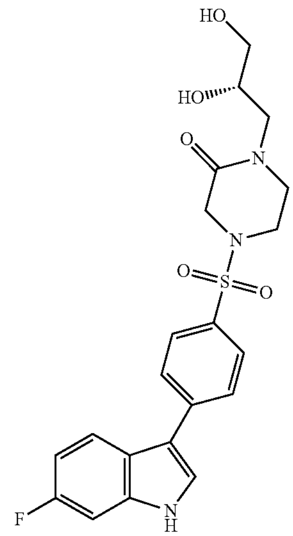 [SMILES: O=C1CN(S(=O)(=O)c2ccc(-c3c[nH]c4cc(F)ccc34)cc2)CCN1C[C@H](O)CO] |
| 1-(2-aminoethyl)-4-((4-(6-fluoro-1H-indol-3-yl)phenyl)sulfonyl)piperazin-2-one | 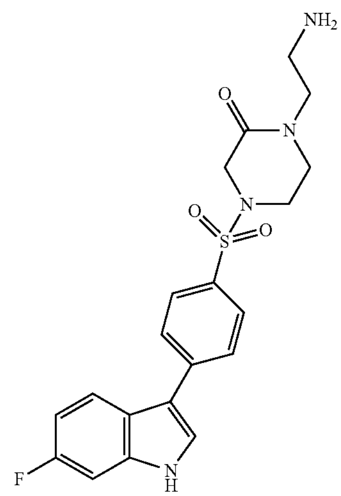 [SMILES: NCCN1CCN(S(=O)(=O)c2ccc(-c3c[nH]c4cc(F)ccc34)cc2)CC1=O] |
| 1-(2-(dimethylamino)ethyl)-4-((4-(6-fluoro-1H-indol-3-yl)phenyl)sulfonyl)piperazin-2-one | 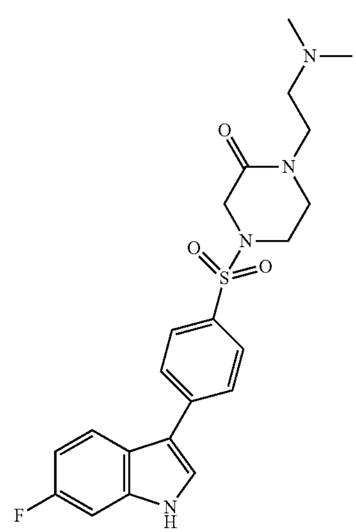 [SMILES: CN(C)CCN1CCN(S(=O)(=O)c2ccc(-c3c[nH]c4cc(F)ccc34)cc2)CC1=O] |

| Compound-IUPAC name | Structure |
|---|---|
| 4-((4-(6-fluoro-1H-indol-3-yl)phenyl)sulfonyl)-1-(2-(methylamino)ethyl)piperazin-2-one | 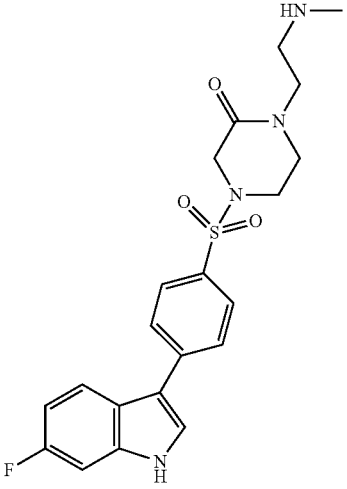 [SMILES: CNCCN1CCN(S(=O)(=O)c2ccc(-c3c[nH]c4cc(F)ccc34)cc2)CC1=O] |
| 4-((4-(6-fluoro-1H-indol-3-yl)phenyl)sulfonyl)-1-(2-hydroxyethyl)piperazin-2-one | 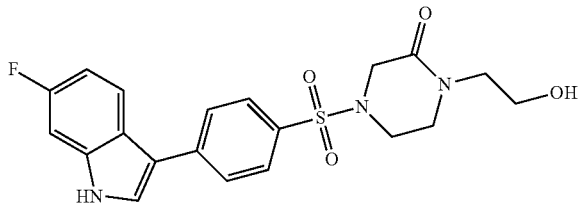 [SMILES: O=C1CN(S(=O)(=O)c2ccc(-c3c[nH]c4cc(F)ccc34)cc2)CCN1CCO] |
| 1-(3-aminopropyl)-4-((4-(6-fluoro-1H-indol-3-yl)phenyl)sulfonyl)piperazin-2-one | 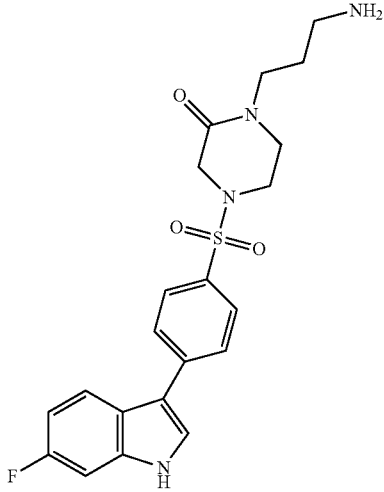 [SMILES: NCCCN1CCN(S(=O)(=O)c2ccc(-c3c[nH]c4cc(F)ccc34)cc2)CC1=O] |
| 4-((4-(6-fluoro-1H-indol-3-yl)phenyl)sulfonyl)-1-(3-(methylamino)propyl)piperazin-2-one | 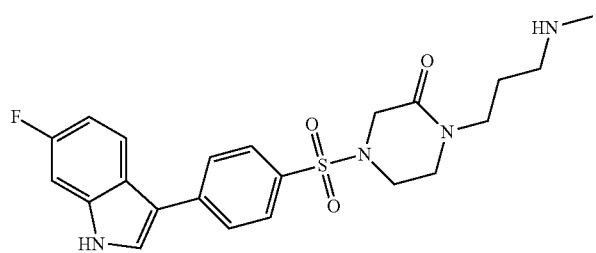 [SMILES: CNCCCN1CCN(S(=O)(=O)c2ccc(-c3c[nH]c4cc(F)ccc34)cc2)CC1=O] |

| Compound-IUPAC name | Structure |
|---|---|
| 1-(3-(dimethylamino)propyl)-4-((4-(6-fluoro-1H-indol-3-yl)phenyl)sulfonyl)piperazine-2-one | 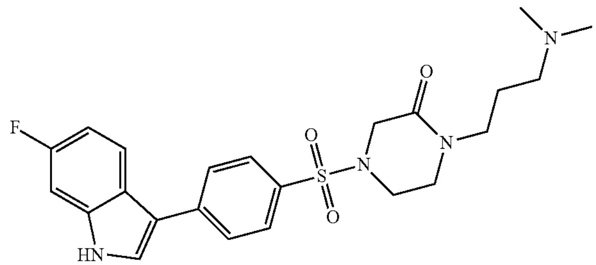 [SMILES: CN(C)CCCN1CCN(S(=O)(=O)c2ccc(-c3c[nH]c4cc(F)ccc34)cc2)CC1=O] |
| 4-(6-fluoro-1H-indol-3-yl)-N-((3-methyl-1,2,4-oxadiazol-5-yl)methyl)benzenesulfonamide | 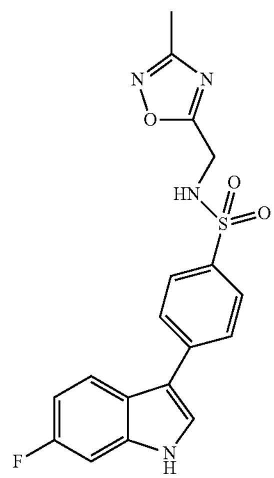 [SMILES: Cc1noc(CNS(=O)(=O)c2ccc(-c3c[nH]c4cc(F)ccc34)cc2)n1] |
| N-((1,2,4-oxadiazol-3-yl)methyl)-4-(6-fluoro-1H-indol-3-yl) benzenesulfonamide | 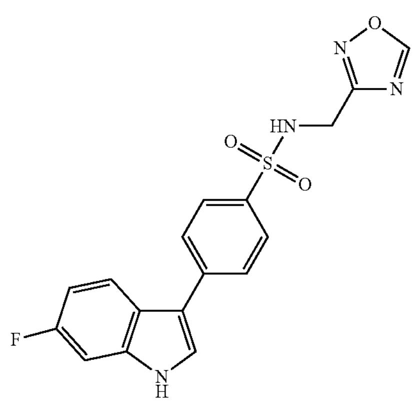 [SMILES: O=S(=O)(NCc1ncon1)c1ccc(-c2c[nH]c3cc(F)ccc23)cc1] |
| 4-(6-fluoro-1H-indol-3-yl)-N-(2-hydroxyethyl)benzenesulfonamide | 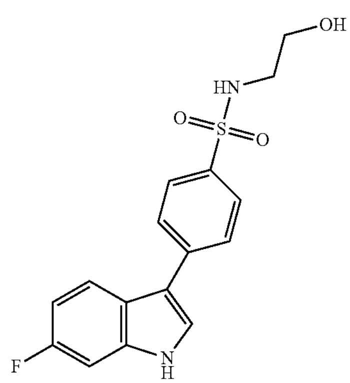 [SMILES: O=S(=O)(NCCO)c1ccc(-c2c[nH]c3cc(F)ccc23)cc1] |

-continued

| Compound-IUPAC name | Structure |
|---|---|
| 3-chloro-4-(6-fluoro-1H-indol-3-yl)-N-(2-hydroxyethyl)benzenesulfonamide | 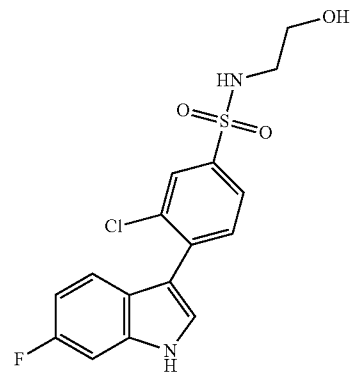 [SMILES: O=S(=O)(NCCO)c1ccc(-c2c[nH]c3cc(F)ccc23)c(Cl)c1] |
| (−)-4-(6-fluoro-1H-indol-3-yl)-N-(2-(methylsulfinyl)ethyl)benzenesulfonamide | 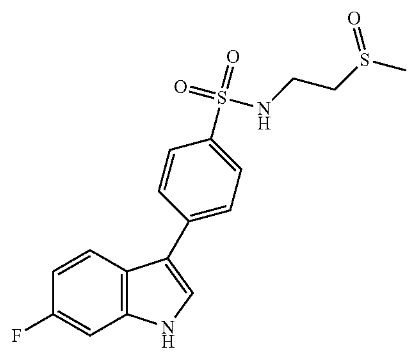 [SMILES: CS(=O)CCNS(=O)(=O)c1ccc(-c2c[nH]c3cc(F)ccc23)cc1] |
| (+)-4-(6-fluoro-1H-indol-3-yl)-N-(2-(methylsulfinyl)ethyl)benzenesulfonamide | 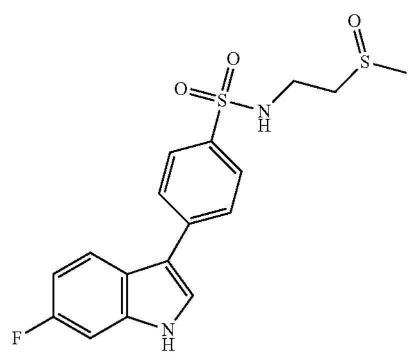 [SMILES: CS(=O)CCNS(=O)(=O)c1ccc(-c2c[nH]c3cc(F)ccc23)cc1] |
| 4-(6-fluoro-1H-indol-3-yl)-N-(2-(2-methyl-1H-imidazol-4-yl)ethyl)benzenesulfonamide | 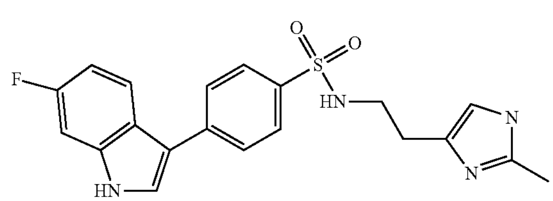 [SMILES: Cc1nc(CCNS(=O)(=O)c2ccc(-c3c[nH]c4cc(F)ccc34)cc2)c[nH]1] |

| Compound-IUPAC name | Structure |
|---|---|
| 3-(2-ethyl-4-(6-fluoro-1H-indol-3-yl)phenyl-sulfonamido)propanamide | 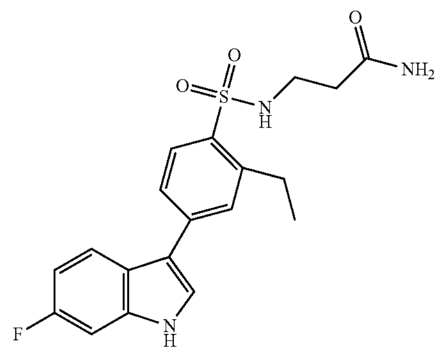 [SMILES: CCc1cc(-c2c[nH]c3cc(F)ccc23)ccc1S(=O)(=O)NCCC(N)=O] |
| 3-((4-(6-fluoro-1H-indol-3-yl)-2-isopropylphenyl)sulfonamido)propanamide | 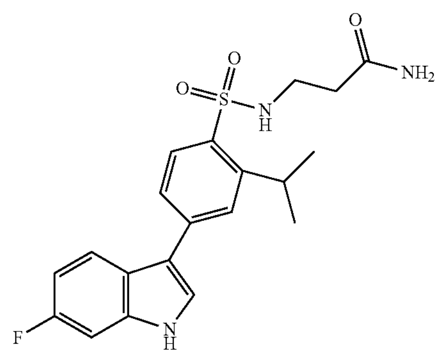 [SMILES: CC(C)c1cc(-c2c[nH]c3cc(F)ccc23)ccc1S(=O)(=O)NCCC(N)=O] |
| 3-((4-(6-fluoro-1H-indol-3-yl)-2-isobutylphenyl)sulfonamido)propanamide | 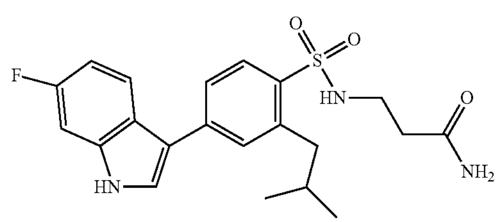 [SMILES: CC(C)Cc1cc(-c2c[nH]c3cc(F)ccc23)ccc1S(=O)(=O)NCCC(N)=O] |
| 3-((4-(6-fluoro-1H-indol-3-yl)-2-(methoxymethyl)phenyl)sulfonamido)propanamide | 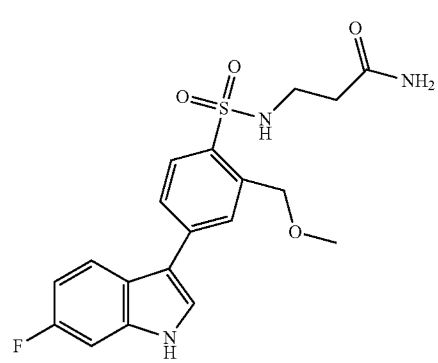 [SMILES: COCc1cc(-c2c[nH]c3cc(F)ccc23)ccc1S(=O)(=O)NCCC(N)=O] |

| Compound-IUPAC name | Structure |
|---|---|
| 3-((4-(6-fluoro-1H-indol-3-yl)-2-isopropoxyphenyl)sulfonamido)propanamide | 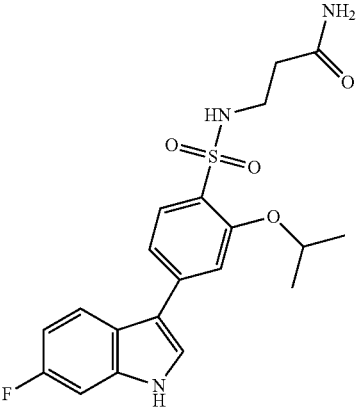 [SMILES: CC(C)Oc1cc(-c2c[nH]c3cc(F)ccc23)ccc1S(=O)(=O)NCCC(N)=O] |
| 3-((4-(6-fluoro-1H-indol-3-yl)-2-(hydroxymethyl)phenyl)sulfonamido)propanamide | 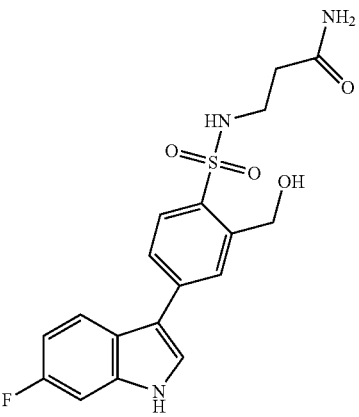 [SMILES: NC(=O)CCNS(=O)(=O)c1ccc(-c2c[nH]c3cc(F)ccc23)cc1CO] |
| 3-((4-(6-fluoro-1H-indol-3-yl)-2-(trifluoromethyl)phenyl)sulfonamido)propanamide | 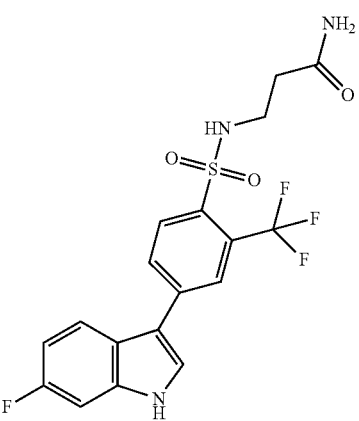 [SMILES: NC(=O)CCNS(=O)(=O)c1ccc(-c2c[nH]c3cc(F)ccc23)cc1C(F)(F)F] |

| Compound-IUPAC name | Structure |
|---|---|
| N-(3-((cis)-3,4-dihydroxypyrrolidin-1-yl)-3-oxo-propyl)-4-(6-fluoro-1H-indol-3-yl)benzenesulfonamide | 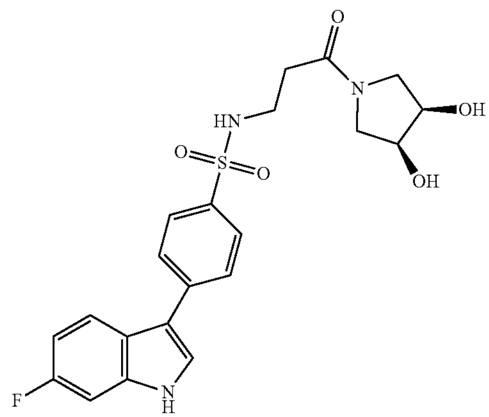 [SMILES: O=C(CCNS(=O)(=O)c1ccc(-c2c[nH]c3cc(F)ccc23)cc1)N1C[C@@H](O)[C@@H](O)C1] |
| (−)-N-(3-((3S,4S)-3,4-dihydroxypyrrolidin-1-yl)-3-oxopropyl)-4-(6-fluoro-1H-indol-3-yl)benzenesulfonamide | 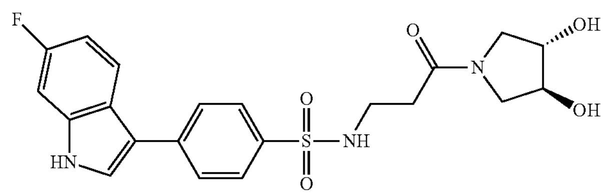 [SMILES: O=C(CCNS(=O)(=O)c1ccc(-c2c[nH]c3cc(F)ccc23)cc1)N1C[C@H](O)[C@@H](O)C1] |
| (−)-N-(3-((3S,4R)-3-amino-4-fluoropyrrolidin-1-yl)-3-oxopropyl)-4-(6-fluoro-1H-indol-3-yl)benzenesulfonamide | |
| (+)-N-(3-((3S,4R)-3-amino-4-fluoropyrrolidin-1-yl)-3-oxopropyl)-4-(6-fluoro-1H-indol-3-yl)benzenesulfonamide | 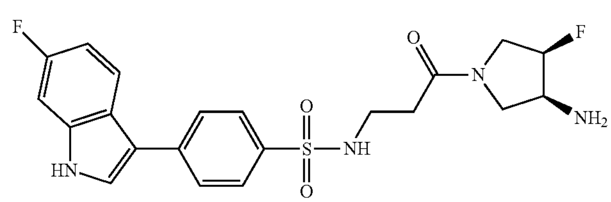 [SMILES: N[C@H]1CN(C(=O)CCNS(=O)(=O)c2ccc(-c3c[nH]c4cc(F)ccc34)cc2)C[C@H]1F] |
| (+)-N-(3-((3R,4R)-3-amino-4-fluoropyrrolidin-1-yl)-3-oxopropyl)-4-(6-fluoro-1H-indol-3-yl)benzenesulfonamide | 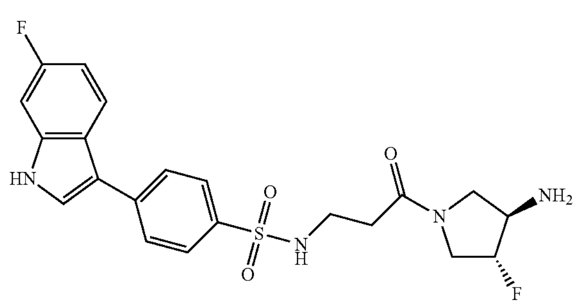 [SMILES: N[C@@H]1CN(C(=O)CCNS(=O)(=O)c2ccc(-c3c[nH]c4cc(F)ccc34)cc2)C[C@H]1F] |

| Compound-IUPAC name | Structure |
|---|---|
| 3-((2-(2,2-difluoroethyl)-4-(6-fluoro-1H-indol-3-yl)phenyl)sulfonamido)propanamide | 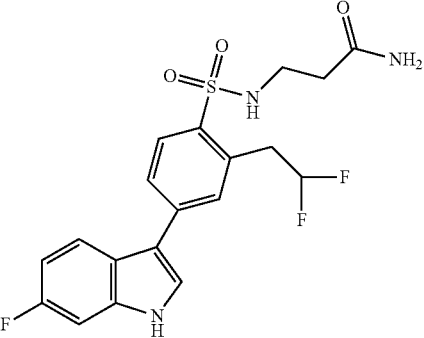 [SMILES: NC(=O)CCNS(=O)(=O)c1ccc(-c2c[nH]c3cc(F)ccc23)cc1CC(F)F] |
| 4-(6-fluoro-1H-indol-3-yl)-2-(hydroxymethyl)benzenesulfonamide | 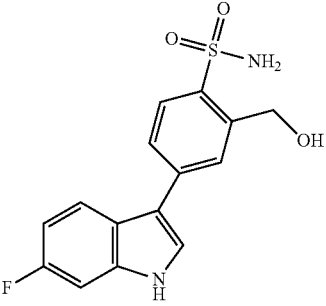 |
| 2-(aminomethyl)-4-(6-fluoro-1H-indol-3-yl)benzenesulfonamide | 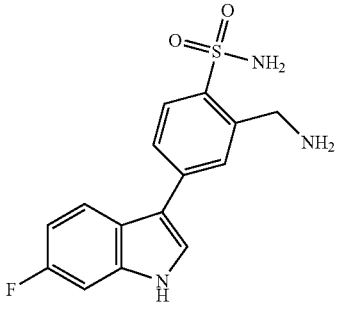 [SMILES: NCc1cc(-c2c[nH]c3cc(F)ccc23)ccc1S(N)(=O)=O] |
| (5-(6-fluoro-1H-indol-3-yl)-2-(methylsulfonyl)phenyl)methanamine | 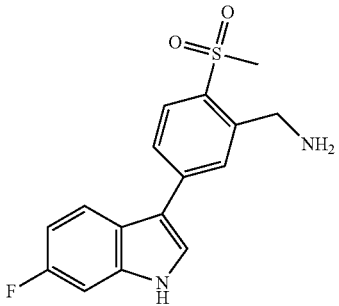 [SMILES: CS(=O)(=O)c1ccc(-c2c[nH]c3cc(F)ccc23)cc1CN] |

| Compound-IUPAC name | Structure |
|---|---|
| 2-(5-(6-fluoro-1H-indol-3-yl)-2-(methylsulfonyl)phenyl)ethanol | | or pharmaceutically acceptable enantiomers, salts and solvates thereof. In one embodiment, a compound which is an enantiomer is selected. In another embodiment, a compound which is a salt is selected. In further embodiment, a compound which is a solvate is selected. In still another embodiment, a compound of Table 1, Formula I (or its subformulae) is selected which is a free base (non-salt). Also encompassed herein are salts of the given Formulae, salts of enantiomers, and solvates of such salts.

The compounds of Table 1 were named using ChemBioDraw® Ultra version 12.0 (PerkinElmer).

The compounds of Formula I and subformulae thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of "pharmaceutically acceptable salts". Pharmaceutically acceptable salts of the compounds of Formula I include the acid addition and base salts thereof. Suitable acid addition salts are formed from acids which form non-toxic salts. Examples include the acetate, lactobionate, benzenesulfonate, laurate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandalate, bitartrate, methylbromide, bromide, methylnitrate, calcium edetate, mucate, napsylate, chloride, clavulanate, Butyl(N) oleate, edetate, estolate, pantothenate, polygalacuronate, salicylate, glutamate, glycollylarsanilate, sulfate, hexylrosorcinate, subacetate, hydrabamine, hydroxynaphthaloate, etolate, triethiodide, valerate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminum, arginine, benzathine, calcium, choline, diethylamine, diolamine, glycine, lysine, magnesium, meglumine, olamine, ornithine, N, N-dibenzyethelenediamine, piperazine, tris(hydroxymethyl)aminomethane, tetramethylammonium hydroxide, methylglucamine, ammonium salt, potassium, sodium, tromethamine, 2-(diethylamino)ethanol, ethanolamine, morpholine, 4-(2-hydroxyethyl)-morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:

(i) by reacting the compound of Formula I with the desired acid;

(ii) by reacting the compound of Formula I with the desired base;

(iii) by removing an acid- or base-labile protecting group from a suitable precursor of the compound of Formula I or by ring-opening a suitable cyclic precursor, for example, a lactone or lactam, using the desired acid; or (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the present invention may be administered in the form of pharmaceutically acceptable salts, which are as defined above. These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Process for Manufacturing

The compounds of Formula I can be prepared by different ways with reactions known to a person skilled in the art.

The invention further relates to a first process for manufacturing of compounds of Formula I

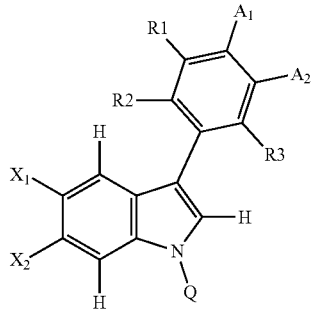

and pharmaceutically acceptable enantiomers, salts and solvates thereof, wherein $X^1$, $X^2$, $R^1$, $R^2$, $R^3$, $A^1$, $A^2$ and Q are as defined in Formula I;

comprising:

(a1) reacting a compound of Formula (i)

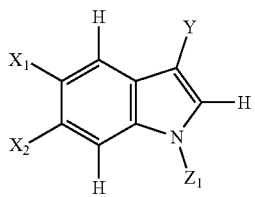

wherein $X^1$ and $X^2$ are as defined in Formula I;

$Z^1$ represents Q or an amino protecting group such as for example an arylsulphonyl, a tert-butoxy carbonyl, a methoxymethyl, a para-methoxy benzyl, a benzyl or any other suitable protecting group known to those skilled in the art Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art with a compound of Formula (ii)

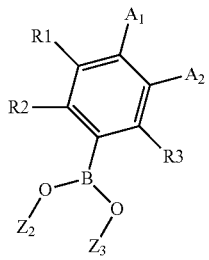

(ii) wherein $R^1$, $R^2$, $R^3$, $A^1$, $A^2$ and $A^3$ are as defined in Formula I;

$Z^2$ and $Z^3$ represent H or alkyl groups, with the possibility for $Z^2$ and $Z^3$ to form a ring;

so as to obtain a compound of Formula (iii),

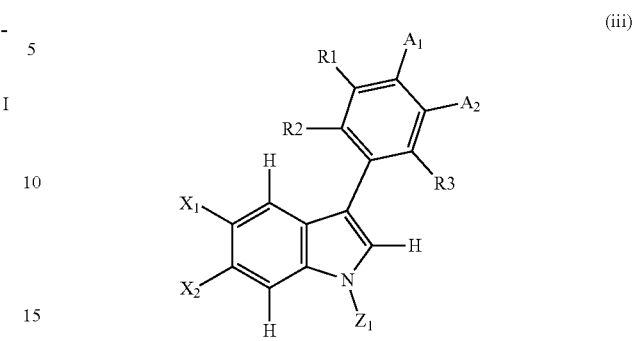

wherein $X^1$, $X^2$, $R^1$, $R^2$, $R^3$, $A^1$, $A^2$ and $Z^1$ are as defined above;

and (b1) in the case wherein $Z^1$ is not Q, deprotecting the indole amine of compound of Formula (iii), to afford compound of Formula I.

According to one embodiment, step (a1) may be performed with or without a catalyst such as but not limited to $Pd_2(dba)_3$, $Pd(PPh_3)_4$, dichlorobis-(triphenylphosphine)palladium(II) or 1,1'-bis(diphenylphosphino)ferrocene-dichloro palladium(II), $Pd(OAc)_2$, or Pd/C in the presence or absence of an additional ligand, such as but not limited to X-Phos, S-Phos, $P(oTol)_3$, $PPh_3$, BINAP, $P(tBu)_3$ or any other suitable phosphine ligand known to those skilled in the art.

According to one embodiment, step (a1) may be performed in the presence of bases such as but not limited to $K_3PO_4$, $K_2CO_3$, $Na_2CO_3$.

According to one embodiment, step (a1) may be performed in the presence of a suitable solvent such as but not limited to dioxane, THF, DMF, water or mixtures thereof, preferably in a mixture of dioxane or THF and water.

According to one embodiment, step (a1) may be performed at a temperature ranging from 20° C. to about 180° C., with or without microwave irradiation, for a period ranging from 10 minutes to a few hours, e.g. 10 minutes to 24 h.

According to one embodiment, the deprotection (b1) may be performed, depending on the nature of the group $Z^1$, by treatment with bases, such as but not limited to sodium hydroxide, potassium hydroxide, potassium carbonate. According to one embodiment, the deprotection may be performed in the presence or absence of a suitable solvent such as but not limited to methanol, ethanol, isopropanol, tert-butanol, THF, DMF, Dioxane, water or a mixture thereof. According to one embodiment, the deprotection may be performed at a temperature ranging from 20° C. to 100° C., preferably at about 85° C., for a few hours, e.g. one hour to 24 h.

According to an alternative embodiment, the deprotection (b1) may be performed, depending on the nature of the group $Z^1$ in the presence of strong acids, such as but not limited to HCl, TFA, HF, HBr. According to one embodiment, the deprotection may be performed in the presence or absence of a suitable solvent such as methanol, ethanol, isopropanol, tert-butanol, THF, DMF, Dioxane, water or a mixture thereof. According to one embodiment, the deprotection may be performed at a temperature between about 20° C. to about 100° C., for a period comprised between 10 minutes and a few hours, e.g. 10 minutes to 24 h.

Also provided is a second process of manufacturing of compounds of Formula I

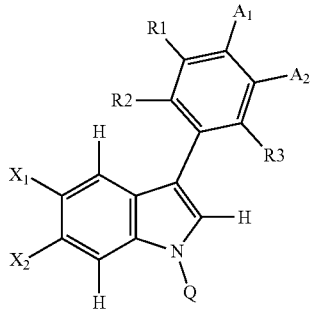

(I)

and pharmaceutically acceptable enantiomers, salts and solvates thereof, wherein $X^1$, $X^2$, $R^1$, $R^2$, $R^3$, $A^1$, $A^2$ and Q are as defined in Formula I;

comprising:

(a2) reacting a compound of Formula (iv)

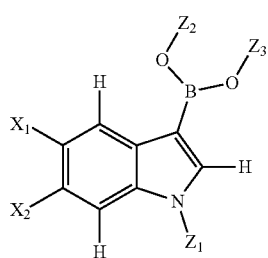

(iv)

wherein $X^1$ and $X^2$ are as defined in Formula I;

$Z^1$ represents Q or an amino protecting group such as for example an arylsulphonyl, a tert-butoxy carbonyl, a methoxymethyl, a para-methoxy benzyl, a benzyl or any other suitable protecting group known to those skilled in the art $Z^2$ and $Z^3$ represent H or alkyl groups, with the possibility for $Z^2$ and $Z^3$ to form a ring;

with a compound of Formula (v)

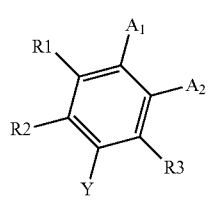

(v)

wherein $R^1$, $R^2$, $R^3$, $A^1$ and $A^2$ are as defined in Formula I;

Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art so as to obtain a compound of Formula (vi),

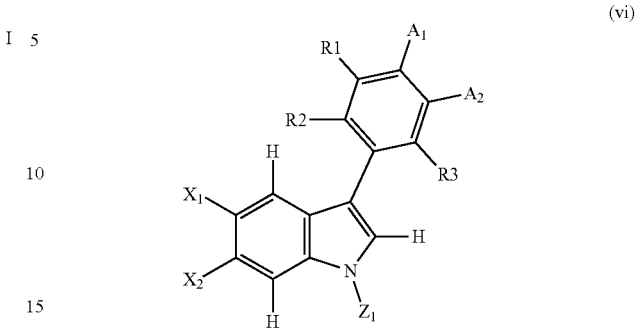

(vi)

wherein $X^1$, $X^2$, $R^1$, $R^2$, $R^3$, $A^1$, $A^2$ and $Z^1$ are as defined above;

and (b2) in the case wherein $Z^1$ is not Q, deprotecting the indole amine of compound of Formula (xii), to afford compound of Formula I (or its subformulae).

According to one embodiment, step (a2) may be performed with or without a catalyst such as but not limited to $Pd_2(dba)_3$, $Pd(PPh_3)_4$, dichlorobis-(triphenylphosphine)palladium(II) or 1,1'-bis(diphenylphosphino)ferrocene-dichloro palladium(II), $Pd(OAc)_2$, or Pd/C in the presence or absence of an additional ligand, such as but not limited to X-Phos, S-Phos, $P(oTol)_3$, $PPh_3$, BINAP, $P(tBu)_3$ or any other suitable phosphine ligand known to those skilled in the art.

According to one embodiment, step (a2) may be performed in the presence of bases such as but not limited to $K_3PO_4$, $K_2CO_3$, $Na_2CO_3$.

According to one embodiment, step (a2) may be performed in the presence of a suitable solvent such as but not limited to dioxane, THF, DMF, water or mixtures thereof, preferably in a mixture of dioxane or THF and water.

According to one embodiment, step (a2) may be performed at a temperature ranging from 20° C. to about 180° C., with or without microwave irradiation, for a period ranging from 10 minutes to a few hours, e.g. 10 minutes to 24 h.

According to one embodiment, the deprotection step (b2) may be performed in conditions described above for deprotection (b1).

In general, the synthesis pathways for any individual compound of Formula (I) will depend on the specific substituents of each molecule and upon the ready availability of intermediates necessary; again such factors being appreciated by those of ordinary skill in the art.

According to a further general process, compounds of Formula I can be converted to alternative compounds of Formula I, employing suitable interconversion techniques well known by a person skilled in the art.

Compounds of the Formula I and related formulae can furthermore be obtained by liberating compounds of the Formula I from one of their functional derivatives by treatment with a solvolysing or hydrogenolysing agent.

Preferred starting materials for the solvolysis or hydrogenolysis are those which conform to the Formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the Formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy¬carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the Formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethyl benzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl¬formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Applications

A compound of Formula I (inclusive of its subformulae, e.g., Formulae Ia, Ib, and II) or pharmaceutically acceptable enantiomers, salts and solvates are useful as the active ingredient in a pharmaceutical composition or preparation. In one embodiment, a compound is used as a TDO2 inhibitor.

Accordingly, in a particularly preferred embodiment, the compounds of Formula I and subformulae, including without limitation, those of Table 1 above, or pharmaceutically acceptable enantiomers, salts and solvates thereof, are used as TDO2 inhibitors.

Accordingly, in another aspect, these compounds or enantiomers, salts and solvates thereof are used in the synthesis of pharmaceutical active ingredients, such as TDO2 inhibitors.

In one embodiment, compounds of Formula I and subformulae in particular those of Table 1 above, or pharmaceutically acceptable enantiomers, salts and solvates thereof, are used for increasing immune recognition and destruction of the cancer cells.

The compounds of Formula I and subformulae are useful as medicaments, in particular in the prevention and/or treatment of cancer.

In one embodiment, the compounds described herein or pharmaceutically acceptable enantiomers, salts or solvates thereof are for use in the treatment and/or prevention of cancer, neurodegenerative disorders such as Parkinson's disease, Alzheimer's disease and Huntington's disease, chronic viral infections such as HCV and HIV, depression, and obesity.

Also provided is a method for treatment or prevention of cancer, neurodegenerative disorders such as Parkinson's disease, Alzheimer's disease and Huntington's disease, chronic viral infections such as HCV and HIV, depression, and obesity, which comprises administering to a mammalian species in need thereof a therapeutically effective amount of the compound according to the invention or a pharmaceutically acceptable enantiomers, salts or solvates thereof.

Various cancers are known in the art. The cancer may be metastatic or non-metastatic. The cancer may be may be familial or sporadic. In some embodiments, the cancer is selected from the group consisting of: leukemia and multiple myeloma. Additional cancers that can be treated using the methods of the invention include, for example, benign and malignant solid tumors and benign and malignant non-solid tumors.

Examples of solid tumors include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumour), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, and thyroid cancer (including thyroid adenocarcinoma and medullary carcinoma).

Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

The invention also provides for a method for delaying in patient the onset of cancer comprising the administration of a pharmaceutically effective amount of a compound of Formula I or pharmaceutically acceptable enantiomer, salt and solvate thereof to a patient in need thereof.

Preferably, the patient is a warm-blooded animal, more preferably a human.

The compounds of the invention are especially useful in the treatment and/or prevention of cancer.

In a specific embodiment, the compounds of the invention are especially useful in the treatment and/or prevention of cancer.

The invention further provides the use of a compound of Formula I or a pharmaceutically acceptable enantiomer, salt and solvate thereof for the manufacture of a medicament for treating and/or preventing cancer.

According to a further feature of the present invention there is provided a method for modulating TDO2 activity, in a patient, preferably a warm blooded animal, preferably a mammal, and even more preferably a human, in need of such treatment, which comprises administering to said patient an effective amount of compound of the present invention, or a pharmaceutically acceptable enantiomer, salt and solvate thereof.

In a further embodiment, the invention provides use of a compound of Formula I (or a subformulae thereof), or a pharmaceutically acceptable enantiomer, salt or solvate thereof for use in the treatment and/or prevention of cancer. In one embodiment, the cancer is bladder carcinoma. In another embodiment, the cancer is hepatocarcinoma. In a further embodiment, the cancer is melanoma. In another embodiment, the cancer is mesothelioma. In a further embodiment, the cancer is a neuroblastoma. In another embodiment, the cancer is a sarcoma. In a further embodiment, the cancer is breast carcinoma. In still another embodiment, the cancer is leukemia. In a further embodiment, the cancer is a renal cell carcinoma. In a further embodiment, the cancer is a colorectal carcinoma. In still another embodiment, the cancer is head & neck carcinoma. In another embodiment, the cancer is lung carcinoma. In still another embodiment, the cancer is a brain tumor. In a further embodiment, the cancer is a glioblastoma. In still another embodiment, the cancer is an astrocytoma. In a further embodiment, the cancer is a myeloma. In yet another embodiment, the cancer is pancreatic carcinoma.

In another embodiment, the invention provides use of a compound of Formula I (or a subformulae thereof), or a pharmaceutically acceptable enantiomer, salt or solvate thereof for use in the treatment of a neurodegenerative disorder. In one embodiment, the disorder is Parkinson's disease. In another embodiment, the disorder is Alzheimer's disease. In a further embodiment, the disorder is Huntington's disease.

In still another embodiment, use of a compound of Formula I (or a subformulae thereof), or a pharmaceutically acceptable enantiomer, salt or solvate thereof) in the treatment of chronic viral infections such as HCV and HIV is provided.

In another embodiment, use of a compound of Formula I (or a subformulae thereof), or a pharmaceutically acceptable enantiomer, salt or solvate thereof) in the treatment of depression is provided.

In another embodiment, use of a compound of Formula I (or a subformulae thereof), or a pharmaceutically acceptable enantiomer, salt or solvate thereof) in the treatment of obesity is provided.

For use in such treatments, the compounds provided herein may be formulated as follows.

Formulations

The invention also provides pharmaceutical compositions comprising one or more compounds of Formula I and/or a subformula thereof, or a pharmaceutically acceptable enantiomer, salt and solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable enantiomer, salt and solvate thereof as active ingredient, additional therapeutic agents and/or active ingredients.

Another object of this invention is a medicament comprising at least one compound of the invention, or a pharmaceutically acceptable enantiomer, salt and solvate thereof, as active ingredient.

According to a further feature of the present invention there is provided the use of a compound of Formula I or a pharmaceutically acceptable enantiomer, salt and solvate thereof for the manufacture of a medicament for modulating TDO2 activity in a patient, in need of such treatment, which comprises administering to said patient an effective amount of compound of the present invention, or a pharmaceutically acceptable enantiomer, salt and solvate thereof.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, disintegrants, bulking agents, fillers, preserving agents, sweetening agents, flavoring agents, flow regulators, release agents, etc. The compositions may also be formulated so as to provide rapid, sustained or delayed release of the active compound(s) contained therein.

In one embodiment, at least one compound of Formula I, its subformulae, or an enantiomer, salt or solvate thereof, is delivered to a subject in an amount ranging from about 0.01 mg/kg to about 600 mg/kg, or a dose of about 1 mg to about 500 mg. However, higher or lower amounts may be selected, e.g., taking consideration such factors as the indication being treated, and/or the age and weight of the patient.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

Definitions

As used herein, the following terms have the following meanings:

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano haloalkoxy, and haloalkyl. In certain embodiments, more than one substituent may be on the same atom of a group (e.g., a dimethyl substitution on a N or C). In other embodiments, other substituents may be selected, such as are described and/or illustrated in the examples.

The term "halogen" means fluoro (F), chloro (Cl), bromo (Br), or iodo (I).

The following definitions are used in connection with the compounds described herein. In general, the number of carbon atoms present in a given group is designated "Cx to Cy", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

The term "alkyl" by itself or as part of another substituent refers to a hydrocarbyl radical of Formula $C_nH_{2n+1}$ wherein n is a number greater than or equal to 1. Alkyl groups may contain 1 to 10 carbons (inclusive), i.e., C1, C2, C3, C4, C5, C6, C7, C8, C9 or C10, i.e., C1-C10 alkyl. In certain embodiments, alkyl groups of this invention comprise from 1 to 6 carbon atoms, preferably from 1 to 4 carbon atoms, more preferably from 1 to 3 carbon atoms. Alkyl groups may be linear or branched and may be substituted as indicated herein. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

The term "haloalkyl" alone or in combination, refers to an alkyl radical having the meaning as defined above wherein one or more hydrogens are replaced with a halogen as defined above. Non-limiting examples of such haloalkyl radicals include fluoromethyl, difluoromethyl, trifluoro methyl and the like. In one example, the haloalkyl is a C1 to C6 alkyl group substituted with at least one halogen. In another example, the haloalkyl is a C1 to C4 alkyl group substituted with at least one halogen. Each halogen substitution may be independently selected.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

The term "heteroatom" refers to a sulfur, nitrogen or oxygen atom.

Where at least one carbon atom in a cycloalkyl group is replaced with a heteroatom, the resultant ring is referred to herein as "heterocyclyl".

The terms "heterocyclyl" or "heterocycle" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. The heterocycle may contain 3 to 7 carbon atoms (inclusive), or an integer therebetween. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. In one embodiment, a heterocycle is a 4, 5 or 6 membered ring, with 1, 2 or 3 heteroatoms in its backbone selected from one or more N or O. In one embodiment, the heterocycle is a 5-membered ring having 3 N. As used herein, when the number of heteroatoms is specified, the remaining members of the heterocycle backbone are C atoms. Non limiting exemplary heterocyclic groups include piperidinyl, azetidinyl, tetrahydropyranyl, piperazinyl, imidazolinyl, morpholinyl, oxetanyl, pyrazolidinyl imidazolidinyl, isoxazolinyl, oxazolidinyl, isoxazolidinyl, thiazolidinyl, isothiazolidinyl, indolyl, indolinyl, isoindolinyl, tetrahydrofuranyl, tetrahydroquinolinyl, thiomorpholinyl, thiomorpholinylsulfoxide, thiomorpholinylsulfone, pyrrolizinyl.

The term "aryl" as used herein refers to a polyunsaturated, aromatic hydrocarbyl group having a single ring (i.e. phenyl) or multiple aromatic rings fused together (e.g. naphthyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic (carbon-containing ring) systems enumerated herein. Non-limiting examples of aryl comprise phenyl, biphenylyl, biphenylenylnaphthalenyl, indenyl.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyridazinyl, pyridinyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, oxazinyl, dioxinyl, thiazinyl, triazinyl, indolyl, indolizinyl, isoindolyl, benzofuranyl, isobenzofuranyl, benzothiophenyl, isobenzothiophenyl, indazolyl, benzimidazolyl, quinolinyl, isoquinolinyl, cinnolinyl, quinazolinyl, quinoxalinyl.

The term "arylalkyl" refers to any group -alkyl-aryl. The term "alkylaryl" refers to any group -aryl-alkyl.

The term "heteroarylalkyl" refers to any group -alkyl-heteroaryl. The term "alkylheteroaryl" refers to any group -heteroaryl-alkyl.

The term "alkoxy" refers to any group O-alkyl. The term "haloalkoxy" refers to any group O-haloalkyl.

The term "oxo" refers to a =O moiety.

The term "amino" refers to a —NH$_2$ group or any group derived thereof by substitution of one or two hydrogen atom by an organic aliphatic or aromatic group. Preferably, groups derived from —NH$_2$ are "alkylamino" groups, i.e. N-alkyl groups, comprising monoalkylamino and dialkylamino. Non-limited examples of the term "amino" include NH$_2$, NHMe or NMe$_2$, NHCOOH, NH COOCH$_3$, NHCOCH$_3$; or N(CH3)COCH3.

The term "amino-protecting group" refers to a protecting group for an amine function. According to a preferred embodiment, the amino-protecting group is selected in the groups comprising: arylsulphonyl, tert-butoxy carbonyl, methoxymethyl, para-methoxy benzyl or benzyl.

The term "leaving group" refers to a molecular fragment that departs with a pair of electrons in heterolytic bond cleavage. According to a preferred embodiment, the leaving group is selected in the groups comprising: halogen, preferably iodine, bromine or chlorine; alkylsulfonyloxy having 1-6 carbon atoms, preferably methylsulfonyloxy or trifluoromethylsulfonyloxy; or arylsulfonyloxy having 6-10 carbon atoms, preferably phenyl- or p-tolylsulfonyloxy.

The term "solvate" is used herein to describe a compound in this invention that contains stoichiometric or sub-stoichiometric amounts of one or more pharmaceutically acceptable solvent molecule, e.g., ethanol. Typically, a solvate does not significantly alter the physiological activity or toxicity of the compounds, and as such may function as pharmacological equivalents to non-solvate compounds of Formula I and its subformula as defined herein. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. "Solvate" may encompass solvates of salts of the compounds of Formula I.

The term "hydrate" refers to when the solvent molecule is water and may be an inorganic salt containing $nH_2O$, wherein n is the number of water molecules per formula unit of the salt. N may be ½, 1½, or an integer from 1 to 10. A hydrate which has lost water.

The compounds of the invention include compounds of Formula I as hereinbefore defined, including all polymorphs and crystal habits thereof, prodrugs and prodrugs thereof and isotopically-labeled compounds of Formula I.

The invention also generally covers all pharmaceutically acceptable predrugs and prodrugs of the compounds of Formula I.

The term "prodrug" as used herein means the pharmacologically acceptable derivatives of compounds of Formula I, such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient that is sufficient to achieve the desired therapeutic or prophylactic effect in the patient to which/whom it is administered.

The term "administration", or a variant thereof (e.g. "administering"), means providing the active agent or active ingredient, alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

EXAMPLES

The present invention will be better understood with reference to the following examples. These examples are intended to representative of specific embodiments of the invention, and are not intended as limiting the scope of the invention.

I. Chemistry Examples

The mass spectrometry (MS) data provided in the examples described below were obtained as followed: Mass spectrum: LC/MS Agilent 6110 (Electron Spray Ionization, ESI) or a Waters Acquity SQD (ESI).

The NMR data provided in the examples described below were obtained as followed: Bruker Ultrashield™ 400 PLUS and Bruker Fourier 300 MHz and TMS was used as an internal standard.

The microwave chemistry was performed on a single mode microwave reactor Initiator Microwave System EU from Biotage.

Preparative High Performance Liquid Chromatography (HPLC) purifications were performed with a mass directed autopurification Fractionlynx from Waters equipped with a Xbridge™ Prep C18 OBD column 19×150 mm 5 μm, unless otherwise reported. All HPLC purifications were performed with a gradient of $CH_3CN/H_2O/NH_4HCO_3$ (5 mM), $CH_3CN/H_2O/TFA$ (0.1%), or $CH_3CN/H_2O/NH_3$ $H_2O$ (0.1%).

The following abbreviations are used herein and have the indicated definitions: ACN is acetonitrile; DMSO is dimethylsulfoxide; DCM is dichloromethane; DIPEA is diisopropylethylamine; DMF is N,N-dimethylformamide; dppf is 1,1'-bis(diphenylphosphino)ferrocene; EtOH is ethanol; HATU is 2-(1H-7-azabenzotriazol-1-yl)-1,1,3,3-tetramethyl uronium hexafluorophosphate methanaminium; Hz is hertz; KOAc is potassium acetate; MeOH is methanol; MeNH2 is methylamide; BH3MeS is borane dimethyl sulfide. BuOK is potassium tert-butoxide. MeI is methylodid. MHz is megahertz; mM is millimolar; mL is milliliter; min is minutes; mol is moles; M+ is molecular ion; [M+H]+ is protonated molecular ion; N is normality; NMR is nuclear magnetic resonance; PE is petrol ether; EA is ethyl acetate. PPh3 is triphenylphosphine; psi is pound per square inch; PPM is parts per million; qd po means daily by mouth; rt is room temperature; RT is retention time; TLC is thin layer chromatography; TFA is trifluoroacetic acid; TEA is trimethylamine; SFC is supercritical fluid chromatography. LCMS (also LC-MS) is liquid chromatography-mass spectrometry. HPLC is High Performance Liquid Chromatography. TBAF is tetra-n-butylammonium fluoride. AIBN is azobisisobutyronitrile; BNS is benzenesulfonic acid; TBDPSCI is tert-butyldiphenylchlorosilane.

Intermediate 1: tert-butyl 6-fluoro-3-(4,4,5,5-tetramethyl-1,3,2-dioxaborolan-2-yl)-1H-indole-1-carboxylate Step 1: tert-butyl 6-fluoro-1H-indole-1-carboxylate To a solution of 6-fluoro-1H-indole (10.0 g, 74.0 mmol) in DCM (200 mL) were added $(Boc)_2O$ (19.4 g, 88.9 mmol), TEA (11.2 g, 15.4 mmol) and DMAP (1.81 g, 14.8 mmol). The reaction was stirred at 18° C. for 18 h. The mixture was washed with aq HCl (1 M, 100 mL) and brine. The organic layer was dried, filtered and concentrated to afford 17.4 g of the crude product which was used for next step without purification.

Step 2: tert-butyl 3-bromo-6-fluoro-1H-indole-1-carboxylate

To a solution of tert-butyl 6-fluoro-1H-indole-1-carboxylate (17.4 g, 74.0 mmol) in DCM (200 mL) was added NBS (15.8 g, 88.8 mmol). The reaction was stirred at 40° C. for 6 h. The mixture was washed with water and brine. The organic layer was dried, filtered and concentrated. The residue was purified by silica gel chromatography (PE/EtOAc=10:1) to afford the title compound as a white solid.

Step 3: tert-butyl 6-fluoro-3-(4,4,5,5-tetramethyl-1,3,2-dioxaborolan-2-yl)-1H-indole-1-carboxylate To a solution of tert-butyl 3-bromo-6-fluoro-1H-indole-1-carboxylate (10.0 g, 32.0 mmol) in dioxane (150 mL) were added 4,4,4',4',5,5,5',5'-octamethyl-2,2'-bi(1,3,2-dioxaborolane) (12.0 g, 47.0 mmol), KOAc (9.30 g, 95.0 mmol) and Pd(dppf)Cl$_2$ (2.30 g, 3.10 mmol). The reaction was stirred at 90° C. for 5 h. The solvent was removed and DCM (300 mL) was added. The mixture was washed with brine, dried and filtered. The filtrate was concentrated and purified by silica gel chromatography (PE/EtOAc=10:1) to afford the title compound (6.00 g, 50%) as a white solid.

Example 1: 6-Fluoro-3-(4-methanesulfonyl-phenyl)-1H-indole

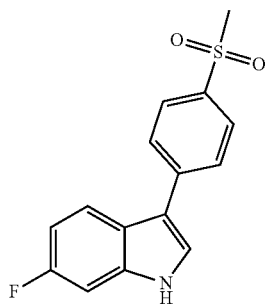 [SMILES: CS(=O)(=O)c1ccc(-c2c[nH]c3cc(F)ccc23)cc1]

Step 1: 6-fluoro-3-(4-(methylsulfonyl)phenyl)-1-(phenylsulfonyl)-1H-indole

To a solution of 1-benzenesulfonyl-6-fluoro-3-iodo-1H-indole (Prepared according to the method described in WO2010/136491A1; 300 mg, 0.75 mmol) in dioxane/H$_2$O (10 mL/1 mL) were added 4-boronophenylmethylsulfone (195 mg, 0.97 mmol), K$_3$PO$_4$ (477 mg, 2.25 mmol) and Pd(dppf)Cl$_2$(20 mg). The mixture was stirred at 100° C. for 3 hr. The solution was poured into water (10 mL) and extracted with EtOAc (3×10 mL). The organic layer was dried over anhydrous Na$_2$SO$_4$ and concentrated. The residue was purified by silica gel chromatography (PE/EtOAc=15/1) to afford the title compound (180 mg, 56%) as a white solid.

Step 2: 6-Fluoro-3-(4-methanesulfonyl-phenyl)-1H-indole

A mixture of 1-Benzenesulfonyl-6-fluoro-3-(4-methanesulfonyl-phenyl)-1H-indole (160 mg, 0.372 mmol) and NaOH (74 mg, 1.86 mmol) in CH$_3$OH (20 mL) was stirred at 80° C. for 2 hr. The solution was poured into water (10 mL) and extracted with EtOAc (3×20 mL). The organic layer was dried over anhydrous Na$_2$SO$_4$, filtered and concentrated. The residue was purified by silica gel chromatography (PE/EtOAc=10/1) and further purified by prep-HPLC to afford the title compound (25 mg, yield: 23%) as a white solid. LC-MS for C$_{15}$H$_{12}$FNO$_2$S—H$^-$ [M−H]$^-$: calcd: 288.1; found: 288.0. $^1$H NMR (400 MHz, DMSO-d$_6$) δ [ppm] 11.7 (s, 1H), 8.00-7.90 (m, 6H), 7.28 (dd, J=10.0, 2.4 Hz, 1H), 7.05-7.00 (m, 1H), 3.24 (s, 3H).

Example 2: N-(2-aminoethyl)-4-(6-fluoro-1H-indol-3-yl)benzamide

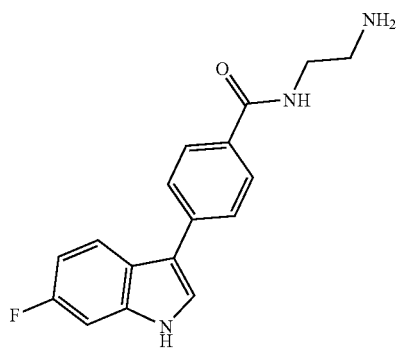 [SMILES: NCCNC(=O)c1ccc(-c2c[nH]c3cc(F)ccc23)cc1]

Step 1: methyl 4-(6-fluoro-1-(phenylsulfonyl)-1H-indol-3-yl)benzoate

The solution of 1-Benzenesulfonyl-6-fluoro-3-iodo-1H-indole (4.0 g, 10 mmol), (4-boronic acid)-benzoic acid methyl ester (2.16 g, 12.0 mmol) and K$_3$PO$_4$ (6.36 g, 30.0 mmol) in dioxane/H$_2$O (200 mL/20 mL) was degassed with N$_2$ for 10 min. Then Pd(dppf)Cl$_2$ (82 mg, 1 mmol) was added. The mixture was stirred at 90° C. for 4 h before it was diluted with EtOAc (200 mL). The organic layer was washed with water (200 mL×3), dried over Na$_2$SO$_4$, and filtered. The filtrate was concentrated and purified by silica gel chromatography (PE:EtOAc=10:1) to afford the title compound (4.0 g, 75% yield) as a brown solid. LC-MS for C$_{22}$H$_{16}$FNO$_4$S—H$^-$ [M−H]$^-$: calcd: 408.1; found: 408.4. $^1$H NMR (400 MHz, DMSO-d$_6$) δ [ppm] 8.33 (s, 1H), 8.19-8.16 (m, 2H), 8.06 (d, J=8.8 Hz, 2H), 7.93-7.89 (m, 3H), 7.84 (dd, J=10, 2.0 Hz, 1H), 7.76-7.62 (m, 1H), 7.64 (t, J=6.4 Hz, 2H), 7.26 (dt, J=9.6, 2.8 Hz, 1H), 3.89 (s, 3H).

Step 2: 4-(6-fluoro-1H-indol-3-yl)benzoic acid

To the solution of 4-(1-Benzenesulfonyl-6-fluoro-1H-indol-3-yl)-benzoic acid methyl ester (400 mg, 1.0 mmol) in MeOH/H$_2$O (20 mL/5 mL) was added NaOH (200 mg, 5.0 mmol). The mixture was stirred at 80° C. for 2 h. The mixture was concentrated, diluted with NaHCO$_3$ (sat, aq) (20 mL) and extracted with EtOAc (20 mL×3). The organic layer was washed with brine (10 mL), dried over Na$_2$SO$_4$ and concentrated in vacuum to afford the product (595 mg, 86%) as a pink solid. LC-MS for $C_{15}H_{10}FNO_2-H^-$ [M−H]⁻: calcd: 254.1; found: 254.4.

Step 3: tert-butyl (2-(4-(6-fluoro-1H-indol-3-yl)benzamido)ethyl)carbamate

To a solution of 4-(6-Fluoro-1H-indol-3-yl)-benzoic acid (255 mg, 1.0 mmol) in THF/DMF (20 mL/2 mL) was added HATU (760 mg, 2.0 mmol) and DIPEA (387 mg, 3.0 mmol). The mixture was stirred at room temperature for 10 min. Then (2-Amino-ethyl)-carbamic acid tert-butyl ester (192 mg, 1.2 mmol) was added. The mixture was stirred at room temperature for 4 h. The resulting mixture was concentrated and diluted with EtOAc (20 mL), washed with water (20 mL×4), dried over $Na_2SO_4$ and filtered. The filtrate was concentrated to give a white solid (399 mg, overweight) which was used in the next step without further purification. LC-MS for $C_{22}H_{24}FN_3O_3-C_4H_8+H^+$ [M−56+H]⁺: calcd: 341.2; found: 341.9

Step 4: N-(2-aminoethyl)-4-(6-fluoro-1H-indol-3-yl)benzamide

The solution of {2-[4-(6-Fluoro-1H-indol-3-yl)-benzoylamino]-ethyl}-carbamic acid tert-butyl ester (399 mg, 1.0 mmol) in HCl/EtOAc (2 M, 20 mL) was stirred at room temperature for 1 h. The resulting mixture was diluted with aqueous $NaHCO_3$ (50 mL) and extracted with EtOAc (20 mL×4). The organic layer was dried over $Na_2SO_4$, concentrated and purified by prep-HPLC to afford the product (9 mg, 3%) as a white solid. LC-MS for $C_{17}H_{16}FN_3O+H^+$ [M+H]⁺: calcd: 298.1; found: 298.1. ¹H NMR (400 MHz, DMSO-$d_6$) δ [ppm] 11.57 (s, 1H), 8.48 (s, 1H), 7.94-7.88 (m, 3H), 7.83 (s, 1H), 7.77 (d, J=8.4 Hz, 2H), 7.25 (dd, J=10.0, 2.0 Hz, 1H), 6.98 (dt, J=10.0, 2.4 Hz, 1H), 3.32-3.29 (m, 2H), 2.73 (t, J=6.4 Hz, 2H).

Example 3: (4-(6-fluoro-1H-indol-3-yl)phenyl)(piperazin-1-yl)methanone

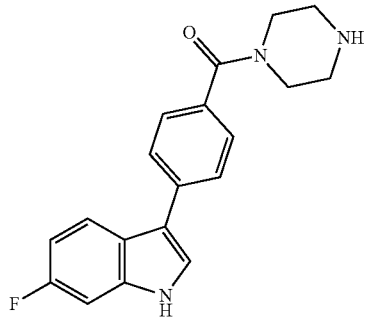 [SMILES: O=C(c1ccc(-c2c[nH]c3cc(F)ccc23)cc1)N1CCNCC1]

Step 1: tert-butyl 4-(4-(6-fluoro-1H-indol-3-yl)benzoyl)-piperazine-1-carboxylate To a mixture of 4-(6-Fluoro-1H-indol-3-yl)-benzoic acid (intermediate 2 in Example 2, 255 mg, 1.0 mmol) in THF (20 mL) and DMF (2 mL) were added HATU (760 mg, 2.0 mmol) and DIPEA (387 mg, 3.0 mmol). The mixture was stirred at room temperature for 10 min. Piperazine-1-carboxylic acid tert-butyl ester (223 mg, 1.2 mmol) was added. The reaction was stirred at room temperature for 4 h. The mixture was concentrated and diluted with EtOAc (20 mL). The organic layer was washed with water (20 mL×4), dried, filtered and concentrated to afford 4-[4-(6-Fluoro-1H-indol-3-yl)-benzoyl]-piperazine-1-carboxylic acid tert-butyl ester (358 mg, crude) as a yellow solid. LC-MS for C24H26FN3O3+H+ [M+H]+: calcd: 424.2; found: 424.7.

Step 2: (4-(6-fluoro-1H-indol-3-yl)phenyl)(piperazin-1-yl)methanone

A mixture of 4-[4-(6-Fluoro-1H-indol-3-yl)-benzoyl]-piperazine-1-carboxylic acid tert-butyl ester (358 mg, 0.84 mmol) in HCl/EtOAc (20 mL, 1 M) was stirred for 1 h at room temperature. The mixture was diluted with aqueous $NaHCO_3$ (20 mL) and extracted with EtOAc (20 mL×3). The organic layer was washed with brine, dried over $Na_2SO_4$ and filtered. The filtrate was concentrated and purified by prep-HPLC to afford the product (126 mg, 43%) as a white solid. LC-MS for $C_{19}H_{18}FN_3O+H^+$ [M+H]⁺: calcd: 324.1; found: 324.1. ¹H NMR (400 MHz, DMSO-$d_6$) δ [ppm] 11.52 (s, 1H), 7.87 (dd, J=8.8, 5.2 Hz, 1H), 7.77 (d, J=2.4 Hz, 1H), 7.73 (d, J=8.4 Hz, 2H), 7.43 (d, J=8.4 Hz, 2H), 7.23 (dd, J=9.6, 2.4 Hz, 1H), 6.97 (td, J=9.6, 2.4 Hz, 1H), 3.48-3.31 (m, 4H), 2.74-2.60 (m, 4H).

Example 4: 6-fluoro-3-(4-(piperazin-1-ylsulfonyl)phenyl)-1H-indole

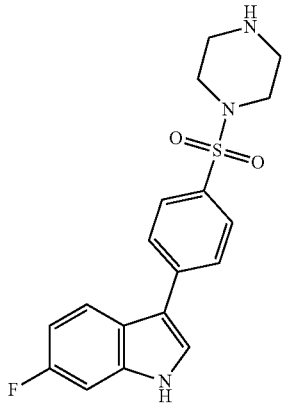 [SMILES: O=S(=O)(c1ccc(-c2c[nH]c3cc(F)ccc23)cc1)N1CCNCC1]

Step 1: tert-butyl 4-((4-bromophenyl)sulfonyl)piperazine-1-carboxylate

To a solution of 4-bromobenzene-1-sulfonyl chloride (1 g, 3.91 mmol) in DCM (30 mL) at 0° C. were added TEA (1.08 mL, 7.83 mmol) and tert-butyl piperazine-1-carboxylate (873 mg, 4.69 mmol). The reaction was stirred at room temperature for 1 hr under $N_2$. The mixture was diluted with aqueous $NH_4Cl$ (30 mL) and extracted with DCM (30 mL×2). The organic layer was washed with brine (30 mL×3), dried over anhydrous $Na_2SO_4$, filtered, and concentrated to afford tert-butyl 4-((4-bromophenyl)sulfonyl)piperazine-1-carboxylate (1.74 g, 100%) as a white solid. ¹H NMR (400 MHz, DMSO-$d_6$) δ [ppm]: 7.90-7.85 (m, 2H), 7.69-7.65 (m, 2H), 3.40 (t, J=4.8 Hz, 4H), 2.88 (t, J=4.8 Hz, 4H), 1.39 (s, 9H).

Step 2: tert-butyl 4-((4-(6-fluoro-1H-indol-3-yl)phenyl)sulfonyl)piperazine-1-carboxylate

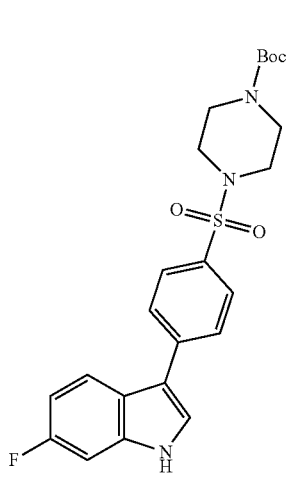 [SMILES: CC(C)(C)OC(=O)N1CCN(S(=O)(=O)c2ccc(-c3c[nH]c4cc(F)ccc34)cc2)CC1]

To a solution of tert-butyl 6-fluoro-3-(4,4,5,5-tetramethyl-1,3,2-dioxaborolan-2-yl)-1H-indole-1-carboxylate (Intermediate 1; 366 mg, 1.0 mmol), tert-butyl 4-((4-bromophenyl)sulfonyl)piperazine-1-carboxylate (450 mg, 1.11 mmol) and $K_2CO_3$ (418 mg, 3.03 mmol) in dioxane/water (20 mL/5 mL) was added $Pd(dppf)Cl_2.DCM$ (82 mg, 0.101 mmol) under nitrogen. The mixture was stirred at 100° C. for 4.5 hrs under $N_2$. The mixture was filtered through Celite, diluted with EtOAc (100 mL) and aqueous of $NH_4Cl$ (60 mL). The aqueous layer was extracted with EtOAc (80 mL×3). The combined organic layer was washed with brine, dried over anhydrous $Na_2SO_4$, filtered, concentrated, and purified by silica gel chromatography (petroleum ether/EtOAc=6/1–3/1) to afford tert-butyl 4-((4-(6-fluoro-1H-indol-3-yl)phenyl)sulfonyl)piperazine-1-carboxylate (292 mg, 63%) as a yellow solid. LC-MS for C23H26FN3O4S—C4H8+H+ [M−56+H]+: calcd: 404.1; found: 404.6. 1H NMR (400 MHz, DMSO-d6) δ [ppm]: 11.70 (s, 1H), 7.95 (m, 4H), 7.75 (d, J=8.5 Hz, 2H), 7.27 (dd, J=9.8, 2.3 Hz, 1H), 7.01 (td, J=9.4, 2.4 Hz, 1H), 3.45-3.40 (m, 4H), 2.94-2.86 (m, 4H), 1.33 (s, 9H).

Step 3: 6-fluoro-3-(4-(piperazin-1-ylsulfonyl)phenyl)-1H-indole

To a solution of tert-butyl 4-((4-(6-fluoro-1H-indol-3-yl)phenyl)sulfonyl)-piperazine-1-carboxylate (253 mg, 0.55 mmol) in DCM (18 mL) was added TFA (5 mL). The resulting mixture was stirred for 20 mins at rt. The reaction mixture was poured into aqueous $NaHCO_3$ (90 mL) and extracted with EtOAc (60 mL×3). The organic layer was dried over anhydrous $Na_2SO_4$, filtered, concentrated and purified by prep-HPLC to afford 6-fluoro-3-(4-(piperazin-1-ylsulfonyl)phenyl)-1H-indole (55 mg, 28%) as a white solid. LC-MS for $C_{18}H_{18}FN_3O_2S$+H+ [M+H]+: calca: 360.1; found: 360.6. 1H NMR (400 MHz, DMSO-$d_6$) δ [ppm]11.68 (brs, 1H), 7.99-7.92 (m, 4H), 7.73 (d, J=8.5 Hz, 2H), 7.27 (dd, J=9.8, 2.4 Hz, 1H), 7.01 (td, J=9.3, 2.4 Hz, 1H), 2.85-2.79 (m, 4H), 2.76-2.70 (m, 4H), 2.24 (br s, 1H).

Example 5: 4-((4-(6-fluoro-1H-indol-3-yl)phenyl)sulfonyl)morpholine

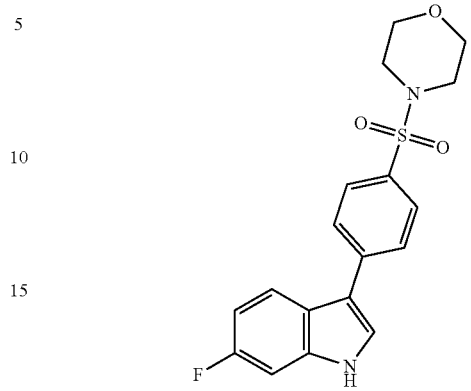

Following the general method as outlined in Example 4, starting from morpholine, the title compound was obtained as a white solid. LC-MS for $C_{18}H_{17}FN_2O_3S$—H− [M−H]−: calcd: 359.1; found: 359.8. 1H NMR (400 MHz, DMSO-$d_6$) δ [ppm]: 11.69 (s, 1H), 7.99-7.93 (m, 4H), 7.75 (d, J=8.5 Hz, 2H), 7.27 (dd, J=9.8, 2.4 Hz, 1H), 7.02 (td, J=9.4, 2.4 Hz, 1H), 3.65 (t, J=4.8 Hz, 4H), 2.91 (t, J=4.8 Hz, 4H).

Example 6: 4-(6-fluoro-1H-indol-3-yl)benzenesulfonamide

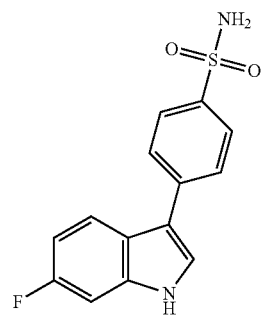 [SMILES: NS(=O)(=O)c1ccc(-c2c[nH]c3cc(F)ccc23)cc1]

Following the general method as outlined in Example 4, the title compound was obtained as a white solid. LC-MS for $C_{14}H_{11}FN_2O_2S$—H− [M−H]−: calcd: 289.1; found: 289.0. 1H NMR (400 MHz, DMSO-$d_6$) δ [ppm] 11.61 (s, 1H), 7.95-7.83 (m, 6H), 7.32 (s, 2H), 7.26 (dd, J=9.9, 2.4 Hz, 1H), 7.00 (td, J=9.5, 2.4 Hz, 1H).

Example 7: 6-fluoro-3-(3-(piperazin-1-ylsulfonyl)phenyl)-1H-indole

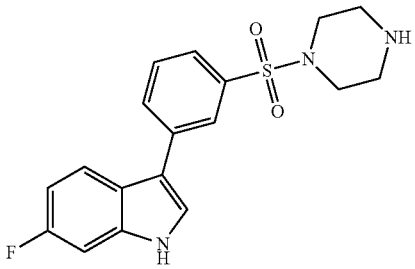 [SMILES: O=S(=O)(c1cccc(-c2c[nH]c3cc(F)ccc23)c1)N1CCNCC1]

Following the general method as outlined in Example 4, starting from tert-butyl piperazine-1-carboxylate and 3-bromobenzene-1-sulfonyl chloride, title compound was obtained as a white solid. LC-MS for $C_{18}H_{18}FN_3O_2S+H^+$ $[M+H]^+$: calcd: 360.1; found: 360.1. $^1H$ NMR (400 MHz, DMSO-$d_6$) δ [ppm] 11.64 (s, 1H), 8.02 (d, J=7.6 Hz, 1H), 7.90 (d, J=9.6 Hz, 2H), 7.81 (dd, J=5.2, 8.8 Hz, 1H), 7.71 (t, J=7.6 Hz, 1H), 7.56 (d, J=8.0 Hz, 1H), 7.26 (dd, J=10.0, 2.0 Hz, 1H), 7.02 (td, J=9.6, 2.4 Hz, 1H), 2.84 (t, J=4.4 Hz, 4H), 2.72 (t, J=4.4 Hz, 4H), 2.16 (s, 1H).

Example 8: N-(2-aminoethyl)-4-(6-fluoro-1H-indol-3-yl)-benzenesulfonamide

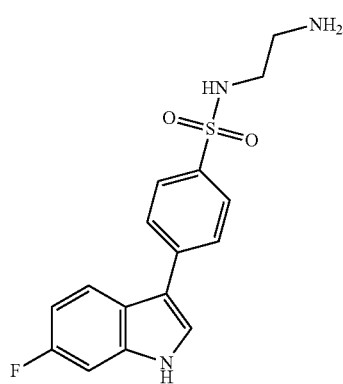 [SMILES: NCCNS(=O)(=O)c1ccc(-c2c[nH]c3cc(F)ccc23)cc1]

Following the general method as outlined in Example 4, starting from tert-butyl (2-aminoethyl) carbamate, the title compound was obtained as a white solid. LC-MS for $C_{16}H_{16}FN_3O_2S+H^+$ $[M+H]^+$: calcd: 334.1; found: 334.0. $^1H$ NMR (400 MHz, DMSO-$d_6$) δ [ppm]11.65 (br s, 1H), 7.96-7.89 (m, 4H), 7.81 (d, J=8.5 Hz, 2H), 7.26 (dd, J=9.8, 2.4 Hz, 1H), 7.02-6.98 (m, 1H), 2.82-2.73 (m, 2H), 2.56-2.50 (m, 2H).

Example 9: N-(2-aminoethyl)-3-(6-fluoro-1H-indol-3-yl)benzenesulfonamide

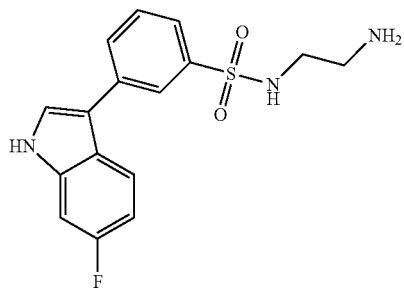 [SMILES: NCCNS(=O)(=O)c1cccc(-c2c[nH]c3cc(F)ccc23)c1]

Step 1: tert-butyl (2-(3-bromophenylsulfonamido)ethyl)carbamate

To a mixture of 3-bromo-benzenesulfonyl chloride (1.00 g, 3.93 mol) and (2-Amino-ethyl)-carbamic acid tert-butyl ester (1.2 g, 11.7 mmol) in DCM (10 mL) was added $Et_3N$ (1.18 mmol, 11.7 mmol). The reaction mixture was stirred at room temperature for 16 h. The reaction mixture was concentrated and the residue was purified by silica gel chromatography (PE/EtOAc=3/1) to afford the title compound (1.2 g, yield: 80%) as a white solid. $^1H$ NMR (400 MHz, DMSO-$d_6$) δ [ppm] 7.92-7.78 (m, 3H), 7.59-7.55 (m, 1H), 6.78 (br s, 1H), 2.95 (t, J=6.4 Hz, 2H), 2.78 (t, J=6.4 Hz, 2H), 1.35 (s, 9H).

Step 2: tert-butyl3-(3-(N-(2-((tert-butoxycarbonyl)amino)ethyl)-sulfamoyl)phenyl)-6-fluoro-1H-indole-1-carboxylate To a solution of [2-(3-Bromo-benzenesulfonylamino)-ethyl]-carbamic acid tert-butyl ester (163 mg, 0.43 mol), 6-Fluoro-3-(4,4,5,5-tetramethyl-[1,3,2]-dioxaborolan-2-yl)-indole-1-carboxylic acid tert-butyl ester (Intermediate 1, 120 mg, 0.33 mmol) and $Na_2CO_3$ (135 mg, 1.29 mmol) in dioxane (10 mL) and $H_2O$ (0.5 mL) was added $Pd(dppf)Cl_2$ (20 mg). The reaction was stirred at 70° C. under $N_2$ atmosphere for 10 h. Then the mixture was concentrated and purified by silica gel chromatography (PE/EtOAc=5/1) to afford the title compound (100 mg, yield: 33%) as a white solid.

Step 3: N-(2-aminoethyl)-3-(6-fluoro-1H-indol-3-yl) benzenesulfonamide

A mixture of 3-[3-(2-tert-Butoxycarbonylamino-ethylsulfamoyl)phenyl]-6-fluoro-indole-1-carboxylic acid tert-butyl ester (350 mg, 0.65 mmol) in TFA (5 mL) and DCM (5 mL) was stirred at r.t for 16 h. The mixture was poured into ice water (20 mL) and the pH was adjusted to 8 with aqueous saturated $Na_2CO_3$. The mixture was extracted with DCM (40 mL×3), dried over anhydrous $Na_2SO_4$ and filtered. The filtrate was concentrated and purified by prep-HPLC (5-95% acetonitrile in water) to afford the title compound (14 mg, yield: 6%) as a white solid. LC-MS for $C_{16}H_{16}FN_3O_2S+H^+$ $[M+H]^+$: calcd: 334.1; found: 334.1. $^1H$ NMR (400 MHz, DMSO-$d_6$) δ [ppm] 11.58 (br s, 1H), 8.06 (s, 1H), 7.95-7.83 (m, 3H), 7.64-7.61 (m, 2H), 7.26 (dd, J=10.0, 2.0 Hz, 1H), 7.04-6.99 (dd, J=9.6, 2.4 Hz, 1H), 2.82-2.76 (m, 2H), 2.56-2.51 (m, 2H).

Example 10: 3-(6-fluoro-1H-indol-3-yl)benzenesulfonamide

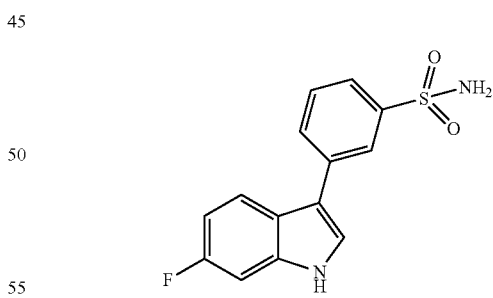

Step 1: 3-bromobenzenesulfonamide

To a solution of 3-Bromo-benzenesulfonyl chloride (1.0 g, 3.92 mmol) in DCM (3 mL) at 0° C., was added $NH_3$—$H_2O$ (3 mL). The reaction was stirred at 0° C. for 4 h. The mixture was filtered to afford 3-Bromo-benzenesulfonamide (0.9 g, 97%) as a white solid. $^1H$ NMR (400 MHz, DMSO-$d_6$) δ [ppm] 7.99 (s, 1H), 7.83 (dd J=8.4, 1.2 Hz, 2H), 7.55 (t, J=8.0 Hz, 1H), 7.48 (s, 2H).

Step 2: tert-butyl 6-fluoro-3-(3-sulfamoylphenyl)-1H-indole-1-carboxylate

To a solution of 6-Fluoro-3-(4,4,5,5-tetramethyl-[1,3,2]dioxaborolan-2-yl)-indole-1-carboxylic acid tert-butyl ester (Intermediate 1, 100 mg, 0.276 mmol) in dioxane/H$_2$O (3/0.3 mL) were added 3-Bromo-benzenesulfonamide (65 mg, 0.276 mmol), Pd(dppf)Cl$_2$ (20 mg, 0.0276 mmol) and Na$_2$CO$_3$(88 mg, 0.828 mmol). The mixture was stirred at 100° C. under N$_2$ in the microwave reactor for 1.5 h. The mixture was filtered and concentrated. The residue was purified by silica gel chromatography (PE-EtOAc=10/1~6/1) to afford the title compound (95 mg, 88%) as a yellow solid. LC-MS for Cl$_{19}$H$_{19}$FN$_2$O$_4$S+H$^+$ [M+H]$^+$: calca: 391.1; found: 391.1.

Step 3: 3-(6-fluoro-1H-indol-3-yl)benzenesulfonamide

To a solution of 6-Fluoro-3-(3-sulfamoyl-phenyl)-indole-1-carboxylic acid tert-butyl ester (190 mg, 0.487 mmol) in DCM (3 mL) was added TFA (1 mL). The mixture was stirred at room temperature for 6 h. The mixture was concentrated and the residue was purified by prep-HPLC to afford the title compound (60 mg, 42%) as a white solid. LC-MS for C$_{14}$H$_{11}$FN$_2$O$_2$S—H$^-$[M–H]$^-$. calca: 289.1; found: 289.0. $^1$H NMR (400 MHz, DMSO-d$_6$) δ [ppm] 11.57 (s, 1H), 8.12 (s, 1H), 7.90-7.87 (m, 2H), 7.80 (d, J=2.4 Hz, 1H), 7.68 (d, J=7.6 Hz, 1H), 7.60 (t, J=7.6 Hz, 1H), 7.39 (s, 2H), 7.25 (dd, J=10.0, 2.4 Hz 1H), 7.00 (td, J=9.2, 2.4 Hz, 1H).

Example 11: 3-(4-(((cis)-3,5-dimethylpiperazin-1-yl)sulfonyl)phenyl)-6-fluoro-1H-indole

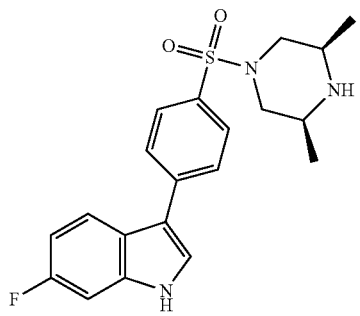 [SMILES: C[C@@H]1CN(S(=O)(=O)c2ccc(-c3c[nH]c4cc(F)ccc34)cc2)C[C@H](C)N1]

Step 1: (cis)-1-((4-bromophenyl)sulfonyl)-3,5-dimethylpiperazine

To a stirred solution of cis-2, 6-dimethyl-piperazine (228 mg, 2.0 mmol) in DCM (20 mL) at 0° C. was added 4-bromo-benzenesulfonyl chloride (511 mg, 2.0 mmol). TEA (202 mg, 2.0 mmol) was added dropwise and the mixture was stirred at room temperature for 1 hr. The mixture was concentrated and purified by silica gel chromatography (from DCM to EtOAc) to afford 560 mg (84%) of the title compound as a white solid. $^1$H NMR (400 MHz, CDCl$_3$) δ [ppm]7.67 (d, J=8.8 Hz, 2H), 7.60 (d, J=8.8 Hz, 2H), 3.61 (dd, J=11.2, 1.2 Hz, 2H), 3.02-2.91 (m, 2H), 1.83 (t, J=10.8 Hz, 2H), 1.03 (d, J=6.0 Hz, 6H).

Step 2: tert-butyl 3-(4-(((cis)-3,5-dimethylpiperazin-1-yl)sulfonyl)phenyl)-6-fluoro-1H-indole-1-carboxylate A mixture of 1-(4-bromo-benzenesulfonyl)-3,5-dimethyl-piperazine (200 mg, 0.60 mmol), 6-fluoro-3-(4,4,5,5-tetramethyl-[1,3,2]dioxaborolan-2-yl)-indole-1-carboxylic acid tert-butyl ester (Intermediate 1, 261 mg, 0.72 mmol), K$_2$CO$_3$ (248 mg, 1.80 mmol) and Pd(dppf)Cl$_2$ (22 mg, 0.030 mmol) in dioxane/water (10 mL/2 mL) was stirred at 100° C. under N$_2$ for 3 hours. The mixture was cooled, concentrated and redissolved with EtOAc (60 mL). The organic layer was dried over anhydrous Na$_2$SO$_4$ and filtered. The filtrate was concentrated and purified by silica gel chromatography (petroleum ether/EtOAc=5/1to 3/1) to afford 216 mg (74%) of the title compound as a white solid. $^1$H NMR (400 MHz, CDCl$_3$) δ [ppm] 7.96 (d, J=9.2 Hz, 1H), 7.83 (d, J=8.4 Hz, 2H), 7.76 (d, J=8.4 Hz, 2H), 7.77-7.75 (m, 1H), 7.71 (dd, J=8.8, 5.2 Hz, 1H), 7.08 (td, J=9.2, 2.4 Hz, 1H), 3.67 (dd, J=10.8, 2.4 Hz, 2H), 3.05-2.96 (m, 2H), 1.90 (t, J=10.8 Hz, 2H), 1.70 (s, 9H), 1.05 (d, J=6.4 Hz, 6H).

Step 3: 3-(4-(((cis)-3,5-dimethylpiperazin-1-yl)sulfonyl)phenyl)-6-fluoro-1H-indole A mixture of cis-3-[4-(3, 5-dimethyl-piperazine-1-sulfonyl)-phenyl]-6-fluoro-indole-1-carboxylic acid tert-butyl ester (100 mg, 0.205 mmol) in HCl/EtOAc (5 mL, 2M) was stirred at room temperature for 16 hours. The mixture was diluted with EtOAc (100 mL) and washed with aq.NaHCO$_3$ (20 mL×2) and brine (20 mL×2). The organic layer was dried over anhydrous Na$_2$SO$_4$ and filtered. The filtrate was concentrated and purified by preparative TLC (petroleum ether/EtOAc=1/2) to afford 52 mg (66%) of the title compound as a white solid. LC-MS for C$_{20}$H$_{22}$FN$_3$O$_2$S+H$^+$ [M+H]$^+$: calcd: 388.1; found: 388.1. $^1$H NMR (400 MHz, DMSO-d$_6$) δ [ppm] 11.68 (brs, 1H), 7.96 (d, J=8.4 Hz, 2H), 7.95-7.92 (m, 2H), 7.74 (d, J=8.4 Hz, 2H), 7.26 (dd, J=9.6, 2.4 Hz, 1H), 7.01 (td, J=8.4, 2.4 Hz, 1H), 3.52 (d, J=9.6 Hz, 2H), 2.87-2.75 (m, 2H), 1.77 (t, J=10.4 Hz, 2H), 0.95 (d, J=6.0, 6H).

Example 12: (4-((4-(6-fluoro-1H-indol-3-yl)phenyl)sulfonyl)piperazin-2-yl)-methanol

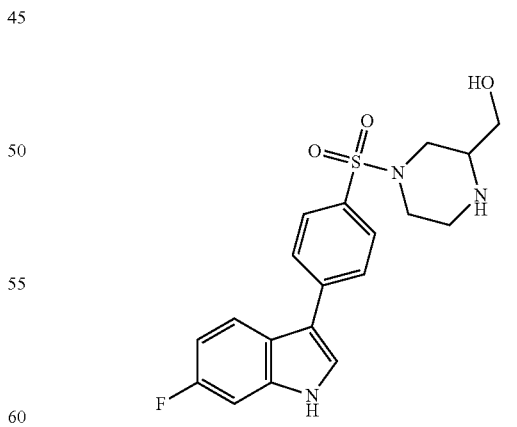

Step 1: 1-tert-butyl 2-methyl 4-((4-bromophenyl)sulfonyl)piperazine-1,2-dicarboxylate To a stirred solution of piperazine-1, 2-dicarboxylic acid 1-tert-butyl ester 2-methyl ester (977 mg, 4.0 mmol) in DCM (20 mL) at 0° C. was added 4-bromo-benzenesulfonyl chloride (1.02 mg, 4.0 mmol). Then TEA (404 mg, 4.0 mmol) was added dropwise and the mixture was stirred at room temperature for 1 hr. The mixture was concentrated and purified by silica gel chromatography (petroleum ether/ EtOAc=20/1to 5/1) to afford 1.66 g (90%) of the title compound as a white solid. $^1$H NMR (400 MHz, CDCl$_3$) δ [ppm] 7.69 (d, J=8.8 Hz, 2H), 7.61 (d, J=8.8 Hz, 2H), 4.89-4.60 (m, 1H), 4.27-4.20 (m, 1H), 4.04-3.82 (m, 1H), 3.77 (s, 3H), 3.76-3.61 (m, 1H), 3.35-3.11 (m, 1H), 2.51 (dd, J=11.6, 4.0 Hz, 1H), 2.33 (td, J=11.6, 4.0 Hz, 1H), 1.44 (s, 9H).

Step 2: tert-butyl 4-((4-bromophenyl)sulfonyl)-2-(hydroxymethyl)-piperazine-1-carboxylate To a stirred solution of 4-(4-bromo-benzenesulfonyl)-piperazine-1, 2-dicarboxylic acid 1-tert-butyl ester 2-methyl ester (1.66 g, 3.59 mmol) in anhydrous THF (20 mL) at 0° C. was added LiAlH$_4$ (137 mg, 3.59 mmol). The mixture was stirred at room temperature for 1 hr before it was diluted with EtOAc (100 mL) and water (0.5 mL). The organic mixture was dried over anhydrous Na$_2$SO$_4$ and filtered. The filtrate was concentrated and purified by silica gel chromatography (petroleum ether/EtOAc=5/1to 3/1) to afford 910 mg (58%) of the title compound as a white solid. $^1$H NMR (300 MHz, CDCl$_3$) δ [ppm] 7.69 (d, J=8.8 Hz, 2H), 7.61 (d, J=8.8 Hz, 2H), 4.28-4.20 (m, 1H), 4.04-3.93 (m, 1H), 3.91-3.71 (m, 3H), 3.70-3.64 (m, 1H), 3.19-3.09 (m, 1H), 2.44-2.27 (m, 2H), 1.99 (t, J=5.7 Hz, 1H), 1.42 (s, 9H).

Step 3: tert-butyl 3-(4-((4-(tert-butoxycarbonyl)-3-(hydroxymethyl)piperazin-1-yl)sulfonyl)phenyl)-6-fluoro-1H-indole-1-carboxylate A mixture of 4-(4-bromo-benzenesulfonyl)-2-hydroxymethyl-piperazine-1-carboxylic acid tert-butyl ester (120 mg, 0.277 mmol), 6-fluoro-3-(4,4,5,5-tetramethyl-[1,3,2]dioxaborolan-2-yl)-indole-1-carboxylic acid tert-butyl ester (Intermediate 1, 100 mg, 0.277 mmol), K$_2$CO$_3$ (114 mg, 0.831 mmol) and Pd(dppf)Cl$_2$ (20 mg, 0.028 mmol) in dioxane/water (10 mL/2 mL) was stirred at 90° C. under N$_2$ for 4 hours. The mixture was cooled and diluted with EtOAc (60 mL). The organic layer was dried with anhydrous Na$_2$SO$_4$ and filtered. The filtrate was concentrated and purified by silica gel chromatography (petroleum ether/EtOAc=5/1to 3/1) to afford 120 mg (74%) of the title compound as a white solid. $^1$H NMR (400 MHz, CDCl$_3$) δ [ppm]7.97 (d, J=9.2 Hz, 1H), 7.83 (d, J=8.8 Hz, 2H), 7.81-7.74 (m, 3H), 7.08 (td, J=8.8, 2.4 Hz, 1H), 4.29-4.21 (m, 1H), 4.02-3.95 (m, 1H), 3.95-3.79 (m, 2H), 3.79-3.71 (m, 2H), 3.17 (t, J=12.8 Hz, 1H), 2.49 (dd, J=12.0, 4.0 Hz, 1H), 2.41 (td, J=12.0, 4.0 Hz, 1H), 2.02 (brs, 1H), 1.70 (s, 9H), 1.42 (s, 9H).

Step 4: (4-((4-(6-fluoro-1H-indol-3-yl)phenyl)sulfonyl)-piperazin-2-yl) methanol To a stirred solution of 3-[4-(4-tert-butoxycarbonyl-3-hydroxymethyl-piperazine-1-sulfonyl)-phenyl]-6-fluoro-indole-1-carboxylic acid tert-butyl ester (120 mg, 0.204 mmol) in anhydrous DCM (5 mL) was added TFA (3 mL) dropwise at 0° C. The mixture was stirred at room temperature for 3 hours before EtOAc (60 mL) and TEA (5 mL) was added. The mixture was washed with water (20 mL) and brine (20 mL×2). The organic layer was dried over anhydrous Na$_2$SO$_4$ and filtered. The filtrate was concentrated and purified by preparative HPLC (NH$_3$ H$_2$O as additive) to afford 36 mg (46%) of the title compound as a white solid. LC-MS for Cl$_{19}$H$_{20}$FN$_3$O$_3$S+H$^-$[M+H]$^+$: calcd: 390.1; found: 390.1. $^1$H NMR (400 MHz, DMSO-d$_6$) δ [ppm]11.67 (brs, 1H), 7.99-7.91 (m, 4H), 7.72 (d, J=8.4 Hz, 2H), 7.26 (dd, J=10.0, 2.0 Hz, 1H), 7.01 (td, J=8.8, 2.4 Hz, 1H), 4.67 (t, J=5.2 Hz, 1H), 3.58 (d, J=10.0 Hz, 1H), 3.45 (t, J=11.2 Hz, 1H), 3.27-3.16 (m, 1H), 2.91 (d, J=12.0 Hz, 1H), 2.70-2.60 (m, 2H), 2.21-2.13 (m, 1H), 1.89 (t, J=10.8 Hz, 1H).

Example 13: (1-((4-(6-fluoro-1H-indol-3-yl)phenyl)sulfonyl)piperazin-2-yl)methanol

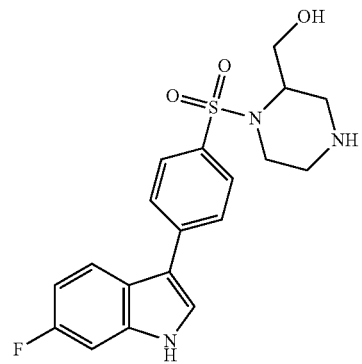 [SMILES: O=S(=O)(c1ccc(-c2c[nH]c3cc(F)ccc23)cc1)N1CCNCC1CO]

Following the general method as outlined in Example 12, starting from 1-tert-butyl 3-methyl piperazine-1,3-dicarboxylate, the title compound was obtained as a white solid. LC-MS for C$_{19}$H$_{20}$FN$_3$O$_3$S—H$^-$[M–H]$^-$: calcd: 388.1; found: 388.1. $^1$H NMR (400 MHz, DMSO-d$_6$) δ [ppm] 11.66 (br s, 1H), 7.95-7.91 (m, 4H), 7.83 (d, J=8.4 Hz, 2H), 7.26 (dd, J=10.0, 2.4 Hz, 1H), 7.01 (td, J=8.8, 2.4 Hz, 1H), 4.76 (br s, 1H), 3.77-3.72 (m, 1H), 3.68-3.64 (m, 1H), 3.51-3.48 (m, 1H), 3.37-3.29 (m, 2H), 3.04-2.92 (m, 2H), 2.71-2.68 (m, 1H), 2.49-2.40 (m, 2H).

Example 14: (3R,5R)-3-[4-(3,5-dimethyl-piperazine-1-sulfonyl)-phenyl]-6-fluoro-1H-indole

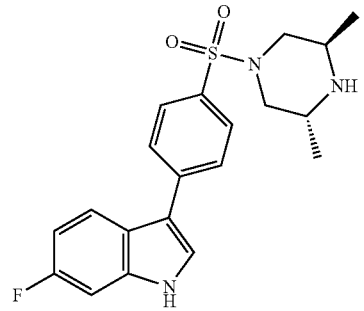 [SMILES: C[C@@H]1CN(S(=O)(=O)c2ccc(-c3c[nH]c4cc(F)ccc34)cc2)C[C@@H](C)N1]

Following the general method as outlined in Example 11, starting from (2R, 6R)-2, 6-dimethyl-piperazine, the title compound was obtained as a white solid. LC-MS for C$_{20}$H$_{22}$FN$_3$O$_2$S+H$^+$ [M+H]$^+$: calca: 388.1; found: 388.3. $^1$H NMR (300 MHz, DMSO-d$_6$) δ [ppm]11.69 (brs, 1H), 8.00-7.91 (m, 4H), 7.71 (d, J=8.1 Hz, 2H), 7.26 (dd, J=9.6, 2.4 Hz, 1H), 7.01 (td, J=9.3, 2.1 Hz, 1H), 3.14-3.03 (m, 2H), 2.91-2.82 (m, 2H), 2.49-2.44 (m, 2H), 2.01 (brs, 1H), 1.02 (d, J=6.6 Hz, 6H).

Example 15: 3-(4-(((3S,5S)-3,5-dimethyl piperazin-1-yl)sulfonyl) phenyl)-6-fluoro-1H-indole

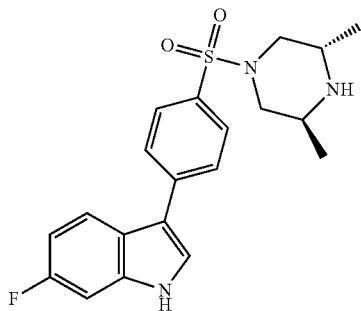 [SMILES: C[C@H]1CN(S(=O)(=O)c2ccc(-c3c[nH]c4cc(F)ccc34)cc2)C[C@H](C)N1]

Following the general method as outlined in Example 11, starting from (2S, 6S)-2, 6-dimethyl-piperazine, the title compound was obtained as a white solid. LC-MS for $C_{20}H_{22}FN_3O_2S+H^+$ [M+H]$^+$: calcd: 388.1; found: 388.3. $^1$H NMR (400 MHz, DMSO-d$_6$) δ [ppm]11.69 (brs, 1H), 7.96-7.93 (m, 4H), 7.71 (d, J=8.8 Hz, 2H), 7.26 (dd, J=9.6, 2.4 Hz, 1H), 7.01 (td, J=9.6, 2.4 Hz, 1H), 3.11-3.07 (m, 2H), 2.89-2.86 (m, 2H), 2.48-2.47 (m, 2H), 2.01 (brs, 1H), 1.02 (d, J=6.4 Hz, 6H).

Example 16: N-(2-(4-(6-fluoro-1H-indol-3-yl)phenylsulfonamido)-ethyl)acetamide

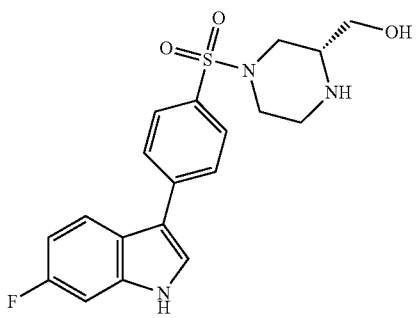

Following the general method as outlined in Example 11, starting from N-(2-aminoethyl) acetamide, the title compound was obtained as a white solid. LC-MS for $C_{18}H_{18}FN_3O_3S+H^+$[M+H]$^+$: calcd: 376.1; found: 376.1. $^1$H NMR (400 MHz, DMSO-d$_6$) δ [ppm] 11.65 (s, 1H), 7.95-7.87 (m, 5H), 7.81 (d, J=8.4 Hz, 2H), 7.64 (br s, 1H), 7.26 (dd, J=10.0, 2.4 Hz, 1H), 7.00 (td, J=10.0, 2.0 Hz, 1H), 3.09 (q, J=6.4 Hz, 2H), 2.79 (q, J=6.4 Hz, 2H), 1.75 (s, 3H).

Example 17: (R)-(4-((4-(6-fluoro-1H-indol-3-yl)phenyl)sulfonyl)piperazin-2-yl)methanol

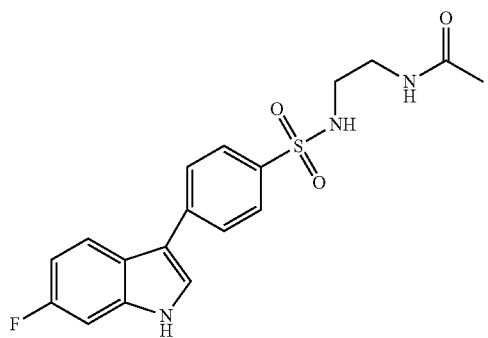 [SMILES: CC(=O)NCCNS(=O)(=O)c1ccc(-c2c[nH]c3cc(F)ccc23)cc1]

Following the general method as outlined in Example 12, starting from (S)-1-tert-butyl 2-methyl piperazine-1,2-dicarboxylate, the title compound was obtained as a white solid. LC-MS for $C_{19}H_{20}FN_3O_3S+H^-$[M+H]$^+$: calcd: 390.1; found: 390.1. $^1$H NMR (400 MHz, DMSO-d$_6$) δ [ppm]11.69 (brs, 1H), 7.99-7.91 (m, 4H), 7.73 (d, J=8.4 Hz, 2H), 7.26 (dd, J=10.0, 2.0 Hz, 1H), 7.01 (td, J=8.8, 2.4 Hz, 1H), 4.76 (t, J=5.2 Hz, 1H), 3.58 (d, J=10.0 Hz, 1H), 3.45 (t, J=11.2 Hz, 1H), 3.27-3.16 (m, 1H), 2.91 (d, J=12.0 Hz, 1H), 2.70-2.60 (m, 2H), 2.21-2.13 (m, 1H), 1.89 (t, J=10.8 Hz, 1H).

Example 18: (S)-(4-((4-(6-fluoro-1H-indol-3-yl)phenyl)sulfonyl)piperazin-2-yl)methanol

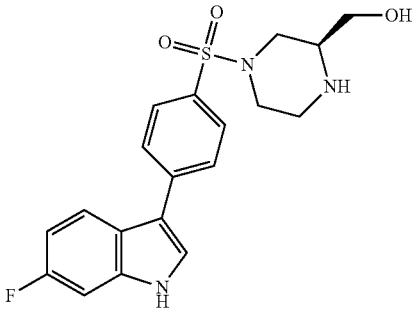 [SMILES: O=S(=O)(c1ccc(-c2c[nH]c3cc(F)ccc23)cc1)N1CCN[C@H](CO)C1]

Following the general method as outlined in Example 12, starting from (S)-1-tert-butyl 2-methyl piperazine-1,2-dicarboxylate, the title compound was obtained as a white solid. LC-MS for $C_{19}H_{20}FN_3O_3S+H^+$ [M+H]$^+$: calcd: 390.1; found: 390.1. $^1$H NMR (400 MHz, DMSO-d$_6$) δ [ppm] 11.69 (brs, 1H), 7.99-7.91 (m, 4H), 7.73 (d, J=8.4 Hz, 2H), 7.26 (dd, J=10.0, 2.0 Hz, 1H), 7.01 (td, J=8.8, 2.4 Hz, 1H), 4.76 (t, J=5.2 Hz, 1H), 3.58 (d, J=10.0 Hz, 1H), 3.45 (t, J=11.2 Hz, 1H), 3.27-3.16 (m, 1H), 2.91 (d, J=12.0 Hz, 1H), 2.70-2.60 (m, 2H), 2.21-2.13 (m, 1H), 1.89 (t, J=10.8 Hz, 1H).

Example 19: 6-fluoro-3-(4-((4-(methylsulfonyl)piperazin-1-yl)sulfonyl)phenyl)-1H-indole

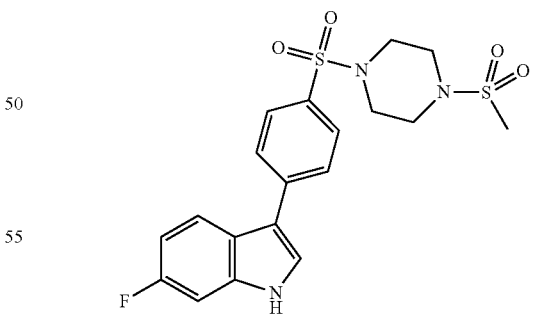

Following the general method as outlined in Example 11, starting from 1-methanesulfonyl-piperazine, the title compound was obtained as a white solid.

LC-MS for $C_{19}H_{20}FN_3O_4S_2$—H$^-$ [M–H]$^-$: calca: 436.1; found: 436.1. $^1$H NMR (400 MHz, DMSO-d$_6$) δ [ppm] 11.72 (s, 1H), 7.98-7.93 (m, 4H), 7.76 (m, 2H), 7.24 (dd, J=10.0 Hz, 2.4 Hz, 1H), 7.01 (td, J=9.2, 2.4 Hz, 1H), 3.23 (t, J=4.4 Hz, 4H), 3.06-3.02 (m, 4H), 2.89 (s, 3H).

Example 20:
3-(4-(piperazin-1-ylsulfonyl)phenyl)-1H-indole

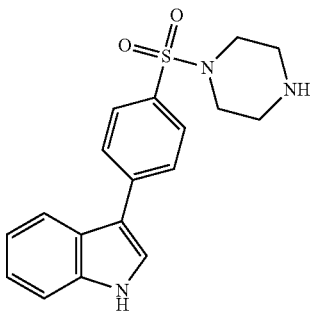 [SMILES: O=S(=O)(c1ccc(-c2c[nH]c3ccccc23)cc1)N1CCNCC1]

Following the general method as outlined in Example 11, starting from 1H-Indole and piperazine-1-carboxylic acid tert-butyl ester, the title compound was obtained as a white solid. LC-MS for $C_{18}H_{19}N_3O_2S+H^+$ [M+H]$^+$: calca: 342.1; found: 341.8. $^1$H NMR (300 MHz, CDCl$_3$) δ [ppm] 11.63 (d, J=1.8 Hz, 1H), 7.99-7.93 (m, 4H), 7.73 (d, J=8.4 Hz, 2H), 7.49 (d, J=8.4 Hz, 1H), 7.21-7.15 (m, 2H). 2.82-2.73 (m, 4H), 2.54-2.46 (m, 4H).

Example 21: 4-(6-fluoro-1H-indol-3-yl)-N-(2-(methylsulfonamido)-ethyl)benzenesulfonamide

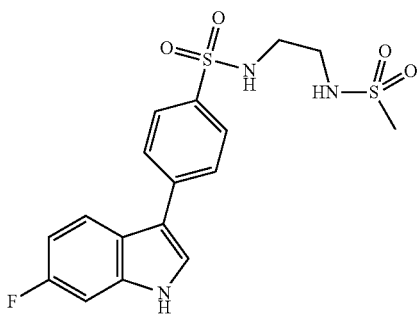 [SMILES: CS(=O)(=O)NCCNS(=O)(=O)c1ccc(-c2c[nH]c3cc(F)ccc23)cc1]

Following the general method as outlined in Example 11, starting from (2-aminoethyl-methyl-sulfonyl)amine, the title compound was obtained as a white solid. LC-MS for $C_{17}H_{18}FN_3O_4S_2+H^+$ [M+H]$^+$: calcd: 412.1; found: 411.8.
$^1$H NMR (400 MHz, DMSO-d$_6$) δ [ppm] 11.66 (s, 1H), 7.95-7.90 (m, 4H), 7.80(d, J=8.4 Hz, 2H), 7.26(d, J=10.0 Hz, 1H), 7.00(t, J=8.8 Hz, 1H), 3.01(t, J=6.0Hz, 2H), 2.86 (m, 5H).

Example 22: 6-fluoro-3-(2-fluoro-4-(piperazin-1-ylsulfonyl)-phenyl)-1H-indole

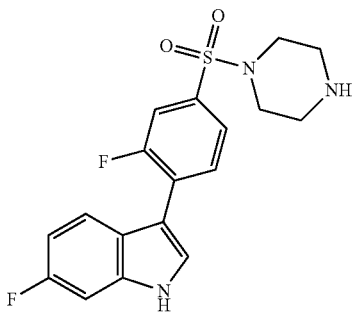 [SMILES: O=S(=O)(c1ccc(-c2c[nH]c3cc(F)ccc23)c(F)c1)N1CCNCC1]

Following the general method as outlined in Example 4, starting from tert-butyl piperazine-1-carboxylate and 4-bromo-3-fluorobenzene-1-sulfonyl chloride, the title compound was obtained as a white solid. LC-MS for $C_{18}H_{17}F_2N_3O_2S+H^+$ [M+H]$^+$: calcd: 378.1; found: 377.8. $^1$H NMR (400 MHz, DMSO-d$_6$) δ [ppm] 11.87 (s, 1H), 8.69 (d, J=10.4 Hz, 1H), 8.08 (t, J=7.8 Hz, 1H), 7.86 (t, J=2.4 Hz, 1H), 7.78-7.74 (m, 2H), 7.68 (dd, J=8.4, 2.0 Hz, 1H), 7.31 (dd, J=10.0, 2.4 Hz, 1H), 7.03 (td, J=8.4, 2.0 Hz, 1H), 3.28-3.23 (m, 8H).

Example 23: 3-(4-chloro-3-(piperazin-1-ylsulfonyl)phenyl)-6-fluoro-1H-indole

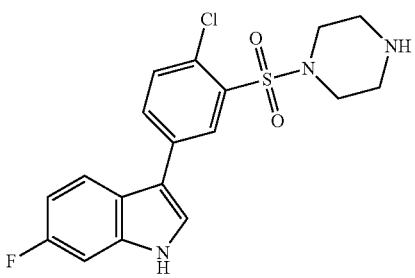 [SMILES: O=S(=O)(c1cc(-c2c[nH]c3cc(F)ccc23)ccc1Cl)N1CCNCC1]

Following the general method as outlined in Example 4, starting from tert-butyl piperazine-1-carboxylate and 5-bromo-2-chlorobenzene-1-sulfonyl chloride, the title compound was obtained as a white solid. LC-MS for $C_{18}H_{17}ClFN_3O_2S+H^+$ [M+H]$^+$: calcd: 394.1; found: 393.9. $^1$H NMR (400 MHz, DMSO-d$_6$) δ [ppm] 11.69 (s, 1H), 8.17 (d, J=2.4 Hz, 1H), 7.97 (dd, J=8.4, 2.0 Hz, 1H), 7.91(d, J=2.4 Hz, 1H), 7.79(dd, J=9.2, 5.6 Hz, 1H), 7.73(d, J=8.4 Hz, 1H), 7.27 (dd, J=9.6, 2.0 Hz, 1H), 7.03 (td, J=9.2, 2.0 Hz, 1H), 3.10 (t, J=4.8 Hz, 4H), 2.75 (t, J=4.8 Hz, 4H).

Example 24: 6-fluoro-3-(4-(piperazin-1-ylsulfonyl)-3-(trifluoromethyl)-phenyl)-1H-indole

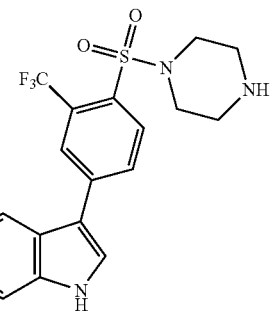

Following the general method as outlined in Example 4, starting from tert-butyl piperazine-1-carboxylate and 4-bromo-2-(trifluoromethyl)benzene-1-sulfonyl chloride, the title compound was obtained as a white solid. LC-MS for $C_{19}H_{17}F_4N_3O_2S+H^+$ [M+H]$^+$: calcd: 428.1; found: 427.9. $^1$H NMR (400 MHz, DMSO-d$_6$) δ [ppm] 11.87 (s, 1H), 8.23 (s, 1H), 8.21 (s, 1H), 8.14 (d, J=2.4 Hz, 1H), 8.05 (d, J=8.8 Hz, 1H), 7.93(dd, J=9.2, 5.2 Hz,1H), 7.29 (dd, J=9.6, 2.4 Hz, 1H), 7.06 (td, J=9.6, 2.4 Hz, 1H), 3.06 (t, J=4.8 Hz, 4H), 2.74 (t, J=4.8 Hz, 4H).

Example 25: 6-fluoro-3-(2-methyl-4-(piperazin-1-ylsulfonyl)-phenyl)-1H-indole

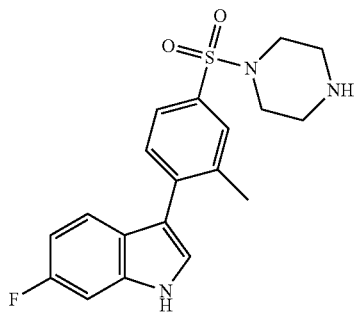 [SMILES: Cc1cc(S(=O)(=O)N2CCNCC2)ccc1-c1c[nH]c2cc(F)ccc12]

Following the general method as outlined in Example 4, starting from tert-butyl piperazine-1-carboxylate and 4-bromo-3-methylbenzene-1-sulfonyl chloride, the title compound was obtained as a white solid. LC-MS for $C_{19}H_{20}FN_3O_2S+H^+$ [M+H]$^+$: calcd: 374.1; found: 373.9. $^1$H NMR (400 MHz, DMSO-d$_6$) δ [ppm] 11.58 (s, 1H), 7.67-7.57 (m, 4H), 7.46 (dd, J=8.8, 5.2 Hz, 1H), 7.25 (dd, J=9.6, 2.0 Hz, 1H), 6.94 (td, J=9.6, 2.4 Hz, 1H), 2.84 (t, J=4.4 Hz, 4H), 2.76 (t, J=4.4 Hz, 4H), 2.43 (s, 3H).

Example 26: 3-(4-(6-fluoro-1H-indol-3-yl)phenyl-sulfonamido)propanamide

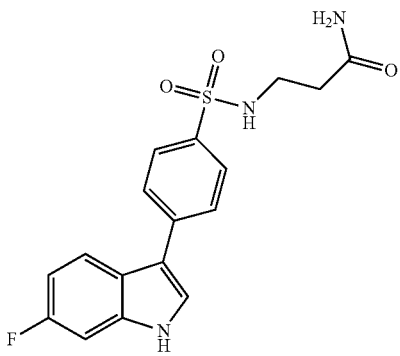 [SMILES: NC(=O)CCNS(=O)(=O)c1ccc(-c2c[nH]c3cc(F)ccc23)cc1]

Following the general method as outlined in Example 4, starting from 3-amino-propionamide, the title compound was obtained as a white solid. LC-MS for $C_{17}H_{16}FN_3O_3S+H^+$ [M+H]$^+$: calcd: 362.1; found: 361.8. $^1$H NMR (400 MHz, DMSO-d$_6$) δ [ppm]11.67 (s, 1H), 7.96-7.90 (m, 4H), 7.82-7.80 (m, 2H), 7.59 (t, J=5.6 Hz, 1H), 7.36 (br s, 1H), 7.26 (dd, J=9.6, 2.4 Hz, 1H), 7.00 (td, J=9.2, 2.4 Hz, 1H), 6.86 (br s, 1H), 2.94 (dd, J=13.2, 7.2 Hz, 2H), 2.25 (t, J=7.2 Hz, 2H).

Example 27: 3-(4-(6-fluoro-1H-indol-3-yl)-N-methylphenylsulfonamido)-propanamide

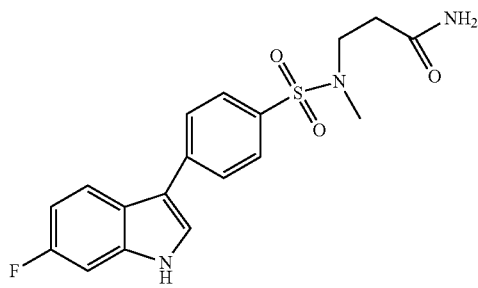 [SMILES: CN(CCC(N)=O)S(=O)(=O)c1ccc(-c2c[nH]c3cc(F)ccc23)cc1]

Following the general method as outlined in Example 4, starting from 3-methylamino-propionamide, the title compound was obtained as a white solid. LC-MS for $Cl_{18}H_{18}FN_3O_3S+H^+$ [M+H]$^+$: calcd: 376.1; found: 375.9. $^1$H NMR (400 MHz, DMSO-d$_6$) δ [ppm]11.70 (br s, 1H), 7.96-7.94 (m, 4H), 7.78 (d, J=8.0 Hz, 2H), 7.42 (br s, 1H), 7.27 (dd, J=9.6, 2.4 Hz, 1H), 7.01 (m, 1H), 6.92 (br s, 1H), 3.18 (t, J=7.2 Hz, 2H), 2.70 (s, 3H), 2.35 (t, J=7.2 Hz, 2H).

Example 28: 6-fluoro-3-(3-fluoro-4-(piperazin-1-ylsulfonyl)-phenyl)-1H-indole

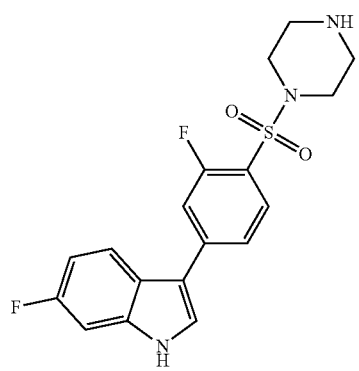 [SMILES: O=S(=O)(c1ccc(-c2c[nH]c3cc(F)ccc23)cc1F)N1CCNCC1]

Following the general method as outlined in Example 4, starting from piperazine-1-carboxylic acid tert-butyl ester and 4-bromo-2-fluoro-benzene-sulfonyl chloride, the title compound was obtained as a white solid. LC-MS for $C_{18}H_{17}F_2N_3O_2S+H^+$ [M+H]$^+$: calcd: 378.1; found: 377.9. $^1$H NMR (400 MHz, DMSO-d$_6$) δ [ppm] 11.82 (s, 1H), 8.05 (s, 1H), 8.05-7.96 (m, 1H), 7.79-7.73 (m, 3H), 7.28 (dd, J=9.6, 2.4 Hz, 1H), 7.03 (td, J=9.6, 2.4 Hz, 1H), 2.96 (d, J=4.4 Hz, 4H), 2.74 (d, J=4.8 Hz, 4H).

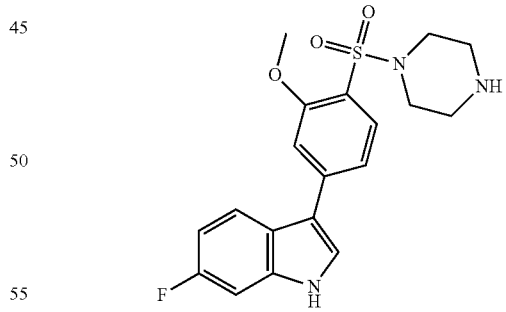

Following the general method as outlined in Example 4, starting from tert-butyl piperazine-1-carboxylate and 4-bromo-2-methoxybenzene-1-sulfonyl chloride the, title compound was obtained as a white solid. LC-MS for $C_{19}H_{20}FN_3O_3S+H^+$ [M+H]$^+$: calcd: 390.1; found: 389.9. $^1$H NMR (400 MHz, DMSO-d$_6$) δ [ppm] 11.70 (br s, 1H), 7.98-7.93 (m, 2H), 7.73 (d, J=8.0 Hz, 1H), 7.45-7.42 (m, 2H), 7.26 (dd, J=9.6, 2.0 Hz, 1H), 7.01 (td, J=9.6, 2.0 Hz, 1H), 3.98 (s, 3H), 3.06-3.01 (m, 4H), 2.78-2.74 (m, 4H).

Example 30: N-(2-aminoethyl)-3-(6-fluoro-1H-indol-3-yl)-5-methyl-benzenesulfonamide

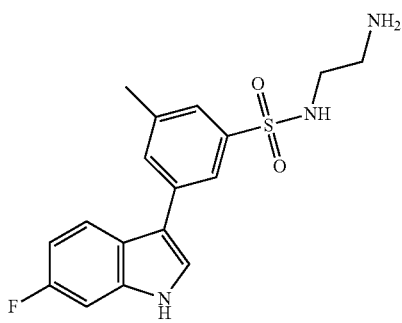

Following the general method as outlined in Example 4, starting from tert-butyl (2-aminoethyl)carbamate and 3-bromo-5-methylbenzene-1-sulfonyl chloride, the title compound was obtained as a white solid. LC-MS for $C_{17}H_{18}FN_3O_2S+H^+$ [M+H]$^+$: calcd: 348.1; found: 347.9. $^1$H NMR (400 MHz, DMSO-d$_6$) δ [ppm] 11.59 (s, 1H), 7.87 (m, 2H), 7.81 (s, 1H), 7.75 (s, 1H), 7.46 (s, 1H), 7.25 (dd, J=10.0, 1.6 Hz, 1H), 7.01 (td, J=9.2, 2.0 Hz, 1H), 2.77 (t, J=7.0 Hz, 2H), 2.54 (m, 2H), 2.46 (s, 3H).

Example 31: 6-fluoro-3-(3-(methylsulfonyl)phenyl)-1H-indole

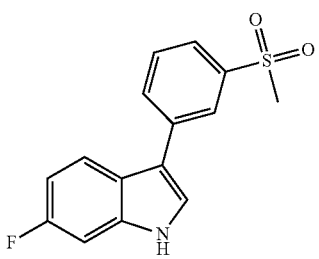 [SMILES: CS(=O)(=O)c1cccc(-c2c[nH]c3cc(F)ccc23)c1]

Step 1: 6-fluoro-3-(3-(methylsulfonyl)phenyl)-1-(phenylsulfonyl)-1H-indole

To a solution of 1-benzenesulfonyl-6-fluoro-3-iodo-1H-indole (400 mg, 1 mmol) and 3-(methylsulfonyl)phenylboronic acid (221 mg, 1.1 mmol) in dioxane/H$_2$O (10 mL/1 mL) were added K$_3$PO$_4$ (636 mg, 3 mmol) and Pd(dppf)Cl$_2$ (40 mg) under N$_2$ atmosphere. The reaction was stirred at 85° C. overnight. The mixture was concentrated in vacuum and the residue was purified by silica gel chromatography (PE/DCM=100/1-1/2) to afford 6-fluoro-3-(3-(methylsulfonyl)-phenyl)-1-(phenylsulfonyl)-1H-indole (318 mg, 74%) as a yellow solid. $^1$H NMR (400 MHz, DMSO-d$_6$) δ [ppm] 8.41 (s, 1H), 8.22 (s, 1H), 8.17 (d, J=7.2 Hz, 2H), 8.10 (d, J=7.6 Hz, 1H), 7.94-7.83 (m, 3H), 7.79-7.73 (m, 2H), 7.64 (t, J=7.2 Hz, 2H), 7.29 (dt, J=9.2, 2.4 Hz, 1H), 3.32 (s, 3H).

Step 2: 6-fluoro-3-(3-(methylsulfonyl)phenyl)-1H-indole

To a solution of NaOH (70 mg, 1.75 mmol) in MeOH (10 mL) was added 6-fluoro-3-(3-(methylsulfonyl)phenyl)-1-(phenylsulfonyl)-1H-indole (150 mg, 0.35 mmol). The reaction was stirred at 75° C. for 45 min. The mixture was concentrated and the residue was purified by prep-TLC (DCM/PE=6/1) to afford 6-fluoro-3-(3-(methylsulfonyl)phenyl)-1H-indole (112 mg, 100%) as a yellow solid. LC-MS for $C_{15}H_{12}FNO_2S$—H$^-$ [M−H]$^-$: calcd: 288.1; found: 287.9. $^1$H NMR (400 MHz, DMSO-d$_6$) δ [ppm] 11.65 (s, 1H), 8.15 (s, 1H), 8.04 (d, J=7.6 Hz, 1H), 7.91-7.86 (m, 2H), 7.78 (d, J=8.0 Hz, 1H), 7.70 (t, J=8.0 Hz, 2H), 7.26 (d, J=9.6 Hz, 2H), 6.99 (t, J=8.8Hz, 1H), 3.29 (s, 3H).

Example 32: 5-(6-Fluoro-1H-indol-3-yl)-2-(piperazine-1-sulfonyl)-benzonitrile

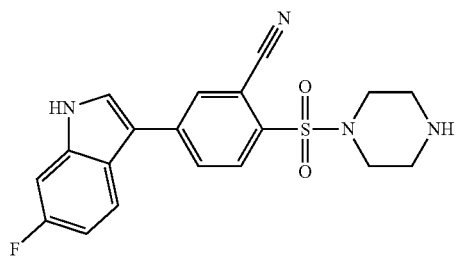 [SMILES: N#Cc1cc(-c2c[nH]c3cc(F)ccc23)ccc1S(=O)(=O)N1CCNCC1]

Following the general method as outlined in Example 4, starting from tert-butyl piperazine-1-carboxylate and 4-bromo-2-cyanobenzene-1-sulfonyl chloride, the title compound was obtained as a white solid. LC-MS for $C_{19}H_{17}FN_4O_2S+H+[M+H]^+$: calcd: 385.1; found: 384.8. $^1$H NMR (400 MHz, DMSO-d$_6$) δ [ppm] 11.89 (s, 1H), 8.43 (s, 1H), 8.27 (d, J=8.4 Hz, 1H), 8.15 (s, 1H), 8.06-7.92 (m, 2H), 7.29 (d, J=9.6 Hz, 1H), 7.05 (t, J=9.6 Hz, 1H), 3.05-2.95 (m, 4H), 2.76-2.73 (m, 4H).

Example 33: N-(2-Amino-ethyl)-5-(6-fluoro-1H-indol-3-yl)-2-methyl-benzenesulfonamide

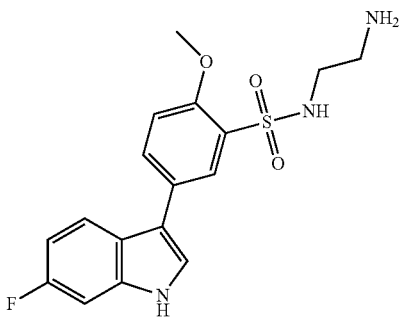 [SMILES: COc1ccc(-c2c[nH]c3cc(F)ccc23)cc1S(=O)(=O)NCCN]

Following the general method as outlined in Example 4, starting from tert-butyl (2-aminoethyl)carbamate and 5-bromo-2-methoxy-benzenesulfonyl chloride, the title compound was obtained as a white solid. LC-MS for $C_{17}H_{18}FN_3O_3S+H^+$ [M+H]$^+$: calcd: 364.1; found 363.9. $^1$H NMR (400 MHz, DMSO-d$_6$) δ [ppm] 11.47 (s, 1H), 7.98 (s, 1H), 7.87 (d, J=8.4 Hz, 1H), 7.74 (dd, J=8.8, 5.2 Hz, 1H), 7.70 (s, 1H), 7.30 (d, J=8.8 Hz, 1H), 7.22 (d, J=9.6 Hz, 1H), 6.99 (t, J=8.8 Hz, 1H), 3.94 (s, 3H), 2.78 (t, J=6.2 Hz, 2H), 2.53 (t, J=6.4 Hz, 2H).

Example 34: 6-fluoro-3-(3-methyl-4-(piperazin-1-ylsulfonyl)-phenyl)-1H-indole

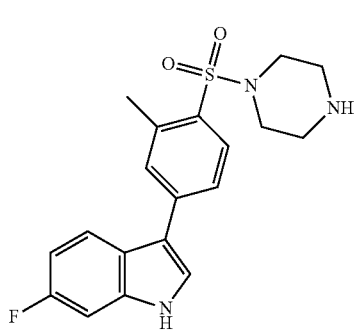 [SMILES: Cc1cc(-c2c[nH]c3cc(F)ccc23)ccc1S(=O)(=O)N1CCNCC1]

Following the general method as outlined in Example 4, starting from tert-butyl piperazine-1-carboxylate and 4-bromo-2-methyl-benzenesulfonyl chloride, the title compound was obtained as a white solid. LC-MS for $C_{19}H_{20}FN_3O_2S+H^+$ [M+H]$^+$: calcd: 374.1; found: 373.9. $^1$H NMR (400 MHz, DMSO-d$_6$) δ [ppm] 11.75 (s, 1H), 8.80 (brs, 1H), 7.98-7.95 (m, 2H), 7.85-7.77 (m, 3H), 7.27 (d, J=10.0 Hz, 1H), 7.02 (t, J=9.2 Hz, 1H), 3.27-3.25 (m, 4H), 3.15-3.13 (m, 4H), 2.64 (s, 3H).

Example 35: 5-(6-fluoro-1H-indol-3-yl)-2-(piperazin-1-ylsulfonyl)phenol

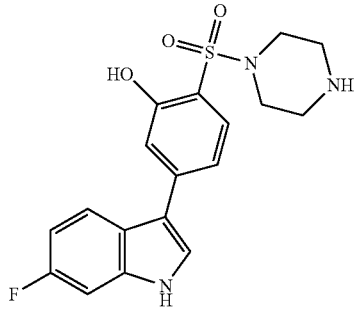 [SMILES: O=S(=O)(c1ccc(-c2c[nH]c3cc(F)ccc23)cc1O)N1CCNCC1]

To a solution of 6-fluoro-3-(3-methoxy-4-(piperazin-1-ylsulfonyl)-phenyl)-1H-indole (Example 29, 100 mg, 0.25 mmol) in DCM was added dropwise BBr$_3$ (94 mg, 0.375 mmol) in DCM (2 mL) at −50° C. The mixture was stirred at room temperature overnight before it was quenched with NaHCO$_3$ solution (30 mL). The pH was adjusted to 8-10. The mixture was extracted with DCM (30 mL×3). The organic layer was dried over anhydrous Na$_2$SO$_4$ and filtered. The filtrate was concentrated and purified by prep-HPLC (NH$_4$HCO$_3$ as additive) to afford the title compound (40 mg, 43%) as a white solid. LC-MS for $C_{18}H_{18}FN_3O_3S+H^+$ [M+H]$^+$: calcd: 376.1; found: 375.8. $^1$H NMR (400 MHz, DMSO-d$_6$) δ [ppm] 11.63 (br s, 1H), 7.89-7.83 (m, 2H), 7.61 (d, J=8.0 Hz, 1H), 7.40 (s, 1H), 7.26 (d, J=8.4 Hz, 2H), 7.01 (td, J=11.6, 2.8 Hz, 1H), 3.03 (s, 4H), 2.74 (s, 4H).

Example 36: N-(2-aminoethyl)-2-chloro-5-(6-fluoro-1H-indol-3-yl)-benzenesulfonamide

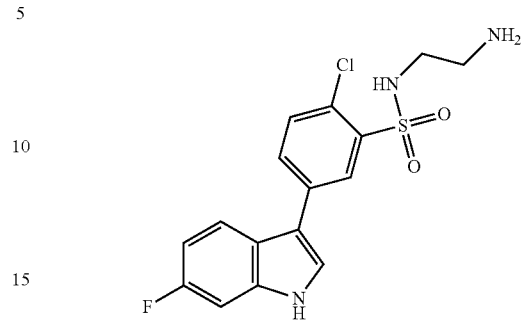

Following the general method as outlined in Example 4, starting from tert-butyl (2-aminoethyl)carbamate and 5-bromo-2-chloro-benzenesulfonyl chloride, the title compound was obtained as a white solid. LC-MS for $C_{16}H_{15}ClFN_3O_2S+H^+$ [M+H]$^+$: calcd: 368.1; found: 367.8. $^1$H NMR (400 MHz, DMSO-d$_6$) δ [ppm] 11.75 (s, 1H), 8.23 (s, 1H), 8.03-7.97 (m, 3H), 7.95-7.92 (m, 2H), 7.85-7.82 (m, 1H), 7.72 (d, J=8.4 Hz, 1H), 7.28 (d, J=10.0 Hz, 1H) 7.05 (t, J=9.2 Hz, 1H), 3.13 (t, J=6.4 Hz, 2H), 2.88 (t, J=6.4 Hz, 2H).

Example 37: 2-(6-fluoro-1H-indol-3-yl)-5-(piperazin-1-ylsulfonyl)benzonitrile

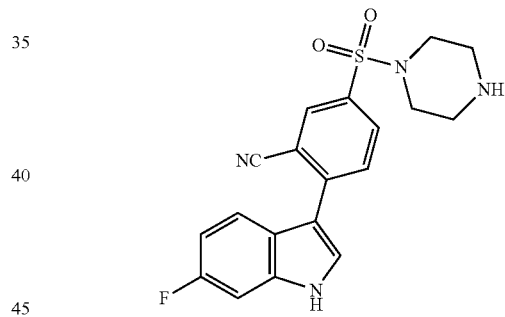

Step 1: 4-bromo-3-cyanobenzene-1-sulfonyl chloride

Water (13 mL) was added dropwise to thionyl chloride (2.1 mL, 28.96 mmol) at 0° C. over 1 h, and the solution was allowed to warm to room temperature over 18 h. CuCl (50 mg, 0.29 mmol) was added and the mixture was stirred for 15 min at −5° C. (solution A).

To a solution of 5-amino-2-bromo-benzonitrile (234 mg, 1.2 mmol) in HCl (12 M, 1.53 mL) at 0° C. was added dropwise over 5 mins a solution of NaNO$_2$ (118 mg) in water (0.5 mL). The resulting mixture was stirred at −5° C. for 10 min before solution A was added dropwise. The reaction was stirred at 0° C. for 2 hrs. The mixture was filtered and washed with water. The filtered cake was dissolved in EtOAc and concentrated to afford 379 mg of the title compound as yellow oil. $^1$H NMR (400 MHz, DMSO-d$_6$) δ [ppm] 7.96 (s, 1H), 7.87 (d, J=8.4 Hz, 1H), 7.80 (d, J=8.4 Hz, 1H).

Step 2: tert-butyl 4-((4-bromo-3-cyanophenyl)sulfonyl)piperazine-1-carboxylate To a stirred solution of piperazine-1-carboxylic acid tert-butyl ester (150 mg, 0.805 mmol) in DCM (20 mL) at 0° C. was added 4-bromo-3-cyanobenzene-1-sulfonyl chloride (204 mg, 0.731 mmol). DIEA (141 mg, 1.09 mmol)) was added dropwise and the mixture was stirred at room temperature overnight. The solvent was removed under reduced pressure and the residue was purified by silica gel chromatography (PE/EtOAc=10/1-3/1) to afford 210 mg (65%) of the title compound as a yellow solid. $^1$H NMR (400 MHz, DMSO-$d_6$) δ [ppm] 8.26 (s, 1H), 8.15 (d, J=8.4 Hz, 1H), 7.90 (d, J=8.4 Hz, 1H), 3.39 (t, J=4.4 Hz, 4H), 2.95 (t, J=4.4 Hz, 4H), 1.35 (s, 9H).

Step 3: tert-butyl 3-(4-((4-(tert-butoxycarbonyl)piperazin-1-yl)sulfonyl)-2-cyanophenyl)-6-fluoro-1H-indole-1-carboxylate A mixture of tert-butyl 4-((4-bromo-3-cyanophenyl)sulfonyl)-piperazine-1-carboxylate (210 mg, 0.49 mmol), 6-fluoro-3-(4,4,5,5-tetramethyl-[1,3,2]dioxaborolan-2-yl)-indole-1-carboxylic acid tert-butyl ester (Intermediate 1, 265 mg, 0.73 mmol), $K_2CO_3$ (202 mg, 1.47 mmol) and Pd(dppf)Cl$_2$ (18 mg, 0.024 mmol) in DMF (4 mL) was heated at 95° C. for 2 hrs in a microwave reactor. The mixture was cooled and diluted with EtOAc (60 mL). The organic layer was washed with brine (30 mL×2), dried over anhydrous $Na_2SO_4$ and filtered. The filtrate was concentrated and purified by prep-TLC (PE/EtOAc=4/1) to afford 181 mg (64%) of the title compound as yellow oil. LC-MS for $C_{29}H_{33}FN_4O_6S$+H$^+$ [M+H]$^+$: calcd: 585.2; found: 585.1.

Step 4: 2-(6-fluoro-1H-indol-3-yl)-5-(piperazin-1-ylsulfonyl)benzonitrile

A mixture of tert-butyl 3-(4-((4-(tert-butoxycarbonyl)piperazin-1-yl)-sulfonyl)-2-cyanophenyl)-6-fluoro-1H-indole-1-carboxylate (181 mg, 0.310 mmol) in HCl/MeOH (2 M, 10 mL) was stirred at room temperature overnight. The solvent was removed under reduced pressure. The residue was basified with aqueous NaHCO$_3$ (20 mL) and extracted with EtOAc (30 mL×2). The combined organic layer was washed with brine (30 mL×2), dried over anhydrous $Na_2SO_4$ and filtered. The filtrate was evaporated and purified by prep-HPLC (NH$_4$HCO$_3$ as additive) to afford 5.5 mg of the title compound as a white solid. LC-MS for $C_{19}H_{17}FN_4O_2S$+H$^+$ [M+H]$^+$: calcd: 385.1; found: 384.8. $^1$H NMR (400 MHz, DMSO) δ [ppm] 11.93 (brs, 1H), 8.21 (s, 1H), 8.02-7.97 (m, 3H), 7.75-7.72 (m, 1H), 7.35-7.32 (m, 1H), 7.04 (t, J=8.4 Hz, 1H), 2.88-2.79 (m, 4H), 2.75-2.70 (m, 4H).

Example 38: N-(2-aminoethyl)-3-chloro-5-(6-fluoro-1H-indol-3-yl)-benzenesulfonamide

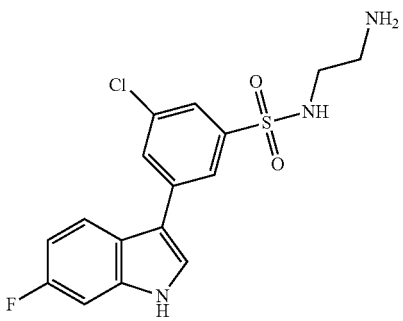 [SMILES: NCCNS(=O)(=O)c1cc(Cl)cc(-c2c[nH]c3cc(F)ccc23)c1]

Step 1: 3-bromo-5-chlorobenzene-1-sulfonyl chloride

Water (13 mL) was added dropwise to thionyl chloride (2.1 mL, 28.96 mmol) at 0° C. over 1 h, and the solution was allowed to warm to room temperature over 18 h. CuCl (50 mg, 0.29 mmol) was added and the mixture was stirred for 15 min at −5° C. (solution A). To a mixture of 3-Bromo-5-chloro-phenylamine (250 mg, 1.2 mmol) in concentrated HCl (1 mL) at 0° C. was added the solution of NaNO$_2$ (125.6 mg, 1.8 mmol) in H$_2$O (2 mL). The reaction mixture was stirred for 20 min at −5° C. before it was added dropwise over 3 min to solution A. The reaction was stirred at 0° C. for 1 h. The reaction mixture was filtered, and the solid was dried at 50° C. under vacuum to afford the title product (200 mg, 58%) as a yellow solid, which was used for next step without further purification.

Step 2: tert-butyl (2-(3-bromo-5-chlorophenylsulfonamido)ethyl)carbamate

To a stirred solution of (2-amino-ethyl)-carbamic acid tert-butyl ester (122 mg, 0.75 mmol) in DCM (10 mL) were added 3-bromo-5-chloro-benzenesulfonyl chloride (200 mg, 0.69 mmol) and DIEA (133 mg, 1.03 mmol) at rt. The mixture was stirred at room temperature for 3 hrs before it was diluted with H$_2$O (30 mL) and extracted with DCM (30 mL×3). The combined organic layer was dried, filtered, concentrated and purified by prep-TLC (PE/EtOAc=1/3) to afford 300 mg (crude) of the title compound as light yellow oil.

Step 3: tert-butyl (2-(3-chloro-5-(6-fluoro-1H-indol-3-yl)phenylsulfon-amido)ethyl)carbamate A mixture of 6-fluoro-3-(4,4,5,5-tetramethyl-[1,3,2]dioxaborolan-2-yl)-indole-1-carboxylic acid tert-butyl ester (Intermediate 1, 300 mg, 0.83 mmol), tert-butyl (2-(3-bromo-5-chlorophenylsulfonamido)ethyl)carbamate (344 mg, 0.83 mmol), $K_2CO_3$ (172 mg, 1.24 mmol) and Pd(dppf)Cl$_2$ (30 mg, 0.04 mmol) in dioxane/H$_2$O (10 mL/2 mL) was stirred at 95° C. under N$_2$ overnight. The mixture was cooled before it was extracted with DCM (30 mL×3). The organic layer was washed with brine (30 mL), dried over anhydrous $Na_2SO_4$ and filtered. The filtrate was concentrated and purified by silica gel chromatography (PE/EtOAc=1/1) to afford tert-butyl (2-(3-bromo-5-chlorophenylsulfonamido)-ethyl)carbamate (350 mg) as light yellow oil, which was used directly without further purification.

Step 4: N-(2-aminoethyl)-3-chloro-5-(6-fluoro-1H-indol-3-yl)benzenesulfonamide A mixture of {2-[3-Chloro-5-(6-fluoro-1H-indol-3-yl)-benzenesulfonylamino]-ethyl}-carbamic acid tert-butyl ester (350 mg, 0.95 mmol) in EtOAc/HCl (5 mL) was stirred at room temperature overnight. The solvent was removed under reduced pressure. The residue was purified by prep-HPLC (NH$_4$HCO$_3$ as additive) to afford N-(2-aminoethyl)-3-chloro-5-(6-fluoro-1H-indol-3-yl)-benzenesulfonamide (23 mg, 6%) as a yellow solid. LC-MS for $C_{16}H_{15}ClFN_3O_2S$+H$^+$ [M+H]$^+$: calcd: 368.1; found: 367.9. $^1$H NMR (400 MHz, DMSO-$d_6$) δ [ppm] 11.76 (s, 1H), 8.02 (s, 1H), 7.99 (s, 2H), 7.86 (dd, J=8.4, 5.2 Hz, 1H), 7.62 (s, 1H), 7.27 (dd, J=9.6, 2.0 Hz, 1H), 7.05 (t, J=9.6 Hz, 1H), 2.80 (t, J=6.4 Hz, 1H), 2.55 (t, J=6.4 Hz, 1H).

Example 39: N-(2-aminoethyl)-5-(6-fluoro-1H-indol-3-yl)-2-hydroxy-benzenesulfonamide

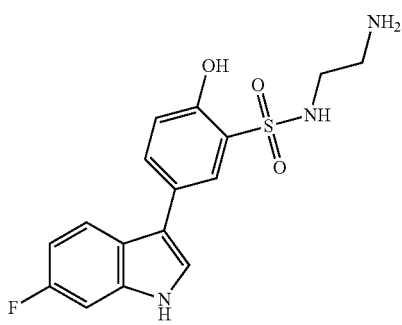 [SMILES: NCCNS(=O)(=O)c1cc(-c2c[nH]c3cc(F)ccc23)ccc1O]

To a solution of N-(2-Amino-ethyl)-5-(6-fluoro-1H-indol-3-yl)-2-methoxy-benzenesulfonamide (Example 38, 500 mg, 1.08 mmol) in DCM at −50° C. was added dropwise BBr$_3$ (540.5 mg, 2.15 mmol) in DCM (2 mL). The mixture was stirred at room temperature overnight. The resulting mixture was quenched with H$_2$O (50 mL) and NaHCO$_3$ solution. The pH was adjusted to 8. The mixture was extracted with EtOAc. The organic layer was dried, filtered and concentrated. The residue was purified by prep-HPLC (NH$_4$HCO$_3$ as additive) to afford 50 mg (13.2%) of the title compound as a white solid. LC-MS for C$_{16}$H$_{16}$FN$_3$O$_3$S+H$^+$ [M+H]$^+$: calcd: 350.1; found 349.8. $^1$H NMR (400 MHz, DMSO-d$_6$) δ [ppm] 11.31 (br s, 1H), 7.82 (d, J=3.2 Hz, 1H), 7.71 (dd, J=11.6, 7.6 Hz, 1H), 7.59 (dd, J=12.0, 2.4Hz, 1H), 7.53 (s, 1H), 7.19 (dd, J=13.6, 2.8Hz, 1H), 6.98-6.86 (m, 2H), 2.96-2.92 (m, 2H), 2.68-2.63(m, 2H).

Example 40: 4-((4-(6-fluoro-1H-indol-3-yl)phenyl)sulfonyl)piperazin-2-one

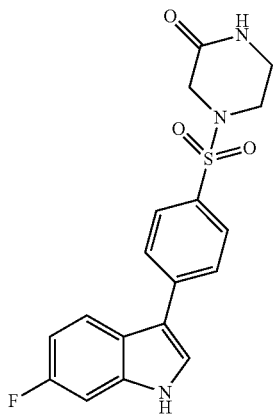 [SMILES: O=C1CN(S(=O)(=O)c2ccc(-c3c[nH]c4cc(F)ccc34)cc2)CCN1]

Following the general method as outlined in Example 4, starting from piperazin-2-one and 4-bromo-benzenesulfonyl chloride, the title compound was obtained as a white solid. LC-MS for C$_{18}$H$_{16}$FN$_3$O$_3$S—H$^-$ [M−H]$^-$: calcd: 372.1; found: 371.8. $^1$H NMR (400 MHz, DMSO-d$_6$) δ [ppm] 11.72 (s, 1H), 8.08 (s, 1H), 7.96 (m, 4H), 7.82 (d, J=8.2 Hz, 2H), 7.27 (d, J=9.5 Hz, 1H), 7.02 (t, J=9.1 Hz, 1H), 3.54 (s, 2H), 3.23 (s, 4H).

Example 41: 5-(6-fluoro-1H-indol-3-yl)-2-(piperazin-1-ylsulfonyl)benzamide

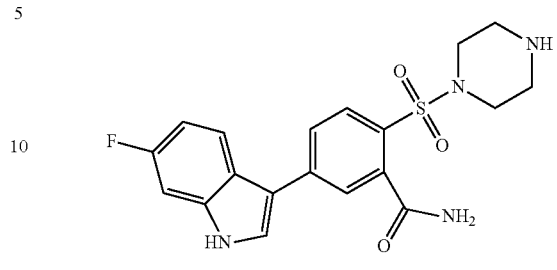

Step 1: tert-butyl 4-((4-bromo-2-carbamoylphenyl)sulfonyl)piperazine-1-carboxylate A mixture of 4-(4-Bromo-2-cyano-benzenesulfonyl)-piperazine-1-carboxylic acid tert-butyl ester (intermediate 2 in Example 32, 800 mg, 1.86 mmol) in DMSO (5 mL) was added K$_2$CO$_3$ (333 mg, 2.42 mmol) and H$_2$O$_2$(274 mg, 2.42 mmol, 30% in water) at 0° C. The reaction was stirred for 30 min. The reaction mixture was poured into water (50 mL) and extracted with EtOAc (50 mL×3). The organic layer was washed with brine (20 mL×3), dried over anhydrous Na$_2$SO$_4$ and filtered. The filtrate was concentrated to afford the title compound (570 mg, yield: 68%) as a white solid. $^1$H NMR (400 MHz, DMSO-d$_6$): δ 7.92 (s, 1H), 7.83 (dd, J=8.4, 2.0 Hz, 1H), 7.72 (d, J=8.8 Hz, 1H), 7.68 (s, 1H), 7.65 (s, 1H), 3.36-3.34 (m, 4H), 3.06-3.03 (m, 4H).

Step 2 and Step 3 were performed with similar procedures as for Example 37. The title compound was obtained as a white solid. LC-MS for C$_{19}$H$_{19}$FN$_4$O$_3$S+H$^+$ [M+H]$^+$: calcd: 403.1; found: 403.0. $^1$H NMR (400 MHz, DMSO-d$_6$) δ [ppm] 11.7 (s, 1H), 7.99 (s, 1H), 7.95-7.90 (m, 2H), 7.87 (s, 1H), 7.78 (d, J=8.4 Hz, 1H), 7.69 (s, 1H), 7.52 (s, 1H), 7.26 (d, J=8.8 Hz, 1H), 7.06-7.00 (m, 1H), 3.01-2.95 (m, 4H), 2.74-2.71 (m, 4H).

Example 42: 4-((4-(6-fluoro-1H-indol-3-yl)phenyl)sulfonyl)-1-methylpiperazin-2-one

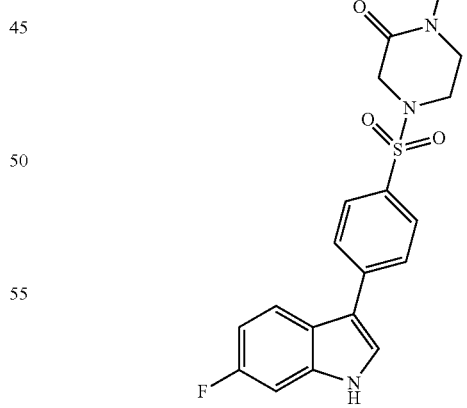

Following the general method as outlined in Example 4, starting from 1-methylpiperazin-2-one and 4-bromo-benzenesulfonyl chloride, the title compound was obtained as a white solid. LC-MS for C$_{19}$H$_{18}$FN$_3$O$_3$S+H$^+$ [M+H]$^+$: calcd: 388.1; found: 388.0. $^1$H NMR (400 MHz, DMSO-d$_6$) δ [ppm] 11.73 (s, 1H), 7.98 (d, J=7.8 Hz, 3H), 7.96-7.92 (m, 1H), 7.82 (d, J=7.9 Hz, 2H), 7.27 (d, J=9.6 Hz, 1H), 7.02 (t, J=8.9 Hz, 1H), 3.58 (s, 2H), 3.34-3.28 (m, 4H), 2.77 (s, 3H).

Example 43: N-(2-aminoethyl)-2-fluoro-5-(6-fluoro-1H-indol-3-yl)-benzenesulfonamide

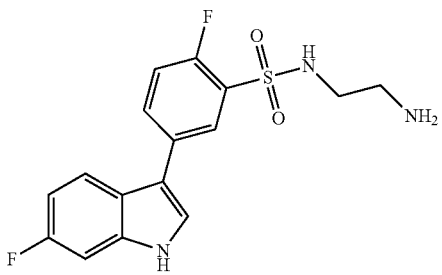 [SMILES: NCCNS(=O)(=O)c1cc(-c2c[nH]c3cc(F)ccc23)ccc1F]

Following the general method as outlined in Example 4, starting from tert-butyl (2-aminoethyl)carbamate and 5-bromo-2-fluoro-benzenesulfonyl chloride, the title compound was obtained as a white solid. LC-MS for $C_{16}H_{15}F_2N_3O_2S+H^+$ [M+H]$^+$: calcd: 352.1; found: 351.9. $^1$H NMR (400 MHz, DMSO-d$_6$) δ [ppm] 11.60 (br s, 1H), 8.00 (d, J=6.4 Hz, 1H), 7.98-7.94 (m, 1H), 7.81-7.77 (m, 2H), 7.50 (t, J=9.6 Hz, 1H), 7.26 (d, J=9.6 Hz, 1H), 7.02 (t, J=9.2 Hz, 1H), 3.48 (brs, 2H), 2.89 (t, J=6.4 Hz, 2H), 2.56 (t, J=6.4 Hz, 2H).

Example 44: N-(2-aminoethyl)-3-fluoro-5-(6-fluoro-1H-indol-3-yl)-benzenesulfonamide

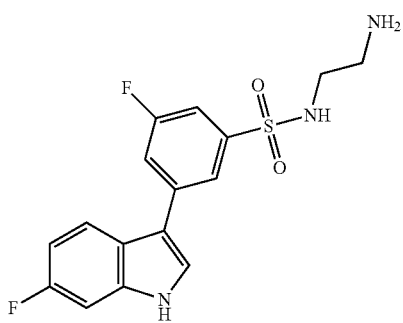 [SMILES: NCCNS(=O)(=O)c1cc(F)cc(-c2c[nH]c3cc(F)ccc23)c1]

Following the general method as outlined in Example 4, starting from tert-butyl (2-aminoethyl)carbamate and 3-bromo-5-fluorobenzene-1-sulfonyl chloride, the title compound was obtained as a white solid. LC-MS for $C_{16}H_{15}F_2N_3O_2S+H^+$ [M+H]$^+$: calcd: 352.1; found: 351.8. $^1$H NMR (400 MHz, CD$_3$OD) δ [ppm] 7.97 (s, 1H), 7.86-7.82 (m, 1H), 7.67-7.61 (m, 2H), 7.42 (d, J=8.0 Hz, 1H), 7.16 (dd, J=9.2, 1.2 Hz, 1H), 6.96 (td, J=8.8, 2.4 Hz, 1H), 2.98 (t, J=6.0 Hz, 2H), 2.71 (t, J=6.2 Hz, 2H).

Example 45: 3-(3-chloro-4-(piperazin-1-ylsulfonyl)phenyl)-6-fluoro-1H-indole

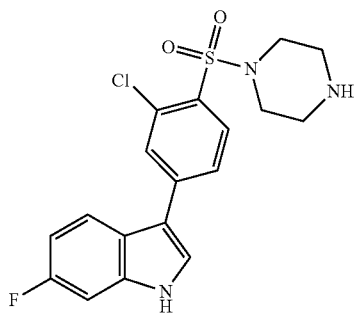 [SMILES: O=S(=O)(c1ccc(-c2c[nH]c3cc(F)ccc23)cc1Cl)N1CCNCC1]

Following the general method as outlined in Example 4, starting from tert-butyl piperazine-1-carboxylate and 4-bromo-2-chlorobenzene-1-sulfonyl chloride, the title compound was obtained as a white solid. LC-MS for $C_{18}H_{17}ClFN_3O_2S+H^+$ [M+H]$^+$: calcd: 394.1; found: 393.8. $^1$H NMR (400 MHz, DMSO-d$_6$) δ [ppm] 11.82 (s, 1H), 8.07 (d, J=2.4 Hz, 1H), 7.97-7.89 (m, 4H), 7.27 (dd, J=9.6, 2.0 Hz, 1H), 7.03 (td, J=9.2, 2.0 Hz, 1H), 3.10 (t, J=4.4 Hz, 4H), 2.75 (t, J=4.4 Hz, 4H).

Example 46: 4-(6-fluoro-1H-indol-3-yl)-N-(tetrahydro-pyran-4-yl)-benzenesulfonamide

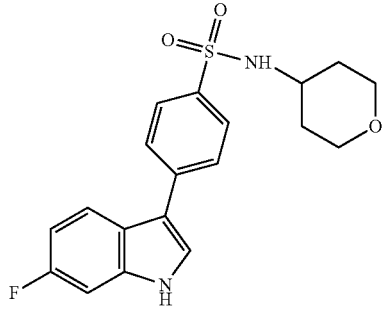 [SMILES: O=S(=O)(NC1CCOCC1)c1ccc(-c2c[nH]c3cc(F)ccc23)cc1]

Following the general method as outlined in Example 4, starting from tetrahydro-2H-pyran-4-amine, the title compound was obtained as a white solid. LC-MS for $C_{19}H_{19}FN_2O_3S+H^+$ [M+H]$^+$: calcd: 375.1; found: 374.9. $^1$H NMR (400 MHz, DMSO-d$_6$) δ [ppm]11.69 (br s, 1H), 7.96-7.93 (m, 4H), 7.84 (d, J=8.0 Hz, 2H), 7.78 (d, J=7.2 Hz, 1H), 7.26 (d, J=9.2 Hz, 1H), 7.01 (t, J=9.6 Hz, 1H), 3.74-3.71 (m, 2H), 3.26-3.18 (m, 3H), 1.57-1.54 (m, 2H), 1.42-1.33 (m, 2H).

Example 47: 6-fluoro-N,N-dimethyl-3-(4-(piperazin-1-ylsulfonyl)phenyl)-1H-indole-1-carboxamide

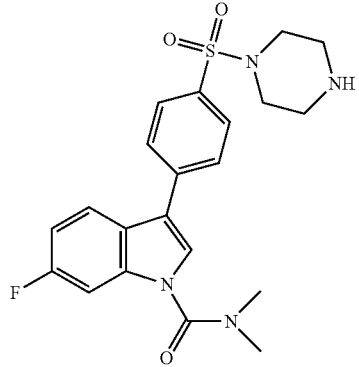 [SMILES: CN(C)C(=O)n1cc(-c2ccc(S(=O)(=O)N3CCNCC3)cc2)c2ccc(F)cc21]

Step 1: tert-butyl 4-((4-(6-fluoro-1-(phenylsulfonyl)-1H-indol-3-yl)phenyl)sulfonyl)-piperazine-1-carboxylate To a stirred solution of 6-fluoro-3-iodo-1-(phenylsulfonyl)indole (2.5 g, 6.2 mmol) in 1,4-dioxane (20 mL), tert-butyl 4-{[4-(4,4,5,5-tetramethyl-1,3,2-dioxaborolan-2-yl)phenyl]sulfonyl} piperazinecarboxylate (2.8 g, 6.2 mmol), Pd(dppf)Cl$_2$ (0.23 g, 0.31 mmol) and K$_2$CO$_3$ were added. The mixture was stirred overnight at 80° C. under N$_2$. The solvent was evaporated and the residue was purified by silica gel chromatography (EtOAc:PE=1:2) to afford 2.8 g (75%) of the title compound. $^1$H NMR (400 MHz, CDCl$_3$) δ [ppm]

7.95 (d, J=7.2 Hz,2H), 7.84-7.67 (m, 7H), 7.60 (d, J=7.6 Hz, 1H), 7.51(t, J=8.0 Hz,2H), 7.11(t, J=6.8 Hz, 1H), 3.54 (t, J=4.8Hz, 4H), 3.03 (t, J=4.0Hz, 4H), 1.40 (s, 9H).

Step 2: tert-butyl 4-((4-(6-fluoro-1H-indol-3-yl) phenyl)sulfonyl)piperazine-1-carboxylate To a stirred solution of tert-butyl4-({4-[6-fluoro-1-(phenylsulfonyl) indol-3-yl]phenyl}sulfonyl) piperazinecarboxylate 6-fluoro-3-iodoindole (2.8 g, 4.65 mmol) in MeOH (30 mL), was added NaOH (200 mg, 5.0 mmol). The mixture was stirred at 80° C. for 1 h. The solvent was evaporated and the residue was purified by silica gel chromatography (EtOAc:PE=1:2) to afford 2.1 g of the title compound.

Step 3: tert-butyl 4-((4-(1-(dimethylcarbamoyl)-6-fluoro-1H-indol-3-yl)phenyl)-sulfonyl)piperazine-1-carboxylate To a stirred solution of tert-butyl 4-((4-(6-fluoro-1H-indol-3-yl)phenyl)-sulfonyl)-piperazine-1-carboxylate (250 mg, 0.55 mmol) in THF (5.0 mL) at 0° C. was added NaH (40 mg, 1.05 mmol). The mixture was stirred for 1 h at rt. Then dimethylcarbamic chloride (64.5 mg, 0.6 mmol) was added and the mixture was stirred for 1 h at R.T. The solvent was evaporated and the residue was purified by silica gel chromatography (EtOAc:PE=1:2) to afford 250 mg of the title compound. LC-MS for $C_{26}H_{31}FN_4O_5S+Na^+[M+Na]^+$: calcd: 553.2; found: 552.8.

Step 4: 6-fluoro-N,N-dimethyl-3-(4-(piperazin-1-ylsulfonyl)phenyl)-1H-indole-1-carboxamide To a stirred solution of tert-butyl 4-((4-(1-(dimethylcarbamoyl)-6-fluoro-1H-indol-3-yl)phenyl)sulfonyl)piperazine-1-carboxylate (250 mg, 0.47 mmol) in $Et_2O$ (25 mL) was added $HCl/Et_2O$ (1 mL, 2M). The mixture was stirred for 1 hour at rt. The solvent was evaporated and the residue was purified by prep-HPLC to afford 51.8 mg of the title compound. LC-MS for $C_{21}H_{23}FN_4O_3S+H^+$ $[M+H]^+$: calcd: 431.1; found: 430.9. $^1$H NMR (400 MHz, $CDCl_3$) δ [ppm] 8.15 (s, 1H), 8.02-7.94 (m, 3H), 7.80 (d, J=8.0 Hz, 2H), 7.50(dd, J=9.6 Hz, 1.6Hz, 1H), 7.19(t, J=9.6 Hz, 1H), 3.08 (s, 6H), 2.86 (d, J=4.0Hz, 4H), 2.79 (d, J=3.6Hz, 4H).

Example 48: 4-(6-fluoro-1H-indol-3-yl)-N-(2-(5-oxo-4,5-dihydro-1,3,4-oxadiazol-2-yl)ethyl)benzenesulfonamide

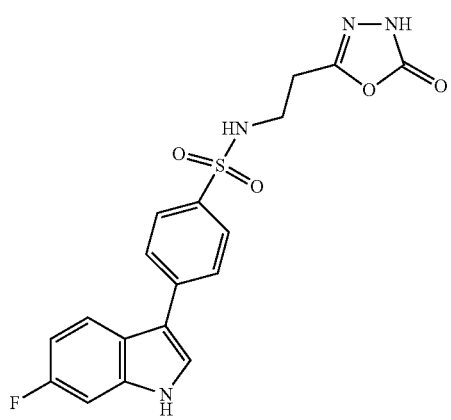 [SMILES: O=c1[nH]nc(CCNS(=O)(=O)c2ccc(-c3c[nH]c4cc(F)ccc34)cc2)o1]

Step 1 was performed according to Step 1 in Example 4

Step 2: 4-bromo-N-(3-hydrazinyl-3-oxopropyl)benzenesulfonamide

To a solution of 3-(4-bromo-benzenesulfonylamino)-propionic acid methyl ester (900 mg, 2.79 mmol) in EtOH (30 mL) was added hydrazine hydrate (210 mg, 4.19 mmol) at room temperature under $N_2$. The resulting mixture was stirred for 24 hrs at 87° C. under $N_2$. The reaction mixture was cooled, filtered and washed with EtOH (10 mL×2) to afford 4-bromo-N-(3-hydrazinyl-3-oxopropyl)-benzenesulfonamide (609 mg, 68%) as a white solid. LC-MS for $C_9H_{12}BrN_3O_3S+H^+$ $[M+H]^+$: calcd: 322.0; found: 322.0. $^1$H NMR (300 MHz, DMSO-$d_6$) δ [ppm] 9.02 (s, 1H), 7.83 (d, J=8.5 Hz, 2H), 7.80-7.74 (m, 1H), 7.71 (d, J=8.5 Hz, 2H), 4.15 (br s, 2H), 2.93 (m, 2H), 2.17 (t, J=7.3 Hz, 2H).

Step 3: 4-bromo-N-(2-(5-oxo-4,5-dihydro-1,3,4-oxadiazol-2-yl)ethyl)benzene-sulfonamide To the solution of 4-bromo-N-(3-hydrazinyl-3-oxopropyl)-benzenesulfonamide (509 mg, 1.58 mmol) in DCM (30 mL) at 0° C. under $N_2$ was added carbonic acid ditrichloromethyl ester (352 mg, 1.18 mmol) in DCM (10 mL). The reaction was stirred at 43° C. for 9 hrs under $N_2$. The mixture was cooled to rt, filtered and the solid was washed with DCM (10 mL×2) to afford 460 mg (84%) of the title compound as a white solid. LC-MS for $C_{10}H_{10}BrN_3O_4S+H^+$ $[M+H]^+$: calcd: 348.0; found: 348.0.

Steps 4 and 5 were performed according to the protocols described for Step 2 and Step 3 in Example 4. LC-MS for $C_{18}H_{15}FN_4O_4S-H^-$ $[M-H]^-$: calcd: 401.1; found: 401.0. $^1$H NMR (400 MHz, DMSO-$d_6$) δ [ppm] 7.98-7.86 (m, 4H), 7.81 (d, J=8.4 Hz, 2H), 7.26 (dd, J=9.9, 2.0 Hz, 1H), 7.01 (td, J=9.3, 2.3 Hz, 1H), 6.08 (br s, 1H), 3.06 (t, J=6.7 Hz, 2H), 2.66 (t, J=6.7 Hz, 2H).

Example 49: 3-(4-(6-fluoro-1H-indol-3-yl)phenylsulfonamido)-N,N-dimethylpropanamide

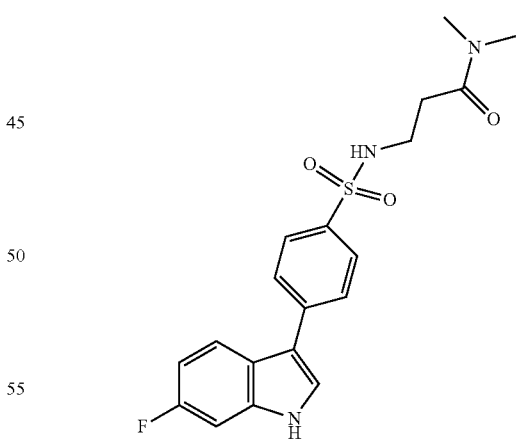

Following the general method as outlined in Example 4, starting from 3-amino-N,N-dimethylpropanamide and 4-bromo-benzenesulfonyl chloride, the title compound was obtained as a white solid. LC-MS for $C_{19}H_{20}FN_3O_3S+H^+$ $[M+H]^+$: calcd: 390.1; found: 389.9. $^1$H NMR (400 MHz, MeOD) δ [ppm] 7.90-7.86 (m, 5H), 7.65 (s, 1H), 7.15 (dd, J=9.7, 2.3 Hz, 1H), 6.94 (td, J=9.3, 2.3 Hz, 1H), 3.17 (t, J=6.8 Hz, 2H), 2.96 (s, 3H), 2.88 (s, 3H), 2.56 (t, J=6.8 Hz, 2H).

Example 50: 3-(4-(6-fluoro-1H-indol-3-yl)phenyl-sulfonamido)-N-methylpropanamide

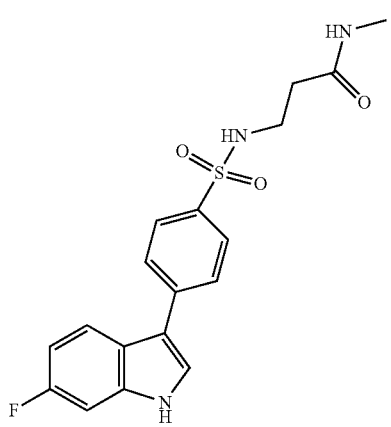 [SMILES: CNC(=O)CCNS(=O)(=O)c1ccc(-c2c[nH]c3cc(F)ccc23)cc1]

Following the general method as outlined in Example 4, starting from 3-amino-N-methylpropanamide, the title compound was obtained as a white solid. LC-MS for $C_{18}H_{18}FN_3O_3S+H^+$ [M+H]$^+$: calcd: 376.1; found: 376.3. $^1$H NMR (400 MHz, DMSO-d$_6$) δ [ppm]11.66 (s, 1H), 7.97-7.89 (m, 4H), 7.81 (d, J=8.4 Hz, 3H), 7.60 (t, J=5.8 Hz, 1H), 7.26 (dd, J=9.8, 2.3 Hz, 1H), 7.00 (td, J=9.4, 2.3 Hz, 1H), 2.96 (q, J=7.0 Hz, 2H), 2.53 (d, J=4.5 Hz, 3H), 2.25 (t, J=7.2 Hz, 2H).

Example 51: 1-(6-fluoro-3-(4-(piperazin-1-ylsulfonyl)phenyl)-1H-indol-1-yl)-propan-1-one

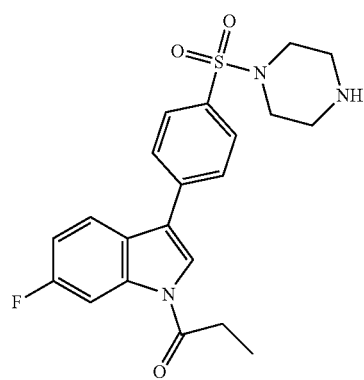 [SMILES: CCC(=O)n1cc(-c2ccc(S(=O)(=O)N3CCNCC3)cc2)c2ccc(F)cc21]

Following the general method as outlined in Example 47, starting from propionyl chloride, the title compound was obtained as a white solid.

LC-MS for $C_{21}H_{22}FN_3O_3S+H^+$ [M+H]$^+$: calcd: 416.1; found: 415.8. $^1$H NMR (400 MHz, CDCl$_3$) δ [ppm] 8.32 (dd, J=10.4, 2.0 Hz, 1H), 7.86 (d, J=8.4 Hz, 2H), 7.77(d, J=8.4 Hz, 2H), 7.70 (d, J=8.4, 5.2 Hz, 1H), 7.63 (s, 1H), 7.13 (t, J=2.4 Hz, 1H), 3.07-2.95 (m, 10H), 1.39 (t, J=7.2Hz, 3H).

Example 52: 1-(6-fluoro-3-(4-(piperazin-1-ylsulfonyl)phenyl)-1H-indol-1-yl)-3-methylbutan-1-one

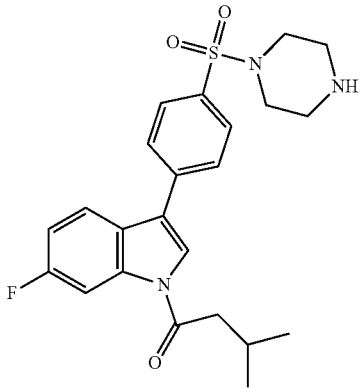 [SMILES: CC(C)CC(=O)n1cc(-c2ccc(S(=O)(=O)N3CCNCC3)cc2)c2ccc(F)cc21]

Following the general method as outlined in Example 47, starting from 3-methylbutanoyl chloride, the title compound was obtained as a white solid.

LC-MS for $C_{23}H_{26}FN_3O_3S+H$[M+H]$^+$: calc: 444.2; found: 443.9. $^1$H NMR (400 MHz, CDCl$_3$) δ [ppm] 8.34 (dd, J=10.4, 2.0 Hz, 1H), 7.86 (d, J=8.4 Hz, 2H), 7.77 (d, J=8.4 Hz, 2H), 7.72-7.69 (m, 1H), 7.61 (s, 1H), 7.13 (td, J=8.4Hz, 2.0 Hz, 1H), 3.06 (t, J=4.0 Hz, 4H), 2.97 (t, J=4.8 Hz, 4H), 2.85 (d, J=7.2 Hz, 2H), 2.42-2.39 (m, 1H), 1.11 (d, J=6.8Hz, 6H).

Example 53: 4-(4-(6-fluoro-1H-indol-3-yl)phenyl-sulfonamido)butanamide

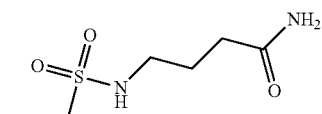

Following the general method as outlined in Example 4, starting from 4-(4-bromophenylsulfonamido)butanamide, the title compound was obtained as a white solid. LC-MS for $C_{18}H_{18}FN_3O_3S+H^+$ [M+H]$^+$: calcd: 376.1; found: 376.0. $^1$H NMR (400 MHz, DMSO-d$_6$) δ [ppm] 11.65 (s, 1H), 7.95-7.89 (m, 4H), 7.80 (d, J=8.4 Hz, 2H), 7.58 (t, J=6.4 Hz, 1H), 7.27-7.24 (m, 2H), 7.03-6.97 (m, 1H), 6.73 (s, 1H), 2.75 (q, J=6.8 Hz, 2H), 2.06 (t, J=7.2 Hz, 2H), 1.61 (t, J=7.2 Hz, 2H),

Example 54: 4-(4-(6-fluoro-1H-indol-3-yl)-N-methylphenylsulfonamido)-butanamide

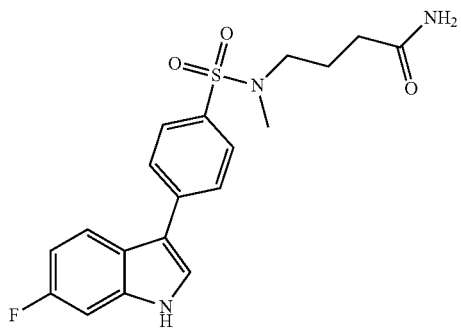 [SMILES: CN(CCCC(N)=O)S(=O)(=O)c1ccc(-c2c[nH]c3cc(F)ccc23)cc1]

Following the general method as outlined in Example 4, starting from 4-(4-bromo-N-methylphenylsulfonamido)butanamide, the title compound was obtained as a white solid. LC-MS for $C_{19}H_{20}FN_3O_3S+H^+$ [M+H]$^+$: calcd: 390.1; found: 390.1. $^1$H NMR (400 MHz, DMSO-d$_6$) δ [ppm] 11.68 (s, 1H), 7.94-7.92 (m, 4H), 7.77 (d, J=8.4 Hz, 2H), 7.30-7.25 (m, 2H), 7.04-6.99 (m, 1H), 6.77 (s, 1H), 2.96 (t, J=6.8 Hz, 2H), 2.68 (s, 3H), 2.12-2.08 (m, 2H), 1.74-1.69 (m, 2H).

Example 55: (R)-4-(6-fluoro-1H-indol-3-yl)-N-(tetrahydrofuran-3-yl)-benzenesulfonamide

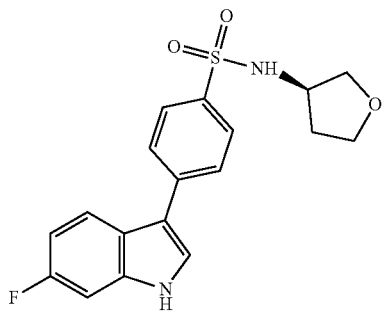 [SMILES: O=S(=O)(N[C@@H]1CCOC1)c1ccc(-c2c[nH]c3cc(F)ccc23)cc1]

Following the general method as outlined in Example 4, starting from (R)-tetrahydrofuran-3-amine, the title compound was obtained as a white solid. LC-MS for $C_{18}H_{17}FN_2O_3S+H^+$ [M+H]$^+$: calcd: 361.1; found: 360.8. $^1$H NMR (400 MHz, DMSO-d$_6$) δ [ppm]11.69 (brs, 1H), 7.96-7.89 (m, 5H), 7.84 (d, J=8.0 Hz, 2H), 7.26 (dd, J=9.6, 2.4 Hz, 1H), 7.01 (td, J=9.3, 2.4 Hz, 1H), 3.73-3.57 (m, 4H), 3.43-3.34 (m, 1H), 1.94-1.89 (m, 1H), 1.67-1.64 (m, 1H).

Example 56: N-(2-aminoethyl)-5-(6-fluoro-1H-indol-3-yl)-2-methylbenzenesulfonamide

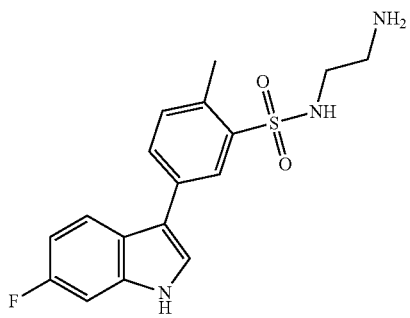 [SMILES: Cc1ccc(-c2c[nH]c3cc(F)ccc23)cc1S(=O)(=O)NCCN]

Following the general method as outlined in Example 4, starting from tert-butyl (2-aminoethyl)carbamate and 5-bromo-2-methylbenzene-1-sulfonyl chloride, the title compound was obtained as a white solid. LC-MS for $C_{17}H_{18}FN_3O_3S+H^+$ [M+H]$^+$: calcd: 348.1; found: 347.9. $^1$H NMR (400 MHz, CD$_3$OD) δ [ppm] 8.20 (d, J=2.4 Hz, 1H), 7.82-7.77 (m, 2H), 7.54 (s, 1H), 7.43 (d, J=7.6 Hz, 1H), 7.13 (dd, J=9.2, 1.6 Hz, 1H), 6.92 (td, J=9.6, 1.6 Hz, 1H), 2.98 (t, J=6.2 Hz, 2H), 2.71 (t, J=6.0 Hz, 2H).

Example 57: 5-(6-fluoro-1H-indol-3-yl)-N-methyl-2-(piperazin-1-ylsulfonyl)-benzamide

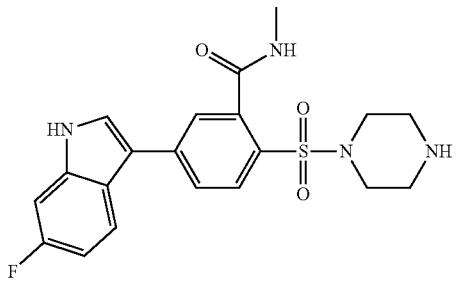 [SMILES: CNC(=O)c1cc(-c2c[nH]c3cc(F)ccc23)ccc1S(=O)(=O)N1CCNCC1]

Step 1: tert-butyl 4-((4-bromo-2-((tert-butoxycarbonyl)-carbamoyl)phenyl)sulfonyl)-piperazine-1-carboxylate A mixture of 4-(4-Bromo-2-carbamoyl-benzenesulfonyl)-piperazine-1-carboxylic acid tert-butyl ester (intermediate 1 in Example 41, 1.60 g, 3.57 mmol), (Boc)$_2$O (933 mg, 428 mmol), DMAP (435 mg, 3.57 mmol) and TEA (2 mL) in THF (30 mL) was stirred at 60° C. for overnight.

The reaction mixture was concentrated and diluted with DCM. The mixture was washed with brine, dried, and filtered. The filtrate was concentrated and purified by silica gel chromatography (PE/EtOAc=10/1) to afford 1.05 g (54%) of the title compound as a white solid. $^1$H NMR (400 MHz, DMSO-d$_6$) δ [ppm] 10.91 (s, 1H), 7.89-7.81 (m, 2H), 7.69 (d, J=8.4 Hz, 1H), 3.42-3.35 (m, 4H), 3.14-3.05 (m, 4H), 1.35-1.20 (m, 18H).

Step 2: tert-butyl 4-((4-bromo-2-((tert-butoxycarbonyl)(methyl)carbamoyl)-phenyl)sulfonyl)piperazine-1-carboxylate The mixture of 4-(4-Bromo-2-tert-butoxycarbonylaminocarbonyl-benzenesulfonyl)-piperazine-1-carboxylic acid tert-butyl ester (250 mg, 0.456 mmol), CH$_3$1 (78 mg, 0.55 mmol) and NaH (27 mg, 0.68 mmol, 60% in oil) in anhydrous THF (5 mL) was stirred at room temperature overnight. The reaction mixture was quenched with aqueous NH$_4$Cl and extracted with EtOAc (30 mL×4). The organic layer was dried, filtered and concentrated to give the crude product which was further purified by prep-TLC to afford 130 mg (51%) of the title compound as a white solid. $^1$H NMR (400 MHz, DMSO-d$_6$) δ [ppm] 7.86-7.81 (m, 2H), 7.70 (d, J=9.2 Hz, 1 H), 3.38-3.34 (m, 4H), 3.17 (s, 3H), 3.01-2.95 (m, 4H), 1.36 (s, 9H), 1.01 (s, 9H).

Step 3: tert-butyl 3-(3-((tert-butoxycarbonyl)(methyl)carbamoyl)-4-((4-(tert-butoxycarbonyl)piperazin-1-yl)sulfonyl)phenyl)-6-fluoro-1H-indole-1-carboxylate The mixture of 4-[4-Bromo-2-(tert-butoxycarbonyl-methyl-aminocarbonyl)-benzenesulfonyl]-piperazine-1-carboxylic acid tert-butyl ester (130 mg, 0.231 mmol), 6-Fluoro-3-(4,4,5,5-tetramethyl-[1,3,2]dioxaborolan-2-yl)-indole-1-carboxylic acid tert-butyl ester (Intermediate 1, 100 mg, 0.277 mmol), $K_2CO_3$ (95.0 mg, 0.693 mmol and Pd(dppf)$Cl_2$ in the solution of 1,4-Dioxane/$H_2O$ (10 mL/1 mL) was stirred at 80° C. overnight under $N_2$ atmosphere. The reaction mixture was extracted with EtOAc (30 mL×4). The combined organic layer was dried, filtered and concentrated to give the crude product which was purified by prep -TLC to afford 100 mg (61%) of the title compound as a white solid.

Step 4: 5-(6-fluoro-1H-indol-3-yl)-N-methyl-2-(piperazin-1-ylsulfonyl)benzamide

The mixture of 3-[3-(tert-Butoxycarbonyl-methyl-aminocarbonyl)-4-(4-tert-butoxycarbonyl-piperazine-1-sulfonyl)-phenyl]-6-fluoro-indole-1-carboxylic acid tert-butyl ester (100 mg, 0.139 mmol) in the solution of HCl/$CH_3OH$ (10 mL) was stirred at room temperature for 5 h. The reaction mixture was concentrated to give the crude product which was purified by prep-HPLC to afford the 10.3 mg of (17%) title compound as a white solid. LC-MS for $C_{20}H_{21}FN_4O_3S+H^+$ [M+H]$^+$: calcd: 417.1; found: 416.8. $^1$H NMR (400 MHz, DMSO-$d_6$) δ [ppm]11.73 (br s, 1H), 8.27 (t, J=4.4 Hz, 1H), 8.00 (d, J=1.6 Hz 1H), 7.99-7.85 (m, 2H), 7.78 (d, J=8.4 Hz, 1H), 7.68 (s, 1H), 7.29-7.23 (m, 1H), 7.03 (t, J=8.8 Hz, 1H), 3.03-2.95 (m, 4H), 2.78-2.70 (m, 7H).

Example 58: (cis)-1-((4-(6-fluoro-1H-indol-3-yl)phenyl)sulfonyl)-pyrrolidine-3,4-diol

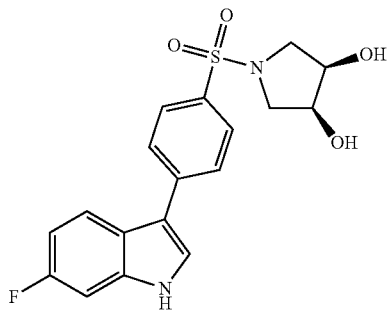 [SMILES: O=S(=O)(c1ccc(-c2c[nH]c3cc(F)ccc23)cc1)N1C[C@@H](O)[C@@H](O)C1]

Step 1: 1-((4-bromophenyl)sulfonyl)-2,5-dihydro-1H-pyrrole

To a solution of 4-bromo-benzenesulfonyl chloride (5.00 g, 22.6 mmol) in pyridine (30 mL) at room temperature was added 2,5-dihydro-1H-pyrrole (1.20, 17.6 mmol). The reaction mixture was stirred overnight. The mixture was poured into water (200 mL) and extracted with DCM (100 mL×3). The organic layer was washed with HCl (2 M, 200 mL) and brine (50 mL×3), dried over anhydrous $Na_2SO_4$, filtered, and concentrated to afford 3.6 g (55%) of the title compound as a white solid. $^1$H NMR (400 MHz, DMSO-$d_6$) δ [ppm] 7.84 (d, J=8.8 Hz, 2H), 7.76 (d, J=8.4 Hz, 2H), 5.73 (s, 2H), 4.04 (s, 4H).

Step 2: (cis)-1-((4-bromophenyl)sulfonyl)pyrrolidine-3,4-diol

A mixture of 1-(4-bromo-benzenesulfonyl)-2,5-dihydro-1H-pyrrole (3.60 g, 5.52 mmol), 4-methyl-morpholine 4-oxide (3.64 g, 6.62 mmol) and $K_2OsO_4$ (780 mg, 2.34 mmol) in THF/$H_2O$/t-Butanol (36 mL/36 mL/4 mL) was stirred at r.t for 72 h. The reaction mixture was concentrated. The residue was dissolved in DCM (300 mL), washed with brine (50 mL×3), dried over anhydrous $Na_2SO_4$ and filtered. The filtrate was concentrated to give the crude compound which was triturated from PE/EtOAc (15/1, 50 mL) to afford 1.9 g (47%) of the title compound as a grey solid. $^1$H NMR (400 MHz, DMSO-$d_6$) δ [ppm] 7.82 (d, J=8.4 Hz, 2H), 7.71 (d, J=8.4 Hz, 2H), 5.01-4.92 (m, 2H), 3.89-3.80 (m, 2H), 3.28-3.32 (m, 2H), 3.01-2.90 (m, 2H).

Step 3: (cis)-1-((4-bromophenyl)sulfonyl)-3,4-bis((2-(trimethylsilyl)ethoxy)-methoxy)pyrrolidine A mixture of (cis)-1-(4-Bromo-benzenesulfonyl)-pyrrolidine-3,4-diol (300 mg, 0.931 mmol), SEM-Cl (466 mg, 2.79 mmol) and DIEA (0.687 mL) in DCM (10 mL) was stirred at r t for 3 h. The reaction mixture was concentrated and the residue was purified by silica gel chromatography (PE/EtOAc=15/1) to afford 380 mg (70%) of the title compound as a white solid.

Step 4: tert-butyl 3-(4-((cis)-3,4-bis((2-(trimethylsilyl)ethoxy)methoxy)-pyrrolidin-1-yl)sulfonyl)phenyl)-6-fluoro-1H-indole-1-carboxylate A mixture of 1-(4-Bromo-benzenesulfonyl)-3,4-bis-(2-trimethylsilanyl-ethoxymethoxy)-pyrrolidine (380 mg, 0.652 mmol), 6-Fluoro-3-(4,4,5,5-tetramethyl-[1,3,2]dioxaborolan-2-yl)-indole-1-carboxylic acid tert-butyl ester (282 mg, 0.783 mmol), $K_2CO_3$ (269 mg, 1.69 mmol) and Pd(dppf)$Cl_2$(50 mg) in 1,4-Dioxane/$H_2O$ (10 mL/1 mL) was stirred at 80° C. for overnight under $N_2$ atmosphere. The mixture was diluted with EtOAc (100 mL). The organic layer was washed with brine, dried over anhydrous $Na_2SO_4$ and filtered. The filtrate was concentrated and the residue was purified by silica gel chromatography (PE/EtOAc=10/1) to afford 330 mg (69%) of the title compound as colorless oil.

Step 5: (cis)-1-((4-(6-fluoro-1H-indol-3-yl)phenyl)sulfonyl)-pyrrolidine-3,4-diol A mixture of (cis)-3-{4-[3,4-Bis-(2-trimethylsilanyl-ethoxymethoxy)-pyrrolidine-1-sulfonyl]-phenyl}-6-fluoro-indole-1-carboxylic acid tert-butyl ester (330 mg, 0.447 mmol) in HCl (10 mL, in $CH_3OH$) was stirred at r. t for overnight. The reaction mixture was concentrated and the residue was purified by prep-HPLC to afford 12.1 mg (7%) of the title compound as a white solid. LC-MS for $C_{18}H_{17}FN_2O_4S+H^+$ [M+H]$^+$: calcd: 377.1; found: 376.8. $^1$H NMR (300 MHz, DMSO-$d_6$) δ [ppm] 11.69 (s, 1H), 7.97-7.90 (m, 4H), 7.80 (d, J=8.4 Hz, 2H), 7.26 (d, J=8.4 Hz, 1H), 7.01 (t, J=9.2 Hz, 1H), 4.97 (d, J=4.4 Hz, 2H), 3.87 (d, J=3.6 Hz, 2H), 3.39-3.34 (m, 2H), 3.07-3.00 (m, 2H).

Example 59: 4-(6-fluoro-1H-indol-3-yl)-N-(2-(3-methyl-1,2,4-oxadiazol-5-yl)-ethyl)benzenesulfonamide

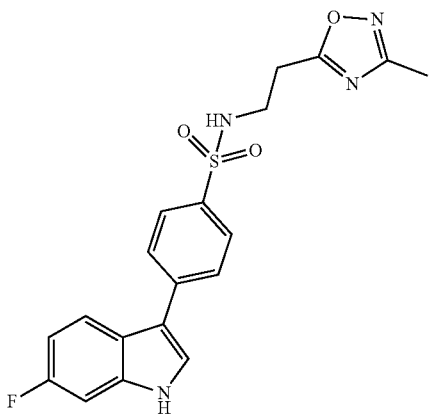 [SMILES: Cc1noc(CCNS(=O)(=O)c2ccc(-c3c[nH]c4cc(F)ccc34)cc2)n1]

Step 1: tert-butyl 6-fluoro-3-(4-(N-(3-methoxy-3-oxopropyl)-sulfamoyl)phenyl)-1H-indole-1-carboxylate To a solution of 6-Fluoro-3-(4,4,5,5-tetramethyl-[1,3,2]dioxaborolan-2-yl)-indole-1-carboxylic acid tert-butyl ester (Intermediate 1, 300 mg, 0.83 mmol), 3-(4-Bromo-benzenesulfonylamino)-propionic acid methyl ester (268 mg, 0.83 mmol) and $K_2CO_3$ (172 mg, 1.25 mmol) in dioxane (30 mL)/water (5 mL) under nitrogen was added Pd(dppf)Cl$_2$ (31 mg, 0.042 mmol). The reaction was stirred at 100° C. for 2 h under $N_2$. The mixture was diluted with EtOAc (100 mL) and aqueous of $NH_4Cl$ (60 mL). The aqueous layer was extracted with EtOAc (80 mL×3). The organic layer was washed with brine, dried over anhydrous $Na_2SO_4$ and filtered. The filtrate was concentrated and purified by silica gel chromatography (PE/EtOAc=3/1-0/1) to afford 319 mg (80%) of the title compound as yellow oil. LC-MS for $C_{23}H_{25}FN_2O_6S+H^+$ $[M+H]^+$:calcd: 477.1; found: 477.4

Step 2: methyl 3-(4-(6-fluoro-1H-indol-3-yl)phenylsulfonamido)propanoate

To a solution of 6-Fluoro-3-[4-(2-methoxycarbonyl-ethylsulfamoyl)-phenyl]-indole-1-carboxylic acid tert-butyl ester (196 mg, 0.63 mmol) in DCM (20 mL) was added TFA (6 mL). The resulting mixture was stirred for 2 h at room temperature. The mixture was poured into aqueous $NaHCO_3$ (90 mL) and extracted with EtOAc (60 mL×3). The organic layer was dried over anhydrous $Na_2SO_4$, filtered and concentrated to afford 220 mg (87%) of the title compound as red oil.

Step 3: (E)-N'-hydroxyacetimidamide

To a mixture of Hydroxylamine hydrochloride (2.00 g, 28.78 mmol) in water (5 mL), were added NaOH (1.15 g, 28.78 mmol) in water (5 ml) and MeCN (30 mL). The mixture was stirred for 24 h at rt and then concentrated. The residue was suspended in EtOH (80 mL), dried over $Na_2SO_4$ and filtered. The filtration was concentrated to afford the title compound (1.37 g, 64.3%) as a white solid. $^1$H NMR (400 MHz, DMSO-d6) δ[ppm] 8.69 (s, 1H), 5.36 (s, 2H), 1.62 (s, 3H).

Step 4: 4-(6-fluoro-1H-indol-3-yl)-N-(2-(3-methyl-1,2,4-oxadiazol-5-yl)-ethyl)benzenesulfonamide To a mixture of N-Hydroxy-acetamidine (47.6 mg, 0.64 mmol) in THF (15 mL) under $N_2$ was added NaH (24.5 mg, 0.61 mmol). The mixture was stirred for 1 h at 0° C. Then 3-[4-(6-Fluoro-1H-indol-3-yl)-benzenesulfonylamino]-propionic acid methyl ester (220 mg, 0.58 mmol) in THF (5 mL) was added. The mixture was refluxed for 12 h under $N_2$ before it was quenched with saturated aqueous $NH_4Cl$ and extracted with EtOAc (30 mL×3). The combined organic layer was washed with brine, dried over $Na_2SO_4$, filtered and concentrated. The residue was purified by prep-HPLC to afford the title compound (35 mg, 15%) as a yellow solid. LC-MS for $C_{19}H_{17}FN_4O_3S+H^+$ $[M+H]^+$: calcd: 401.1; found: 400.8. $^1$H NMR (400 MHz, DMSO-d$_6$) δ [ppm]11.67 (s, 1H), 7.98-7.88 (m, 4H), 7.81 (d, J=7.8 Hz, 2H), 7.27 (d, J=9.7 Hz, 1H), 7.01 (t, J=9.2 Hz, 1H), 3.20 (t, J=6.6 Hz, 2H), 3.05 (t, J=6.1 Hz, 2H), 2.28 (s, 3H).

Example 60: 6-fluoro-N-methyl-3-(4-(piperazin-1-ylsulfonyl)phenyl)-1H-indole-1-carboxamide

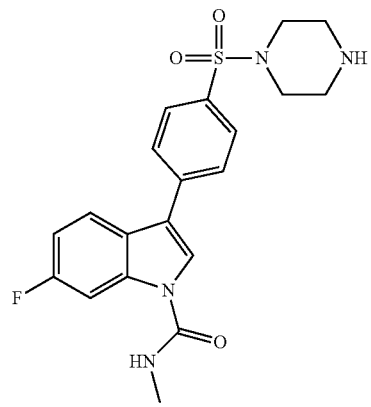 [SMILES: CNC(=O)n1cc(-c2ccc(S(=O)(=O)N3CCNCC3)cc2)c2ccc(F)cc21]

The Title compound was prepared following the general method as outlined in Example 47. $^1$H NMR (400 MHz, CDCl$_3$) δ [ppm] 8.00 (dd, J=10.0, 2.0 Hz, 1H), 7.80 (d, J=8.0 Hz, 2H), 7.74-7.70 (m, 2H), 7.62 (s, 1H), 7.08 (td, J=8.8, 2.0 Hz, 1H), 5.82 (d, J=4.0 Hz, 1H), 3.11(d, J=4.8Hz, 3H), 3.04-3.03 (m, 4H), 2.95 (t, J=4.4Hz, 4H). LC-MS for $C_{20}H_{21}FN_4O_3S+H^+$ $[M+H]^+$: calcd.: 417.1; found: 417.0

Example 61: N-(2-aminoethyl)-3-(6-fluoro-1H-indol-3-yl)-5-methoxybenzene-sulfonamide

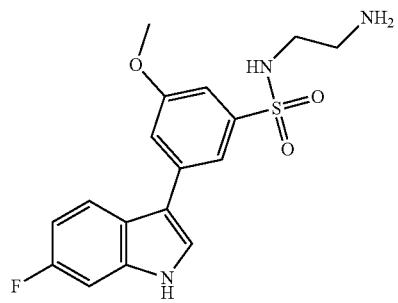 [SMILES: COc1cc(-c2c[nH]c3cc(F)ccc23)cc(S(=O)(=O)NCCN)c1]

Following the general method as outlined in Example 37, starting from tert-butyl (2-aminoethyl)carbamate and 3-bromo-5-methoxy-phenylamine, the title compound was obtained as a white solid. LC-MS for $C_{17}H_{18}FN_{33}S+H^+$ [M+H]$^+$: calcd: 364.1; found: 363.9. $^1$H NMR (400 MHz, DMSO-d$_6$) δ [ppm] 11.62 (s, 1H), 7.86-7.83 (m, 2H), 7.66 (s, 1H), 7.42 (s, 1H), 7.25 (dd, J=2.4, 9.6 Hz, 1H), 7.17 (s, 1H), 7.04-6.99 (m, 1H), 3.89 (s, 3H), 2.78 (t, J=6.4 Hz, 2H), 2.54 (t, J=6.4 Hz, 2H).

Example 62: N-(2-aminoethyl)-4-fluoro-3-(6-fluoro-1H-indol-3-yl)benzene-sulfonamide

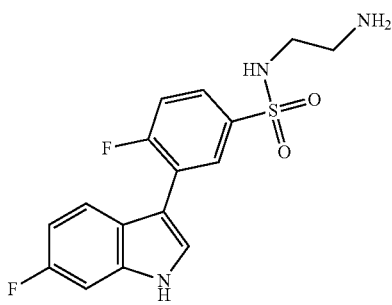 [SMILES: NCCNS(=O)(=O)c1ccc(F)c(-c2c[nH]c3cc(F)ccc23)c1]

Following the general method as outlined in Example 37, starting from tert-butyl (2-aminoethyl) carbamate and 3-bromo-4-fluorobenzene-1-sulfonyl chloride, the title compound was obtained as a white solid. LC-MS for $C_{16}H_{15}F_2N_3O_2S+H^+$ [M+H]$^+$: calcd: 352.1; found: 351.8. $^1$H NMR (400 MHz, MeOD) δ [ppm] 8.21 (dd, J=6.5, 2.0 Hz, 1H), 7.78-7.76 (m, 1H), 7.72-7.69 (m, 1H), 7.62 (d, J=1.9 Hz, 1H), 7.42 (t, J=9.6 Hz, 1H), 7.18-7.16 (m, 1H), 6.94 (td, J=8.9, 1.7 Hz, 1H), 3.01 (t, J=6.1 Hz, 2H), 2.81 (t, J=6.0 Hz, 2H).

Example 63: (1-((4-(6-fluoro-1H-indol-3-yl)phenyl)sulfonyl)-azetidin-3-yl)methanol

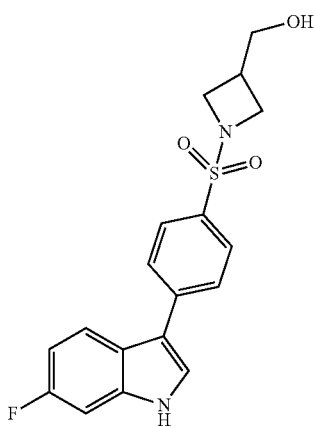 [SMILES: O=S(=O)(c1ccc(-c2c[nH]c3cc(F)ccc23)cc1)N1CC(CO)C1]

Step 1: methyl azetidine-3-carboxylate

To a solution of azetidine-3-carboxylic acid (1.00 g, 9.89 mmol) in MeOH at 0° C. was added thionyl chloride (1.44 ml, 19.78 mmol). The reaction was warmed to room temperature, and then refluxed for 2 h. The reaction mixture was concentrated to give the title compound (1.14 g, 100%) as yellow oil which was used for the next step without further purification.

Step 2: methyl 1-((4-bromophenyl)sulfonyl)azetidine-3-carboxylate

A mixture of 4-Bromo-benzenesulfonyl chloride (2.52 g, 9.89 mmol), azetidine-3-carboxylic acid methyl ester (1.14 g, 9.89 mmol) and TEA (2.75 mL) in DCM (20 mL) was stirred at room temperature for 2 h. Then the mixture was diluted with EtOAc (60 mL). The organic layer was washed with NH$_4$Cl (60 mL×3), dried over Na$_2$SO$_4$, filtered and concentrated. The residue was purified by silica gel chromatography (PE:EtOAc=6:1-3:1) to afford the title compound (2.71 g, 82%) as a white solid. $^1$H NMR (400 MHz, DMSO-d$_6$) δ [ppm] 7.92 (d, J=8.4 Hz, 2H), 7.76 (d, J=8.5 Hz, 2H), 3.95 (t, J=8.7 Hz, 2H), 3.80-3.73 (m, 2H), 3.53 (s, 3H), 3.42-3.32 (m, 1H).

Step 3: tert-butyl 6-fluoro-3-(4-((3-(methoxycarbonyl)azetidin-1-yl)sulfonyl)-phenyl)-1H-indole-1-carboxylate A mixture of compound 1-(4-Bromo-benzenesulfonyl)-azetidine-3-carboxylic acid methyl ester (369 mg, 1.11 mmol), 6-Fluoro-3-(4,4,5,5-tetramethyl-[1,3,2]-dioxaborolan-2-yl)-indole-1-carboxylic acid tert-butyl ester (Intermediate 1, 400 mg, 1.11 mmol), Pd(dppf)Cl$_2$ (40.61 mg, 0.05 mmol) and K$_2$CO$_3$ (230 mg, 1.67 mmol) in dioxane/H$_2$O (30 mL/5 mL) was stirred at 100° C. for 2 h under N$_2$ atmosphere. The reaction mixture was diluted with EtOAc (100 mL), dried, filtered and concentrated. The residue was purified by silica gel chromatography (PE/EtOAc=6/1-3/1) to afford the title compound (322 mg, 59%) as yellow oil. LC-MS for $C_{24}H_{25}FN_2O_6S+H^+$ [M+H]$^+$: calcd: 489.1; found: 489.0

Step 4: methyl 1-((4-(6-fluoro-1H-indol-3-yl)phenyl)sulfonyl)azetidine-3-carboxylate To a solution of 6-Fluoro-3-[4-(3-methoxycarbonyl-azetidine-1-sulfonyl)-phenyl]-indole-1-carboxylic acid tert-butyl ester (322 mg, 0.65 mmol) in DCM (20 mL) was added TFA (6 mL). The resulting mixture was stirred at room temperature for 3 h. The reaction mixture was poured into aqueous NaHCO$_3$ (90 mL) and extracted with EtOAc (60 mL×3). The organic layer was dried over anhydrous Na$_2$SO$_4$, filtered, and concentrated to afford 256 mg (100%) of the title compound as yellow oil. LC-MS for $C_{19}H_{17}FN_2O_4S+H^+$ [M+H]$^+$: calcd: 389.1; found: 389.0.

Step 5: (1-((4-(6-fluoro-1H-indol-3-yl)phenyl)sulfonyl)-azetidin-3-yl)methanol

To the mixture of LiAlH$_4$ (29.6 mg, 0.78 mmol) in anhydrous THF (100 mL) at 0° C. was added 1-[4-(6-Fluoro-1H-indol-3-yl)-benzenesulfonyl]-azetidine-3-carboxylic acid methyl ester (256.0 mg, 0.65 mol) under N$_2$. The mixture was stirred at room temperature for 2 h under N$_2$. The reaction mixture was quenched with water (2 mL) and diluted with EtOAc (60 mL). The mixture was dried and filtered. The filtrate was concentrated and purified by prepare HPLC to afford the title compound (16.0 mg, 6.8%) as a white solid. LC-MS for $C_{18}H_{17}FN_2O_3S+H^+$ [M+H]$^+$: calcd: 361.1; found: 360.8. $^1$H NMR (400 MHz, DMSO-d6) δ[ppm] 8.04-7.95 (m, 4H), 7.82 (d, J=8.3 Hz, 2H), 7.27 (dd, J=9.8, 2.3 Hz, 1H), 7.03 (td, J=9.1, 2.7 Hz, 1H), 4.69-4.65 (m, 1H), 3.74 (t, J=8.2 Hz, 2H), 3.49-3.44 (m, 3H), 3.25-3.20 (m, 2H).

Example 64: (S)-4-(6-fluoro-1H-indol-3-yl)-N-(tetrahydrofuran-3-yl)-benzenesulfonamide

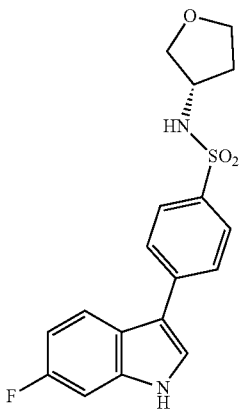 [SMILES: O=S(=O)(N[C@H]1CCOC1)c1ccc(-c2c[nH]c3cc(F)ccc23)cc1]

Following the general method as outlined in Example 4, starting from (S)-tetrahydrofuran-3-amine and 4-bromo-benzenesulfonyl chloride, the title compound was obtained as a white solid. LC-MS for $C_{18}H_{17}FN_2O_3S$—H$^-$[M−H]$^-$: calcd: 359.1; found: 359.0. $^1$H NMR (400 MHz, DMSO-d6) δ[ppm] 11.66 (s, 1H), 7.96-7.90 (m, 5H), 7.83 (d, J=8.8 Hz, 2H), 7.26 (dd, J=9.6, 2.0 Hz,1H), 7.00 (td, J=9.6, 2.0 Hz,1H), 3.74-3.67 (m, 2H), 3.65-3.56 (m, 2H), 3.39 (dd, J=8.8, 4.0 Hz,1H), 1.94-1.89 (m, 1H), 1.68-1.64 (m, 1H).

Example 65: 1-((4-(6-fluoro-1H-indol-3-yl)phenyl)sulfonyl)azetidin-3-ol

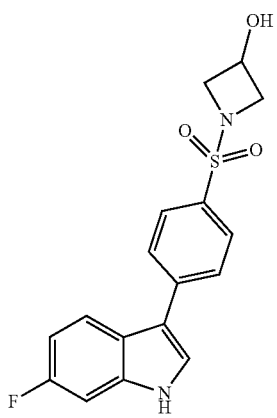 [SMILES: O=S(=O)(c1ccc(-c2c[nH]c3cc(F)ccc23)cc1)N1CC(O)C1]

Following the general method as outlined in Example 4, starting from azetidin-3-yl acetate and 4-bromo-benzenesulfonyl chloride, the title compound was obtained as a white solid. LC-MS for $C_{17}H_{15}FN_2O_3S+H^+$ [M+H]$^+$:calcd: 347.1; found: 346.8. $^1$H NMR (400 MHz, DMSO-d$_6$) δ [ppm] 11.73 (s, 1H), 8.06-7.95 (m, 4H), 7.82 (d, J=8.0 Hz, 2H), 7.28 (dd, J=9.8, 2.2 Hz, 1H), 7.03 (td, J=9.2, 2.2 Hz, 1H), 5.77 (d, J=5.9 Hz, 1H), 4.36-4.26 (m, 1H), 3.91 (t, J=7.4 Hz, 2H), 3.40 (s, 2H).

Example 66: (3S,4S) 1-[4-(6-Fluoro-1H-indol-3-yl)-benzenesulfonyl]-pyrrolidine-3,4-diol

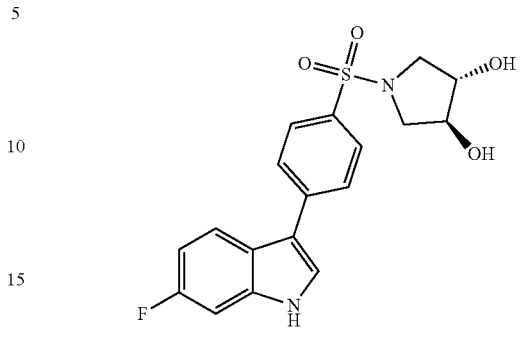

Step 1: (3R,4R) 1-Benzyl-3,4-dihydroxy-pyrrolidine-2,5-dione

To a two-neck round bottom flask with a Dean-stark apparatus were added (2R,3R)-2,3-dihydroxysuccinic acid (7.0 g, 46.6 mmol), BnNH$_2$ (7.5 g, 70.0 mmol) and xylene (300 mL). The reaction mixture was refluxed for overnight. The mixture was cooled to room temperature and filtered. The residue was triturated with PE/EtOAc (PE/EtOAc=5/1, 200 mL) to afford 5.5 g (54%) of the title compound as a white solid.

Step 2: (3S,4S)-1-benzylpyrrolidine-3,4-diol

To a mixture of LiAlH$_4$ (2.8 g, 74.6 mmol) in anhydrous THF (50 mL) was added 1-Benzyl-3, 4-dihydroxy-pyrrolidine-2,5-dione (5.5 g, 24.9 mmol). The reaction mixture was refluxed for 3 h. After being cooled to room temperature, the mixture was quenched with H$_2$O (2 mL) and aq NaOH (2 mL, 15% in water). EtOAc (150 mL) was added and the mixture was dried, filtered and concentrated to afford 2.5 g (52%) of the title compound as colorless oil.

Step 3: (3S,4S)-1-benzylpyrrolidine-3,4-diyl diacetate

A mixture of 1-Benzyl-pyrrolidine-3,4-diol (3.40 g, 17.5 mmol), DMAP (10 mg), Ac$_2$O (4.46 g, 4.38 mmol) and TEA (3 mL) in anhydrous DCM (50 mL) was stirred at r t for 3 h. The reaction mixture was diluted with DCM (100 mL), washed with brine (20 mL×3), dried over anhydrous Na$_2$SO$_4$, filtered and concentrated to give the crude product which was further purified by flash column to afford 2.9 g (60%) of the title compound as colorless oil. $^1$H NMR (400 MHz, DMSO-d$_6$) δ [ppm] 7.38-7.23 (m, 5H), 4.99-4.93 (m, 2H), 3.58 (s, 2H), 2.95 (dd, J=10.4, 6.4 Hz, 2H), 2.43 (dd, J=10.4, 4.0 Hz, 2H), 2.00 (s, 6H).

Step 4: (3S,4S)-pyrrolidine-3,4-diyl diacetate

A mixture of Acetic acid 4-acetoxy-1-benzyl-pyrrolidin-3-yl ester (1.2 g, 4.33 mmol) and Pd/C (20 mg) in CH$_3$OH (20 mL) was stirred at room temperature for overnight under H$_2$ atmosphere. The reaction mixture was filtered and concentrated to give 800 mg (99%) of the title compound as colorless oil.

Step 5: (3S,4S)-1-((4-bromophenyl)sulfonyl)pyrrolidine-3,4-diyl diacetate

A mixture of acetic acid 4-acetoxy-pyrrolidin-3-yl ester (0.80 g, 4.28 mmol), 4-Bromo-benzenesulfonyl chloride (1.31 g, 5.13 mmol) and TEA (1.29 g, 12.8 mmol) in DCM (20 mL) was stirred at r t for 3 h. The reaction mixture was concentrated and the residue was purified by silica gel chromatography (PE/EtOAc=5/1) to afford 1.21 g (63%) of the title compound as a white solid. $^1$H NMR (400 MHz, DMSO-d$_6$) δ [ppm] 7.88 (d, J=8.4 Hz, 2H), 7.78 (d, J=8.4 Hz, 2H), 4.99-4.93 (m, 2H), 3.52 (dd, J=12.3, 3.6 Hz, 2H), 3.44-3.35 (m, 2H), 1.81 (s, 6H).

Step 6: (3S,4S)-1-((4-(1-(tert-butoxycarbonyl)-6-fluoro-1H-indol-3-yl) phenyl)sulfonyl)pyrrolidine-3,4-diyl diacetate A mixture of acetic acid 4-acetoxy-1-(4-bromo-benzenesulfonyl)-pyrrolidin-3-yl ester (300 mg, 0.74 mmol), 6-fluoro-3-(4,4,5,5-tetramethyl-[1,3,2]-dioxaborolan-2-yl)-indole-1-carboxylic acid tert-butyl ester (Intermediate 1, 320 mg, 0.89 mmol), Pd(dppf)Cl$_2$ (20 mg) and K$_2$CO$_3$ (305 mg, 2.21 mmol) in dioxane/H$_2$O (10 mL/1 mL) was stirred at 80° C. for overnight under N$_2$ atmosphere. The reaction mixture was diluted with DCM (100 mL), washed with brine (20 mL×3), dried over anhydrous Na$_2$SO$_4$ and filtered. The filtrate was concentrated and purified by prep-TLC (PE/EtOAc=1/1) to afford the title compound (130 mg) as a white solid. $^1$H NMR (400 MHz, DMSO-d$_6$) δ [ppm] 8.12 (s, 1H), 8.02 (d, J=8.4 Hz, 2H), 7.96-7.90 (m, 4H), 7.27 (dt, J=8.4 Hz, 1H), 5.00-4.97 (m, 2H), 3.65-3.52 (m, 2H), 3.41 (d, J=12.4 Hz, 2H), 1.78 (s, 6H), 1.66 (s, 9H).

Step 7: tert-butyl 3-(4-(((3S,4S)-3,4-dihydroxypyrrolidin-1-yl)sulfonyl)phenyl)-6-fluoro-1H-indole-1-carboxylate A mixture of 3-[4-(3-Acetoxy-4-hydroxy-pyrrolidine-1-sulfonyl)-phenyl]-6-fluoro-indole-1-carboxylic acid tert-butyl ester (130 mg, 0.251 mmol) and K$_2$CO$_3$ (103 mg, 0.753 mmol) in CH$_3$OH (10 mL) was stirred at r.t for 2 h. The reaction mixture was concentrated and the residue was dissolved in EtOAc (20 mL). The organic layer was washed with brine (20 mL×3), dried over anhydrous Na$_2$SO$_4$, filtered and concentrated to afford 94 mg (100%) of the title compound as a white solid which was used for next step without further purification.

Step 8: (3S,4S)-1-((4-(6-fluoro-1H-indol-3-yl)phenyl)-sulfonyl)pyrrolidine-3,4-diol A mixture of 3-[4-(3,4-Dihydroxy-pyrrolidine-1-sulfonyl)-phenyl]-6-fluoro-indole-1-carboxylic acid tert-butyl ester (204 mg, 0.428 mmol) in HCl (10 mL, in CH$_3$OH) was stirred at r.t for 3 h. The reaction mixture was concentrated and the residue was purified by prep-HPLC to afford 30 mg (19%) of the title compound as a white solid. LC-MS for C$_{18}$H$_{17}$FN$_2$O$_4$S—H$^−$ [M−H]$^−$: calcd: 375.1; found: 375.0. $^1$H NMR (400 MHz, DMSO-d$_6$) δ [ppm]11.66 (s, 1H), 7.96-7.87 (m, 4H), 7.82-7.75 (m, 2H), 7.26 (dd, J=14.4, 2.4Hz, 1H), 7.03-6.98 (m, 1H), 5.11 (brs, 2H), 3.86-3.83 (m, 2H), 3.35-3.33 (m, 2H), 3.11 (d, J=10.8Hz, 2H).

Example 67: 1-((4-(6-fluoro-1H-indol-3-yl)phenyl)sulfonyl)azetidine-3-carboxamide

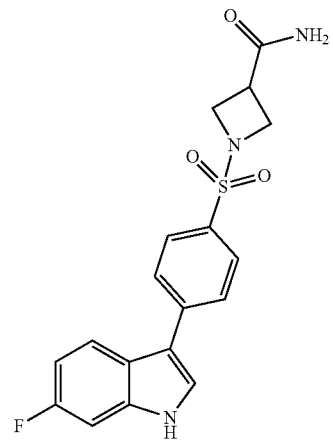 [SMILES: NC(=O)C1CN(S(=O)(=O)c2ccc(-c3c[nH]c4cc(F)ccc34)cc2)C1]

Step 1: 1-((4-(6-fluoro-1H-indol-3-yl)phenyl)sulfonyl)azetidine-3-carboxylic acid A mixture of 6-Fluoro-3-[4-(3-methoxycarbonyl-azetidine-1-sulfonyl)-phenyl]-indole-1-carboxylic acid tert-butyl ester (intermediate 3 in Example 63, 553.0 mg, 1.13 mmol), and NaOH (90.4 mg, 2.26 mmol) in MeOH (30 ml)/water (3 mL) was stirred at room temperature for 2 h. The mixture was acidified with 12M HCl to pH=5. The mixture was diluted with EtOAc (80 mL). The organic layer was washed with water (60 mL×3), dried over anhydrous Na$_2$SO$_4$, filtered and concentrated to afford 422 mg (100%) of the title compound as a white solid. LC-MS for C$_{18}$H$_{15}$FN$_2$O$_4$S+H$^+$ [M+H]$^+$: calcd: 375.1; found: 374.8.

Step 2: 1-((4-(6-fluoro-1H-indol-3-yl)phenyl)sulfonyl)-azetidine-3-carboxamide A mixture of 1-[4-(6-Fluoro-1H-indol-3-yl)-benzenesulfonyl]-azetidine-3-carboxylic acid (422 mg, 1.13 mmol), HATU (557 mg, 1.46 mmol) and DIEA (0.4 mL, 2.26 mmol) in THF/DMF (30 mL/5 mL) was stirred for 10 min. NH$_4$Cl (66 mg, 1.24 mmol) was added and the mixture was stirred overnight at room temperature under N$_2$. The mixture was diluted with EtOAc (80 mL). The organic layer was washed with water (60 mL×3), dried over anhydrous Na$_2$SO$_4$ and filtered. The filtrate was concentrated and purified by prepare HPLC to afford the title compound (100 mg, 23.7%) as a white solid. LC-MS for C$_{18}$H$_{16}$FN$_3$O$_3$S+H$^+$ [M+H]$^+$: calcd: 374.1; found: 373.8. $^1$H NMR (400 MHz, DMSO-d6) δ [ppm] 11.72 (s, 1H), 8.05-7.95 (m, 4H), 7.83 (d, J=8.4 Hz, 2H), 7.35 (br s, 1H), 7.28 (dd, J=9.8, 2.3 Hz, 1H), 7.03 (td, J=9.4, 2.3 Hz, 1H), 6.98 (s, 1H), 3.84-3.76 (m, 4H), 3.23-3.12 (m, 1H).

Example 68: N-(azetidin-3-yl)-4-(6-fluoro-1H-indol-3-yl)benzenesulfonamide

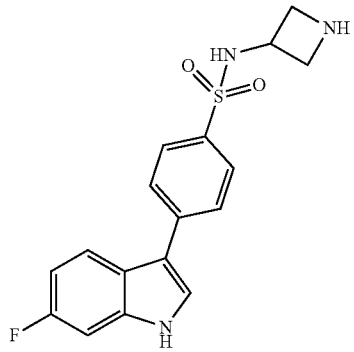 [SMILES: O=S(=O)(NC1CNC1)c1ccc(-c2c[nH]c3cc(F)ccc23)cc1]

Following the general method as outlined in Example 4, starting from azetidin-3-ylamine and 4-bromo-benzenesulfonyl chloride, the title compound was obtained as a white solid. LC-MS for $C_{17}H_{16}FN_3O_2S+H^+$ [M+H]$^+$: calcd: 346.1; found: 345.8. $^1$H NMR (400 MHz, DMSO-d$_6$) δ [ppm]11.72 (s, 1H), 8.05-7.89 (m, 4H), 7.81 (d, J=8.2 Hz, 2H), 7.29-7.26 (m, 1H), 7.03 (td, J=9.2, 2.0 Hz, 1H), 3.87 (dt, J=14.8, 3.9 Hz, 2H), 3.58-3.41 (m, 2H), 3.35-3.24 (m, 3H).

Example 69: N-(2-aminoethyl)-3-(6-fluoro-1H-indol-3-yl)-5-hydroxy-benzenesulfonamide

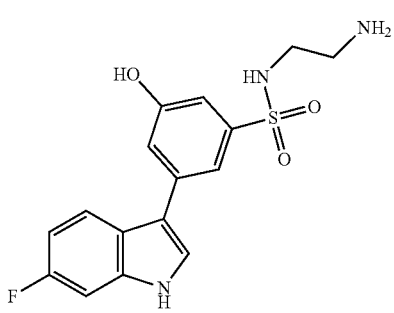 [SMILES: NCCNS(=O)(=O)c1cc(O)cc(-c2c[nH]c3cc(F)ccc23)c1]

To a solution of N-(2-Amino-ethyl)-3-(6-fluoro-1H-indol-3-yl)-5-methoxy-Benzenesulfonamide (Example 61, 100 mg, 0.27 mmol) in DCM (6 mL) was added BBr$_3$ (103 mg, 0.41 mmol) at 0° C. The mixture was stirred at room temperature overnight and concentrated to dryness. The residue was purified by prep-HPLC to afford the title compound (31 mg, 32%) as a white solid. LC-MS for $C_{16}H_{16}FN_3O_3S+H^+$[M+H]$^+$: calcd: 350.1; found: 349.8. $^1$H NMR (400 MHz, MeOD) δ [ppm] 7.86-7.82 (m, 1H), 7.60 (s, 1H), 7.56 (s, 1H), 7.33(s, 1H), 7.18-7.15 (m, 2H), 6.94 (dt, J=8.8, 1.6 Hz, 1H), 3.01 (t, J=6.4 Hz, 2H), 2.75 (t, J=6.4 Hz, 2H).

Example 70: 1-(6-fluoro-3-(4-(piperazin-1-ylsulfonyl)phenyl)-1H-indol-1-yl)ethanone

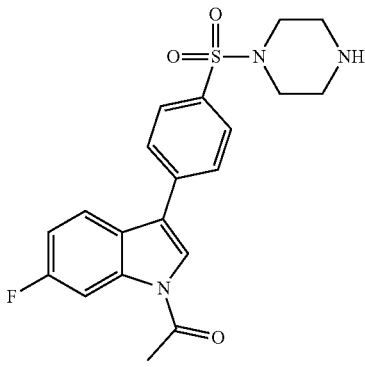 [SMILES: CC(=O)n1cc(-c2ccc(S(=O)(=O)N3CCNCC3)cc2)c2ccc(F)cc21]

The title compound was prepared following the general method as outlined in Example 47. $^1$H NMR (400 MHz, DMSO-d$_6$) δ [ppm] 8.41 (s, 1H), 8.35 (br s, 1H), 8.20 (dd, J=10.4, 2.0 Hz, 1H), 8.09 (d, J=8.4Hz, 2H), 7.96 (d, J=3.2 Hz, 1H), 7.89 (d, J=8.4 Hz, 2H), 7.29 (t, J=2.4 Hz, 1H), 3.13(s, 8H), 2.75 (s, 3H). LC-MS for $C_{20}H_{20}FN_3O_3S+H^+$ [M+H]$^+$: calcd.: 402.1; found: 401.8.

Example 71: 3-(3,5-dimethyl-4-(piperazin-1-ylsulfonyl)phenyl)-6-fluoro-1H-indole

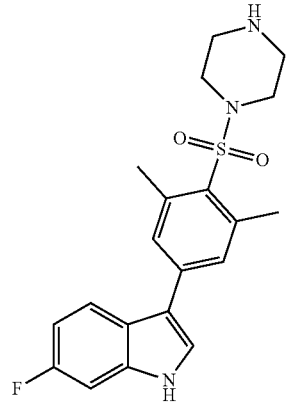 [SMILES: Cc1cc(-c2c[nH]c3cc(F)ccc23)cc(C)c1S(=O)(=O)N1CCNCC1]

Step 1: 4-bromo-2,6-dimethylbenzene-1-sulfonyl chloride

To a solution of 1-Bromo-3,5-dimethyl-benzene (370 mg, 2.0 mmol) in CHCl$_3$ (15 mL) at 0° C. was added HOSO$_2$Cl (1.45 g, 12.5 mmol). The solution was stirred at 0° C. for 2 h. The reaction mixture was poured into ice water (50 mL) and extracted with DCM (100 mL). The organic layer was washed with water and brine, dried over Na$_2$SO$_4$ and filtered. The filtrate was concentrated to afford the crude product (544 mg, 96%) as a yellow solid which was used in the next step without further purification.

Step 2: tert-butyl 4-((4-bromo-2,6-dimethylphenyl)sulfonyl)piperazine-1-carboxylate To a solution of 4-Bromo-2,6-dimethyl-benzenesulfonyl chloride (540 mg, 1.9 mmol) and piperazine-1-carboxylic acid tert-butyl ester (428 mg, 2.3 mmol) in DCM (20 mL) was added TEA (385 mg, 3.8 mmol). The solution was stirred at room temperature for 30 min and then water (30 mL) was added. The organic layer was washed with brine, dried over $Na_2SO_4$ and filtered. The filtrate was concentrated and purified by silica gel chromatography (PE:DCM=1:1 to 1:2, then MeOH:DCM=1:20) to afford the product (798 mg, 97%) as white solid.

$^1$H NMR (400 MHz, $CDCl_3$) δ [ppm] 7.33 (s, 2H), 3.46 (t, J=5.2Hz, 4H), 3.13 (t, J=5.2Hz, 4H), 2.63 (s, 6H), 1.45 (s, 9H).

Step 3: tert-butyl 3-(4-((4-(tert-butoxycarbonyl)piperazin-1-yl)sulfonyl)-3,5-dimethylphenyl)-6-fluoro-1H-indole-1-carboxylate To a solution of 6-fluoro-3-(4,4,5,5-tetramethyl-[1,3,2]dioxaborolan-2-yl)-indole-1-carboxylic acid tert-butyl ester (Intermediate 1, 433 mg, 1.2 mmol), 4-(4-bromo-2,6-dimethyl-benzenesulfonyl)-piperazine-1-carboxylic acid tert-butyl ester (433 mg, 1.0 mmol), $K_2CO_3$ (207 mg, 1.5 mmol) in dioxane/$H_2O$ (10 mL/2 mL) was added Pd(dppf)$Cl_2$ (30 mg) under $N_2$. The mixture was stirred at 60° C. overnight under $N_2$. The solvent was removed and the mixture was extracted with DCM (30 mL×4). The organic layer was washed with water and brine, dried over $Na_2SO_4$ and filtered. The filtrate was concentrated and the residue was purified with silica gel chromatography (PE:EtOAc=10:1 to 6:1) to afford the product (325 mg, 46% yield) as a yellow solid.

Step 4: 3-(3,5-dimethyl-4-(piperazin-1-ylsulfonyl)phenyl)-6-fluoro-1H-indole

To a solution of 3-[4-(4-tert-Butoxycarbonyl-piperazine-1-sulfonyl)-3,5-dimethyl-phenyl]-6-fluoro-indole-1-carboxylic acid tert-butyl ester (340 mg, 0.58 mmol) in DCM (15 mL) was added HCl/$Et_2O$ (15 mL). The reaction mixture was stirred at room temperature for 4 h. The solvent was removed and water (20 mL) was added. The pH was adjusted to 8 with $Na_2CO_3$ solution. The mixture was extracted with DCM (100 mL×3). The organic layer was washed with water and brine, dried over $Na_2SO_4$ and filtered. The filtrate was concentrated and the residue was purified by prep-HPLC to afford the product (120 mg, 53.6% yield) as a yellow solid. LC-MS for $C_{20}H_{22}FN_3O_2S$ [M+H]$^+$: calcd: 388.1; found: 387.9. $^1$H NMR (400 MHz, DMSO-$d_6$) δ [ppm] 11.65 (br s, 1H), 7.96 (dd, J=8.8, 5.6 Hz, 1H), 7.91 (d, J=2.4 Hz, 1H), 7.59 (s, 1H), 7.24 (dd, J=10.0, 2.4 Hz, 1H), 6.99 (dt, J=9.6, 2.4 Hz, 1H), 2.98 (t, J=4.8 Hz, 4H), 2.70 (t, J=4.8 Hz, 4H), 2.66 (s, 6H).

Example 72: N-(2-(1H-1,2,3-triazol-4-yl)ethyl)-4-(6-fluoro-1H-indol-3-yl)benzenesulfonamide

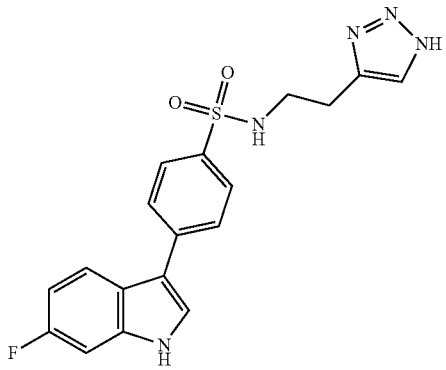 [SMILES: O=S(=O)(NCCc1c[nH]nn1)c1ccc(-c2c[nH]c3cc(F)ccc23)cc1]

Step 1: 4-bromo-N-(but-3-yn-1-yl)benzenesulfonamide

To a stirred solution of 4-bromo-benzenesulfonyl chloride (4.8 g, 18.8 mmol) in DCM (100 mL) at 0° C. was added 3-butynylamine HCl salt (2.0 g, 19.0 mmol). Then DIEA (7.3 g, 56.3 mmol) was added dropwise and the mixture was stirred at room temperature for 2 h. The mixture was diluted with water (30 mL) and extracted with DCM (50 mL×3). The organic layer was washed with brine (30 mL), dried over anhydrous $Na_2SO_4$ and filtered. The filtrate was concentrated and purified by silica gel chromatography (PE/EtOAc=5/1) to afford 300 mg (62.8%) of the title compound as a white solid. $^1$H NMR (400 MHz, DMSO-$d_6$) δ [ppm] 7.96 (t, J=5.8 Hz,1H), 7.82 (d, J=8.8 Hz, 2H), 7.72 (d, J=8.4 Hz, 2H), 2.90-2.84 (m, 3H), 2.30-2.26 (m, 2H).

Step 2: N-(2-(1H-1,2,3-triazol-4-yl)ethyl)-4-bromobenzenesulfonamide

To a stirred solution of 4-bromo-N-but-3-ynyl-benzenesulfonamide (1.0 g, 3.47 mmol) in DMF (10 mL) at room temperature was added CuI (33 mg, 0.17 mmol) and TMSN$_3$ (2.0 g, 17.36 mmol). The mixture was stirred at 90° C. for 6 h before it was cooled. The mixture was diluted with water (30 mL) and extracted with EtOAc (50 mL×3). The organic layer was washed with brine (30 mL), dried over anhydrous $Na_2SO_4$ and filtered. The filtrate was concentrated and purified by silica gel chromatography to afford 0.8 g (70.0%) of the title compound as a yellow solid. $^1$H NMR (400 MHz, DMSO-$d_6$) δ [ppm] 7.85 (br s, 1H), 7.77 (d, J=8.4 Hz, 2H), 7.67 (d, J=8.0 Hz, 2H), 7.55 (br s, 1H), 2.98 (q, J=6.8 Hz, 2H), 2.74-2.70 (m, 2H).

Step 3: tert-butyl 3-(4-(N-(2-(1H-1,2,3-triazol-4-yl)ethyl)-sulfamoyl)phenyl)-6-fluoro-1H-indole-1-carboxylate A mixture of 4-bromo-N-[2-(1H-[1,2,3]triazol-4-yl)-ethyl]-benzenesulfonamide (600 mg, 1.82 mmol), 6-fluoro-3-(4,4,5,5-tetramethyl-[1,3,2]dioxaborolan-2-yl)-indole-1-carboxylic acid tert-butyl ester (Intermediate 1, 656 mg, 1.82 mmol), $K_2CO_3$ (376 mg, 2.73 mmol) and Pd(dppf)$Cl_2$ (133 mg, 0.18 mmol) in dioxane/$H_2O$ (10 mL/2 mL) was stirred at 100° C. under $N_2$ overnight. The mixture was diluted with water (30 mL) and extracted with DCM (50 mL×3). The organic layer was washed with brine (30 mL), dried over anhydrous Na$_2$SO$_4$ and filtered. The filtrate was concentrated and purified by prep-TLC (PE/EtOAc=2/1) to afford 300 mg of the title compound as a light yellow solid.

Step 4: N-(2-(1H-1,2,3-triazol-4-yl)ethyl)-4-(6-fluoro-1H-indol-3-yl)benzenesulfonamide To the mixture of 6-fluoro-3-{4-[2-(1H-[1,2,3]triazol-4-yl)-ethylsulfamoyl]-phenyl}-indole-1-carboxylic acid tert-butyl ester (300 mg, 0.41 mmol) in DCM (2 mL) was added TFA (3 mL). The reaction was stirred at room temperature for 2 h. The mixture was quenched with aq NaHCO$_3$ and the pH was adjusted to 8-10. The solvent was removed and the residue was purified by prep-HPLC (NH$_4$HCO$_3$ as additive) to afford 14.5 mg (9.2%) of the title compound as a white powder. LC-MS for C$_{18}$H$_{16}$FN$_5$O$_2$S+H$^+$ [M+H]$^+$: calcd: 386.1; found: 385.8. $^1$H NMR (400 MHz, DMSO-d$_6$) δ [ppm] 11.67 (br s, 1H), 7.97-7.89 (m, 5H), 7.83-7.74 (m, 3H), 7.25 (dd, J=9.6, 2.4 Hz, 1H), 7.03-6.97 (m, 1H), 3.32 (s, 1H), 3.07-3.01 (m, 2H), 2.82-2.77 (m, 2H).

Example 73: N-(2-(1H-imidazol-2-yl)ethyl)-4-(6-fluoro-1H-indol-3-yl)benzenesulfonamide

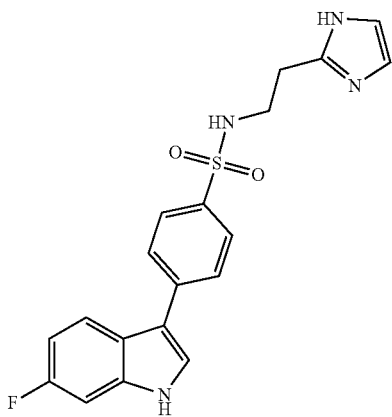 [SMILES: O=S(=O)(NCCc1ncc[nH]1)c1ccc(-c2c[nH]c3cc(F)ccc23)cc1]

Step 1: tert-butyl 2-(2-((tert-butoxycarbonyl)amino)ethyl)-1H-imidazole-1-carboxylate The mixture of 2-(1H-imidazol-2-yl)ethanamine hydrochloride (480 mg, 3.25 mmol), tert-butyldicarbonate (1.56 g, 7.15 mmol) and TEA (1.64 g, 16.30 mmol) in DCM (20 mL) was stirred at room temperature overnight. The mixture was diluted with DCM (50 mL), washed with brine, dried over Na$_2$SO$_4$, filtered and concentrated. The residue was purified by silica gel chromatography (PE/EtOAc=5/1) to afford the title compound (720 mg, 71%) as colorless oil. $^1$H NMR (400 MHz, DMSO-d$_6$) δ [ppm] 7.43 (s, 1H), 6.84 (s, 1H), 6.79 (br s, 1H), 3.33-3.26 (m, 2H), 3.02 (t, J=9.2 Hz, 2H), 1.57 (s, 9H), 1.20 (s, 9H).

Step 2: tert-butyl 2-(2-(4-bromo-N-(tert-butoxycarbonyl-phenylsulfonamido)-ethyl)-1H-imidazole-1-carboxylate To a solution of 2-(2-tert-Butoxycarbonylamino-ethyl)-imidazole-1-carboxylic acid tert-butyl ester (720 mg, 2.3 mmol) in dry THF (10 mL) at −78° C. was added LiHMDS (2.12 mL, 2.8 mmol) under N$_2$. The mixture was stirred at −78° C. for 30 min. Then a solution of (4-bromophenyl) chlorosulfone (613 mg, 3.5 mmol) in THF (10 mL) was added. The mixture was stirred at −78° C. for 2 hs before it was quenched with aqueous NH$_4$Cl and extracted with EtOAc (30 mL×3). The combined organic layer was washed with brine, dried over Na$_2$SO$_4$, filtered and concentrated. The residue was purified by silica gel chromatography (PE/EtOAc=5/1) to afford the title compound (958 mg, 78%) as a yellow solid. $^1$H NMR (400 MHz, DMSO-d$_6$) δ [ppm] 7.86 (s, 4H), 7.48 (s, 1H), 6.88 (s, 1H), 4.19 (t, J=6.4 Hz, 2H), 3.29 (t, J=6.4 Hz, 2H), 1.57 (s, 9H), 1.20 (s, 9H).

Step 3: tert-butyl 3-(4-(N-(tert-butoxycarbonyl)-N-(2-(1-(tert-butoxycarbonyl)-1H-imidazol-2-yl)ethyl)sulfamoyl)phenyl)-6-fluoro-1H-indole-1-carboxylate A mixture of tert-butyl 6-fluoro-3-(4,4,5,5-tetramethyl(1,3,2-dioxaborolan-2-yl))indolecarboxylate (652 mg, 1.8 mmol), 2-(2-{(tert-butoxy)-N-[(4-bromophenyl)-sulfonyl]carbonylamino}ethyl)imidazolecarboxylate (958 mg, 1.8 mmol), K$_2$CO$_3$ (745 mg, 5.4 mmol) and Pd(dppf)Cl$_2$ (131 mg, 0.18 mmol) in 1,4-dioxane/H$_2$O (20 mL/2 mL) was stirred at 95° C. under N$_2$ overnight. The mixture was concentrated and the residue was diluted with EtOAc (100 mL). The organic layer was washed with brine, dried over anhydrous Na$_2$SO$_4$, filtered and concentrated to afford the title compound (989 mg, crude) as a brown solid. The solid was used for the next step directly.

Step 4: N-(2-(1H-imidazol-2-yl)ethyl)-4-(6-fluoro-1H-indol-3-yl)benzenesulfonamide The mixture of tert-butyl 3-(4-(N-(tert-butoxycarbonyl)-N-(2-(1-(tert-butoxycarbonyl)-1H-imidazol-2-yl)ethyl)sulfamoyl)phenyl)-6-fluoro-1H-indole-1-carboxylate (989 mg, crude, 1.45 mmol) and TFA (5 mL) in DCM (15 mL) was stirred at room temperature for 4 h. The mixture was concentrated. The residue was neutralized with aqueous NaHCO$_3$, and extracted with EtOAc (30 mL×3). The organic layer was washed with brine, dried over anhydrous Na$_2$SO$_4$, filtered and concentrated. The residue was purified by prep-HPLC to afford the title compound (26.9 mg, 4.8%) as a yellow solid. LC-MS for C$_{19}$H$_{17}$FN$_4$O$_2$S+H$^+$ [M+H]$^+$: calcd: 385.1; found: 384.8. $^1$H NMR (400 MHz, DMSO-d$_6$) δ [ppm] 11.93 (br s, 1H), 11.65 (s, 1H), 7.96-7.89 (m, 4H), 7.81 (d, J=8.4 Hz, 2H), 7.77-7.72 (m, 1H), 7.25 (dd, J=10.0, 2.4 Hz, 1H), 7.00 (td, J=9.2, 2.0 Hz, 1H), 6.88 (s, 2H), 3.10-3.05 (m, 2H), 2.77 (t, J=8.0 Hz, 2H).

Example 74: (3R,4R)-1-((4-(6-fluoro-1H-indol-3-yl)phenyl)-sulfonyl)pyrrolidine-3,4-diol

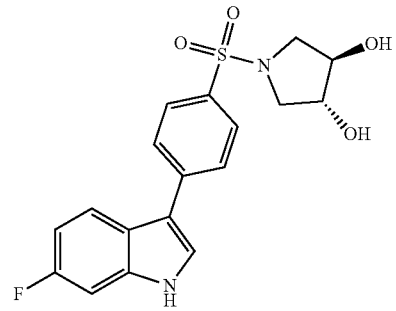 [SMILES: O=S(=O)(c1ccc(-c2c[nH]c3cc(F)ccc23)cc1)N1C[C@@H](O)[C@H](O)C1]

Following the general method as outlined in Example 66, starting from (2S,3S)-2, 3-dihydroxysuccinic acid, the title compound was obtained as a white solid. LC-MS for C$_{18}$H$_{17}$FN$_2$O$_4$S+H$^+$ [M+H]$^+$: calcd: 377.1; found: 376.8. $^1$H NMR (400 MHz, DMSO-d$_6$) δ [ppm]11.67 (br s, 1H), 7.95-7.86 (m, 4H), 7.83-7.77 (m, 2H), 7.30-7.24 (m, 1H), 7.05-6.96 (m, 2H), 5.12-5.09 (m, 2H), 3.89-3.83 (m, 2H), 3.46-3.32 (m, 2H), 3.11 (d, J=10.8 Hz, 2H).

Example 75: 3-(3,5-difluoro-4-(piperazin-1-ylsulfonyl)phenyl)-6-fluoro-1H-indole

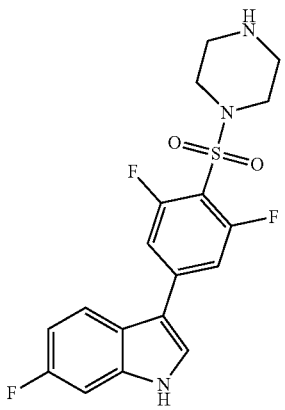 [SMILES: O=S(=O)(c1c(F)cc(-c2c[nH]c3cc(F)ccc23)cc1F)N1CCNCC1]

Following the general method as outlined in Example 76, starting from 1-Bromo-3, 5-difluoro-benzene, the title compound was obtained as a white solid. LC-MS for C$_{18}$H$_{16}$F$_3$N$_3$O$_2$S+H$^+$ [M+H]$^+$: calcd: 396.1; found: 396.0
$^1$H NMR (400 MHz, DMSO-d$_6$) δ [ppm] 11.90 (s, 1H), 8.14 (d, J=2.0 Hz, 1H), 8.01 (dd, J=8.8, 3.6 Hz, 1H), 7.65 (d, J=11.2 Hz, 2H), 7.28 (dd, J=9.6, 2.0 Hz, 1H), 7.04 (dt, J=9.2, 2.4 Hz, 1H), 3.03 (s, 4H), 2.78 (t, J=4.8 Hz, 4H).

Example 76: 3-(3,5-dichloro-4-(piperazin-1-ylsulfonyl)phenyl)-6-fluoro-1H-indole

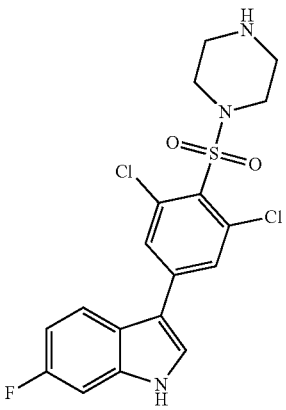 [SMILES: O=S(=O)(c1c(Cl)cc(-c2c[nH]c3cc(F)ccc23)cc1Cl)N1CCNCC1]

Step 1: 4-bromo-2,6-dichlorobenzene-1-sulfonyl chloride

The solution of 1-Bromo-3,5-dichloro-benzene (3.0 g, 13.3 mmol) in HOSO$_2$Cl (10 mL) was stirred at 60° C. for 2 h. The reaction mixture was diluted with DCM (200 mL) and washed with water and brine, dried over Na$_2$SO$_4$ and filtered. The filtrate was concentrated to give the crude product (2.6 g, 60.5%) as a yellow solid which was used in the next step without further purification. Steps 2, 3 and 4 were performed as described for Example 71. The title compound was obtained as a white solid. LC-MS for Cl$_8$H$_{16}$Cl$_2$FN$_3$O$_2$S [M+H]$^+$: calcd: 428.1; found: 427.9. $^1$H NMR (400 MHz, DMSO-d$_6$) δ [ppm] 11.92 (s, 1H), 8.16 (s, 1H), 7.94-7.90 (m, 3H), 7.28 (dd, J=9.6, 2.4 Hz, 1H), 7.06 (dt, J=8.8, 2.0 Hz, 1H), 3.20 (t, J=4.8 Hz, 4H), 2.73 (t, J=4.8 Hz, 4H).

Example 77: (R)-1-((4-(6-fluoro-1H-indol-3-yl)phenyl)sulfonyl)-pyrrolidin-3-ol

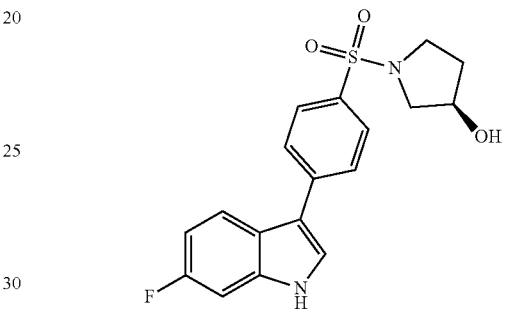

Following the general method as outlined in Example 66, starting from (R)-2-hydroxysuccinic acid, the title compound was obtained as a white solid. LC-MS for C$_{18}$H$_{17}$FN$_2$O$_3$S+H+[M+H]$^+$: calcd: 361.1; found: 360.8. $^1$H NMR (400 MHz, DMSO-d6) δ [ppm]11.67 (s, 1H), 7.95-7.91 (m, 4H), 7.81-7.79 (m, 2H), 7.26 (dd, J=9.6, 2.0 Hz, 1H), 7.01 (td, J=10.0, 2.4 Hz, 1H), 4.93 (d, J=3.2 Hz, 1H), 4.18-4.17 (m, 1H), 3.37-3.23 (m, 3H), 3.04-3.01 (m, 1H), 1.78-1.74 (m, 1H), 1.66-1.64 (m, 1H).

Example 78: 6-fluoro-3-(4-(piperazin-1-ylsulfonyl)phenyl)-1H-indole-1-carboxamide

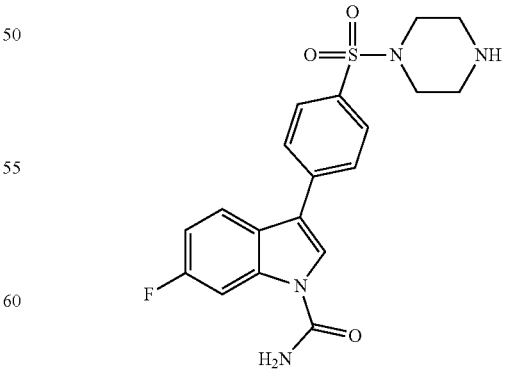

The title compound was prepared following the general method as outlined in Example 47. LC-MS for C$_{19}$H$_{19}$FN$_4$O$_3$S+H[M+H]$^+$: calcd.: 403.1; found: 402.9

$^1$H NMR (400 MHz, DMSO-d$_6$) δ [ppm] 9.33 (br s, 1H), 8.51 (s, 1H), 8.13 (dd, J=10.4, 2.4 Hz, 1H), 8.03 (d, J=8.4Hz, 2H), 7.96-7.87 (m, 4H), 7.20 (td, J=8.8, 2.0Hz, 1H), 3.25-3.15 (m, 8H).

Example 79: (S)-1-((4-(6-fluoro-1H-indol-3-yl)phenyl)sulfonyl)-pyrrolidin-3-ol

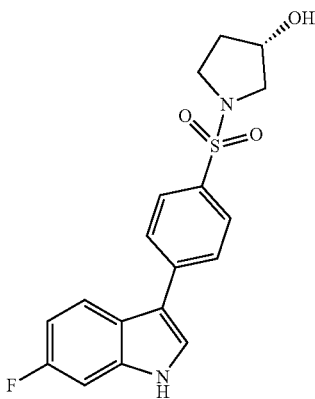 [SMILES: O=S(=O)(c1ccc(-c2c[nH]c3cc(F)ccc23)cc1)N1CC[C@H](O)C1]

Following the general method as outlined in Example 66, starting from (S)-2-hydroxysuccinic acid, the title compound was obtained as a white solid. LC-MS for C$_{18}$H$_{17}$FN$_2$O$_3$S+H$^+$ [M+H]$^+$: calcd: 361.1; found: 360.8. $^1$H NMR (400 MHz, DMSO-d$_6$) δ [ppm]11.68 (s, 1H), 7.98-7.90 (m, 4H), 7.82 (d, J=8.4 Hz, 2H), 7.27 (dd, J=9.8, 2.3 Hz, 1H), 7.02 (td, J=9.4, 2.4 Hz, 1H), 4.94 (d, J=3.5 Hz, 1H), 4.19 (d, J=2.7 Hz, 1H), 3.34-3.21 (m, 3H), 3.05 (dd, J=10.5, 1.4 Hz, 1H), 1.85-1.72 (m, 1H), 1.70-1.60 (m, 1H).

Example 80: (3S,4S)-4-fluoro-1-{[4-(6-fluoro-1H-indol-3-yl)phenyl]sulfonyl}pyrrolidin-3-amine

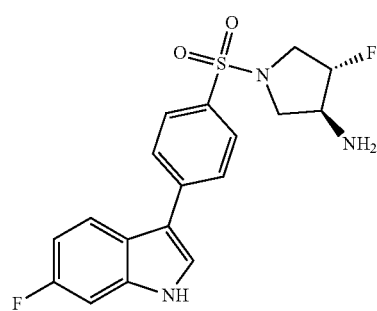 [SMILES: N[C@H]1CN(S(=O)(=O)c2ccc(-c3c[nH]c4cc(F)ccc34)cc2)C[C@@H]1F]

Step 1: tert-butyl ((3S,4S)-1-((4-bromophenyl)sulfonyl)-4-fluoropyrrolidin-3-yl)carbamate To a colorless solution of p-bromophenylsulfonyl chloride (250.3 mg, 0.98 mmol) in DCM (25 mL) was added tert-butyl ((3S,4S)-4-fluoropyrrolidin-3-yl)carbamate (200 mg, 0.98 mmol) and Et$_3$N (99.1 mg, 0.98 mmol) at 0° C. The colorless solution was stirred at 0-20° C. for 1 hour. The reaction was quenched with water (20 mL), washed with saturated NaHCO$_3$ (20 mL), water (20 mL) and brine (20 mL). The organic phase was dried over anhydrous Na$_2$SO$_4$, filtered, and concentrated in vacuum to afford a crude solid (320 mg). The residue was purified by flash chromatography (silica gel, EtOAc/Petroleum Ether=0% to 30%) to afford the title compound (200 mg, yield: 63%) as a white solid.

Step 2: (3S,4S)-4-fluoro-1-((4-(6-fluoro-1H-indol-3-yl)phenyl)sulfonyl)-pyrrolidin-3-amine To a suspension of tert-butyl ((3S, 4S)-1-((4-bromophenyl)sulfonyl)-4-fluoropyrrolidin-3-yl)carbamate (150 mg, 0.415 mmol), tert-butyl 6-fluoro-3-(4,4,5,5-tetramethyl-1,3,2-dioxaborolan-2-yl)-1H-indole-1-carboxylate (Intermediate 1; 134 mg, 0.415 mmol) and Cs$_2$CO$_3$ (271 mg, 0.831 mmol) in dioxane (9 mL) and H$_2$O (3 mL) was added PdCl$_2$(dppf) (30.4 mg, 0.0415 mmol) under N$_2$. The reaction mixture was stirred at 100° C. for 16 hours. The resulting mixture was diluted with water (15 mL) and then extracted with EtOAc (15 mL×2). The organic layer was washed with brine (15 mL), dried over anhydrous Na$_2$SO$_4$, filtered and concentrated under reduced pressure to dryness to give crude solid (197 mg), to which was added DCM (10 mL) and TFA (1 mL). The mixture was stirred for 1 hour at 25° C., concentrated, added the NH$_3$.H$_2$O (3 mL) to pH=9-10 and then extracted with EtOAc (15 mL×2).

The organic layer was washed with brine (10 mL), dried over anhydrous Na$_2$SO$_4$, filtered and concentrated under reduced pressure to dryness to give a crude solid 137 mg, The crude solid was submitted to purification by preparative HPLC. (Column: DuraShell 150*25 mm*5 um, Mobil phase: from 32% CH$_3$CN in H$_2$O (0.05% ammonia-ACN) to 52% CH$_3$CN in H$_2$O (0.05% ammonia-ACN)). Most of MeCN was removed under reduced pressure, and the solvent was removed by lyophilization to afford the title compound (51.62 mg with 98.5% HPLC purity, 30% of yield) as a white solid. $^1$H NMR (400 MHz, DMSO-d6) δ [ppm] 11.68 (br. s., 1H), 7.92 (d, J=6.8 Hz, 4H), 7.82 (d, J=8.3 Hz, 2H), 7.27 (dd, J=2.0, 9.8 Hz, 1H), 7.01 (dt, J=2.3, 9.3 Hz, 1H), 4.85-4.66 (m, 1H), 3.67-3.36 (m, 4H), 3.09 (d, J=10.0 Hz, 1H), 1.68 (br. s., 2H).

Example 81: (+)-(cis)-4-fluoro-1-{[4-(6-fluoro-1H-indol-3-yl)phenyl]-sulfonyl}pyrrolidin-3-amine

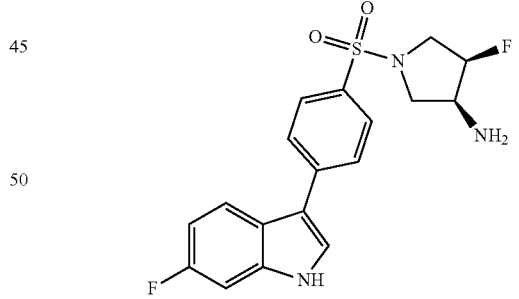

Step 1: tert-butyl ((cis)-1-((4-bromophenyl)sulfonyl)-4-fluoropyrrolidin-3-yl)carbamate To a yellow solution of tert-butyl ((cis)-4-fluoropyrrolidin-3-yl)carbamate (200 mg, 0.98 mmol) and p-bromophenylsulfonyl chloride (300 mg, 1.18 mmol, 1.2 eq.) in CH$_2$Cl$_2$ (9.8 mL) was added TEA (0.27 mL, 1.96 mmol, 2.0 eq.) at 0° C. The yellow solution was warmed to 20° C. and stirred 20° C. for 15 hours. The reaction was quenched with saturated NaHCO$_3$ solution and extracted with EtOAc (15 mL*2). The combined organic layers were washed with brine (15 mL). The solvent was removed in vacuo to afford title compound (467 mg, 100%) as a yellow solid. LC-MS m/z=324.9.

Step 2: tert-butyl ((cis)-4-fluoro-1-((4-(6-fluoro-H-indol-3-yl)-phenyl)sulfonyl)pyrrolidin-3-yl)carbamate A mixture of tert-butyl ((cis)-1-((4-bromophenyl)sulfonyl)-4-fluoropyrrolidin-3-yl)carbamate (467 mg, 0.979 mmol), tert-butyl 6-fluoro-3-(3,3,4,4-tetramethylborolan-1-yl)-1H-indole-1-carboxylate (Intermediate 1, 677 mg, 1.08 mmol), $PdCl_2(dppf)CH_2Cl_2$ (73.1 mg, 0.0979 mmol) and $Cs_2CO_3$ (957 mg, 2.94 mmol) in 1,4-dioxane (8.0 mL) and water (2.0 mL) was bubbled with nitrogen for 1 min and the reaction mixture was stirred at 100° C. for 15 hours. The reaction was concentrated to dryness. The residue was purified by column chromatography (20 g silica gel, MeOH/DCM=1~5%) to afford crude product (488 mg, 100%) as a yellow solid. The crude product was further purified by preparative HPLC. The desired fractions were combined and evaporated in vacuo to afford the title compound (255 mg, 54.5%) as a yellow solid. Separation by chiral SFC afforded the two separated enantiomers, a first eluting (Enantiomer A, peak 1, 134 mg, 52.5%) as a yellow solid and a second eluting (Enantiomer B, peak 2, 179 mg, 70.2%) as a yellow solid.

Step 3: (+)-(cis)-4-fluoro-1-((4-(6-fluoro-H-indol-3-yl)phenyl)-sulfonyl)pyrrolidin-3-amine To a solution of tert-butyl ((cis)-4-fluoro-1-((4-(6-fluoro-1H-indol-3-yl)phenyl)-sulfonyl)pyrrolidin-3-yl)carbamate (Enantiomer A, 134 mg, 0.280 mmol) in $CH_2Cl_2$ (3 mL) was added HCl/EtOAc (4M, 10 mL) at 0° C. and stirred at 0-18° C. for 2 h. The reaction solution was concentrated in vacuo at 20° C. The residue was redissolved in MeOH and basified with ammonia (3 mL). Then, the basified solution was combined with the previous batch. The solvent was then removed in vacuo and purified by prep-HPLC. The desired fractions were combined. The solvent was removed in vacuo and dried by lyophilization to afford the title compound (50 mg, 47.2%) as a white solid. LC-MS m/z=377.9 (M+H)$^+$. $^1$H NMR (400 MHz, DMSO-d6) δ [ppm]11.66 (br. s., 1H), 7.96-7.83 (m, 6H), 7.30-7.22 (m, 1H), 7.00 (dt, J=2.0, 9.3 Hz, 1H), 4.86-4.64 (m, 1H), 3.61-3.46 (m, 2H), 3.16 (dd, J=4.0, 13.6 Hz, 2H), 2.88-2.69 (m, 2H), 2.47-2.39 (m, 1H). $[α]^{20}_D$+67.9° (c=1.085 mg/mL, MeOH).

Example 82: (3R,4R)-4-fluoro-1-{[4-(6-fluoro-1H-indol-3-yl)phenyl]sulfonyl}pyrrolidin-3-amine

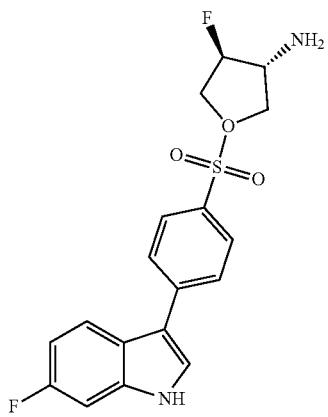

Step 1: tert-butyl ((3R,4R)-1-((4-bromophenyl)sulfonyl)-4-fluoropyrrolidin-3-yl)carbamate This Step was performed as described for Example 81, Step 1.

Step 2: tert-butyl ((trans)-4-fluoro-1-((4-(6-fluoro-1H-indol-3-yl)phenyl)sulfonyl)pyrrolidin-3-yl)carbamate A red suspension of tert-butyl 6-fluoro-3-(4,4,5,5-tetramethyl-1,3,2-dioxaborolan-2-yl)-1H-indole-1-carboxylate (Intermediate 1, 500 mg, 1.38 mmol), tert-butyl ((trans)-1-((4-bromophenyl)sulfonyl)-4-fluoropyrrolidin-3-yl)carbamate (586 mg, 1.38 mmol), $PdCl_2(dppf)$ (101 mg, 0.138 mmol) and $Cs_2CO_3$ (902 mg, 2.77 mmol) in dioxane (12 mL) and $H_2O$ (4 mL) was stirred at 100° C. under $N_2$ atmosphere for 6 hours. The reaction was diluted with EtOAc (50 mL) and separation. The organic layer was washed with brine (20 mL), dried over anhydrous $Na_2SO_4$ and concentrated to dryness to give crude tert-butyl ((trans)-4-fluoro-1-((4-(6-fluoro-1H-indol-3-yl)phenyl)sulfonyl)pyrrolidin-3-yl)carbamate (640 mg) as dark oil, which was used for next step directly.

Step 3: (−)-(3R,4R)-4-fluoro-1-((4-(6-fluoro-1H-indol-3-yl)phenyl)-sulfonyl)pyrrolidin-3-amine A solution of tert-butyl ((trans)-4-fluoro-1-((4-(6-fluoro-1H-indol-3-yl)phenyl)-sulfonyl)pyrrolidin-3-yl)carbamate (640 mg, 1.38 mmol) in 4M HCl/EtOAc (30 mL) was stirred at 15° C. for 1 hour. The resulting black reaction mixture was concentrated to dryness. The residue was basified with sat.NaHCO$_3$ (10 mL) and then extracted with EtOAc (30 mL×2). The combined organic layer was washed with brine (30 mL), dried over anhydrous $Na_2SO_4$ and concentrated to dryness to give crude product (500 mg), which was purified with prep-HPLC. The obtained solution was concentrated to give the racemic product (400 mg) as an off-white solid. The racemic product solid was further purified by chiral SFC. The first eluting product was concentrated and then lyophilized to give the title compound as a white solid. LC-MS: 377.8 (M+H)$^+$. $^1$H NMR (400MHz, DMSO-d6) δ [ppm] 11.67 (br. s., 1H), 8.14-7.70 (m, 6H), 7.42-6.83 (m, 2H), 4.99-4.49 (m, 1H), 3.70-3.40 (m, 4H, overlapping with H2O signal), 3.20-3.00 (m, 1H), 1.90-1.55 (m, 2H). $^1$H NMR (400MHz, CD3OD) δ [ppm] 7.92-7.85 (m, 5H), 7.66 (s, 1H), 7.16 (dd, J=2.3, 9.5 Hz, 1H), 6.98-6.90 (m, 1H), 4.90-4.80 (m, 0.5H, overlapping with H2O signal), 4.80-4.65 (m, 0.5H), 3.76-3.61 (m, 1H), 3.57-3.45 (m, 3H), 3.22-3.15 (m, 1H). $[α]^{20}_D$−1.3° (c=1.5 mg/ml, MeOH).

Example 83: (−)-(cis)-4-fluoro-1-((4-(6-fluoro-1H-indol-3-yl)-phenyl)sulfonyl)-pyrrolidin-3-amine

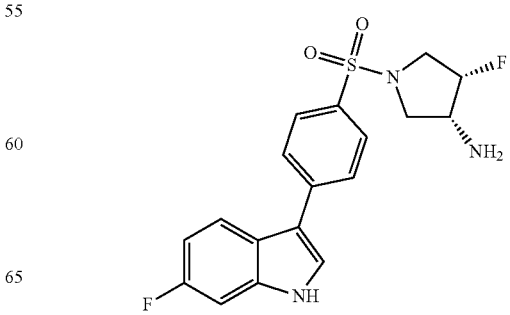

This Example was obtained as described for Example 81, Step 3, starting with the Enantiomer B (second eluting enantiomer) of the Intermediate of Step 2. LC-MS m/z=378.0 (M+H)⁺. ¹H NMR (400MHz, DMSO-d6) δ[ppm] 11.65 (br. s., 1H), 7.97-7.83 (m, 6H), 7.26 (dd, J=2.3, 9.8 Hz, 1H), 7.01 (dt, J=2.3, 9.2 Hz, 1H), 4.85-4.65 (m, 1H), 3.64-3.44 (m, 2H), 3.20-3.03 (m, 2H), 2.87-2.66 (m, 2H), 2.44 (t, J=10.5 Hz, 1H). [α]²⁰$_D$-12.9° (c=0.8 mg/ml, MeOH).

Example 84: 2-[(1-{[4-(6-fluoro-1H-indol-3-yl)phenyl]sulfonyl}piperidin-4-yl)-oxy]acetamide

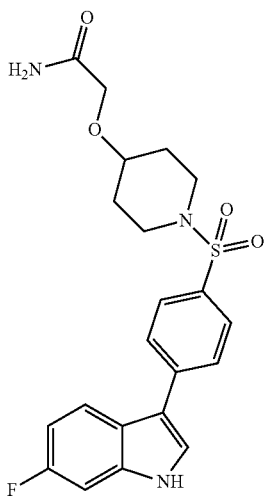 [SMILES: NC(=O)COC1CCN(S(=O)(=O)c2ccc(-c3c[nH]c4cc(F)ccc34)cc2)CC1]

Step 1: 2-((1-((4-bromophenyl)sulfonyl)piperidin-4-yl)oxy)acetamide

To a solution of 2-(piperidin-4-yloxy)acetamide (180 mg, 0.92 mmol) and p-bromophenylsulfonyl chloride (283 mg, 1.11 mmol, 1.2 eq.) in CH₂Cl₂ (9.25 mL) was added TEA (280 mg, 0.39 mL, 2.8 mmol, 3.0 eq.) at 0° C. Then, the yellow solution was warmed to 20° C. and stirred 20° C. for 4 hour. Most of CH₂Cl₂ was removed in vacuo. The residue was diluted with PE and filtered. After washing with PE/EtOAc (30:1), the solid was dried under vacuum to afford a crude (645 mg, >100%) as a white solid, which was used as such for the next step.

Step 2. 2-((1-((4-(6-fluoro-1H-indol-3-yl)phenyl)sulfonyl)piperidin-4-yl)-oxy)acetamide A mixture of tert-butyl 6-fluoro-3-(3,3,4,4-tetramethylborolan-1-yl)-1H-indole-1-carboxylate (Intermediate 1, 200 mg, 0.55 mmol), 2-((1-((4-bromophenyl)sulfonyl)piperidin-4-yl)oxy)acetamide (418 mg), PdCl₂(dppf)CH₂Cl₂(41 mg, 0.055 mmol) and Cs₂CO₃ (722 mg, 2.21 mmol) in 1,4-dioxane (8 mL) and water (2 mL) was bubbled with nitrogen for 1 min and the reaction mixture was stirred at 100° C. for 15 hours. The reaction solution was diluted with MeOH and concentrated in vacuo to dryness. The residue was purified by Column Chromatography (40 g silica gel, MeOH/DCM=1~8%) to give a crude product (248 mg, >100%) as a yellow solid, which was further purified by prep-HPLC. The solvent was removed in vacuo and dried by lyophilization to afford the title compound (90 mg, 37.7%) as a white solid. LC-MS m/z=431.9 (M+H)⁺. ¹H NMR (DMSO-d6, 400MHz): δ [ppm]11.67 (br. s., 1H), 7.89-7.98 (m, 4H), 7.75 (d, J=8.5 Hz, 2H), 7.26 (dd, J=9.8, 2.3 Hz, 1H), 7.19 (br. s., 1H), 7.07 (br. s., 1H), 7.01 (td, J=9.2, 2.3 Hz, 1H), 3.73 (s, 2H), 3.40 (dt, J=7.5, 3.8 Hz, 1H), 3.17-3.26 (m, 2H), 2.78 (t, J=8.3 Hz, 2H), 1.82-1.92 (m, 2H), 1.54-1.69 ppm (m, 2H).

Example 85: 4-(6-fluoro-1H-indol-3-yl)-N-[1-(4-methyl-4H-1,2,4-triazol-3-yl) ethyl]benzenesulfonamide

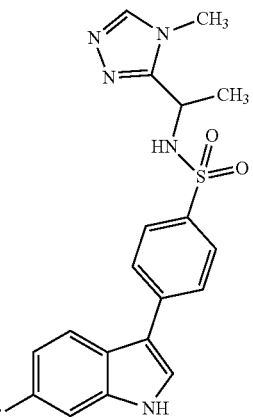

Following the general method as outlined in Example 84, starting from [1-(4-methyl-4H-1,2,4-triazol-3-yl)ethylamine, the title compound was obtained as a white solid. ¹H NMR (400MHz, DMSO-d6): δ [ppm] 11.67 (br. s, 1H), 8.32-8.28 (m, 2H), 7.94-7.88 (m, 4H), 7.81-7.79 (m, 2H), 7.28-7.25 (dd, 1H), 7.04-7.02 (dt, 1H), 4.71-4.66 (m, 1H), 3.58 (s, 3H), 1.32-1.30 (d, 3H); LC-MS: m/z 400.1 [M+H]⁺.

Example 86: 4-(6-fluoro-1H-indol-3-yl)-N-[(4-methyl-5-oxomorpholin-2-yl)methyl]benzenesulfonamide

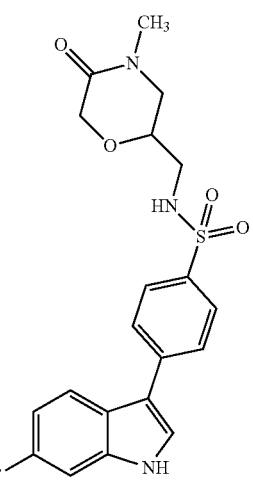

Following the general method as outlined in Example 80, starting from 6-(aminomethyl)-4-methylmorpholin-3-one, the title compound was obtained as a yellow solid. $^1$H NMR (400MHz, DMSO-d6) δ [ppm] 11.67 (br, 1H), 8.00-7.87 (m, 5H), 7.86-7.80 (m, 2H), 7.27 (dd, J=2.3, 9.8 Hz, 1H), 7.06-6.97 (m, 1H), 4.07-3.90 (m, 2H), 3.82 (dd, J=4.9, 8.4 Hz, 1H), 3.27-3.15 (m, 2H), 2.95 (br. s., 2H), 2.82 (s, 3H); LC-MS: m/z 440.2 (M+Na)$^+$.

Example 87: N-(1,1-dioxidotetrahydrothiophen-3-yl)-4-(6-fluoro-1H-indol-3-yl)-benzenesulfonamide

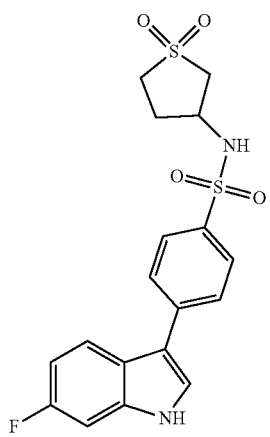 [SMILES: O=S1(=O)CCC(NS(=O)(=O)c2ccc(-c3c[nH]c4cc(F)ccc34)cc2)C1]

Following the general method as outlined in Example 80, starting from 3-aminotetrahydrothiophene 1,1-dioxide, the title compound was obtained as an off-white solid. $^1$H NMR (400MHz, DMSO-d6) δ[ppm] 11.67 (brs, 1H), 8.23 (d, J=4.8 Hz, 1H), 7.98-7.88 (m, 4H), 7.85 (d, J=8.4 Hz, 2H), 7.26 (dd, J=9.6 Hz, 1H), 7.05-6.95 (m, 1H), 4.05-3.88 (m, 1H), 3.30-3.15 (m, 2H), 3.15-3.02 (m, 1H), 2.90-2.80 (m, 1H), 2.30-2.15 (m, 1H), 2.08-1.92 (m, 1H). LC-MS: m/z 430.8.

Example 88: 4-(6-fluoro-1H-indol-3-yl)-N-[2-(methylsulfonyl)ethyl]-benzene-sulfonamide

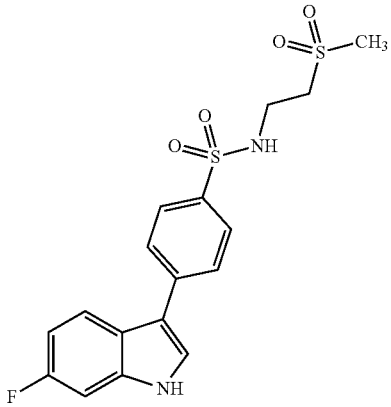 [SMILES: CS(=O)(=O)CCNS(=O)(=O)c1ccc(-c2c[nH]c3cc(F)ccc23)cc1]

Following the general method as outlined in Example 84, starting from 2-(methylsulfonyl)ethanamine, the title compound was obtained as a white solid. LC-MS: m/z 419.0 [M+Na$^+$]$^-$. $^1$H NMR (400MHz, DMSO-d$_6$) δ [ppm] 11.67 (br. s., 1H), 7.98-7.89 (m, 5H), 7.86-7.81 (m, 2H), 7.27 (dd, J=2.5, 9.8 Hz, 1H), 7.01 (dt, J=2.4, 9.2 Hz, 1H), 3.31-3.26 (m, 2H), 3.21-3.14 (m, 2H), 3.03 (s, 3H)

Example 89: 4-(6-fluoro-1H-indol-3-yl)-N-((5-methyl-1,3,4-oxadiazol-2-yl)methyl) benzenesulfonamide

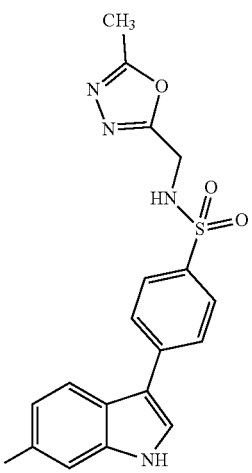

Following the general method as outlined in Example 84, starting from (5-methyl-1,3,4-oxadiazol-2-yl)methanamine, the title compound was obtained as a white solid. LC-MS: m/z 408.8 [M+Na]$^+$. $^1$H NMR (400MHz, DMSO-d6) δ [ppm] 11.66 (br. s., 1H), 8.49 (br. s., 1H), 7.94-7.86 (m, 4H), 7.75 (d, J=8.5 Hz, 2H), 7.26 (dd, J=2.3, 9.8 Hz, 1H), 7.01 (dt, J=2.5, 9.3 Hz, 1H), 4.29 (s, 2H), 2.27 (s, 3H).

Example 90: 1-((4-(6-fluoro-1H-indol-3-yl)phenyl)sulfonyl)-1,4-diazepan-5-one

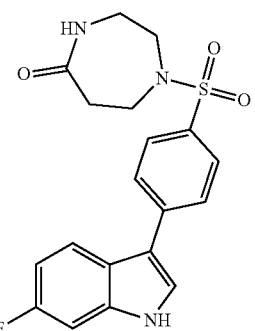

Following the general method as outlined in Example 80, starting from 1,4-diazepan-5-one, the title compound was obtained as a white solid. LC-MS: m/z 388.0 [M+H]$^+$. $^1$H NMR (400MHz, DMSO-d6) δ[ppm] 11.68 (br. s., 1H), 7.97-7.90 (m, 4H), 7.77 (d, J=8.5 Hz, 2H), 7.68 (t, J=5.1 Hz, 1H), 7.26 (dd, J=2.3, 9.8 Hz, 1H), 7.01 (dt, J=2.4, 9.2 Hz, 1H), 3.28-3.15 (m, 6H), 2.58-2.53 (m, 2H).

Example 91: 4-(6-fluoro-1H-indol-3-yl)-N-(1-methyl-1H-pyrazol-5-yl)benzenesulfonamide

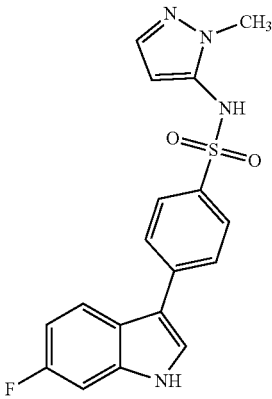 [SMILES: Cn1nccc1NS(=O)(=O)c1ccc(-c2c[nH]c3cc(F)ccc23)cc1]

Step 1: 4-bromo-N-(1-methyl-1H-pyrazol-5-yl)benzenesulfonamide

A solution of 4-bromobenzene-1-sulfonyl chloride (880 mg, 3.44 mmol) and 1-methyl-1H-pyrazol-5-amine (401 mg, 4.13 mmol) in pyridine (10 mL) was stirred at 15° C. for 1 hour. The resulting mixture was concentrated under reduced pressure to dryness. The residue was diluted with water (10 mL) and extracted with EtOAc (30 mL). The organic layer was washed with brine (10 mL), dried over anhydrous $Na_2SO_4$ and concentrated under reduced pressure to dryness to give crude product (1.2 g). The crude product was washed with EtOAc/PE (5 mL/8 mL) to give crude 4-bromo-N-(1-methyl-1H-pyrazol-5-yl)benzenesulfonamide (600 mg, 55.1% yield) as a yellow solid.

Step 2: 4-(6-fluoro-1H-indol-3-yl)-N-(1-methyl-1H-pyrazol-5-yl)benzene-sulfonamide This step was performed according to the protocol described for Step 2 of Example 80. The title compound (45 mg, 14% yield) was obtained as an off-white solid. $^1$H NMR (400MHz, DMSO-d6) δ[ppm] 11.69 (brs, 1H), 10.28 (brs, 1H), 8.00-7.88 (m, 4H), 7.74 (d, J=6.8 Hz, 2H), 7.34-7.20 (m, 2H), 7.10-6.95 (m, 1H), 5.69 (d, J=2.0 Hz, 1H), 3.60 (s, 3H). LC-MS: m/z 370.8 [M+H]$^+$.

Example 92: 4-(6-fluoro-1H-indol-3-yl)-N-[(4-methyl-4H-1,2,4-triazol-3-yl)methyl]-benzenesulfonamide

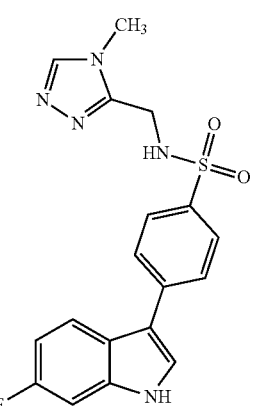

Step 1. N-[(4-methyl-4H-1,2,4-triazol-3-yl)methyl] benzenesulfonamide

This step was performed according to the protocol described for Step 1 of Example 91, starting from (4-methyl-4H-1,2,4-triazol-3-yl)methanamine. The title compound (136 mg, yield: 92%) was obtained as a light yellow solid. LC-MS: m/z 354.9 [M+Na$^+$]$^+$. $^1$H NMR (400MHz, DMSO-d$_6$) δ [ppm] 8.69 (t, J=5.8 Hz, 1H), 8.54 (t, J=7.8 Hz, 1H), 7.87-7.81 (m, 2H), 7.74 (d, J=8.5 Hz, 2H), 4.29 (d, J=5.8 Hz, 2H), 3.69 (s, 3H).

Step 2: 4-(6-fluoro-1H-indol-3-yl)-N-[(4-methyl-4H-1,2,4-triazol-3-yl)methyl]-benzenesulfonamide This step was performed according to the protocol described for Step 2 of Example 84. The title compound (20 mg) was obtained as a white solid. LC-MS: m/z 385.9 [M+H$^+$]$^+$. $^1$H NMR (400MHz, DMSO-d$_6$) δ [ppm] 11.67 (br. s., 1H), 8.37 (s, 1H), 8.23 (br. s., 1H), 7.98-7.89 (m, 4H), 7.84-7.79 (m, 2H), 7.27 (dd, J=2.4, 9.9 Hz, 1H), 7.01 (dt, J=2.4, 9.2 Hz, 1H), 4.18 (s, 2H), 3.64-3.56 (m, 3H).

Example 93: (−)-(R)-4-(6-fluoro-1H-indol-3-yl)-N-(2-hydroxypropyl)-benzenesulfonamide

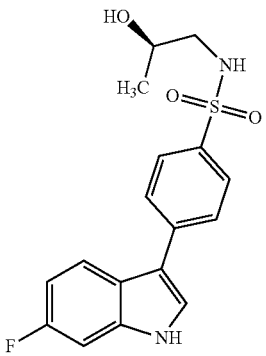 [SMILES: C[C@@H](O)CNS(=O)(=O)c1ccc(-c2c[nH]c3cc(F)ccc23)cc1]

Following the general method as outlined in Example 84, starting from (R)-1-aminopropan-2-ol, the title compound was obtained as a white solid. $^1$H NMR: (400MHz, DMSO-d6) δ [ppm] 11.64 (brs, 1H), 8.00-7.86 (m, 4H), 7.82 (d, J=8.4 Hz, 2H), 7.54 (t, J=6.4 Hz, 1H), 7.26 (dd, J=10.0, 2.4 Hz, 1H), 7.06-6.92 (m, 1H), 4.70 (d, J=4.8 Hz, 1H), 3.70-3.55 (m, 1H), 2.80-2.60 (m, 2H), 1.02 (d, J=6.0 Hz, 3H); LC-MS: m/z 349.1 [M+H]$^+$. $[α]^{20}_D$ −1.3° (c=1.5 mg/ml, MeOH).

Example 94: (+)-(S)-4-(6-fluoro-1H-indol-3-yl)-N-(2-hydroxypropyl)-benzenesulfonamide

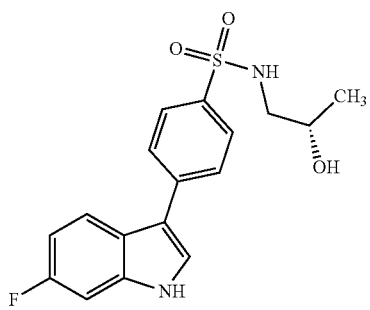 [SMILES: C[C@H](O)CNS(=O)(=O)c1ccc(-c2c[nH]c3cc(F)ccc23)cc1]

Following the genera method as outlined in Example 84, starting from (S)-1-aminopropan-2-ol, the title compound was obtained as a white solid. LC-MS: m/z 348.9 [M+H]$^+$. $^1$H NMR (400MHz, DMSO-d6) δ[ppm] 11.64 (br. s., 1H), 7.98-7.87 (m, 4H), 7.84-7.78 (m, 2H), 7.54 (br. s., 1H), 7.26 (dd, J=2.4, 9.9 Hz, 1H), 7.00 (dt, J=2.3, 9.3 Hz, 1H), 4.69 (d, J=4.8 Hz, 1H), 3.66-3.57 (m, 1H), 2.75-2.60 (m, 2H), 1.01 (d, J=6.3 Hz, 3H). [α]$^{20}_D$+1.2° (c=1.1 mg/ml, MeOH).

Example 95: (cis)-3-(4-(6-fluoro-1H-indol-3-yl)phenylsulfon-amido)cyclobutanecarboxamide

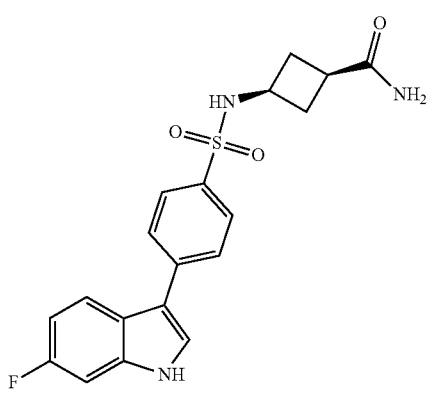 [SMILES: NC(=O)[C@H]1C[C@@H](NS(=O)(=O)c2ccc(-c3c[nH]c4cc(F)ccc34)cc2)C1]

Step 1: (cis)-methyl 3-aminocyclobutanecarboxylate

A solution of (cis)-methyl 3-((tert-butoxycarbonyl)amino)cyclobutane-carboxylate (500 mg, 2.18 mmol) in 4 M HCl/EtOAc (15 mL) was stirred at 15° C. for 1 hour. The resulting mixture was concentrated to dryness to give (cis)-methyl 3-aminocyclobutanecarboxylate hydrochloride (361 mg, quantitative yield) as a white solid.

Step 2: (cis)-methyl 3-(4-bromophenylsulfonamido)cyclobutane-carboxylate

To a solution of 4-bromobenzene-1-sulfonyl chloride (557 mg, 2.18 mmol) and (cis)-methyl 3-aminocyclobutanecarboxylate (361 mg, 2.18 mmol) in anhydrous DCM (15 mL) was added TEA (441 mg, 4.36 mmol) at 15° C. and then the mixture was stirred at 15° C. for 1 hour. The resulting mixture was concentrated to dryness. The residue was stirred in EtOAc (50 mL) and then filtered. The filtrate was concentrated to dryness to give crude (cis)-methyl 3-(4-bromophenylsulfonamido)cyclobutanecarboxylate (800 mg) as colorless oil, which was used for the next step without further purification.

Step 3: (cis)-3-(4-bromophenylsulfonamido)cyclobutanecarboxamide

A colorless solution of (cis)-methyl 3-(4-bromophenylsulfonamido)cyclobutanecarboxylate (759 mg, 2.18 mmol) and NH$_3$.H$_2$O (6110 mg, 43.6 mmol) in MeOH (10 mL) was stirred at 15-20° C. for 16 hours. TLC showed that the material was consumed completely. The suspension was filtered and the filter cake was washed with water (20 mL) and then dried under high vacuum to give the title compound (366 mg, 50.4% yield) as a white solid.

Step 4: (cis)-3-(4-(6-fluoro-1H-indol-3-yl)phenylsulfonamido)-cyclobutanecarboxamide This step was performed according to the protocol described for Example 84, Step 2. (cis)-3-(4-(6-fluoro-1H-indol-3-yl)phenylsulfonamido)cyclobutane-carboxamide (70 mg, 26% yield) was obtained as an off-white solid. LC-MS: m/z 387.9 (M+H)$^+$. $^1$H NMR (400MHz, DMSO-d6) δ[ppm] 11.65 (brs, 1H), 8.10-7.66 (m, 7H), 7.37-6.90 (m, 3H), 6.80-6.55 (m, 1H), 3.68-3.50 (m, 1H), 2.60-2.40 (m, 1H, overlapping with DMSO signal), 2.18-2.00 (m, 2H), 2.00-1.75 (m, 2H).

Example 96: 4-(6-fluoro-1H-indol-3-yl)-N-[(2R)-1-hydroxypropan-2-yl]benzenesulfonamide

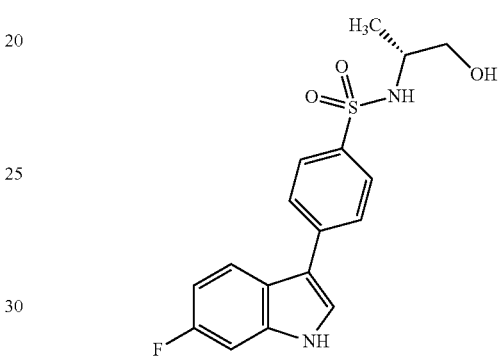

Following the general method as outlined in Example 84, starting from (R)-2-aminopropan-1-ol, the title compound was obtained as a white solid. $^1$H NMR (400MHz, DMSO-d6) d=11.65 (br. s., 1H), 7.99-7.79 (m, 6H), 7.58-7.40 (m, 1H), 7.27 (dd, J=2.3, 9.8 Hz, 1H), 7.05-6.95 (m, 1H), 4.71 (br. s., 1H), 3.22-3.06 (m, 2H), 0.93 (d, J=6.3 Hz, 3H).

Example 97: (Trans)-3-(4-(6-fluoro-1H-indol-3-yl)phenyl-sulfonamido)cyclobutanecarboxamide

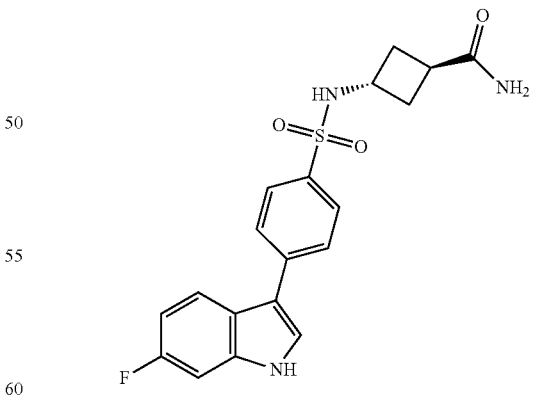

Following the general method as outlined in Example 95, starting from (trans)-methyl 3-aminocyclobutanecarboxylate, the title compound was obtained as a white solid. LC-MS: m/z 388.1 (M+H)$^+$. $^1$H NMR (400MHz, DMSO-d6) δ[ppm] 11.64 (br. s., 1H), 8.00-7.86 (m, 5H), 7.79 (d, J=8.3 Hz, 2H), 7.26 (dd, J=2.0, 9.8 Hz, 1H), 7.17 (br. s., 1H), 7.05-6.94 (m, 1H), 6.73 (br. s., 1H), 3.91-3.76 (m, 1H), 2.71 (t, J=9.5 Hz, 1H), 2.18-2.05 (m, 2H), 2.04-1.90 (m, 2H).

Example 98: 4-(6-fluoro-1H-indol-3-yl)-N-methyl-N-(2-sulfamoylethyl)benzenesulfonamide

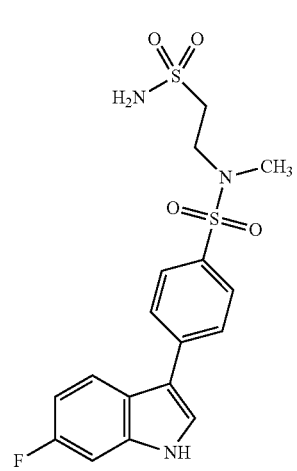 [SMILES: CN(CCS(N)(=O)=O)S(=O)(=O)c1ccc(-c2c[nH]c3cc(F)ccc23)cc1]

Following the general method as outlined in Example 84, starting from 2-(methylamino)ethanesulfonamide, the title compound was obtained as a white solid. ¹H NMR: (400MHz, DMSO-d6) δ[ppm] 11.70 (brs, 1H), 8.05-7.88 (m, 4H), 7.81 (d, J=8.4 Hz, 2H), 7.27 (dd, J=10.0, 2.4 Hz, 1H), 7.10-6.90 (m, 3H), 3.47-3.36 (m, 2H), 3.30-3.20 (m, 2H), 2.76 (s, 3H), HPLC:00709873-0018-01b 98.09% purity; LC-MS: m/z 433.9 (M+Na)⁺.

Example 99: 4-(6-fluoro-1H-indol-3-yl)-N-[2-(1H-1,2,4-triazol-1-yl)-ethyl]benzenesulfonamide

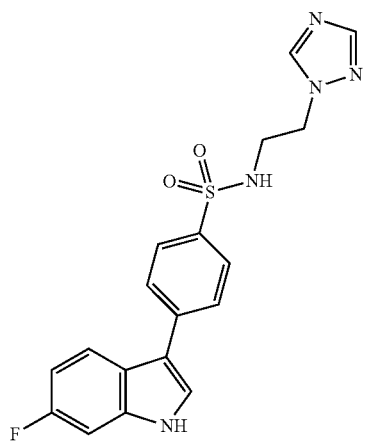 [SMILES: O=S(=O)(NCCn1cncn1)c1ccc(-c2c[nH]c3cc(F)ccc23)cc1]

Following the general method as outlined in Example 84, starting from 2-(1H-1,2,4-triazol-1-yl)ethanamine, the title compound was obtained as a white solid. ¹H NMR (400MHz, DMSO-d6): δ [ppm] 11.65 (br, s, 1H), 8.46 (s, 1H), 8.04-7.65 (m, 8H), 7.95-7.78 (m, 8H), 7.27-7.25 (m, 1H), 7.03-7.01 (m, 1H), 4.27-4.24 (m, 2H), 3.21-3.17 (m, 2H); LC-MS: m/z 386.1 [M+H]⁺.

Example 100: 4-(6-fluoro-1H-indol-3-yl)-N-methyl-N-[2-(methylsulfamoyl)ethyl]benzenesulfonamide

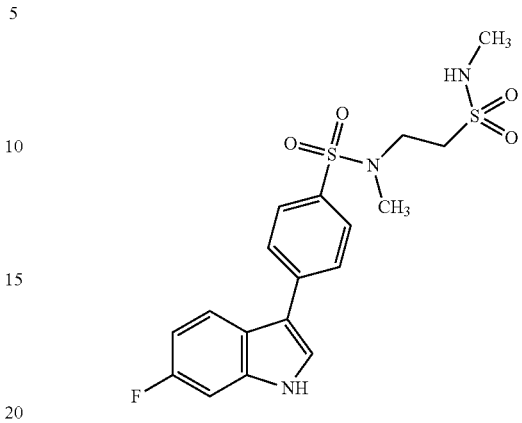

Step 1: N-methylethenesulfonamide

A suspension of 2-chloroethanesulfonyl chloride (5.00 g, 30.67 mmol) in methylamine (40 ml, 2 M in THF) was stirred at 50° C. for 2 days. The yellow suspension was filtered and concentrated under reduced pressure to dryness, and the resulting mixture was purified by silica gel column (Petroleum ether/EtOAc to EtOAc=10/1 to 1/1) to give N-methylethenesulfonamide (1.0 g, 27% yield) as a yellow oil. ¹H NMR (400MHz, CDCl₃) δ [ppm] 6.54-6.42 (m, 1H), 6.28 (d, J=16.6 Hz, 1H), 6.00 (d, J=9.8 Hz, 1H), 2.74 (d, J=5.5 Hz, 3H).

Step 2: N-methyl-2-(methylamino)ethanesulfonamide

A solution of N-methylethenesulfonamide (1.00 g, 8.254 mmol) in methylamine (20 ml, ~40% in EtOH) was stirred at 25° C. for 14 hours. The yellow solution was concentrated under reduced pressure to dryness to give crude N-methyl-2-(methylamino)ethanesulfonamide (1.2 g, 95% yield) as a yellow oil. ¹H NMR (400MHz, CDCl₃) δ [ppm] 5.61-5.40 (m, 1H), 3.21-3.13 (m, 2H), 3.10-3.00 (m, 2H), 2.84-2.73 (m, 3H), 2.44 (s, 3H).

Step 3: 4-bromo-N-methyl-N-(2-(N-methylsulfamoyl)ethyl)benzene-sulfonamide

To a solution of 4-bromobenzene-1-sulfonyl chloride (500 mg, 1.97 mmol) and N-methyl-2-(methylamino)ethanesulfonamide (300 mg, 1.97 mmol) in anhydrous DCM (20 mL) was added Et₃N (399 mg, 3.94 mmol) at 25° C. and then the yellow solution was stirred at 25° C. for 2 hours. The reaction solution was concentrated in vacuo and purified by flash chromatography (SiO₂, 12 g, petroleum ether/EtOAc=3/1 to 1/3) to give the title compound (450 mg, 61.5% yield) as a yellow gum.

Step 4: 4-(6-fluoro-1H-indol-3-yl)-N-methyl-N-[2-(methylsulfamoyl)ethyl]benzenesulfonamide This step was performed according to the protocol described for Example 80, Step 2, to give the title compound (130 mg, 24.2% yield) as a pale yellow solid. ¹H NMR (400MHz, CDCl₃) δ [ppm] 8.51 (br. s., 1H), 7.88-7.76 (m, 5H), 7.47 (d, J=2.5 Hz, 1H), 7.16 (dd, J=2.4, 9.2 Hz, 1H), 7.01 (dt, J=2.3, 9.2 Hz, 1H), 4.69 (q, J=5.3 Hz, 1H), 3.51-3.44 (m, 2H), 3.38-3.30 (m, 2H), 2.92-2.83 (m, 6H) LC-MS: m/z 447.8 (M+Na)+.

Example 101: (−)-(6-fluoro-1H-indol-3-yl)-N-[(2S)-1-hydroxypropan-2-yl]benzenesulfonamide

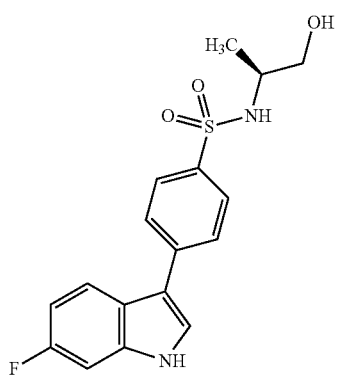 [SMILES: C[C@@H](CO)NS(=O)(=O)c1ccc(-c2c[nH]c3cc(F)ccc23)cc1]

Following the general method as outlined in Example 84, starting from (S)-2-aminopropan-1-ol, the title compound was obtained as a white solid. LC-MS: m/z 371.9 [M+Na+]+. $^1$H NMR (400MHz, DMSO-$d_6$) δ [ppm] 11.64 (br. s., 1H), 7.97-7.88 (m, 4H), 7.86-7.81 (m, 2H), 7.49 (d, J=6.5 Hz, 1H), 7.26 (dd, J=2.4, 9.9 Hz, 1H), 7.00 (dt, J=2.4, 9.2 Hz, 1H), 4.70 (t, J=5.5 Hz, 1H), 3.19-3.05 (m, 2H), 0.93 (d, J=6.3 Hz, 3H). [α]$^{20}_D$–12.2° (c=1.1 mg/ml, MeOH).

Example 102: 4-(6-fluoro-1H-indol-3-yl)-N-(3-oxo-3-(piperazin-1-yl)propyl) benzenesulfonamide

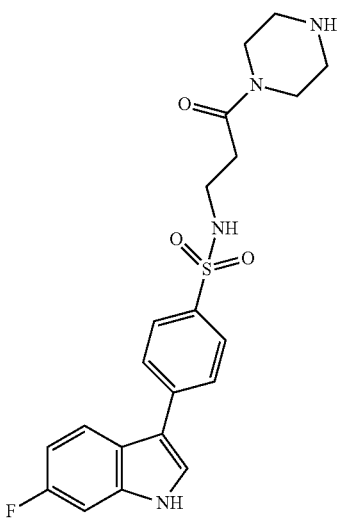 [SMILES: O=C(CCNS(=O)(=O)c1ccc(-c2c[nH]c3cc(F)ccc23)cc1)N1CCNCC1]

Step 1: ethyl 3-(4-bromophenylsulfonamido)propanoate

To a solution of 4-bromobenzene-1-sulfonyl chloride (25 g, 97.841 mmol) and ethyl 3-aminopropanoate (15 g, 1.04 mmol) in anhydrous DCM (200 mL) was added Et$_3$N (19.8 g, 196 mmol) at 15° C. and then the mixture was stirred at 15° C. for 1 hour. The resulting mixture was concentrated under reduced pressure to dryness. The residue was diluted with water (100 mL) and extracted with EtOAc (300 mL). The organic layer was washed with brine (50 mL), dried over anhydrous Na$_2$SO$_4$ and concentrated under reduced pressure to dryness to give crude product (40 g). The crude product was purified by flash chromatography (SiO$_2$, petroleum ether/EtOAc=1/1 to 1/4) to give ethyl 3-(4-bromophenylsulfon-amido)propanoate (32 g, yield 97%) as a yellow gum. $^1$H NMR (400MHz, CDCl$_3$) d=7.76-7.70 (m, 1H), 7.69-7.63 (m, 1H), 5.47-5.14 (m, 1H), 4.13 (q, J=7.2 Hz, 2H), 3.20 (q, J=6.3 Hz, 2H), 2.54 (t, J=5.9 Hz, 2H), 1.33-1.15 (m, 3H)

Step 2: 3-(4-(6-fluoro-1H-indol-3-yl)phenylsulfonamido)propanoic acid

A suspension of ethyl 3-(4-bromophenylsulfonamido) propanoate (597 mg, 1.6 mmol), tert-butyl 6-fluoro-3-(4,4,5,5-tetramethyl-1,3,2-dioxaborolan-2-yl)-1H-indole-1-carboxylate (Intermediate 1; 542 mg, 1.61 mmol), Pd(dppf)Cl$_2$ (118 mg, 0.161 mmol) and K$_3$PO$_4$ (856 mg, 4.03 mmol) in dioxane (20 mL) and water (5 mL) was stirred under N$_2$ atmosphere at 100° C. for 16 hours. The suspension was concentrated to a residue which was purified by Combi Flash (silical gel 4, petroleum ether: EtOAc=1:0 to 2:1) to afford a crude, which was reacted with LiOH.H$_2$O (56.1 mg, 1.34 mmol) in H$_2$O (2.5 mL) and THF (2.5 mL). The mixture was stirred at room temperature for 1 hour. The solution was concentrated to residue. EtOAc (15 mL) and water (10 mL) were added, neutralization was done with diluted hydrochloric acid and the phases were separated, the aqueous layer was separated, extracted with EtOAc (10 mL*2) and the combined organic phases were dried over anhydrous Na$_2$SO$_4$, filtered and concentrated to afford compound the title compound as a crude (224 mg, yield: >100%) which was used in the next step without purification.

Step 3: tert-butyl 4-(3-(4-(6-fluoro-1H-indol-3-yl) phenylsulfonamido)-propanoyl)piperazine-1-carboxylate A solution of 3-(4-(6-fluoro-1H-indol-3-yl)phenylsulfonamido)propanoic acid (80 mg, 0.21 mmol), tert-butyl piperazine-1-carboxylate (38.2 mg, 0.205 mmol), HATU (117 mg, 0.308 mmol) and DIPEA (79.6 mg, 0.616 mmol) in DMF (10 mL) was stirred at room temperature for 1 hour. EtOAc (20 mL) and water (10 ml) were added to the solution, and extracted with EtOAc (20 mL*2), dried over anhydrous Na$_2$SO$_4$, filtered and concentrated to afford the title compound as a crude (100 mg, yield: 92%) which was used in the next step without purification.

Step 4: 4-(6-fluoro-1H-indol-3-yl)-N-(3-oxo-3-(piperazin-1-yl)propyl)-benzenesulfonamide To a solution of tert-butyl 4-(3-(4-(6-fluoro-1H-indol-3-yl)-phenylsulfonamido)propanoyl)piperazine-1-carboxylate (100 mg, 0.204 mmol) in DCM (10 mL) was added Trifluoroacetic acid (2 mL), the resulting solution was stirred at room temperature for 2 hours. The reaction solution was neutralized by diluted Na$_2$CO$_3$ solution, extracted with EtOAc (10 mL*2), the combined organic phases were dried over anhydrous Na$_2$SO$_4$, filtered and concentrated to give a residue which was purified by Flash chromatography (silica gel 4 g, DCM: MeOH=1:0 to 4:1) to afford a crude. The crude compound was submitted to be purified by preparative HPLC. The buffer solution was concentrated at 35° C. in vacuum and lyophilized to give the title compound (52 mg, yield: 59%) as a white solid. LC-MS: m/z 431.0 [M+H]+. 1H NMR (400MHz, CD3OD) δ [ppm] 7.93-7.85 (m, 5H), 7.66 (s, 1H), 7.16 (dd, J=2.3, 9.8 Hz, 1H), 6.94 (dt, J=2.4, 9.2 Hz, 1H), 3.55-3.50 (m, 1H), 3.46-3.41 (m, 1H), 3.19 (t, J=6.8 Hz, 1H), 2.76 (td, J=5.2, 10.5 Hz, 2H), 2.56 (t, J=6.8 Hz, 1H).

Example 103: 4-(6-fluoro-1H-indol-3-yl)-N-(3-(4-methylpiperazin-1-yl)-3-oxopropyl) benzenesulfonamide

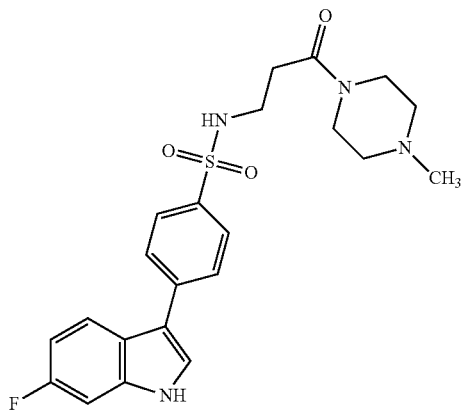 [SMILES: CN1CCN(C(=O)CCNS(=O)(=O)c2ccc(-c3c[nH]c4cc(F)ccc34)cc2)CC1]

Following the general method as outlined in Example 102, the title compound was obtained as a white solid. LC-MS: m/z 445.0 [M+H]+. 1H NMR (400MHz, CDCl3) δ [ppm] 9.04 (br. s., 1H), 7.86 (d, J=8.3 Hz, 2H), 7.78 (dd, J=5.1, 8.7 Hz, 1H), 7.69 (d, J=8.3 Hz, 2H), 7.35 (d, J=2.3 Hz, 1H), 7.13 (dd, J=1.9, 9.4 Hz, 1H), 6.96 (dt, J=2.0, 9.2 Hz, 1H), 5.78 (br. s., 1H), 3.60 (br. s., 2H), 3.41-3.34 (m, 2H), 3.26 (d, J=3.8 Hz, 2H), 2.56 (t, J=5.5 Hz, 2H), 2.34 (t, J=4.6 Hz, 4H), 2.26 (s, 3H).

Example 104: (−)-(S)-3-(4-(6-fluoro-1H-indol-3-yl)phenylsulfonamido)-N-(tetrahydrofuran-3-yl)propanamide

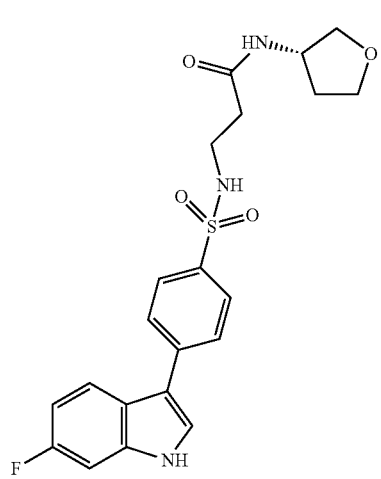 [SMILES: O=C(CCNS(=O)(=O)c1ccc(-c2c[nH]c3cc(F)ccc23)cc1)N[C@H]1CCOC1]

Following the general method as outlined in Example 102, the title compound was obtained as a white solid. LC-MS: m/z 432.0 [M+H]+. 1H NMR (400MHz, DMSO-d6) δ [ppm]11.65 (br. s., 1H), 8.13 (d, J=6.5 Hz, 1H), 7.98-7.87 (m, 4H), 7.84-7.78 (m, 2H), 7.60 (t, J=5.8 Hz, 1H), 7.26 (dd, J=2.3, 9.8 Hz, 1H), 7.00 (dt, J=2.3, 9.3 Hz, 1H), 4.22-4.13 (m, 1H), 3.78-3.60 (m, 3H), 3.41 (dd, J=3.8, 8.8 Hz, 1H), 3.00-2.92 (m, 2H), 2.27 (t, J=7.4 Hz, 2H), 2.07-1.97 (m, 1H), 1.73-1.63 (m, 1H). [α]20D−1.7° (c=1.1 mg/ml, MeOH).

Example 105: (−)-N-(3-((3S,4S)-3-amino-4-fluoropyrrolidin-1-yl)-3-oxopropyl)-4-(6-fluoro-1H-indol-3-yl)benzenesulfonamide

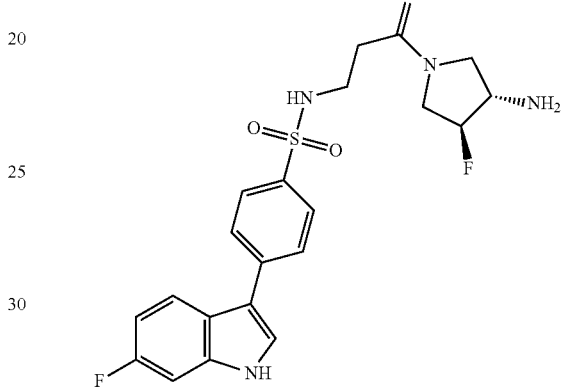

Following the general method as outlined in Example 102, the title compound was obtained as a white solid. LC-MS: m/z 449.1 [M+H]+. 1H NMR (400MHz, CD3OD) δ [ppm] 7.97-7.79 (m, 5H), 7.64 (s, 1H), 7.15 (d, J=9.0 Hz, 1H), 6.93 (t, J=8.5 Hz, 1H), 3.96-3.75 (m, 1H), 3.74-3.41 (m, 4H), 3.36 (d, J=11.0 Hz, 1H), 3.21 (t, J=6.3 Hz, 2H), 2.62-2.43 (m, 2H). [α]20D−4.5° (c=1.1 mg/ml, MeOH).

Example 106: 4-(6-fluoro-1H-indol-3-yl)-N-(3-morpholino-3-oxopropyl)-benzenesulfonamide

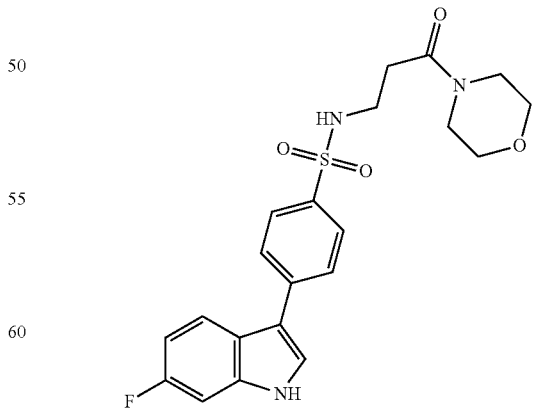

Following the general method as outlined in Example 102, the title compound was obtained as a white solid. LC-MS: m/z 432.2 [M+H]+. 1H NMR (400MHz, CD3OD)

δ [ppm] 7.92-7.84 (m, 2H), 7.65 (s, 1H), 7.16 (dd, J=2.3, 9.5 Hz, 1H), 6.94 (dt, J=2.4, 9.2 Hz, 1H), 3.64-3.56 (m, 4H), 3.55-3.50 (m, 2H), 3.47-3.42 (m, 2H), 3.19 (t, J=6.7 Hz, 2H), 2.56 (t, J=6.8 Hz, 2H).

Example 107: (+)-(R)-3-(4-(6-fluoro-1H-indol-3-yl) phenylsulfonamido)-N-(tetrahydrofuran-3-yl)propanamide

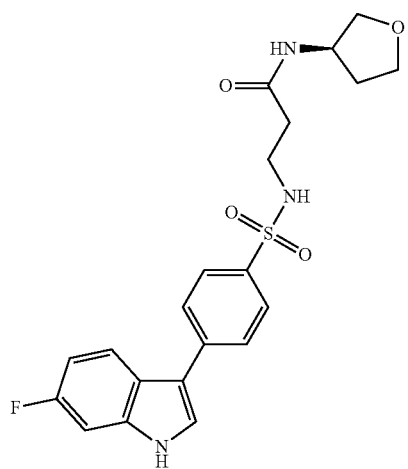 [SMILES: O=C(CCNS(=O)(=O)c1ccc(-c2c[nH]c3cc(F)ccc23)cc1)N[C@@H]1CCOC1]

Following the general method as outlined in Example 102, the title compound was obtained as a white solid. LC-MS m/z 431.7 (M+H)⁺. $^1$H NMR (400MHz, DMSO-d6) δ[ppm]11.65 (br. s., 1H), 8.13 (d, J=6.5 Hz, 1H), 7.98-7.87 (m, 4H), 7.84-7.77 (m, 2H), 7.61 (br. s., 1H), 7.26 (dd, J=2.3, 9.8 Hz, 1H), 7.00 (dt, J=2.4, 9.2 Hz, 1H), 4.23-4.12 (m, 1H), 3.79-3.59 (m, 3H), 3.40-3.38 (m, 1H), 3.05-2.90 (m, 2H), 2.27 (t, J=7.3 Hz, 2H), 2.10-1.95 (m, 1H), 1.73-1.62 (m, 1H). $[\alpha]^{20}_D$+7.3° (c=1.1 mg/ml, MeOH).

Example 108: N-(2-(4-(6-fluoro-1H-indol-3-yl)phenylsulfonamido)ethyl)-morpholine 4-carboxamide

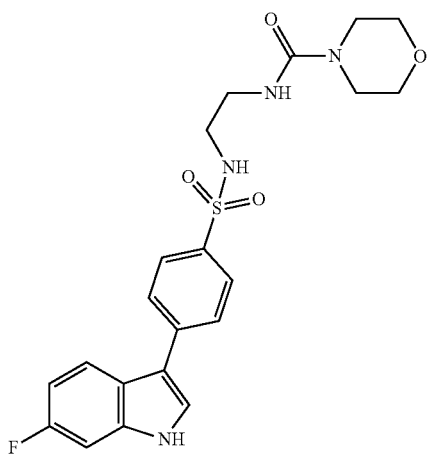 [SMILES: O=C(NCCNS(=O)(=O)c1ccc(-c2c[nH]c3cc(F)ccc23)cc1)N1CCOCC1]

Step 1: tert-butyl (2-(4-bromophenylsulfonamido)ethyl)carbamate

To a solution of 4-bromobenzene-1-sulfonyl chloride (5.11 g, 20 mmol) and TEA (6.07 g, 60 mmol) in DCM (50 mL) was added tert-butyl (2-aminoethyl)-carbamate (3.27 g, 20.4 mmol). The mixture was stirred at 20° C. for 16 h. The yellow solution was concentrated under reduced pressure to dryness, and to the resulting mixture was added EtOAc (200 ml) and 3 N aqueous HCl (200 ml). The organic layer was washed with sat. aq. NaHCO3 solution (100 ml) and brine (100 ml), dried over anhydrous Na$_2$SO$_4$ and concentrated under reduced pressure to give the title compound (6.00 g, 79% yield) as a white solid. $^1$H NMR (400MHz, DMSO-d6) d=7.83-7.77 (m, 3H), 7.72-7.68 (m, 2H), 6.88-6.69 (m, 1H), 2.95 (d, J=6.5 Hz, 2H), 2.76 (d, J=6.5 Hz, 2H), 1.34 (s, 9H).

Step 2: tert-butyl 3-(4-(N-(2-((tert-butoxycarbonyl)amino)ethyl)sulfamoyl)-phenyl)-6-fluoro-1H-indole-1-carboxylate To a solution of tert-butyl (2-(4-bromophenylsulfonamido)ethyl)carbamate (1 g, 3 mmol) and tert-butyl 6-fluoro-3-(4,4,5,5-tetramethyl-1,3,2-dioxaborolan-2-yl)-1H-indole-1-carboxylate (Intermediate 1, 1.08 g, 3 mmol) in dioxane/water (30 mL/10 mL) was added K$_3$PO$_4$ (1.91 g, 9 mmol) and Pd(dppf)Cl$_2$.DCM (220 mg, 0.3 mmol). The yellow solution was stirred at 100° C. for 16 h under nitrogen. The black solution was poured into water (100 mL), and the aqueous layer was extracted twice with DCM (100 ml). The combined organic layer was dried over anhydrous Na$_2$SO$_4$ and concentrated under reduced pressure to give the title compound (1.5 g) as a crude black oil which was used without further purification for the next step.

Step 3: N-(2-aminoethyl)-4-(6-fluoro-1H-indol-3-yl)benzenesulfonamide

To a black solution of tert-butyl 3-(4-(N-(2-((tert-butoxycarbonyl)amino)-ethyl) sulfamoyl)phenyl)-6-fluoro-1H-indole-1-carboxylate 10 (1.5 g, crude) in DCM (20 mL) was added TFA (5 mL) at 20° C. The black solution was stirred at 20° C. for 16 h. The pH of the mixture was adjusted to 8-9 with sat. aq. NaHCO$_3$ solution, and the aqueous layer were extracted with DCM twice (100 ml). The combined organic layer was washed with brine (100 ml), dried over anhydrous Na$_2$SO$_4$ and concentrated under reduced pressure to dryness, the resulting mixture was purified by combi flash (40 g silicagel, DCM/MeOH=1%~10%) to give the title compound (800 mg) as a yellow solid. $^1$H NMR (400MHz, DMSO-d6) d=11.98-11.45 (m, 1H), 7.97-7.88 (m, 4H), 7.87-7.79 (m, 2H), 7.30-7.23 (m, 1H), 7.05-6.96 (m, 1H), 2.80 (s, 2H), 2.60 (s, 2H).

Step 4: phenyl N-{2-[4-(6-fluoro-1H-indol-3-yl) benzenesulfonamido]-ethyl}-N,N'-(phenoxycarbonyl)carbamate To a yellow solution of N-(2-aminoethyl)-4-(6-fluoro-1H-indol-3-yl)benzene sulfonamide (350 mg, 1.05 mmol) and TEA (319 mg, 3.15 mmol) in DCM (30 ml) was added dropwise phenylchloroformate (493 mg, 3.15 mmol) at 0° C. The mixture was stirred at 20° C. for 16 h. To the yellow suspension was added water (50 mL) and the aqueous layer was extracted with EtOAc (50 mL×2). The combined organic layer were washed with brine (50 mL), dried over anhydrous Na$_2$SO$_4$ and concentrated under reduced pressure to dryness, which was purified by combi flash (PE/EtOAc=10%~50%) to give the title compound (300 mg, 63% yield) as a white solid.

Step 5: N-(2-(4-(6-fluoro-1H-indol-3-yl) phenylsulfonamido)ethyl)-morpholine-4-carboxamide A yellow suspension of phenyl N-{2-[4-(6-fluoro-1H-indol-3-yl)-benzenesulfonamido]ethyl}-N,N'-(phenoxycarbonyl)carbamate (150 mg, 0.262 mmol) and morpholine (45.6 mg, 0.523 mmol) in DMF (5 mL) was added $K_2CO_3$ (72.3 mg, 0.523 mmol). The mixture was stirred at 70° C. for 16 h. The yellow suspension was poured into water (50 mL), extracted with EtOAc (50 mL×2). The combined organic layer was washed with brine (50 mL), dried over anhydrous $Na_2SO_4$ and concentrated under reduced pressure to dryness, which was purified by prep-HPLC (0.1% $NH_3.H_2O$ as additive). After most of the solvent was removed, the resulting mixture was lyophilized to give the title compound (51.8 mg, 44% yield) as a white solid. LC-MS: m/z 446.8 (M+H)$^+$. $^1$H NMR (400MHz, DMSO-d6) d=11.65 (br. s., 1H), 7.96-7.89 (m, 4H), 7.85-7.78 (m, 2H), 7.70-7.59 (m, 1H), 7.30-7.23 (m, 1H), 7.04-6.96 (m, 1H), 6.61-6.52 (m, 1H), 3.52-3.47 (m, 4H), 3.23-3.17 (m, 4H), 3.13-3.06 (m, 2H), 2.85-2.78 (m, 2H).

Example 109: N-(2-(4-(6-fluoro-1H-indol-3-yl)phenylsulfonamido)ethyl)piperazine-1-carboxamide

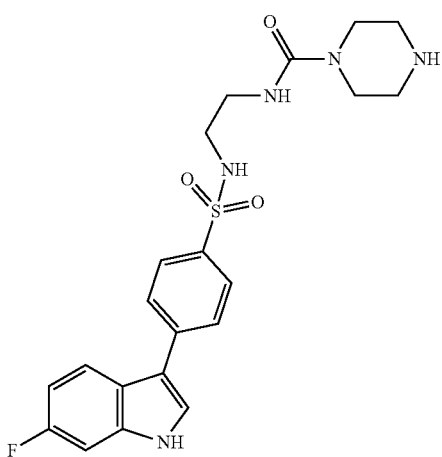 [SMILES: O=C(NCCNS(=O)(=O)c1ccc(-c2c[nH]c3cc(F)ccc23)cc1)N1CCNCC1]

Following the general method as outlined in Example 108, the title compound was obtained as a white solid. LC-MS: m/z 445.9 (M+H)$^+$. $^1$H NMR (400MHz, DMSO-d6) d=11.82-11.55 (m, 1H), 7.96-7.88 (m, 4H), 7.85-7.78 (m, 2H), 7.77-7.46 (m, 1H), 7.26 (dd, J=2.4, 9.9 Hz, 1H), 7.00 (s, 1H), 6.57-6.40 (m, 1H), 3.17-3.03 (m, 6H), 2.86-2.77 (m, 2H), 2.70-2.51 (m, 4H).

Example 110: N-(2-(4-(6-fluoro-1H-indol-3-yl)phenylsulfonamido)ethyl)-4-methylpiperazine-1-carboxamide

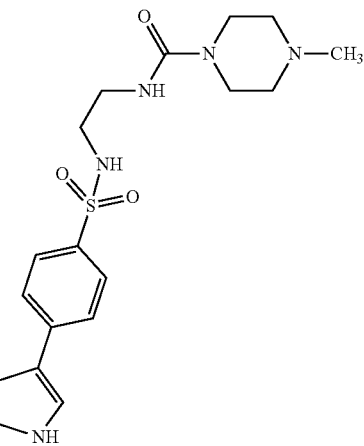

Following the general method as outlined in Example 108, the title compound was obtained as a white solid. LC-MS: m/z 481.9 (M+Na)$^+$. $^1$H NMR (400MHz, DMSO-d6) d=11.64 (br. s., 1H), 7.95-7.88 (m, 4H), 7.83-7.77 (m, 2H), 7.66-7.59 (m, 1H), 7.29-7.22 (m, 1H), 7.03-6.97 (m, 1H), 6.54-6.48 (m, 1H), 3.23-3.17 (m, 4H), 3.08 (d, J=6.0 Hz, 2H), 2.83-2.77 (m, 2H), 2.21-2.16 (m, 4H), 2.12 (s, 3H).

Synthesis of Examples 111-135 follow the general method outlined in Example 4 using the appropriate amine.

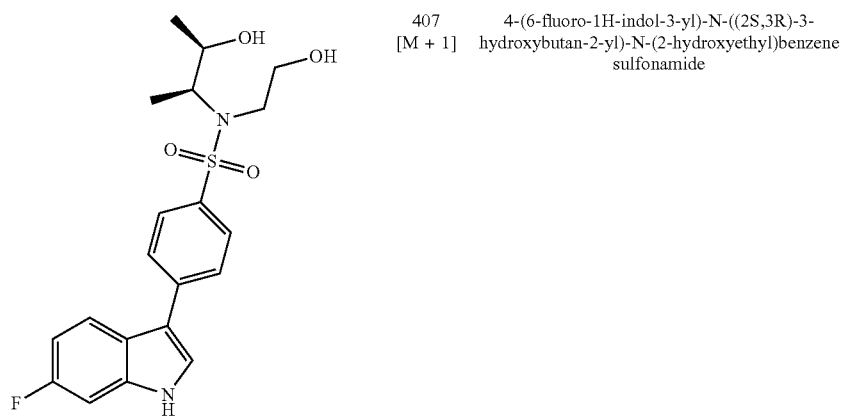

| Example 111 | | 407 [M + 1] | 4-(6-fluoro-1H-indol-3-yl)-N-((2S,3R)-3-hydroxybutan-2-yl)-N-(2-hydroxyethyl)benzenesulfonamide |

-continued
| Example 112 | 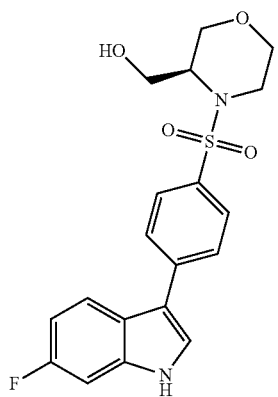 [SMILES: O=S(=O)(c1ccc(-c2c[nH]c3cc(F)ccc23)cc1)N1CCOC[C@@H]1CO] | 391 [M + 1] | (S)-(4-((4-(6-fluoro-1H-indol-3-yl)phenyl)sulfonyl)morpholin-3-yl)methanol |
| Example 113 | 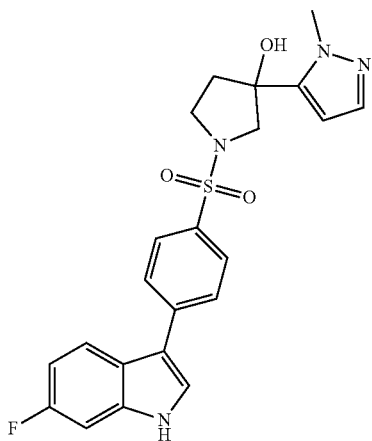 [SMILES: Cn1nccc1C1(O)CCN(S(=O)(=O)c2ccc(-c3c[nH]c4cc(F)ccc34)cc2)C1] | 441 [M + 1] | 1-((4-(6-fluoro-1H-indol-3-yl)phenyl)sulfonyl)-3-(1-methyl-1H-pyrazol-5-yl)pyrrolidin-3-ol |
| Example 114 | 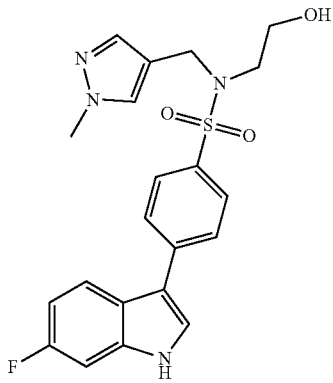 [SMILES: Cn1cc(CN(CCO)S(=O)(=O)c2ccc(-c3c[nH]c4cc(F)ccc34)cc2)cn1] | 429 [M + 1] | 4-(6-fluoro-1H-indol-3-yl)-N-(2-hydroxyethyl)-N-((1-methyl-1H-pyrazol-4-yl)methyl)benzenesulfonamide |
| Example 115 | 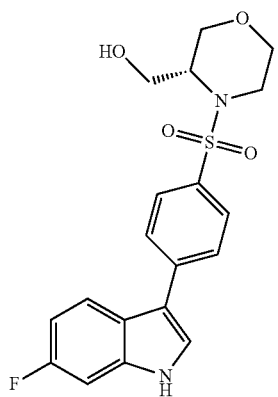 [SMILES: O=S(=O)(c1ccc(-c2c[nH]c3cc(F)ccc23)cc1)N1CCOC[C@H]1CO] | 391 [M + 1] | (R)-(4-((4-(6-fluoro-1H-indol-3-yl)phenyl)sulfonyl)morpholin-3-yl)methanol |

-continued
| Example 116 | 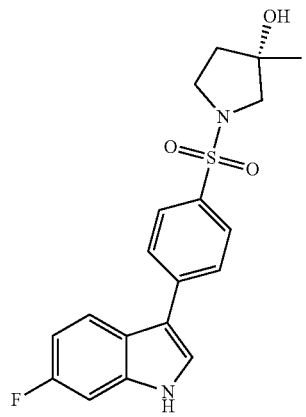 [SMILES: C[C@]1(O)CCN(S(=O)(=O)c2ccc(-c3c[nH]c4cc(F)ccc34)cc2)C1] | 375 [M + 1] | (S)-1-((4-(6-fluoro-1H-indol-3-yl)phenyl)sulfonyl)-3-methylpyrrolidin-3-ol |
| Example 117 | 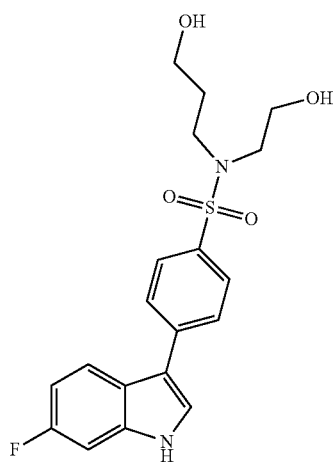 [SMILES: O=S(=O)(c1ccc(-c2c[nH]c3cc(F)ccc23)cc1)N(CCO)CCCO] | 393 [M + 1] | 4-(6-fluoro-1H-indol-3-yl)-N-(2-hydroxyethyl)-N-(3-hydroxypropyl)benzenesulfonamide |
| Example 118 | 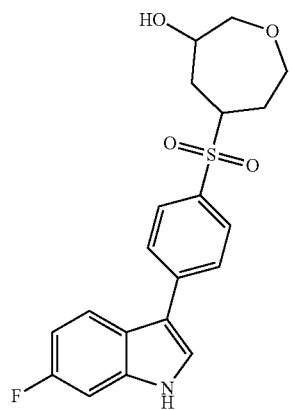 [SMILES: O=S(=O)(c1ccc(-c2c[nH]c3cc(F)ccc23)cc1)C1CCOCC(O)C1] | 391 [M + 1] | 4-((4-(6-fluoro-1H-indol-3-yl)phenyl)sulfonyl)-1,4-oxazepan-6-ol |

-continued
| | | | |
|---|---|---|---|
| Example 119 | 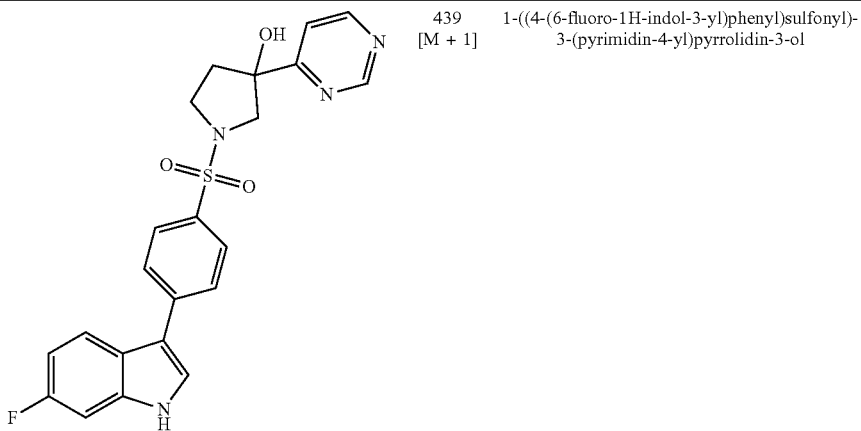 | 439 [M + 1] | 1-((4-(6-fluoro-1H-indol-3-yl)phenyl)sulfonyl)-3-(pyrimidin-4-yl)pyrrolidin-3-ol |
| Example 120 | 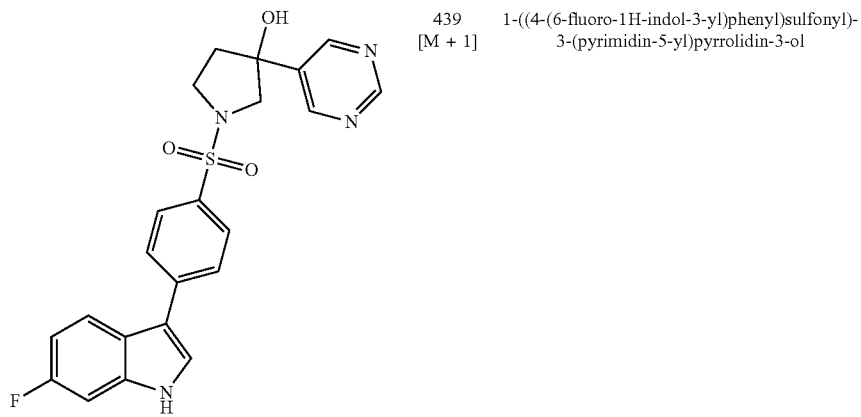 | 439 [M + 1] | 1-((4-(6-fluoro-1H-indol-3-yl)phenyl)sulfonyl)-3-(pyrimidin-5-yl)pyrrolidin-3-ol |
| Example 121 | 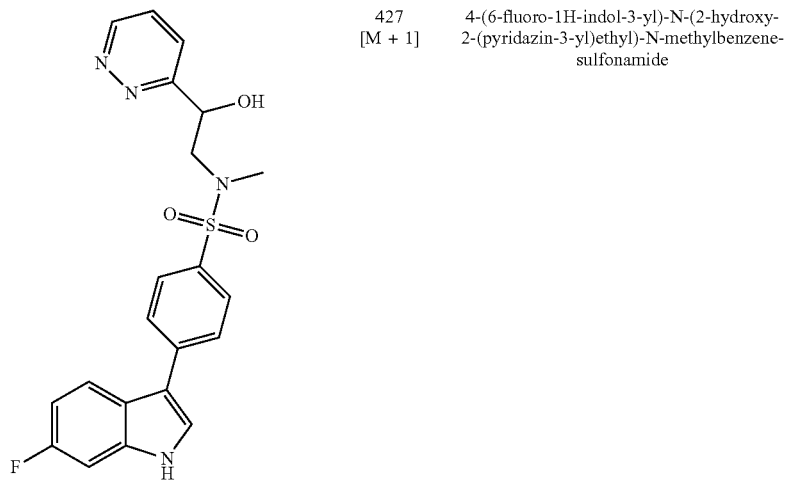 | 427 [M + 1] | 4-(6-fluoro-1H-indol-3-yl)-N-(2-hydroxy-2-(pyridazin-3-yl)ethyl)-N-methylbenzenesulfonamide |

-continued
| | | | |
|---|---|---|---|
| Example 122 | 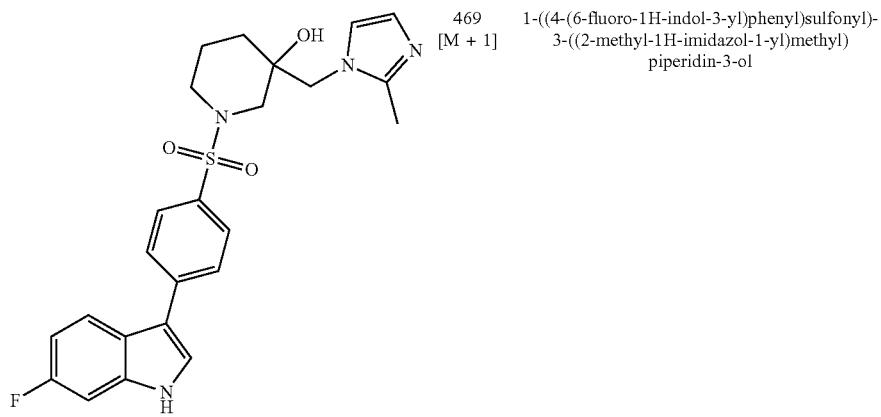 | 469 [M + 1] | 1-((4-(6-fluoro-1H-indol-3-yl)phenyl)sulfonyl)-3-((2-methyl-1H-imidazol-1-yl)methyl)piperidin-3-ol |
| Example 123 | 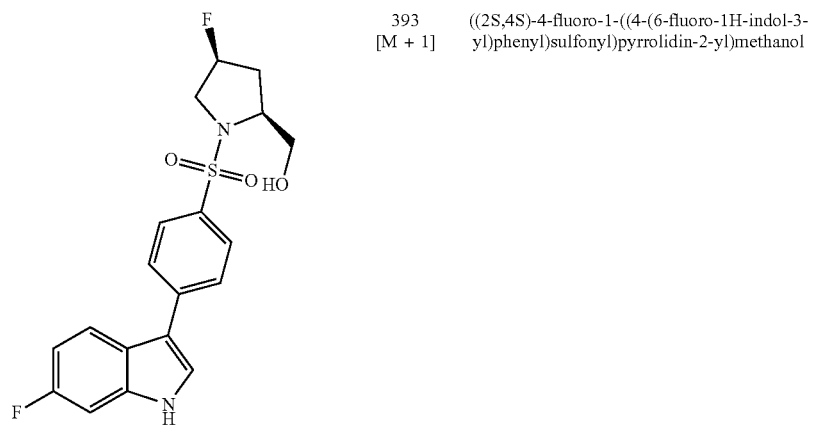 | 393 [M + 1] | ((2S,4S)-4-fluoro-1-((4-(6-fluoro-1H-indol-3-yl)phenyl)sulfonyl)pyrrolidin-2-yl)methanol |
| Example 124 | 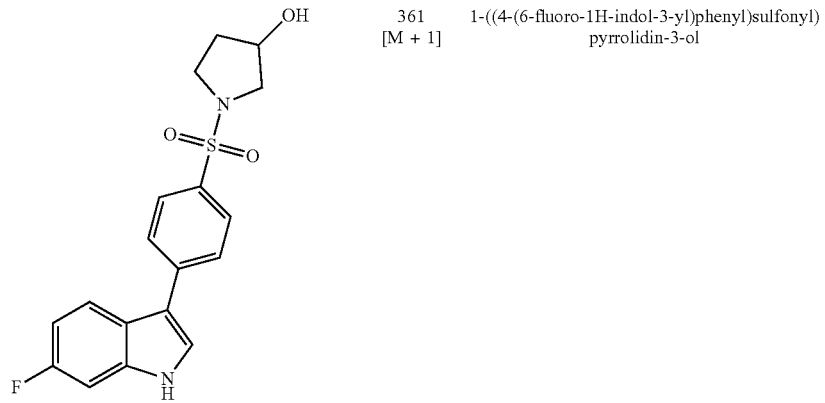 | 361 [M + 1] | 1-((4-(6-fluoro-1H-indol-3-yl)phenyl)sulfonyl)pyrrolidin-3-ol |

-continued
| | | | |
|---|---|---|---|
| Example 125 | 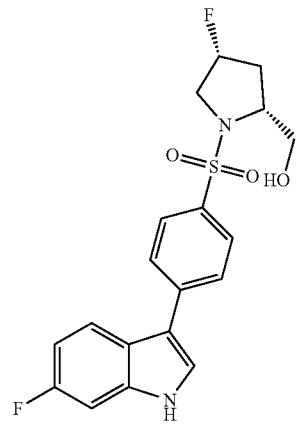 [SMILES: O=S(=O)(c1ccc(-c2c[nH]c3cc(F)ccc23)cc1)N1C[C@H](F)C[C@@H]1CO] | 393 [M + 1] | ((2R,4R)-4-fluoro-1-((4-(6-fluoro-1H-indol-3-yl)phenyl)sulfonyl)pyrrolidin-2-yl)methanol |
| Example 126 | 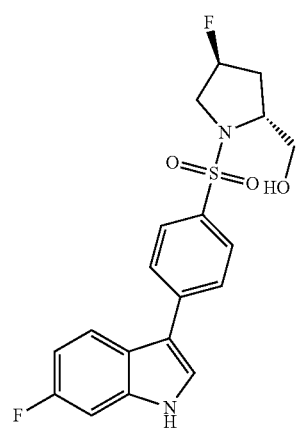 [SMILES: O=S(=O)(c1ccc(-c2c[nH]c3cc(F)ccc23)cc1)N1C[C@@H](F)C[C@@H]1CO] | 393 [M + 1] | ((2R,4S)-4-fluoro-1-((4-(6-fluoro-1H-indol-3-yl)phenyl)sulfonyl)pyrrolidin-2-yl)methanol |
| Example 127 | 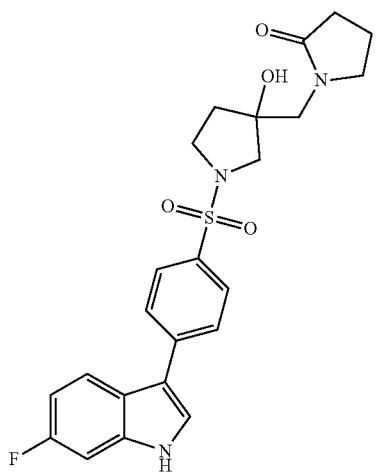 [SMILES: O=C1CCCN1CC1(O)CCN(S(=O)(=O)c2ccc(-c3c[nH]c4cc(F)ccc34)cc2)C1] | 458 [M + 1] | 1-((1-((4-(6-fluoro-1H-indol-3-yl)phenyl)sulfonyl)-3-hydroxypyrrolidin-3-yl)methyl)pyrrolidin-2-one |

-continued
| | | | |
|---|---|---|---|
| Example 128 | 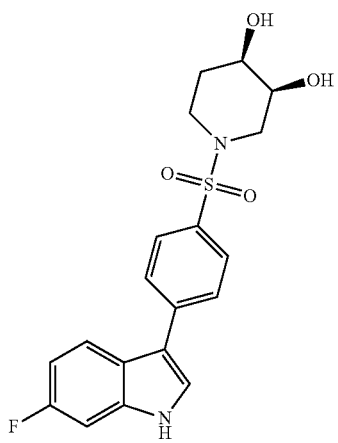 [SMILES: O=S(=O)(c1ccc(-c2c[nH]c3cc(F)ccc23)cc1)N1CC[C@@H](O)[C@@H](O)C1] | 391 [M + 1] | (3S,4R)-1-((4-(6-fluoro-1H-indol-3-yl)phenyl)sulfonyl)piperidine-3,4-diol |
| Example 129 | 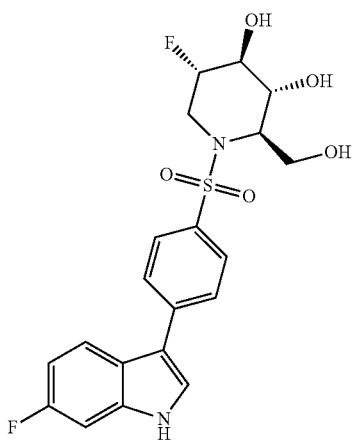 [SMILES: O=S(=O)(c1ccc(-c2c[nH]c3cc(F)ccc23)cc1)N1C[C@H](F)[C@@H](O)[C@H](O)[C@H]1CO] | 439 [M + 1] | (2R,3R,4S,5S)-5-fluoro-1-((4-(6-fluoro-1H-indol-3-yl)phenyl)sulfonyl)-2-(hydroxymethyl)piperidine-3,4-diol |
| Example 130 | 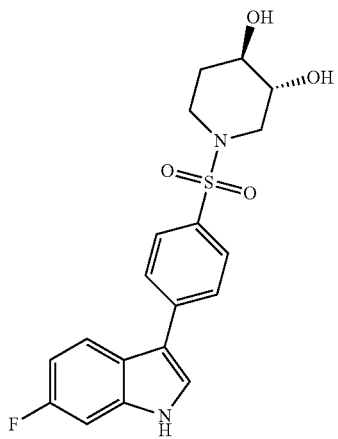 [SMILES: O=S(=O)(c1ccc(-c2c[nH]c3cc(F)ccc23)cc1)N1CC[C@@H](O)[C@H](O)C1] | 391 [M + 1] | (3R,4R)-1-((4-(6-fluoro-1H-indol-3-yl)phenyl)sulfonyl)piperidine-3,4-diol |

| | | | |
|---|---|---|---|
| Example 131 | 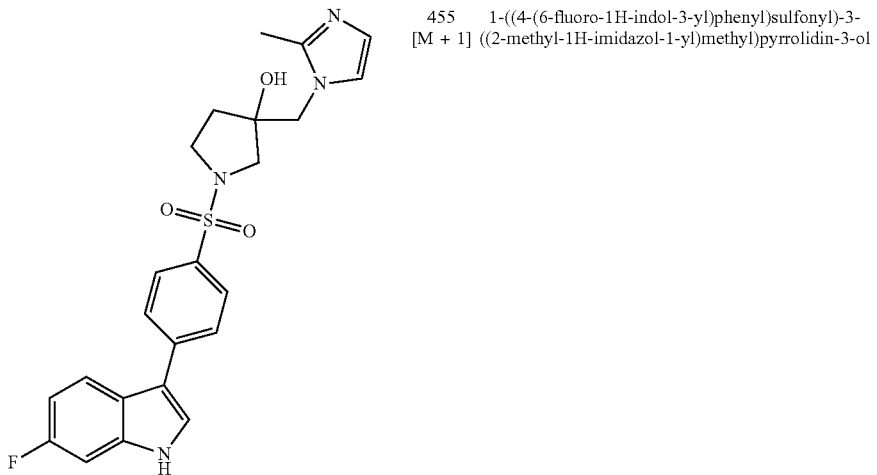 | 455 [M + 1] | 1-((4-(6-fluoro-1H-indol-3-yl)phenyl)sulfonyl)-3-((2-methyl-1H-imidazol-1-yl)methyl)pyrrolidin-3-ol |
| Example 132 | 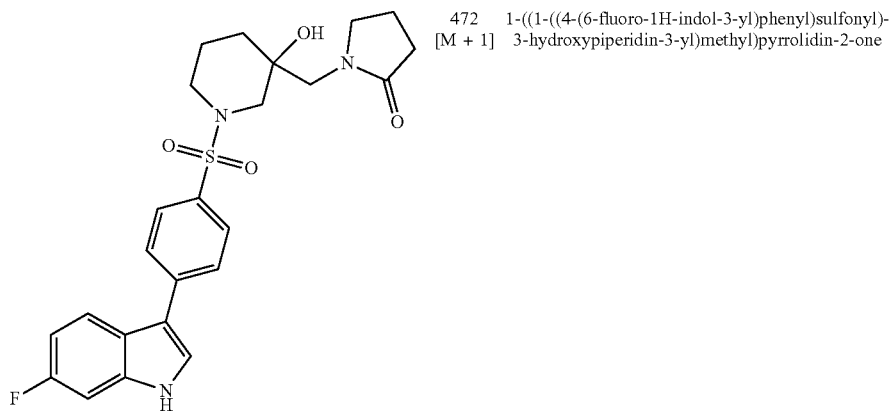 | 472 [M + 1] | 1-((1-((4-(6-fluoro-1H-indol-3-yl)phenyl)sulfonyl)-3-hydroxypiperidin-3-yl)methyl)pyrrolidin-2-one |
| Example 133 | 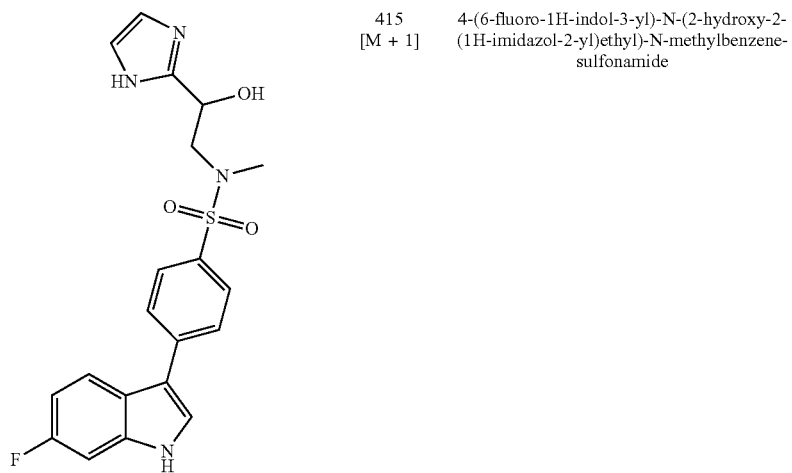 | 415 [M + 1] | 4-(6-fluoro-1H-indol-3-yl)-N-(2-hydroxy-2-(1H-imidazol-2-yl)ethyl)-N-methylbenzene-sulfonamide |

| | | | |
|---|---|---|---|
| Example 134 | 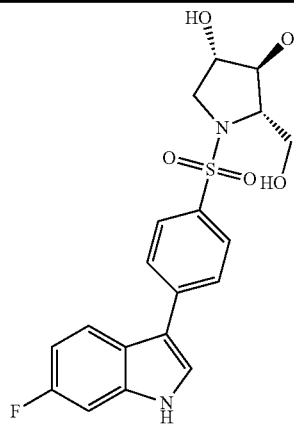 | 407 [M + 1] | (2S,3S,4S)-1-((4-(6-fluoro-1H-indol-3-yl)phenyl)sulfonyl)-2-(hydroxymethyl)pyrrolidine-3,4-diol |
| Example 135 | 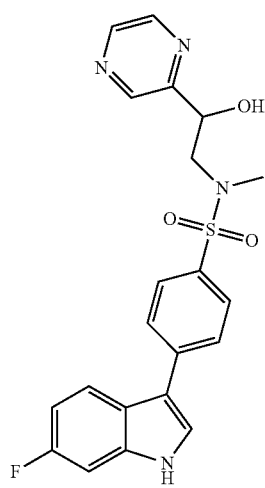 [SMILES: CN(CC(O)c1cnccn1)S(=O)(=O)c1ccc(-c2c[nH]c3cc(F)ccc23)cc1] | 427 [M + 1] | 4-(6-fluoro-1H-indol-3-yl)-N-(2-hydroxy-2-(pyrazin-2-yl)ethyl)-N-methylbenzenesulfonamide |

Example 136: 3-chloro-4-(6-fluoro-1H-indol-3-yl)benzenesulfonamide

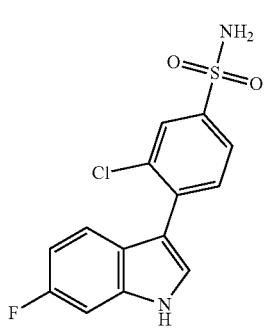 [SMILES: NS(=O)(=O)c1ccc(-c2c[nH]c3cc(F)ccc23)c(Cl)c1]

Step 1: 4-bromo-3-chlorobenzenesulfonamide

To a cooled (ice bath) solution of 4-bromo-3-chlorobenzene-1-sulfonyl chloride (300 mg, 0.98 mmol) in DCM (5 mL) was slowly added NH$_3$H$_2$O (413 mg, 0.459 mL, 2.95 mmol). The reaction was stirred at 15° C. for 1 h then quenched with water (10 mL) and concentrated to remove dichloromethane. The mixture was extracted with EtOAc (15 mL×3). The combined organic layers were washed with water (10 mL) and brine (10 mL) then dried over anhydrous Na$_2$SO$_4$, filtered, and concentrated to afford 4-bromo-3-chlorobenzenesulfonamide (269 mg, 100%) as a white solid.

Step 2: tert-butyl 3-(2-chloro-4-sulfamoylphenyl)-6-fluoro-1H-indole-1-carboxylate A mixture of 4-bromo-3-chlorobenzenesulfonamide (265 mg, 0.92 mmol), tert-butyl 6-fluoro-3-(4,4,5,5-tetramethyl-1,3,2-dioxaborolan-2-yl)-1H-indole-1-carboxylate (333 mg, 0.92 mmol), PdCl$_2$(dppf)CH$_2$Cl$_2$ (68.7 mg, 0.092 mmol), and K$_3$PO$_4$ (586 mg, 2.76 mmol) in 1,4-dioxane (8 mL) and water (2 mL) was sparged with nitrogen for 1 minute. The reaction was stirred at 80° C. for 12 h then cooled and extracted with EtOAc (15 mL×3). The combined organic layers were washed with water (15 mL) and brine (15 mL) then dried over anhydrous Na$_2$SO$_4$, filtered, and concentrated to give crude tert-butyl 3-(2-chloro-4-sulfamoylphenyl)-6-fluoro-1H-indole-1-carboxylate (450 mg) as a brown solid, which was used for next step without further purification.

Step 3: 3-chloro-4-(6-fluoro-1H-indol-3-yl)benzenesulfonamide

A brown solution of tert-butyl 3-(2-chloro-4-sulfamoylphenyl)-6-fluoro-1H-indole-1-carboxylate (crude 450 mg, 0.80 mmol) in MeNH$_2$/EtOH (30% w/w, 10 mL) was stirred at 50° C. for 1 h. The resulting black mixture was concentrated and purified by column chromatography to afford 3-chloro-4-(6-fluoro-1H-indol-3-yl)benzenesulfonamide (219 mg, 84%) as a pale-yellow solid. ¹H NMR (400 MHz, DMSO-d₆) δ [ppm] 11.67 (br, 1H), 7.98 (d, J=2.0 Hz, 1H), 7.84-7.72 (m, 3H), 7.53-7.49 (m, 3H), 7.27 (dd, J=2.3, 9.8 Hz, 1H), 6.99-6.94 (m, 1H); MS: m/z 325.0 (M+H)⁺.

Example 137: 3,5-dichloro-4-(6-fluoro-H-indol-3-yl)-benzenesulfonamide

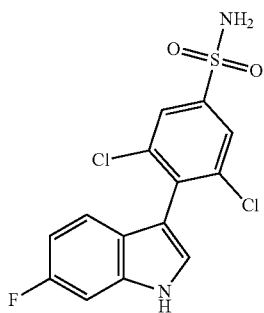 [SMILES: NS(=O)(=O)c1cc(Cl)c(-c2c[nH]c3cc(F)ccc23)c(Cl)c1]

Following the general methods as outlined in Example 136, starting from 4-bromo-3,5-dichlorobenzene-1-sulfonyl chloride, the title compound was isolated as a brown solid. ¹H NMR (400 MHz, DMSO-d₆) δ [ppm] 11.70-11.60 (m, 1H), 7.96 (s, 2H), 7.71 (s, 2H), 7.57 (d, J=2.5 Hz, 1H), 7.27 (dd, J=2.3, 9.8 Hz, 1H), 7.18 (dd, J=5.4, 8.9 Hz, 1H), 6.96-6.86 (m, 1H); LC-MS: m/z 358.9 (M+H)⁺.

Example 138: 2-(5-(6-fluoro-1H-indol-3-yl)-2-sulfamoylphenyl)-N,N-dimethylacetamide

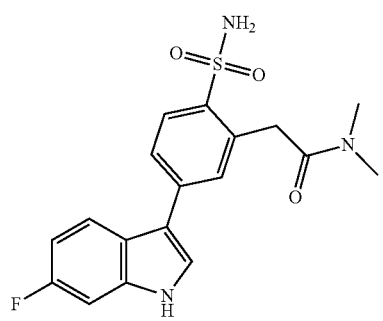 [SMILES: CN(C)C(=O)Cc1cc(-c2c[nH]c3cc(F)ccc23)ccc1S(N)(=O)=O]

Step 1: 2-(5-bromo-2-(N-(tert-butyl)sulfamoyl)phenyl)acetic acid

To a solution of methyl 2-(5-bromo-2-(N-(tert-butyl)sulfamoyl)-phenyl)acetate (700 mg, 1.92 mmol) in MeOH (10 mL) and H₂O (3 mL) was added NaOH (154 mg, 3.84 mmol). The reaction was stirred at 50° C. for 16 h then concentrated and diluted with water (20 mL). The mixture was adjusted to pH 4 with 1 N HCl then extracted with EtOAc (30 mL×2). The combined organic layers were washed with brine (20 mL) then dried over anhydrous Na₂SO₄, filtered and concentrated to give crude 2-(5-bromo-2-(N-(tert-butyl)sulfamoyl)phenyl)acetic acid (550 mg, 82%) as yellow oil, which was used in the next step without further purification.

Step 2: 2-(5-bromo-2-(N-(tert-butyl)sulfamoyl)phenyl)-N,N-dimethylacetamide

A solution of 2-(5-bromo-2-(N-(tert-butyl)sulfamoyl)phenyl)acetic acid (550 mg, 1.51 mmol), dimethylamine hydrochloride (123 mg, 1.51 mmol), HATU (689 mg, 1.81 mmol) and DIEA (585 mg, 4.53 mmol) in DMF (10 mL) was stirred at 20° C. for 16 hrs. The reaction was diluted with water (25 mL) and extracted with EtOAc (30 mL×2). The combined organic layers were washed with brine (40 mL×2) then dried over anhydrous Na₂SO₄, filtered and concentrated. The crude residue was purified by column chromatography (silica gel, 30-40% EtOAc in PE) to give 2-(5-bromo-2-(N-(tert-butyl)sulfamoyl)phenyl)-N,N-dimethylacetamide (300 mg, 53%) as clear oil.

Step 3: tert-butyl 3-(4-(N-(tert-butyl)sulfamoyl)-3-(2-(dimethylamino)-2-oxoethyl)phenyl)-6-fluoro-1H-indole-1-carboxylate A suspension of 2-(5-bromo-2-(N-(tert-butyl)sulfamoyl)phenyl)-N,N-dimethylacetamide (250 mg, 0.663 mmol), tert-butyl 6-fluoro-3-(4,4,5,5-tetramethyl-1,3,2-dioxaborolan-2-yl)-1H-indole-1-carboxylate (311 mg, 0.861 mmol), PdCl₂(dppf)CH₂Cl₂ (50 mg, 0.0663 mmol), and K₃PO₄ (281 mg, 1.33 mmol) in 1,4-dioxane (8 mL) and water (2 mL) was sparged with nitrogen for 1 minute. The reaction was stirred at 80° C. for 2 h then diluted with water (10 mL) and extracted with EtOAc (20 mL). The layers were separated and the organic layer was washed with brine (15 mL) then dried over anhydrous Na₂SO₄, filtered and concentrated. The crude residue was purified by column chromatography to give tert-butyl 3-(4-(N-(tert-butyl)sulfamoyl)-3-(2-(dimethylamino)-2-oxoethyl)phenyl)-6-fluoro-1H-indole-1-carboxylate (300 mg, 85%) as yellow oil.

Step 4: 2-(5-(6-fluoro-1H-indol-3-yl)-2-sulfamoylphenyl)-N,N-dimethylacetamide

A solution of tert-butyl 3-(4-(N-(tert-butyl)sulfamoyl)-3-(2-(dimethylamino)-2-oxoethyl)phenyl)-6-fluoro-1H-indole-1-carboxylate (300 mg, 0.564 mmol) in TFA (8 mL) and DCM (5 mL) was stirred at 30° C. for 2 h. The reaction was neutralized to pH 7 with NaHCO₃ (sat) then extracted with EtOAc (30 mL×2). The combined organic layers were washed with brine (15 mL) then dried over anhydrous Na₂SO₄, filtered and concentrated. The crude residue was purified by column chromatography to give 2-(5-(6-fluoro-1H-indol-3-yl)-2-sulfamoylphenyl)-N,N-dimethylacetamide (32 mg, 15%) as an off-white solid. ¹H NMR (400 MHz, DMSO-d₆) δ [ppm] 11.61 (br, 1H), 7.94-7.81 (m, 3H), 7.73 (dd, J=1.8, 8.3 Hz, 1H), 7.63 (d, J=1.8 Hz, 1H), 7.31-7.19 (m, 3H), 7.00 (dt, J=2.5, 9.3 Hz, 1H), 4.16 (s, 2H), 3.07 (s, 3H), 2.89 (s, 3H); LC-MS: m/z 376.0 (M+H)⁺.

Example 139: 4-(6-fluoro-1H-indol-3-yl)-2-(2-hydroxyethyl)-benzenesulfonamide

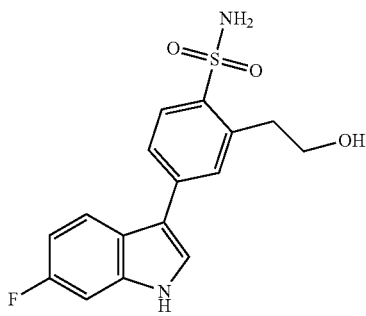 [SMILES: NS(=O)(=O)c1ccc(-c2c[nH]c3cc(F)ccc23)cc1CCO]

Step 1: 3-bromophenethyl acetate

To a cooled (ice bath) solution of 3-bromophenethyl alcohol (5.0 g, 25 mmol) and Et$_3$N (3.0 g, 30 mmol) in DCM (50 mL) was added dropwise AcCl (2.15 g, 27.4 mmol). The reaction was stirred at room temperature for 1 h then poured into water (20 mL) and extracted with DCM (2×20 mL). The combined organic layers were washed with brine (10 mL) then dried over Na$_2$SO$_4$, filtered and concentrated to give 3-bromophenethyl acetate (5.5 g, 91%) as clear oil.

Step 2: 5-bromo-2-(chlorosulfonyl)phenethyl acetate

To a cooled (ice bath) solution of 3-bromophenethyl acetate (2.0 g, 8.2 mmol) in CHCl$_3$ (5 mL) under N$_2$ was added dropwise chlorosulfonic acid (7.67 g, 65.8 mmol). The reaction was stirred in the ice bath for 1.5 h then at room temperature for 18 h. The crude reaction was carefully poured into ice-water (100 mL) and extracted with TBME (2×20 mL). The combined organic layers were washed with brine (5 mL) and NaHCO$_3$ (sat) (5 mL) then dried over Na$_2$SO$_4$, filter and concentrated to crude give 5-bromo-2-(chlorosulfonyl)phenethyl acetate (2.5 g, 89%) as yellow solid.

Step 3: 5-bromo-2-(N-(tert-butyl)sulfamoyl)phenethyl acetate

To a cooled (ice bath) solution of 5-bromo-2-(chlorosulfonyl)phenethyl acetate (2.5 g, 10.3 mmol) in THF (20 mL) was added dropwise tBuNH$_2$ (3.g, 41 mmol). The suspension was stirred at room temperature for 30 min then concentrated. The residue was diluted with water (10 mL) and extracted with EtOAc (3×10 mL). The combined organic layers were dried over Na$_2$SO$_4$, filtered and concentrated to give crude 5-bromo-2-(N-(tert-butyl)sulfamoyl)-phenethyl acetate (2.2 g, 57%) as yellow gum. $^1$H NMR (400 MHz, CDCl$_3$) δ [ppm] 7.90-7.95 (m, 1 H), 7.45-7.52 (m, 2 H), 5.04 (s, 1 H), 4.28-4.39 (m, 2 H), 3.30-3.38 (m, 2 H), 2.06-2.14 (m, 3 H), 1.24-1.27 (m, 9 H).

Step 4: 4-bromo-N-(tert-butyl)-2-(2-hydroxyethyl) benzenesulfonamide

To a solution of 5-bromo-2-(N-(tert-butyl)sulfamoyl) phenethyl acetate (2.2 g, 5.8 mmol) in THF (10 mL) was added a solution of NaOH (930 mg, 23.3 mmol) in H$_2$O (2 mL). The reaction was stirred at room temperature for 1 h then concentrated. The residue was diluted with water (10 mL) and extracted with TBME (2×10 mL). The combined organic layers were dried over Na$_2$SO$_4$, filtered and concentrated to give crude 4-bromo-N-(tert-butyl)-2-(2-hydroxyethyl)-benzenesulfonamide (0.9 g, 46%).

Step 5: tert-butyl 3-(4-(N-(tert-butyl)sulfamoyl)-3-(2-hydroxyethyl)phenyl)-6-fluoro-1H-indole-1-carboxylate A solution of the 4-bromo-N-(tert-butyl)-2-(2-hydroxyethyl)-benzenesulfonamide (850 mg, 2.53 mmol) and tert-butyl 6-fluoro-3-(4,4,5,5-tetramethyl-1,3,2-dioxaborolan-2-yl)-1H-indole-1-carboxylate (1.0 g, 2.8 mmol) in dioxane (10 mL) was added Cs$_2$CO$_3$ (1.65 g, 5.06 mmol, 2 M in water) and Pd(dppf)$_2$Cl$_2$ (92.5 mg, 0.126 mmol). The reaction was sparged with N$_2$ for 2 min then sealed and heated to 90° C. for 2 h. The crude reaction was concentrated and purified by column chromatography to give tert-butyl 3-(4-(N-(tert-butyl)sulfamoyl)-3-(2-hydroxyethyl)phenyl)-6-fluoro-1H-indole-1-carboxylate (650 mg, 52%) as yellow solid. $^1$H NMR (400 MHz, CDCl$_3$) δ [ppm] 8.09-8.18 (m, 1 H), 7.87-8.02 (m, 1 H), 7.75-7.81 (m, 1 H), 7.68-7.74 (m, 1 H), 7.62-7.65 (m, 1 H), 7.58 (dd, J=8.16, 1.63 Hz, 1 H), 7.07 (td, J=8.97, 2.38 Hz, 1 H), 4.81 (s, 1 H), 4.05 (t, J=6.15 Hz, 2 H), 3.38 (t, J=6.40 Hz, 2 H), 1.95 (br s, 1 H), 1.66-1.75 (m, 9 H), 1.26-1.33 (m, 9 H).

Step 6: 4-(6-fluoro-1H-indol-3-yl)-2-(2-hydroxyethyl)benzenesulfonamide

A solution of tert-butyl 3-(4-(N-(tert-butyl)sulfamoyl)-3-(2-hydroxyethyl)phenyl)-6-fluoro-1H-indole-1-carboxylate (438 mg, 0.983 mmol) in neat TFA (10 mL) was stirred at 50° C. for 2 hrs. The reaction was concentrated then diluted EtOAc (50 mL) and washed with NaHCO$_3$ (sat) (10 ml) and H$_2$O (10 mL). The organic phase was dried over Na$_2$SO$_4$, filtered and concentrated. The crude residue was purified by prep HPLC to give 4-(6-fluoro-1H-indol-3-yl)-2-(2-hydroxyethyl)benzenesulfonamide (70 mg, 23%) as a red solid. $^1$H NMR (400 MHz, DMSO-d$_6$) δ [ppm] 11.77-11.56 (m, 1H), 8.01-7.94 (m, 1H), 7.93-7.88 (m, 2H), 7.80 (d, J=1.8 Hz, 1H), 7.75 (dd, J=1.8, 8.3 Hz, 1H), 7.53 (s, 2H), 7.26 (dd, J=2.4, 9.9 Hz, 1H), 7.06-6.96 (m, 1H), 3.96 (t, J=7.4 Hz, 2H), 3.50 (t, J=7.4 Hz, 2H); LCMS: m/z 353.0 (M+H+H$_2$O)$^+$.

Example 140: 4-(6-fluoro-1H-indol-3-yl)-2-(2-(methylamino)ethyl)-benzenesulfonamide

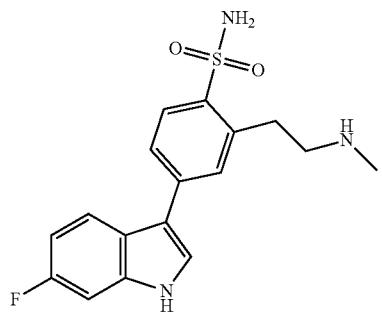 [SMILES: CNCCc1cc(-c2c[nH]c3cc(F)ccc23)ccc1S(N)(=O)=O]

Step 1: tert-butyl3-(4-(N-(tert-butyl)sulfamoyl)-3-(2-((methylsulfonyl)oxy)ethyl)phenyl)-6-fluoro-1H-indole-1-carboxylate To a cooled (ice bath) solution of tert-butyl 3-(4-(N-(tert-butyl)sulfamoyl)-3-(2-hydroxyethyl)phenyl)-6-fluoro-1H-indole-1-carboxylate (600 mg, 1.22 mmol) and DIPEA (474 mg, 3.67 mmol) in DCM (10 mL) was added dropwise MsCl (280 mg, 2.45 mmol). The reaction solution was stirred at room temperature for 2 h then poured into ice-water (10 mL) and extracted with DCM (2×10 mL). The combined organic layers were dried over $Na_2SO_4$, filtered and concentrated to give crude tert-butyl3-(4-(N-(tert-butyl)sulfamoyl)-3-(2-((methylsulfonyl)oxy)ethyl)phenyl)-6-fluoro-1H-indole-1-carboxylate (650 mg, 93%) as yellow solid.

Step 2: tert-butyl 3-(4-(N-(tert-butyl)sulfamoyl)-3-(2-(methylamino)-ethyl)phenyl)-6-fluoro-1H-indole-1-carboxylate A solution of tert-butyl 3-(4-(N-(tert-butyl)sulfamoyl)-3-(2-((methylsulfonyl)oxy)ethyl) phenyl)-6-fluoro-1H-indole-1-carboxylate (320 mg, 0.563 mmol) and $MeNH_2$ (2M in THF, 2 mL) in DMF (5 mL) was stirred at room temperature for 14 h. The reaction was poured into water (50 mL) and extracted with EtOAc (3×20 mL). The combined organic layers were dried over $Na_2SO_4$, filtered and concentrated. The crude residue was purified by column chromatography to give tert-butyl 3-(4-(N-(tert-butyl)sulfamoyl)-3-(2-(methylamino)ethyl)phenyl)-6-fluoro-1H-indole-1-carboxylate (100 mg, 35%) as yellow solid.

Step 3: 4-(6-fluoro-1H-indol-3-yl)-2-(2-(methylamino)-ethyl)benzenesulfonamide To a solution of N-(tert-butyl)-4-(6-fluoro-1H-indol-3-yl)-2-(2-(methylamino)ethyl) benzenesulfonamide (60 mg, 0.15 mmol) in DCM (1 mL) was added TFA (4 mL). The reaction was stirred at 40° C. for 2 h then room temperature for 16 h. The crude reaction was concentrated and neutralized with $NaHCO_3$ (sat) (2 mL). The mixture was extracted with EtOAc (3×5 mL). The combined organic layers were dried over $Na_2SO_4$, filtered and concentrated then purified by prep HPLC to give 4-(6-fluoro-1H-indol-3-yl)-2-(2-(methylamino)-ethyl)benzenesulfonamide (22 mg, 43%) as yellow solid. $^1$H NMR (400 MHz, DMSO-$d_6$) δ [ppm] 11.63 (br s, 1 H), 7.82-8.03 (m, 3 H), 7.63-7.79 (m, 2 H), 7.27 (dd, J=9.8, 2.2 Hz, 1 H), 7.01 (td, J=9.3, 2.3 Hz, 1 H), 6.75 (br s, 2 H), 3.22-3.26 (m, 2 H), 2.94-3.04 (m, 2 H), 2.43 (s, 3 H); LCMS: m/z 348.1 (M+H)$^+$.

Example 141: 2-(2-(dimethylamino)ethyl)-4-(6-fluoro-1H-indol-3-yl)benzenesulfonamide

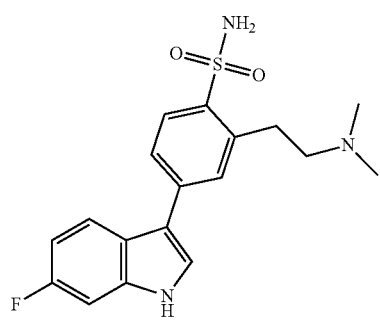 [SMILES: CN(C)CCc1cc(-c2c[nH]c3cc(F)ccc23)ccc1S(N)(=O)=O]

Step 1: tert-butyl3-(4-(N-(tert-butyl)sulfamoyl)-3-(2-(dimethylamino)-ethyl)phenyl)-6-fluoro-1H-indole-1-carboxylate A suspension of tert-butyl 3-(4-(N-(tert-butyl)sulfamoyl)-3-(2-((methylsulfonyl)oxy)ethyl) phenyl)-6-fluoro-1H-indole-1-carboxylate (320 mg, 0.563 mmol), $Me_2NH$—HCl (229 mg, 2.81 mmol) and $K_2CO_3$ (389 mg, 2.81 mmol) in DMF (5 mL) was stirred at room temperature for 12 h. The reaction was poured into water (50 mL) and extracted with EtOAc (3×20 mL). The combined organic layers were dried over $Na_2SO_4$, filtered and concentrated. The crude residue was purified by column chromatography to give tert-butyl3-(4-(N-(tert-butyl)sulfamoyl)-3-(2-(dimethylamino)ethyl) phenyl)-6-fluoro-1H-indole-1-carboxylate (150 mg, 52%) as yellow solid.

Step 2: 2-(2-(dimethylamino)ethyl)-4-(6-fluoro-1H-indol-3-yl)benzenesulfonamide To a solution of tert-butyl 3-(4-(N-(tert-butyl)sulfamoyl)-3-(2-(dimethylamino)ethyl)phenyl)-6-fluoro-1H-indole-1-carboxylate (150 mg, 0.29 mmol) in DCM (2 mL) was added TFA (6 mL). The reaction was stirred at 40° C. for 2 h then at room temperature for 48 h. The reaction was concentrated, neutralized with $NaHCO_3$ (sat) (2 mL) and extracted with EtOAc (3×5 mL). The combined organic layers were dried over $Na_2SO_4$, filtered and concentrated then purified by prep HPLC to give 2-(2-(dimethylamino)ethyl)-4-(6-fluoro-1H-indol-3-yl)benzenesulfonamide (50 mg, 48%) as white solid. $^1$H NMR (400 MHz, DMSO-$d_3$) δ [ppm] 11.61 (br s, 1 H), 7.84-7.96 (m, 3 H), 7.74 (d, J=1.8 Hz, 1 H), 7.68 (d, J=8.0 Hz, 1 H), 7.46 (br s, 2 H), 7.2 (dd, J=10.0, 2.26 Hz, 1 H), 7.01 (td, J=9.2, 2.2 Hz, 1 H), 3.22 (t, J=7.4 Hz, 2 H), 2.74 (m, 2 H), 2.34 (br s, 6 H); LCMS: m/z 362.1 (M+H)$^+$.

Example 142: 4-(6-fluoro-1H-indol-3-yl)-2-(2,2,2-trifluoroethyl)-benzenesulfonamide

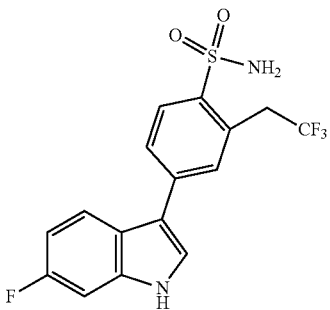 [SMILES: NS(=O)(=O)c1ccc(-c2c[nH]c3cc(F)ccc23)cc1CC(F)(F)F]

Step 1: 4-bromo-2-(2,2,2-trifluoroethyl)benzene-1-sulfonyl chloride

To a cooled (ice bath) solution of 1-bromo-3-(2,2,2-trifluoroethyl)benzene (1.0 g, 4.1 mmol) in $CHCl_3$ (15 mL) was added via addition funnel chlorosulfonic acid (2.84 g, 1.60 mL, 24.3 mmol). The reaction was stirred in the ice bath for 3 h then at 27° C. for 16 h. The reaction was poured into ice (about 20 g) then extracted with dichloromethane (20 mL×3). The combined organic layers were washed with water (15 mL×2) and brine (15 mL) then dried over anhydrous $Na_2SO_4$, filtered and concentrated. The crude residue was purified by column chromatography (silica gel, petroleum ether) to afford 4-bromo-2-(2,2,2-trifluoroethyl)benzene-1-sulfonyl chloride (800 mg, 73%) as a white solid. $^1$H NMR (400 MHz, CDCl$_3$) δ [ppm] 8.06 (d, J=8.8 Hz, 1H), 7.81-7.75 (m, 2H), 4.05 (q, J=10.0 Hz, 2H).

Step 2:
4-bromo-2-(2,2,2-trifluoroethyl)benzenesulfonyl azide

A clear solution of 4-bromo-2-(2,2,2-trifluoroethyl)benzene-1-sulfonyl chloride (800 mg, 2.98 mmol) in water/acetone (1:1, 30 ml) was stirred in an ice bath for 20 min then sodium azide (387 mg, 5.96 mmol) was added in three portions. The reaction was stirred at 28° C. for 1.5 h then concentrated at 25° C. to remove acetone. The mixture was extracted with ethyl acetate (15 ml×3) and the organic phase was washed with brine (10 mL) then dried over anhydrous sodium sulfate, filtered and concentrated to give 4-bromo-2-(2,2,2-trifluoroethyl)benzenesulfonyl azide (938 mg, >100%) as a white solid, which was used directly in the next step. $^1$H NMR (400 MHz, CDCl$_3$) δ [ppm] 8.01 (d, J=8.5 Hz, 1H), 7.80 (s, 1H), 7.74 (dd, J=2.0, 8.5 Hz, 1H), 3.92 (q, J=10.0 Hz, 2H).

Step 3:
4-bromo-2-(2,2,2-trifluoroethyl)benzenesulfonamide

To a yellow solution of 4-bromo-2-(2,2,2-trifluoroethyl)benzenesulfonyl azide (938 mg, 2.74 mmol) in chlorobenzene (0.5 mL) was added 5,10,15,20-tetraphenyl-21H, 23H-porphine(II) (118 mg, 0.17 mmol) under N$_2$. The suspension was sparged with N$_2$ for 2 min then heated to 80° C. for 80 h. The reaction was concentrated and purified by column chromatography (silica gel, 0-50% ethyl acetate/petroleum ether) to give 4-bromo-2-(2,2,2-trifluoroethyl)-benzenesulfonamide (320 mg, 37%) as a yellow solid. $^1$H NMR (400 MHz, CDCl$_3$) δ [ppm] 8.85 (s, 1H), 8.23 (d, J=7.3 Hz, 1H), 7.77 (d, J=7.0 Hz, 1H), 4.17-3.92 (m, 1H).

Step 4: tert-butyl 6-fluoro-3-(4-sulfamoyl-3-(2,2,2-trifluoroethyl)phenyl)-1H-indole-1-carboxylate A yellow solution of 4-bromo-2-(2,2,2-trifluoroethyl)benzenesulfonamide (320 mg, 1.30 mmol), tert-butyl 6-fluoro-3-(4,4,5,5-tetramethyl-1,3,2-dioxaborolan-2-yl)-1H-indole-1-carboxylate (406 mg, 1.12 mmol), PdCl$_2$(dppf)CH$_2$Cl$_2$ (76.3 mg, 0.102 mmol) and K$_3$PO$_4$ (651 mg, 3.07 mmol) in 1,4-dioxane (8.0 mL) and water (2.0 mL) was sparged with N$_2$ for 1 min then stirred at 80° C. for 2 h. The reaction was concentrated and purified by column chromatography (silica gel, 0-30% ethyl acetate/petroleum ether) to afford tert-butyl 6-fluoro-3-(4-sulfamoyl-3-(2,2,2-trifluoroethyl)phenyl)-1H-indole-1-carboxylate (244 mg, 47% yield) as a dark red oil.

Step 5: 4-(6-fluoro-1H-indol-3-yl)-2-(2,2,2-trifluoroethyl)-benzenesulfonamide

To a cooled (ice bath) solution of tert-butyl 6-fluoro-3-(4-sulfamoyl-3-(2,2,2-trifluoroethyl)phenyl)-H-indole-1-carboxylate (244 mg, 0.608 mmol) in dichloromethane (4 mL) was added trifluoroacetic acid (2 mL). The reaction was stirred at 26° C. for 16 h then concentrated and neutralized to pH 7-8 with NH$_3$/H$_2$O. The solution was concentrated and purified by column chromatography (silica gel, 12 g, 0-50% ethyl acetate/petroleum ether) to afford the desired product (120 mg) as a brown solid, which was further purified by prep-HPLC to afford 4-(6-fluoro-1H-indol-3-yl)-2-(2,2,2-trifluoroethyl)benzenesulfonamide (57 mg, 25%) as a white solid. $^1$H NMR (400 MHz, DMSO-d$_6$) δ [ppm] 11.68 (s, 1H), 7.99 (d, J=8.0 Hz, 1H), 7.90-7.83 (m, 4H), 7.58 (s, 2H), 7.27 (dd, J=2.3, 9.8 Hz, 1H), 7.03 (dt, J=2.3, 9.3 Hz, 1H), 4.24-4.16 (m, 2H); LC-MS: m/z 373.1 (M+H)$^+$.

Example 143: 2-(5-(6-fluoro-1H-indol-3-yl)-2-sulfamoylphenyl)-N-methylacetamide

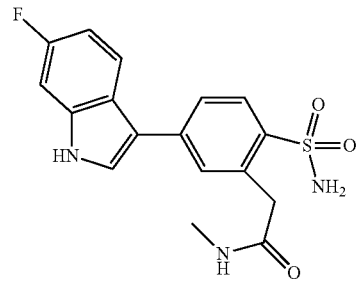 [SMILES: CNC(=O)Cc1cc(-c2c[nH]c3cc(F)ccc23)ccc1S(N)(=O)=O]

Step 1: methyl 2-(5-bromo-2-(chlorosulfonyl)phenyl)acetate

A 100 mL of round bottom flask was purged with N$_2$ and charged with methyl 2-(3-bromophenyl)acetate (2.0 g, 8.7 mmol) then cooled in an ice bath. Chlorosulfonic acid (6.1 g, 52 mmol) was added dropwise and the reaction was stirred under a N$_2$ atmosphere at 5° C. for 4 h then at ambient temperature for 18 h. The reaction was carefully poured into ice-water (100 mL) then extracted with dichloromethane (2×50 mL). The combined organic layers were washed with brine (10 mL) then dried over Na$_2$SO$_4$, filtered and concentrated to give methyl 2-(5-bromo-2-(chlorosulfonyl)phenyl)acetate as light yellow solid, which was directly used in the next reaction.

Step 2: methyl 2-(5-bromo-2-sulfamoylphenyl)acetate

To a cooled (ice bath) yellow solution of methyl 2-(5-bromo-2-(chlorosulfonyl)phenyl)acetate (4.5 g, 14 mmol) in THF (10 ml) was added dropwise NH$_3$/THF (flash prepared, saturated, 10 mL). The reaction was stirred at 10° C. for 1 h then concentrated and diluted with water (20 mL). The mixture was extracted with ethyl acetate (3×20 ml) and the combined organic layers were washed with brine (10 ml) then dried over Na$_2$SO$_4$, filtered and concentrated. The crude residue was purified by column chromatography (silica gel, ethyl acetate/petroleum ether=0-50%) to give methyl 2-(5-bromo-2-sulfamoylphenyl)acetate (1.6 g, 38%) as white solid. $^1$H NMR (400 MHz, DMSO-d$_6$) δ [ppm] 7.76-7.82 (m, 1 H), 7.70-7.74 (m, 2 H), 7.58 (s, 2 H), 4.08 (s, 2 H), 3.56-3.62 (m, 3 H).

Step 3: tert-butyl 6-fluoro-3-(3-(2-methoxy-2-oxoethyl)-4-sulfamoylphenyl)-1H-indole-1-carboxylate A solution of the methyl 2-(5-bromo-2-sulfamoylphenyl)acetate (2.3 g, 7.4 mmol) and tert-butyl 6-fluoro-3-(4,4,5,5- tetramethyl-1,3,2-dioxaborolan-2-yl)-1H-indole-1-carboxylate (3.5 g, 9.7 mmol) in dioxane (30 mL) was added K₃PO₄ (2 M in water, 3.17 mg, 14.9 mmol) and Pd(dppf)₂C₂(546 mg, 0.746 mmol). The reaction was sparged with N₂ for 2 min stirred at 80° C. for 3 h. The reaction was cooled, concentrated and purified by column chromatography (silica gel, ethyl acetate/petroleum ether=0-50%) to give tert-butyl 6-fluoro-3-(3-(2-methoxy-2-oxoethyl)-4-sulfamoylphenyl)-1H-indole-1-carboxylate (1.5 g, 44%) as white solid. ¹H NMR (400 MHz, CDCl₃) δ [ppm] 8.15-8.20 (m, 1 H), 7.91-8.00 (m, 1 H), 7.75-7.80 (m, 1 H), 7.65-7.74 (m, 2 H), 7.55-7.58 (m, 1 H), 7.05-7.12 (m, 1 H), 5.37-5.48 (m, 2 H), 4.30 (s, 2 H), 3.75-3.82 (m, 3 H), 1.71 (s, 9 H).

Step 4: 2-(5-(6-fluoro-1H-indol-3-yl)-2-sulfamoylphenyl)-N-methylacetamide

To a solution of tert-butyl 6-fluoro-3-(3-(2-methoxy-2-oxoethyl)-4-sulfamoylphenyl)-1H-indole-1-carboxylate (150 mg, 0.324 mmol) in EtOH (5 mL) was added MeNH₂ (5 mL, 38% EtOH solution). The reaction was sealed and stirred at 80° C. for 1 h then cooled to ambient temperature and concentrated. The crude residue was purified by prep-HPLC to give 2-(5-(6-fluoro-1H-indol-3-yl)-2-sulfamoylphenyl)-N-methylacetamide (15 mg, 13%) as light yellow solid. ¹H NMR (400 MHz, DMSO-d₆) δ [ppm] 11.59-11.68 (m, 1 H), 8.24 (d, J=4.77 Hz, 1 H), 7.88-7.96 (m, 2 H), 7.78-7.86 (m, 2 H), 7.73 (dd, J=8.28, 1.51 Hz, 1 H), 7.46 (br s, 2 H), 7.27 (dd, J=9.91, 2.38 Hz, 1 H), 7.02 (td, J=9.16, 2.51 Hz, 1 H), 4.01 (s, 2 H), 2.64 (d, J=4.77 Hz, 3 H); LCMS: m/z 383.8 (M+Na)⁺.

Example 144: 2-(5-(6-fluoro-1H-indol-3-yl)-2-sulfamoylphenyl)-acetamide

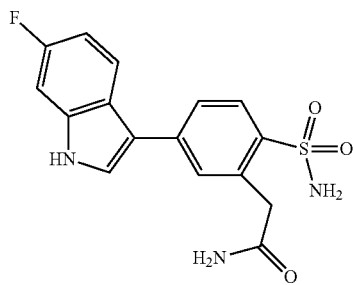 [SMILES: NC(=O)Cc1cc(-c2c[nH]c3cc(F)ccc23)ccc1S(N)(=O)=O]

A solution of tert-butyl 6-fluoro-3-(3-(2-methoxy-2-oxoethyl)-4-sulfamoylphenyl)-1H-indole-1-carboxylate (300 mg, 0.649 mmol) in EtOH (15 mL) was sparged with NH₃ gas for 10 min at −40° C. The reaction was sealed and stirred at 30° C. for 16 h. The reaction was concentrated and purified by prep-HPLC to give 2-(5-(6-fluoro-1H-indol-3-yl)-2-sulfamoylphenyl)acetamide (52 mg, 23%) as a white solid. ¹H NMR (400 MHz, DMSO-d₆) δ [ppm] 11.64 (s, 1 H), 7.88-7.96 (m, 2 H), 7.82-7.87 (m, 1 H), 7.69-7.78 (m, 2 H), 7.43 (s, 2 H), 7.19-7.31 (m, 2 H), 7.01 (d, J=2.26 Hz, 1 H), 3.99 (s, 2 H); LCMS: m/z 370.1 (M+Na)⁺.

Example 145: 4-((4-(6-fluoro-1H-indol-3-yl)phenyl)sulfonyl)-1-methylpiperazine-2,6-dione

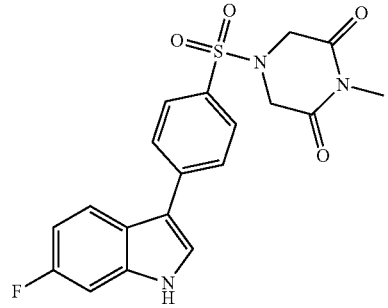 [SMILES: CN1C(=O)CN(S(=O)(=O)c2ccc(-c3c[nH]c4cc(F)ccc34)cc2)CC1=O]

Step 1: 4-((4-bromophenyl)sulfonyl)piperazine-2,6-dione

To a yellow solution of piperazine-2,6-dione (400 mg, 3.50 mmol) and 4-bromobenzenesulfonyl chloride (1.07 g, 4.21 mmol) in CH₂Cl₂ (35 mL) was added Et₃N (0.98 mL, 7.0 mmol) at 20° C. The yellow solution was stirred 20° C. for 2.5 h then quenched with NaHCO₃ (sat) and extracted with ethyl acetate (15 mL×3). The combined organic layers were washed with brine (15 mL) then dried over anhydrous Na₂SO₄, filtered and concentrated. The crude residue was purified by column chromatography (silica gel, petroleum ether/ethyl acetate=8-50% followed by methanol/CH₂Cl₂=1-10%) to give 4-((4-bromophenyl)sulfonyl)piperazine-2,6-dione (585 mg, 50%) as a yellow solid. ¹H NMR (400 MHz, DMSO-d₆) δ [ppm] 11.23 (s, 1H), 7.87 (d, J=8.5 Hz, 2H), 7.78-7.71 (m, 2H), 4.08 (s, 4H).

Step 2: 4-((4-bromophenyl)sulfonyl)-1-methylpiperazine-2,6-dione

A solution of 4-((4-bromophenyl)sulfonyl)piperazine-2,6-dione (585 mg, 0.30 mmol) in DMF (17.6 mL) was cooled to 0° C. and sodium hydride (60% in mineral oil, 84.3 mg, 2.11 mmol) was added. Stirring was continued at 0° C. for 10 min then methyl iodide (299 mg, 2.11 mmol) was added and the reaction was slowly warmed to 20° C. and stirred for 15 h. The reaction was quenched with water and extracted with ethyl acetate (20 mL×2). The combined organic layers were washed with NaHCO₃ (sat) (15 mL×2), water (15 mL×2), and brine (15 mL×2) then dried over anhydrous Na₂SO₄ and concentrated to give crude 4-((4-bromophenyl)sulfonyl)-1-methylpiperazine-2,6-dione (450 mg, 74%) as a yellow solid, which was used in the next step without further purification. ¹H NMR (400 MHz, DMSO-d₆) δ [ppm] 7.91-7.86 (m, 2H), 7.74 (d, J=8.5 Hz, 2H), 4.22 (s, 4H), 2.63 (s, 3H).

Step 3: tert-butyl 6-fluoro-3-(4-((4-methyl-3,5-dioxopiperazin-1-yl)sulfonyl)-phenyl)-1H-indole-1-carboxylate A mixture of 4-((4-bromophenyl)sulfonyl)-1-methylpiperazine-2,6-dione (200 mg, 0.58 mmol), tert-butyl 6-fluoro-3-(4,4,5,5-tetramethyl-1,3,2-dioxaborolan-2-yl)-1H-indole-1-carboxylate (347 mg, 0.576 mmol), PdCl₂(dppf)CH₂Cl₂ (43.0 mg, 0.0576 mmol) and K₃PO₄ (245 mg, 1.15 mmol) in 1,4-dioxane (8 mL) was sparged with N₂ for 1 min then heated at 80° C. for 2 h. The reaction was concentrated and purified by column chromatography (silica gel, ethyl acetate/Petroleum ether=6%~70%) to give tert-butyl 6-fluoro-3-(4-((4-methyl-3,5-dioxopiperazin-1-yl)sulfonyl)phenyl)-1H-indole-1-carboxylate (180 mg, 62%) as a yellow solid.

Step 4: 4-((4-(6-fluoro-1H-indol-3-yl)phenyl)sulfonyl)-1-methylpiperazine-2,6-dione To a yellow solution of tert-butyl 6-fluoro-3-(4-((4-methyl-3,5-dioxopiperazin-1-yl) sulfonyl)phenyl)-1H-indole-1-carboxylate (180 mg, 0.36 mmol) in CH$_2$Cl$_2$ (10 mL) was added trifluoroacetic acid (5 mL) at 20° C. The reaction was stirred for 2 h then neutralized with NaHCO$_3$ (sat) and extracted with CH$_2$Cl$_2$ (15 mL×2). The combined organic layers were washed with water (10 mL) and brine (10 mL) then dried over anhydrous Na$_2$SO$_4$, filtered and concentrated. The crude residue was purified by column chromatography (silica gel, methanol/CH$_2$Cl$_2$=0-3%) then further purified by prep-HPLC and column chromatography (12 g silica gel, methanol/CH$_2$Cl$_2$=0-3%) to afford 4-((4-(6-fluoro-1H-indol-3-yl)phenyl)sulfonyl)-1-methylpiperazine-2,6-dione (20 mg, 14%) as a white solid. $^1$H NMR (400 MHz, DMSO-d$_6$) δ [ppm] 11.73 (br s, 1H), 7.98-7.88 (m, 4H), 7.77 (d, J=8.5 Hz, 2H), 7.27 (dd, J=2.5, 9.5 Hz, 1H), 7.03 (dt, J=2.5, 9.3 Hz, 1H), 4.26 (s, 4H), 2.55 (s, 3H); LC-MS: m/z 402.1 (M+H)$^+$.

Example 146: (R)-1-(2,3-dihydroxypropyl)-4-((4-(6-fluoro-1H-indol-3-yl)phenyl)sulfonyl)piperazin-2-one

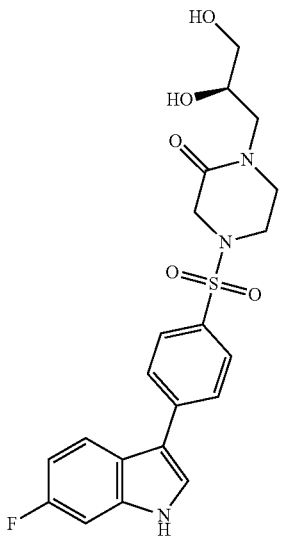 [SMILES: O=C1CN(S(=O)(=O)c2ccc(-c3c[nH]c4cc(F)ccc34)cc2)CCN1C[C@@H](O)CO]

Step 1: benzyl 3-oxopiperazine-1-carboxylate

To a cooled (ice bath) solution of piperazin-2-one (8.0 g, 80 mmol) in THF (25 mL) was added triethylamine (14 mL, 24 mmol) and CbzCl (14 g, 80 mmol). The reaction was stirred for 3 h then concentrated. The crude residue was diluted with petroleum ether and filtered to afford benzyl 3-oxopiperazine-1-carboxylate (14 g, 75%) as a white solid. $^1$H NMR (400 MHz, DMSO-d$_6$) δ [ppm] 8.17-8.03 (m, 1H), 7.47-7.21 (m, 5H), 5.11 (s, 2H), 3.91 (d, J=12.5 Hz, 2H), 3.64-3.46 (m, 2H), 3.21 (dt, J=2.9, 5.3 Hz, 2H), 1.20 (t, J=7.3 Hz, 1H).

Step 2: (R)-benzyl 4-((2,2-dimethyl-1,3-dioxolan-4-yl)methyl)-3-oxopiperazine-1-carboxylate To a cooled (ice bath) yellow solution of benzyl 3-oxopiperazine-1-carboxylate (1.5 g, 5.8 mmol) in dry DMF (20 mL) was added NaH (692 mg, 60% in mineral, 17.3 mmol) in two portions. The reaction was stirred in an ice bath for 20 min then (S)-4-(chloromethyl)-2,2-dimethyl-1,3-dioxolane (1.1 g, 7.0 mmol) was added. Stirring was continued at 70° C. for 44 h. The reaction was diluted with ethyl acetate (30 mL) and H$_2$O (10 mL) then extracted with ethyl acetate (30 mL×3). The combined organic layers were dried over Na$_2$SO$_4$, filtered and concentrated then purified by prep-HPLC to give (R)-benzyl 4-((2,2-dimethyl-1,3-dioxolan-4-yl)methyl)-3-oxopiperazine-1-carboxylate (290 mg, 14%) as a clear oil. $^1$H NMR (400 MHz, CDCl$_3$) δ [ppm] 7.44-7.30 (m, 5H), 5.20-5.11 (m, 2H), 4.34 (dq, J=3.1, 6.7 Hz, 1H), 4.18 (d, J=1.8 Hz, 2H), 4.07 (dd, J=6.4, 8.7 Hz, 1H), 3.88 (dd, J=2.8, 14.1 Hz, 1H), 3.79-3.68 (m, 2H), 3.67-3.59 (m, 2H), 3.49 (s, 1H), 3.21 (dd, J=7.3, 14.1 Hz, 1H), 1.42 (s, 3H), 1.33 (s, 3H).

Step 3: (R)-1-((2,2-dimethyl-1,3-dioxolan-4-yl)methyl)piperazin-2-one

To a yellow solution of (R)-benzyl 4-((2,2-dimethyl-1,3-dioxolan-4-yl)methyl)-3-oxopiperazine-1-carboxylate (290 mg, 0.832 mmol) in methanol (10 mL) was added Pd(OH)$_2$/C (60 mg, 0.085 mmol) under N$_2$. The suspension was evacuated and back-filled with H$_2$ three times then stirred under a H$_2$ atmosphere (30 psi) for 3 h. The suspension was filtered and concentrated to give (R)-1-((2,2-dimethyl-1,3-dioxolan-4-yl)methyl)piperazin-2-one (190 mg, >100%) as a yellow oil. $^1$H NMR (400 MHz, CDCl$_3$) [ppm] 4.34 (dq, J=3.5, 6.7 Hz, 1H), 4.06 (dd, J=6.5, 8.5 Hz, 1H), 3.84 (dd, J=3.5, 14.1 Hz, 1H), 3.66-3.54 (m, 2H), 3.52 (s, 2H), 3.47-3.37 (m, 1H), 3.16 (dd, J=7.0, 14.1 Hz, 1H), 3.11-3.00 (m, 2H), 1.41 (s, 3H), 1.32 (s, 3H).

Step 4: (R)-4-((4-bromophenyl)sulfonyl)-1-((2,2-dimethyl-1,3-dioxolan-4-yl)methyl)piperazin-2-one To a yellow solution of 4-bromobenzene-1-sulfonyl chloride (178 mg, 0.832 mmol) in CH$_2$Cl$_2$ (6 mL) was added trimethylamine (0.232 mL, 1.67 mmol) and (R)-1-((2,2-dimethyl-1,3-dioxolan-4-yl)methyl)piperazin-2-one (213 mg, 0.834 mmol) at 26° C. The reaction was stirred for 2 h then diluted with H$_2$O (10 mL) and extracted with dichloromethane (10 mL×3). The combined organic layers were washed with brine (5 mL×2) then dried over Na$_2$SO$_4$, filtered and concentrated to give crude (R)-4-((4-bromophenyl)sulfonyl)-1-((2,2-dimethyl-1,3-dioxolan-4-yl)methyl)piperazin-2-one (300 mg, 83%) as a gray solid which was used directly in the next step.

Step 5: (R)-4-((4-bromophenyl)sulfonyl)-1-((2,2-dimethyl-1,3-dioxolan-4-yl)methyl)piperazin-2-one To a yellow solution of (R)-4-((4-bromophenyl)sulfonyl)-1-((2,2-dimethyl-1,3-dioxolan-4-yl)methyl)piperazin-2-one (200 mg, 0.462 mmol), tert-butyl 6-fluoro-3-(4,4,5,5-tetramethyl-1,3,2-dioxaborolan-2-yl)-1H-indole-1-carboxylate (132 mg, 0.508 mmol) and Cs$_2$CO$_3$ (301 mg, 0.923 mmol) in dioxane/H$_2$O (8 ml/2 mL) was added Pd(dppf)Cl$_2$ (33.8 mg, 0.0462 mmol) at 25° C. under N$_2$. The reaction was stirred at 100° C. for 6 h then diluted with water (5 mL) and extracted with ethyl acetate (10 mL×3). The combined organic layers were washed with brine (10 mL) then dried over anhydrous Na$_2$SO$_4$, filtered and concentrated. The crude residue was purified by column chromatography (silica gel, 10-70% ethyl acetate/petroleum ether) to give (R)-4-((4-bromophenyl)sulfonyl)-1-((2,2-dimethyl-1,3-dioxolan-4-yl)methyl)piperazin-2-one (100 mg, 37%) as a light yellow oil.

Step 6: (R)-1-(2,3-dihydroxypropyl)-4-((4-(6-fluoro-1H-indol-3-yl)phenyl)sulfonyl)piperazin-2-one To a yellow solution of (R)-4-((4-bromophenyl)sulfonyl)-1-((2,2-dimethyl-1,3-dioxolan-4-yl)methyl)piperazin-2-one (100 mg, 0.17 mmol) in dichloromethane (1 mL) was added trifluoroacetic acid/H$_2$O (0.5 mL/0.5 mL). The reaction was stirred at 28° C. for 6 h then concentrated. The pH was adjusted to 9 with NaHCO$_3$ (sat) and extracted with ethyl acetate (10 mL×3). The combined organic layers were dried over anhydrous Na$_2$SO$_4$, filtered and concentrated. The crude residue was purified by prep-HPLC to give (R)-1-(2,3-dihydroxypropyl)-4-((4-(6-fluoro-1H-indol-3-yl)phenyl)sulfonyl)piperazin-2-one (17 mg, 23%) as a white solid. $^1$H NMR (400 MHz, DMSO-d$_6$) δ [ppm] 7.99-7.91 (m, 4 H), 7.81 (d, J=8.5 Hz, 2 H), 7.27 (d, J=9.0 Hz, 1 H), 7.01 (dt, J=2.4, 9.2 Hz, 1 H), 4.77 (br s, 1 H), 4.52 (br s, 1 H), 3.65-3.38 (m, 7 H), 3.26-3.20 (m, 3 H), 3.06 (dd, J=8.0, 13.6 Hz, 1 H); LC-MS: m/z 469.9 (M+Na)$^+$; [α]$^{20}_D$+6.43° (c=1.4 mg/ml, DMSO).

Example 147: (S)-1-(2,3-dihydroxypropyl)-4-((4-(6-fluoro-1H-indol-3-yl)phenyl)sulfonyl)piperazin-2-one

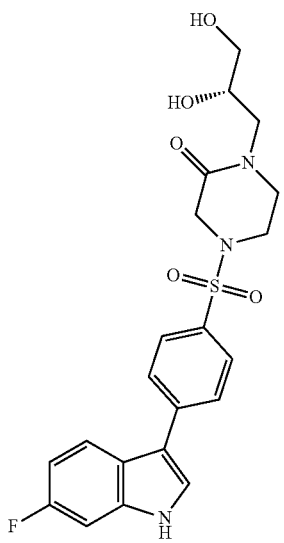 [SMILES: O=C1CN(S(=O)(=O)c2ccc(-c3c[nH]c4cc(F)ccc34)cc2)CCN1C[C@H](O)CO]

Following the general methods as outlined in Example 277, starting from (S)-benzyl 4-((2,2-dimethyl-1,3-dioxolan-4-yl)methyl)-3-oxopiperazine-1-carboxylate, the title compound was isolated as a white solid. $^1$H NMR (400 MHz, DMSO-d$_6$) δ [ppm] 7.99-7.93 (m, 4H), 7.81 (d, J=8.5 Hz, 2H), 7.28 (d, J=9.0 Hz, 1H), 7.01 (dt, J=2.4, 9.2 Hz, 1H), 4.78 (m, 1H), 4.54-4.51 (m, 1H), 3.62-3.40 (m, 7H), 3.25-3.24 (m, 3H), 3.09-3.04 (dd, J=8.0, 13.6 Hz, 1H); LC-MS: m/z 469.9 (M+Na)$^+$; [α]$^{20}_D$−8.27° (c=1.25 mg/ml, DMSO).

Example 148: 1-(2-aminoethyl)-4-((4-(6-fluoro-1H-indol-3-yl)-phenyl)sulfonyl)piperazin-2-one

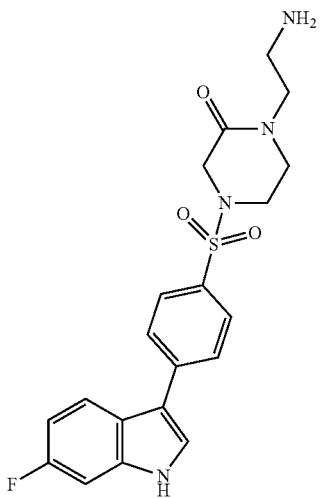 [SMILES: NCCN1CCN(S(=O)(=O)c2ccc(-c3c[nH]c4cc(F)ccc34)cc2)CC1=O]

Step 1: benzyl 4-(2-((tert-butoxycarbonyl)amino)ethyl)-3-oxopiperazine-1-carboxylate To a solution of benzyl 3-oxopiperazine-1-carboxylate (500 mg, 2.13 mmol) in DMF (10 mL), was added t-BuOK (479 mg, 4.27 mmol). The reaction was stirred for 30 min then 2-((tert-butoxycarbonyl)amino)ethyl methanesulfonate (613 mg, 2.56 mmol) was added and the mixture was stirred at 70° C. for 2 h. The suspension was poured into ice-water (10 mL) then extracted with ethyl acetate (20 ml×2). The combined organic layers were washed with brine (10 ml) then dried over Na$_2$SO$_4$, filtered and concentrated. The crude oil was purified by column chromatography (silica gel, 10-70%) ethyl acetate/petroleum ether) to give benzyl 4-(2-((tert-butoxycarbonyl)amino)ethyl)-3-oxopiperazine-1-carboxylate (130 mg, 16%) as a yellow oil.

Step 2: tert-butyl (2-(2-oxopiperazin-1-yl)ethyl)carbamate

To a yellow solution of benzyl 4-(2-((tert-butoxycarbonyl)amino)ethyl)-3-oxopiperazine-1-carboxylate (280 mg, 0.742 mmol) in methanol (10 mL) was added Pd(OH)$_2$/C (60 mg, 20% w/w) under N$_2$. The suspension was evacuated and back-filled with H$_2$ three times then stirred under H$_2$ (30 psi) for 3 h. The suspension was filtered and concentrated to give tert-butyl (2-(2-oxopiperazin-1-yl)ethyl)carbamate (190 mg, >100%) as a light yellow oil. $^1$H NMR (400 MHz, CDCl$_3$) δ [ppm] 4.52-4.43 (m, 2H), 4.37-4.29 (m, 1H), 3.65 (t, J=7.9 Hz, 2H), 3.56-3.48 (m, 3H), 3.41-3.37 (m, 2H), 3.11-3.06 (m, 1H), 1.44 (s, 9H).

Step 3: tert-butyl (2-(4-((4-bromophenyl)sulfonyl)-2-oxopiperazin-1-yl)ethyl)carbamate To a light yellow solution of tert-butyl (2-(2-oxopiperazin-1-yl)ethyl)carbamate (190 mg, 0.62 mmol) in dichloromethane (6 mL) was added triethylamine (0.17 mL, 1.3 mmol) and 4-bromobenzene-1-sulfonyl chloride (160 mg, 0.626 mmol) at 26° C. The reaction was stirred for 2 h then diluted with dichloromethane (30 mL) and washed with H$_2$O (8 mL×2). The organic layer was dried over Na$_2$SO$_4$ then filtered and concentrated. The crude residue was purified by column chromatography (silica gel, 5-30% ethyl acetate/ petroleum ether) to give tert-butyl (2-(4-((4-bromophenyl)sulfonyl)-2-oxopiperazin-1-yl)ethyl)carbamate (150 mg, 52%) as a gray solid.

Step 4: tert-butyl 3-(4-((4-(2-((tert-butoxycarbonyl)amino)ethyl)-3-oxopiperazin-1-yl)sulfonyl)phenyl)-6-fluoro-1H-indole-1-carboxylate To a yellow solution of tert-butyl (2-(2-oxopiperazin-1-yl)ethyl)carbamate (150 mg, 0.325 mmol), tert-butyl 6-fluoro-3-(4,4,5,5-tetramethyl-1,3,2-dioxaborolan-2-yl)-H-indole-1-carboxylate (147 mg, 0.325 mmol) and $Cs_2CO_3$ (212 mg, 0.651 mmol) in Dioxane/$H_2O$ (8 ml/2 mL) was added Pd(dppf)$Cl_2$ (23 mg, 0.03 mmol) at 28° C. under $N_2$. The reaction was stirred at 80° C. for 6 h then diluted with water (5 mL) and extracted with ethyl acetate (10 mL×3). The combined organic layers were dried over anhydrous $Na_2SO_4$ then filtered and concentrated. The crude residue was purified by column chromatography (silica gel, 10-70% ethyl acetate/petroleum ether) to give tert-butyl 3-(4-((4-(2-((tert-butoxycarbonyl)amino)ethyl)-3-oxopiperazin-1-yl)sulfonyl)phenyl)-6-fluoro-1H-indole-1-carboxylate (120 mg, 60%) as a white solid.

Step 5: 1-(2-aminoethyl)-4-((4-(6-fluoro-1H-indol-3-yl)-phenyl)sulfonyl)piperazin-2-one To a yellow solution of tert-butyl 3-(4-((4-(2-((tert-butoxycarbonyl)-amino)ethyl)-3-oxopiperazin-1-yl)sulfonyl)phenyl)-6-fluoro-1H-indole-1-carboxylate (120 mg, 0.195 mmol) in dichloromethane (5 mL) was added trifluoroacetic acid (5 mL). The reaction was stirred at 25° C. for 3 h then concentrated. The residue was diluted with $H_2O$ (5 mL) then neutralized to pH>7 with $NH_3.H_2O$ and extracted with ethyl acetate (15 mL×3). The combined organic layers were washed with brine (10 mL) then dried over anhydrous $Na_2SO_4$, filtered and concentrated. The crude product was purified by prep-HPLC to give 1-(2-aminoethyl)-4-((4-(6-fluoro-1H-indol-3-yl)phenyl)sulfonyl)piperazin-2-one (17 mg, 21%) as a white solid. $^1$H NMR (400 MHz, DMSO-$d_6$) δ [ppm] 11.71 (br s, 1H), 7.99-7.92 (m, 4H), 7.82 (d, J=8.3 Hz, 2H), 7.27 (dd, J=2.5, 9.8 Hz, 1H), 7.01 (dt, J=2.3, 9.3 Hz, 1H), 3.60-3.55 (m, 2H), 3.41-3.38 (m, 2H), 3.21 (m, 4H), 2.57 (t, J=6.4 Hz, 2H); LC-MS: m/z 438.8 (M+Na)$^+$.

Example 149: 1-(2-(dimethylamino)ethyl)-4-((4-(6-fluoro-1H-indol-3-yl)phenyl)sulfonyl)piperazin-2-one

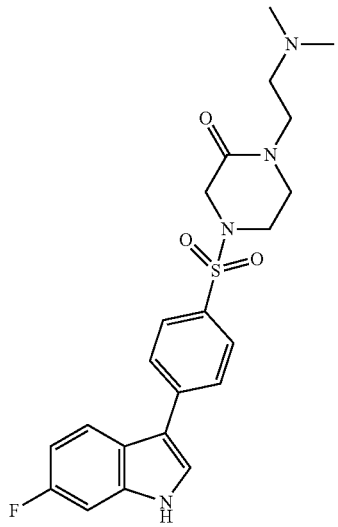 [SMILES: CN(C)CCN1CCN(S(=O)(=O)c2ccc(-c3c[nH]c4cc(F)ccc34)cc2)CC1=O]

A yellow solution of 1-(2-aminoethyl)-4-((4-(6-fluoro-1H-indol-3-yl)phenyl)sulfonyl)piperazin-2-one (58 mg, 0.14 mmol) and formaldehyde (45 mg, 0.56 mmol) in methanol (4 mL) was cooled in an ice bath then NaBH$_4$ (15.9 mg, 0.42 mmol) was added. The reaction was stirred in the ice bath for 4 h, warmed to 28° C. and stirred for 4 h. The resulting yellow solution was diluted with water (20 mL) and extracted with 5% methanol in ethyl acetate (25 ml×2). The combined organic layers were washed with brine (10 ml) then dried over anhydrous Na$_2$SO$_4$, filtered and concentrated. The crude residue was purified by column chromatography (silica gel, 2-10% methanol/dichloromethane) to give the title product which was further purified by prep-TLC (methanol/dichloromethane=1/20) to give 1-(2-(dimethylamino)ethyl)-4-((4-(6-fluoro-1H-indol-3-yl)phenyl)sulfonyl)piperazin-2-one (10 mg, 16%) as a white solid. $^1$H NMR (400 MHz, MeOD) δ [ppm] 7.98-7.82 (m, 4H), 7.69 (s, 1H), 7.27-7.13 (m, 1H), 7.16 (dd, J=2.3, 9.5 Hz, 1H), 6.95 (dt, J=2.4, 9.2 Hz, 1H), 3.74 (s, 2H), 3.48-3.38 (m, 6H), 2.43-2.36 (m, 2H), 2.19 (s, 6H); LC-MS: m/z 445.0 (M+H)$^+$.

Example 150: 4-((4-(6-fluoro-1H-indol-3-yl)phenyl)sulfonyl)-1-(2-(methylamino)ethyl)piperazin-2-one

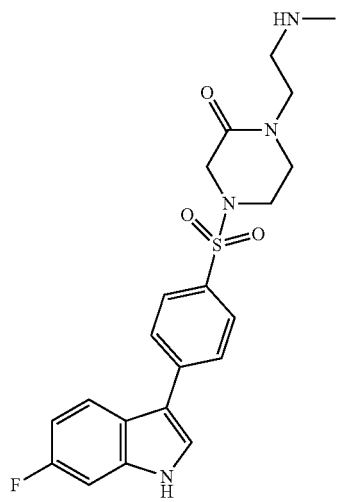 [SMILES: CNCCN1CCN(S(=O)(=O)c2ccc(-c3c[nH]c4cc(F)ccc34)cc2)CC1=O]

Following the general methods as outlined in Example 148, starting from 2-((tert-butoxycarbonyl)(methyl)amino)ethyl methanesulfonate, the title compound was isolated as a white solid. $^1$H NMR (400 MHz, DMSO-$d_6$) δ [ppm] 11.71 (br s, 1H), 7.99-7.92 (m, 4H), 7.82 (d, J=8.5 Hz, 2H), 7.27 (dd, J=2.4, 9.9 Hz, 1H), 7.01 (dt, J=2.4, 9.2 Hz, 1H), 3.59 (s, 2H), 3.39 (br s, 2H), 3.26 (br s, 4H), 2.49-2.45 (m, 2H), 2.16 (s, 3H); LC-MS: m/z 430.9 (M+H)$^+$.

Example 151: 4-((4-(6-fluoro-1H-indol-3-yl)phenyl)sulfonyl)-1-(2-hydroxyethyl)piperazin-2-one

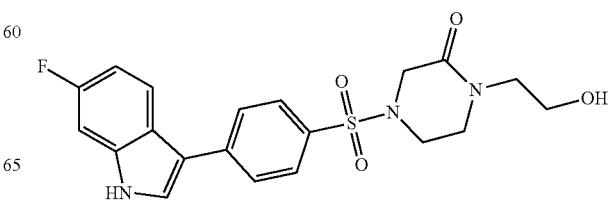

Following the general methods as outlined in Example 148, starting from 2-bromoethyl benzoate, the title compound was isolated as a white solid. $^1$H NMR (400 MHz, DMSO-d$_6$) δ [ppm] 11.71 (br s, 1H), 8.02-7.93 (m, 4H), 7.82 (d, J=8.5 Hz, 2H), 7.27 (dd, J=2.4, 9.9 Hz, 1H), 7.02 (d, J=2.3 Hz, 1H), 4.70 (t, J=5.6 Hz, 1H), 3.58 (s, 2H), 3.44 (t, J=5.8 Hz, 4H), 3.32-3.24 (m, 4H).

Example 152: 1-(3-aminopropyl)-4-((4-(6-fluoro-1H-indol-3-yl)phenyl-)sulfonyl)piperazin-2-one

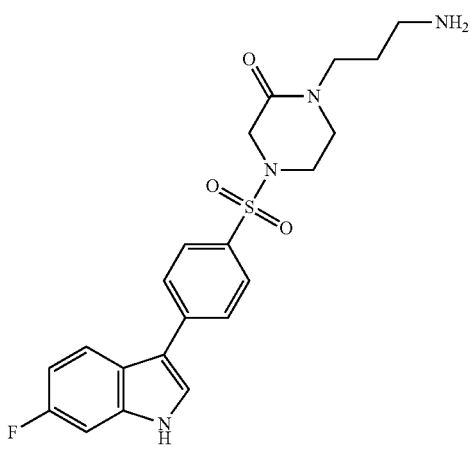 [SMILES: NCCCN1CCN(S(=O)(=O)c2ccc(-c3c[nH]c4cc(F)ccc34)cc2)CC1=O]

Following the general methods as outlined in Example 148, starting from tert-butyl (3-bromopropyl)carbamate, the title compound was isolated as a white solid. $^1$H NMR (400 MHz, MeOD) δ [ppm] 7.97-7.81 (m, 5H), 7.69 (s, 1H), 7.17 (dd, J=2.3, 9.8 Hz, 1H), 6.95 (dt, J=2.3, 9.2 Hz, 1H), 3.75 (s, 2H), 3.52-3.37 (m, 6H), 2.85 (t, J=6.8 Hz, 2H), 1.87 (quin, J=6.7 Hz, 2H); LC-MS: m/z 431.2 (M+H)$^+$.

Example 153: 4-((4-(6-fluoro-1H-indol-3-yl)phenyl)sulfonyl)-1-(3-(methylamino)propyl)piperazin-2-one

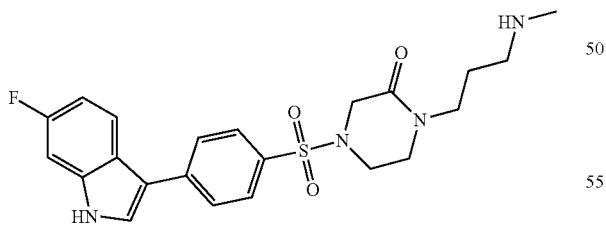

Following the general methods as outlined in Example 148, starting from benzyl 4-(3-((tert-butoxycarbonyl)(methyl)amino)propyl)-3-oxopiperazine-1-carboxylate, the title compound was isolated as a yellow solid. $^1$H NMR (400 MHz, MeOD) δ [ppm] 7.98-7.82 (m, 5H), 7.70 (s, 1H), 7.22-7.14 (m, 1H), 7.00-6.89 (m, 1H), 3.76 (s, 2H), 3.45 (dd, J=6.1, 13.7 Hz, 6H), 2.90 (t, J=6.7 Hz, 2H), 2.64 (s, 3H), 1.90 (br s, 2H).

Example 154: 1-(3-(dimethylamino)propyl)-4-((4-(6-fluoro-1H-indol-3-yl)phenyl)sulfonyl) piperazine-2-one

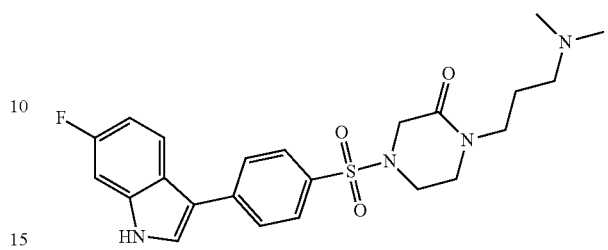

To a yellow solution of 4-((4-(6-fluoro-1H-indol-3-yl)phenyl)sulfonyl)-1-(3-(methylamino)propyl)piperazin-2-one (50 mg, 0.11 mmol) and formaldehyde (6.75 mg, 0.225 mmol) in methanol (2 mL) was added NaBH$_4$ (14.1 mg, 0.225 mmol). The yellow solution was stirred at 20° C. for 4 h then carefully quenched with water (50 mL) and extracted with ethyl acetate (25 mL×2). The combined organic layers were washed with brine (50 mL) then dried over anhydrous Na$_2$SO$_4$, filtered and concentrated. The crude residue was purified by prep-HPLC to give 1-(3-(dimethylamino)propyl)-4-((4-(6-fluoro-1H-indol-3-yl)phenyl)sulfonyl)piperazin-2-one (8.5 mg, 15%) as a yellow solid. $^1$H NMR (400 MHz, MeOD) δ [ppm] 7.98-7.85 (m, 5H), 7.71 (s, 1H), 7.18 (dd, J=2.3, 9.5 Hz, 1H), 7.01-6.92 (m, 1H), 3.76 (s, 2H), 3.53-3.40 (m, 6H), 3.05 (t, J=7.2 Hz, 2H), 2.83 (s, 6H), 1.99-1.89 (m, 2H).

Example 155: 4-(6-fluoro-1H-indol-3-yl)-N-((3-methyl-1,2,4-oxadiazol-5-yl)methyl) benzenesulfonamide

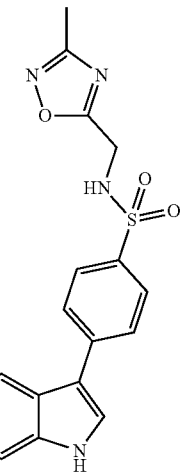

Step 1: 4-bromo-N-((3-methyl-1,2,4-oxadiazol-5-yl)methyl)-benzenesulfonamide

To a cooled (ice bath) solution of (3-methyl-1,2,4-oxadiazol-5-yl)methanamine (246 mg, 1.64 mmol) in pyridine (8 mL) was added 4-bromobenzene-1-sulfonyl chloride (420 mg, 1.64 mmol). The ice bath was removed and the reaction was stirred at 22° C. for 2 h. The reaction was concentrated then diluted with H$_2$O (10 mL) and extracted with ethyl acetate (10 mL×4). The combined organic layers were washed with brine (10 mL) then dried over Na₂SO₄, filtered, and concentrated. The crude residue was triturated with petroleum ether (20 mL) then filtered to afford 4-bromo-N-((3-methyl-1,2,4-oxadiazol-5-yl)methyl)benzenesulfonamide (310 mg, 57%) as a gray solid.

Step 2: tert-butyl 6-fluoro-3-(4-(N-((3-methyl-1,2,4-oxadiazol-5-yl)methyl)sulfamoyl)phenyl)-1H-indole-1-carboxylate To a yellow solution of 4-bromo-N-((3-methyl-1,2,4-oxadiazol-5-yl)methyl)benzenesulfonamide (310 mg, 0.933 mmol), tert-butyl 6-fluoro-3-(4,4,5,5-tetramethyl-1,3,2-dioxaborolan-2-yl)-1H-indole-1-carboxylate (375 mg, 0.933 mmol) and Cs₂CO₃ (608 mg, 1.87 mmol) in Dioxane/H₂O (10 ml/2.5 mL) was added Pd(dppf)Cl₂ (68 mg, 0.09 mmol) at 25° C. under N₂. The red suspension was stirred at 100° C. for 6 h then diluted with ethyl acetate (20 mL) and brine (10 mL). The layers were separated and the organic phase was dried over Na₂SO₄, filtered and concentrated to give crude tert-butyl 6-fluoro-3-(4-(N-((3-methyl-1,2,4-oxadiazol-5-yl)methyl)sulfamoyl)phenyl)-1H-indole-1-carboxylate (400 mg, 88%) which was used directly in the next step.

Step 3: 4-(6-fluoro-1H-indol-3-yl)-N-((3-methyl-1,2,4-oxadiazol-5-yl)methyl)benzenesulfonamide To a solution of tert-butyl 6-fluoro-3-(4-(N-((3-methyl-1,2,4-oxadiazol-5-yl)methyl)sulfamoyl)phenyl)-1H-indole-1-carboxylate (400 mg, 0.27 mmol) in dichloromethane (6 mL) was added trifluoroacetic acid (3 mL) at 25° C. The reaction was stirred at 25° C. for 5 h then concentrated. The crude residue was diluted with ethyl acetate (20 mL) and H₂O (8 mL). The layers were separated and the aqueous layer was back-extracted with ethyl acetate (10 mL×2). The combined organic layers were washed with NaHCO₃ (sat) (10 mL×2), brine (10 mL) then dried over Na₂SO₄, filtered and concentrated. The crude material was purified by column chromatography (silica gel, ethyl acetate/petroleum ether=20-100%) then further purified by prep-HPLC to give 4-(6-fluoro-1H-indol-3-yl)-N-((3-methyl-1,2,4-oxadiazol-5-yl)methyl)benzenesulfonamide (21 mg, 20%) as a white solid. ¹H NMR (400 MHz, MeOD) δ [ppm]7.89-7.79 (m, 5H), 7.65 (s, 1H), 7.18-7.15 (dd, J=2.4, 9.7 Hz, 1H), 6.95-6.93 (m, 1H), 4.42 (s, 2H), 2.16 (s, 3H); LC-MS: m/z 387.1 (M+H)⁺.

Example 156: N-((1,2,4-oxadiazol-3-yl)methyl)-4-(6-fluoro-1H-indol-3-yl)benzenesulfonamide

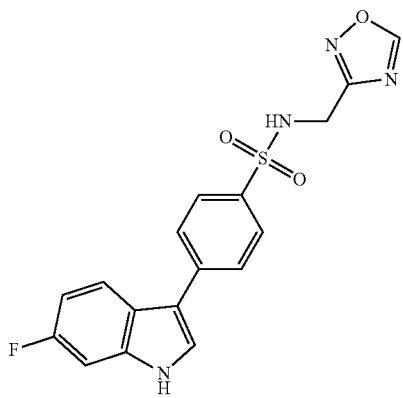 [SMILES: O=S(=O)(NCc1ncon1)c1ccc(-c2c[nH]c3cc(F)ccc23)cc1]

Step 1: 4-bromo-N-(cyanomethyl)benzenesulfonamide

To a solution of 4-bromobenzene-1-sulfonyl chloride (580 mg, 6.26 mmol) and Et₃N (1.9 g, 19 mmol) in anhydrous dichloromethane (20 mL) was added 2-aminoacetonitrile (580 mg, 6.26 mmol) at 20° C. The reaction was stirred at 20° C. for 1 h then concentrated. The residue was stirred in ethyl acetate (50 mL) then the solids were filtered and the filtrate was concentrated. The crude product was purified by column chromatography (silica gel, 30% ethyl acetate/petroleum ether) to give 4-bromo-N-(cyanomethyl)benzenesulfonamide (540 mg, 31%) as a white solid. ¹H NMR (400 MHz, DMSO-d₆) δ [ppm] 8.69 (s, 1H), 7.89-7.81 (m, 2H), 7.80-7.73 (m, 2H), 4.14 (s, 3H).

Step 2: (Z)-2-(4-bromophenylsulfonamido)-N'-hydroxyacetimidamide

To a cooled (ice bath) solution of 4-bromo-N-(cyanomethyl)-benzenesulfonamide (340 mg, 1.24 mmol) in methanol (10 mL) was added NH₂OH.HCl (85.9 mg, 1.24 mmol, 1.0 eq.) and trimethylamine (125 mg, 1.24 mmol). The reaction was stirred at 25° C. for 16 h then concentrated. The crude residue was purified by column chromatography (silica gel, 70% ethyl acetate/petroleum ether) to give (Z)-2-(4-bromophenylsulfonamido)-N'-hydroxyacetimidamide (280 mg, 74%) as a white solid. ¹H NMR (400 MHz, DMSO-d₆) δ [ppm] 9.09 (s, 1H), 7.95 (s, 1H), 7.84-7.76 (m, 2H), 7.74-7.69 (m, 2H), 5.23 (s, 2H), 3.34 (s, 2H).

Step 3: (Z)-tert-butyl 3-(4-(N-(2-amino-2-(hydroxyimino)ethyl)sulfamoyl)-phenyl)-6-fluoro-1H-indole-1-carboxylate A red suspension of tert-butyl 6-fluoro-3-(4,4,5,5-tetramethyl-1,3,2-dioxaborolan-2-yl)-1H-indole-1-carboxylate (715 mg, 1.19 mmol), (Z)-2-(4-bromophenylsulfonamido)-N'-hydroxyacetimidamide (280 mg, 0.909 mmol), PdCl₂(dppf) (58 mg, 0.0792 mmol) and K₃PO₄ (673 mg, 3.17 mmol) in dioxane (10 mL) and H₂O (3 mL) was stirred at 80° C. under a N₂ atmosphere for 16 h. The resulting mixture was diluted with water (10 mL) and extracted with ethyl acetate (15 mL×2). The combined organic layers were washed with brine (10 mL) then dried over anhydrous Na₂SO₄, filtered and concentrated. The crude residue was purified by column chromatography (silica gel, 60% ethyl acetate/petroleum ether) to give (Z)-tert-butyl 3-(4-(N-(2-amino-2-(hydroxyimino)ethyl) sulfamoyl)phenyl)-6-fluoro-1H-indole-1-carboxylate (75 mg, 18%) as yellow oil. ¹H NMR (400 MHz, DMSO-d₆) δ [ppm] 9.12 (s, 1H), 8.10 (s, 1H), 7.99-7.85 (m, 7H), 7.29-7.21 (m, 1H), 5.28 (s, 2H), 3.37 (s, 2H), 1.66 (s, 9H).

Step 4: tert-butyl 3-(4-(N-((1,2,4-oxadiazol-3-yl)methyl)sulfamoyl)phenyl)-6-fluoro-1H-indole-1-carboxylate A solution of (Z)-tert-butyl 3-(4-(N-(2-amino-2-(hydroxyimino)ethyl)-sulfamoyl)phenyl)-6-fluoro-1H-indole-1-carboxylate (75 mg, 0.16 mmol) and TsOH—H₂O (3.08 mg, 0.016 mmol) in CH(OMe)₃ (2 mL) was stirred at 90° C. for 2 h. The solution was directly purified by prep-TLC (petroleum ether/ethyl acetate=1/1) to give tert-butyl 3-(4-(N-((1,2,4-oxadiazol-3-yl)methyl)-sulfamoyl)phenyl)-6-fluoro-1H-indole-1-carboxylate (45 mg, 59%) as an off-white solid. ¹H NMR (400 MHz, DMSO-d₆) δ [ppm] 8.59

(s, 1H), 8.01-7.91 (m, 3H), 7.79-7.66 (m, 5H), 7.10 (dt, J=2.5, 8.9 Hz, 1H), 5.24 (t, J=6.3 Hz, 1H), 4.49 (d, J=6.3 Hz, 2H), 1.71 (s, 9H).

Step 5: N-((1,2,4-oxadiazol-3-yl)methyl)-4-(6-fluoro-1H-indol-3-yl)benzenesulfonamide To a suspension of tert-butyl 3-(4-(N-((1,2,4-oxadiazol-3-yl)methyl)-sulfamoyl)phenyl)-6-fluoro-1H-indole-1-carboxylate (45 mg, 0.10 mmol) in anhydrous dichloromethane (5 mL) was added trifluoroacetic acid (1 mL). The reaction was stirred at 20° C. for 1 h then concentrated. The residue was diluted with 2 M NaHCO₃ (10 mL) and extracted with ethyl acetate (20 mL×2). The combined organic layers were washed with brine (15 mL) then dried over anhydrous Na₂SO₄, filtered and concentrated to give crude N-((1,2,4-oxadiazol-3-yl)methyl)-4-(6-fluoro-1H-indol-3-yl)benzenesulfonamide (23 mg, 65%) as a yellow solid. ¹H NMR (400 MHz, DMSO-d₆) δ [ppm] 11.66 (br s, 1H), 9.49 (s, 1H), 8.43 (br s, 1H), 8.00-7.83 (m, 4H), 7.82-7.75 (m, 2H), 7.26 (dd, J=2.3, 9.8 Hz, 1H), 7.01 (dt, J=2.4, 9.2 Hz, 1H), 4.22 (s, 2H); LC-MS: m/z 395.2 (M+Na)⁺.

Example 157: 4-(6-fluoro-1H-indol-3-yl)-N-(2-hydroxyethyl)-benzenesulfonamide

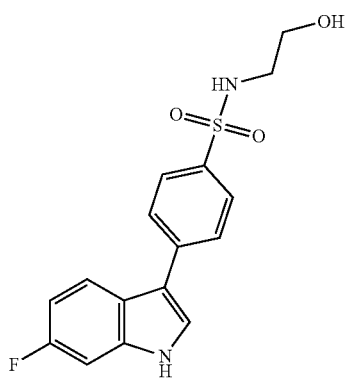 [SMILES: O=S(=O)(NCCO)c1ccc(-c2c[nH]c3cc(F)ccc23)cc1]

Step 1:
4-bromo-N-(2-hydroxyethyl)benzenesulfonamide

To a solution of 4-bromobenzene-1-sulfonyl chloride (500 mg, 1.96 mmol) and TEA (396 mg, 3.91 mmol) in DCM (20 mL) was added 2-aminoethanol (120 mg, 1.96 mmol). The reaction was stirred at 25° C. for 1 h then concentrated to give crude 4-bromo-N-(2-hydroxyethyl)benzenesulfonamide (548 mg, 100%), which was used directly in the next step.

Step 2: tert-butyl 6-fluoro-3-(4-(N-(2-hydroxyethyl)sulfamoyl)-phenyl)-1H-indole-1-carboxylate To a suspension of 4-bromo-N-(2-hydroxyethyl)benzenesulfonamide (300 mg, 1.076 mmol), tert-butyl 6-fluoro-3-(4,4,5,5-tetramethyl-1,3,2-dioxaborolan-2-yl)-1H-indole-1-carboxylate (387 mg, 1.07 mmol) and Cs₂CO₃ (698 mg, 2.14 mmol) in dioxane (10 mL) and H₂O (3 mL) was added PdCl₂(dppf) (78.4 mg, 0.107 mmol) The reaction was stirred at 80° C. under N₂ for 1.5 h then concentrated and purified by column chromatography to give tert-butyl 6-fluoro-3-(4-(N-(2-hydroxyethyl)sulfamoyl)phenyl)-1H-indole-1-carboxylate (600 mg, 100%) as yellow gum.

Step 3: 3,5-dichloro-4-(6-fluoro-1H-indol-3-yl)benzenesulfonamide

A solution of 4-(6-fluoro-1H-indol-3-yl)-N-(2-hydroxyethyl)-benzenesulfonamide (600 mg, 1.38 mmol) in HCl (g)/MeOH (10 mL) was stirred at 30° C. for 2 h. The reaction was concentrated and purified by prep-HPLC to give 4-(6-fluoro-1H-indol-3-yl)-N-(2-hydroxyethyl)benzenesulfonamide (190 mg, 41%) as a yellow solid. ¹H NMR (400 MHz, DMSO-d₆) δ [ppm] 11.64 (br, 1H), 7.96-7.88 (m, 4H), 7.84-7.80 (m, 2H), 7.26 (dd, J=2.4, 9.9 Hz, 1H), 7.01 (dt, J=2.4, 9.2 Hz, 1H), 4.70 (br s, 1H), 3.40 (t, J=6.1 Hz, 2H), 2.82 (t, J=6.4 Hz, 2H); LCMS: m/z 356.9 (M+Na)⁺.

Example 158: 3-chloro-4-(6-fluoro-1H-indol-3-yl)-N-(2-hydroxyethyl)benzenesulfonamide

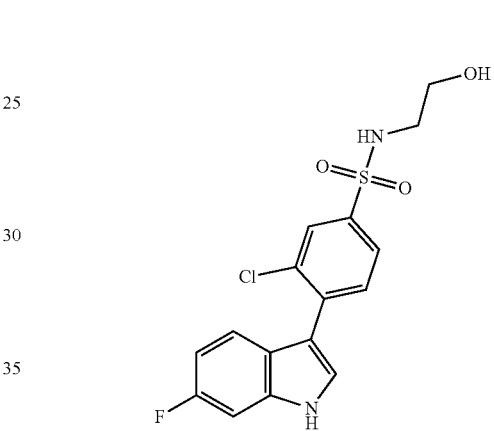

Following the general methods as outlined in Example 157, starting from 4-bromo-3-chlorobenzenesulfonyl chloride, the title compound was isolated as a white solid. ¹H NMR (400 MHz, DMSO-d₅) δ [ppm] 11.68 (br, 1H), 7.94 (t, J=1.0 Hz, 1H), 7.81-7.74 (m, 4H), 7.53 (dd, J=5.3, 8.8 Hz, 1H), 7.27 (dd, J=2.4, 9.9 Hz, 1H), 7.00-6.93 (m, 1H), 4.75 (t, J=5.5 Hz, 1H), 3.42 (q, J=6.1 Hz, 2H), 2.87 (t, J=6.3 Hz, 2H); LC-MS: m/z 390.9 (M+Na)⁺.

Example 159: (−)-4-(6-fluoro-1H-indol-3-yl)-N-(2-(methylsulfinyl)-ethyl)benzenesulfonamide

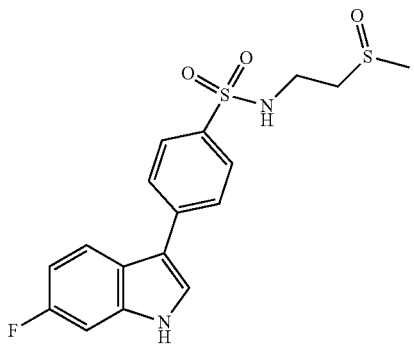 [SMILES: CS(=O)CCNS(=O)(=O)c1ccc(-c2c[nH]c3cc(F)ccc23)cc1]

Step 1: 4-bromo-N-(2-(methylthio)ethyl)benzenesulfonamide

To a yellow solution of 4-bromobenzene sulfonyl chloride (1.68 g, 6.58 mmol) and 2(methylthio)ethylamine (600 mg, 6.58 mmol) in anhydrous dichloromethane (50 mL) was added Et₃N (1.33 g, 13.2 mmol) at 25° C. The yellow suspension was stirred at 25° C. for 14 h then concentrated and purified by column chromatography (silica gel, petroleum ether/ethyl acetate=6/1-3/1) to give 4-bromo-N-(2-(methylthio)ethyl)benzenesulfonamide (2.0 g, 98%) as a yellow solid.

Step 2: 4-bromo-N-(2-(methylsulfinyl)ethyl)benzenesulfonamide

To a yellow solution of 4-bromo-N-(2-(methylthio)ethyl)benzene-sulfonamide (500 mg, 1.61 mmol) in anhydrous dichloromethane (50 mL) was added m-CPBA (327 mg, 1.61 mmol) at −25° C. The yellow suspension was stirred at −25° C. for 1 h then washed with H₂O (10 mL×2), dried over Na₂SO₄, filtered and concentrated. The crude solid was purified by column chromatography (silica gel, petroleum ether/ethyl acetate=6/1-3/1) to give 4-bromo-N-(2-(methylsulfinyl)ethyl)benzenesulfonamide (450 mg, 86%) as a yellow solid.

Step 3: tert-butyl 6-fluoro-3-(4-(N-(2-(methylsulfinyl)ethyl)-sulfamoyl)phenyl)-1H-indole-1-carboxylate A yellow solution of tert-butyl 6-fluoro-3-(4,4,5,5-tetramethyl-1,3,2-dioxaborolan-2-yl)-1H-indole-1-carboxylate (350 mg, 0.969 mmol), 4-bromo-N-(2-(methylsulfinyl)ethyl)benzenesulfonamide (316 mg, 0.969 mmol), PdCl₂(dppf) (71 mg, 0.10 mmol) and Cs₂CO₃ (631 mg, 1.94 mmol) in dioxane (8 mL) and H₂O (2 mL) was stirred at 85° C. under a N₂ atmosphere for 14 h. The resulting black mixture was diluted with ethyl acetate (50 mL) and the layers were separated. The organic layer was washed with brine (20 mL) then dried over anhydrous Na₂SO₄, filtered and concentrated to give crude tert-butyl 6-fluoro-3-(4-(N-(2-(methylsulfinyl)ethyl)sulfamoyl)phenyl)-1H-indole-1-carboxylate as a red gum, which was used in the next step without further purification.

Step 4: (−)-4-(6-fluoro-1H-indol-3-yl)-N-(2-(methylsulfinyl)ethyl)-benzenesulfonamide A red solution of tert-butyl 6-fluoro-3-(4-(N-(2-(methylsulfinyl)ethyl)-sulfamoyl) phenyl)-1H-indole-1-carboxylate (466 mg, 0.969 mmol) and trifluoroacetic acid (5 mL) in dichloromethane (5 mL) was stirred at 20° C. under a N₂ atmosphere for 1 h. The reaction was concentrated then diluted with NaHCO₃(sat) (10 mL) and extracted ethyl acetate (20 mL×3). The combined organic extracts were dried over Na₂SO₄, filtered, and concentrated. The crude residue was purified by column chromatography (silica gel, petroleum ether/ethyl acetate=1/1 to ethyl acetate/methanol=10/1) to give 4-(6-fluoro-1H-indol-3-yl)-N-(2-(methylsulfinyl)ethyl)benzenesulfonamide (200 mg, 54%) as a red solid, which was further purified by prep-HPLC to provide a racemic mixture of the title compound. The enantiomers were separated by prep-chiral SFC to afford (−)-4-(6-fluoro-1H-indol-3-yl)-N-(2-(methylsulfinyl)ethyl)benzenesulfonamide as the first eluting peak (15 mg, 4%) as a pale yellow solid. ¹H NMR (400 MHz, DMSO-d₆) δ [ppm] 11.67 (br s, 1H), 8.00-7.80 (m, 7H), 7.27 (dd, J=2.4, 9.9 Hz, 1H), 7.01 (d, J=1.8 Hz, 1H), 3.25-3.07 (m, 2H), 2.97-2.87 (m, 1H), 2.83-2.74 (m, 1H), 2.56 (s, 3H); LC-MS: m/z 402.9 (M+Na)⁺; [α]²⁰_D−32.7° (c=0.001 g/mL, DMSO).

Example 160: (+)-4-(6-fluoro-1H-indol-3-yl)-N-(2-(methylsulfinyl)-ethyl)benzenesulfonamide

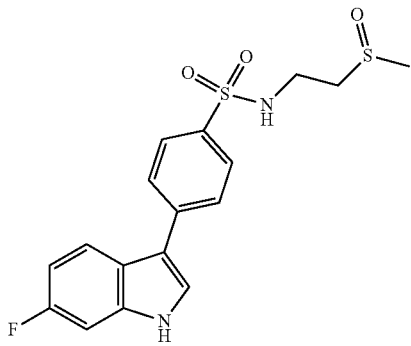

The title compound was obtained as the second eluting peak from the chiral separation described in Example 159 (40 mg, 11%) as a pale yellow solid. ¹H NMR (400 MHz, DMSO-d₆) δ [ppm] 11.67 (br s, 1H), 7.99-7.80 (m, 7H), 7.27 (dd, J=2.3, 9.8 Hz, 1H), 7.01 (dt, J=2.4, 9.2 Hz, 1H), 3.15 (br s, 2H), 2.97-2.87 (m, 1H), 2.84-2.75 (m, 1H), 2.56 (s, 3H); LC-MS: m/z 402.9 (M+Na)⁺; [α]²⁰_D+34.0° (c=0.001 g/mL, DMSO).

Example 161: 4-(6-fluoro-1H-indol-3-yl)-N-(2-(2-methyl-1H-imidazol-4-yl)ethyl)benzenesulfonamide

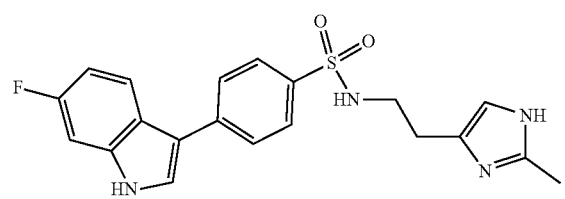 [SMILES: Cc1nc(CCNS(=O)(=O)c2ccc(-c3c[nH]c4cc(F)ccc34)cc2)c[nH]1]

Step 1: N,N,2-trimethyl-1H-imidazole-1-sulfonamide

To a solution of 2-methyl-1H-imidazole (5.0 g, 61 mmol) and dimethylsulfamoyl chloride (9.6 g, 67 mmol) in anhydrous dichloromethane (50 mL) was added triethylamine (12 g, 122 mmol) at 20° C. The reaction was stirred at 20° C. for 16 h then diluted with water (10 mL) and extracted with dichloromethane (50 mL×2). The combined organic layers were washed with brine (20 mL) then dried over anhydrous Na₂SO₄, filtered and concentrated. The crude residue was purified by column chromatography (silica gel, 40 g, 50-70% ethyl acetate/petroleum ether) to give N,N,2-trimethyl-1H-imidazole-1-sulfonamide (11 g, 96%) as colorless oil. ¹H NMR (400 MHz, CDCl₃) δ [ppm] 7.21 (d, J=1.6 Hz, 1H), 6.91 (d, J=1.6 Hz, 1H), 2.89 (s, 6H), 2.61 (s, 3H).

Step 2: 4-(2-hydroxyethyl)-N,N,2-trimethyl-1H-imidazole-1-sulfonamide

To a three neck round-bottom flask, purged and maintained with an inert atmosphere of N₂, was added a solution of N,N,2-trimethyl-1H-imidazole-1-sulfonamide (5.00 g, 26.42 mmol) in anhydrous THF (50 mL) followed by drop-wise addition of n-BuLi (2.5 M in hexane, 12.7 mL, 31.7 mmol) with stirring at −78° C. The clear solution was stirred at −78° C. for 1 h then oxirane (9.31 g, 211 mmol) was added dropwise at −30° C. The reaction was stirred for 4 h at 20° C. then quenched with water (10 mL) and extracted with ethyl acetate (60 mL×2). The combined organic layers were washed with brine (20 mL) then dried over anhydrous $Na_2SO_4$, filtered and concentrated. The crude product was purified by column chromatography (silica gel, 10% methanol/ethyl acetate) to give 4-(2-hydroxyethyl)-N,N,2-trimethyl-1H-imidazole-1-sulfonamide (4.00 g, 65%) as a clear oil. $^1$H NMR (400 MHz, DMSO-$d_6$) δ [ppm] 6.69 (s, 1H), 4.73 (t, J=5.4 Hz, 1H), 3.69-3.56 (m, 2H), 2.87-2.80 (m, 8H), 2.47 (s, 3H).

Step 3: tert-butyl (2-(1-(N, N-dimethylsulfamoyl)-2-methyl-1H-imidazol-4-yl)ethyl)carbamate A solution of 4-(2-hydroxyethyl)-N,N,2-trimethyl-1H-imidazole-1-sulfonamide (1.00 g, 4.29 mmol), DPPA (2.95 g, 10.7 mmol) and $Ph_3P$ (2.81 g, 10.7 mmol) in anhydrous THF (20 mL) was stirred at 0° C. for 15 min then DIAD (2.17 g, 10.7 mmol) was added at 0° C. The reaction was warmed to 20° C., stirred for 16 h then quenched with ammonium chloride (sat) (30 mL) and extracted with ethyl acetate (30 mL×2). The combined organic layers were diluted with THF (60 mL) and water (20 mL) then concentrated to remove most of the ethyl acetate. The reaction was stirred at 80° C. under a $N_2$ atmosphere for 4 h then allowed to stand for 3 days. Concentrated HCl (5 mL) was added to the yellow suspension and stirred at 20° C. for 2 h. The mixture was diluted with water (10 mL) and with ethyl acetate (50 mL×2). The aqueous layer was neutralized to pH=8-9 with solid $Na_2CO_3$. $Boc_2O$ (2.81 g, 12.9 mmol) was added to the aqueous solution and stirred at 20° C. for 2 h. The suspension was extracted with ethyl acetate (30 mL×2) and the combined organic layers were washed with brine (20 mL), dried over anhydrous $Na_2SO_4$, filtered and concentrated. The crude residue was purified by column chromatography (silica gel, 10% methanol/ethyl acetate) to give tert-butyl (2-(1-(N,N-dimethylsulfamoyl)-2-methyl-1H-imidazol-4-yl)ethyl)carbamate (1.9 g, >100%) as a clear oil. $^1$H NMR (400 MHz, $CDCl_3$) δ [ppm] 6.69 (s, 1H), 4.69 (br s, 1H), 3.44-3.36 (m, 2H), 2.94 (t, J=6.8 Hz, 2H), 2.89 (s, 6H), 2.59 (s, 3H), 1.44 (s, 9H).

Step 4: 4-(2-aminoethyl)-N,N,2-trimethyl-1H-imidazole-1-sulfonamide

A clear solution of tert-butyl (2-(1-(N,N-dimethylsulfamoyl)-2-methyl-1H-imidazol-4-yl)ethyl)carbamate (500 mg, 1.50 mmol) and trifluoroacetic acid (2 mL) in dichloromethane (6 mL) was stirred at 20° C. for 1 h. The reaction was concentrated to give crude 4-(2-aminoethyl)-N,N,2-trimethyl-1H-imidazole-1-sulfonamide (521 mg, 100%) as an off-white solid. $^1$H NMR (400 MHz, DMSO-$d_6$) δ [ppm] 7.94 (br s, 3H), 7.15 (s, 1H), 3.13-3.03 (m, 4H), 2.95 (s, 6H), 2.61 (s, 3H).

Step 5: 4-(2-(4-bromophenylsulfonamido)ethyl)-N,N,2-trimethyl-1H-imidazole-1-sulfonamide To a solution of 4-(2-aminoethyl)-N,N,2-trimethyl-1H-imidazole-1-sulfonamide (521 mg, 1.50 mmol) and 4-bromobenzene-1-sulfonyl chloride (384 mg, 1.50 mmol) in anhydrous dichloromethane (20 mL) was added triethylamine (304 mg, 3.01 mmol). The reaction was stirred at 20° C. for 1 h then concentrated. The crude residue was purified by column chromatography (silica gel, 60% ethyl acetate/petroleum ether) to give 4-(2-(4-bromophenylsulfonamido)ethyl)-N,N,2-trimethyl-1H-imidazole-1-sulfonamide (600 mg, 88%) as an off-white solid. $^1$H NMR (400 MHz, DMSO-$d_6$) δ [ppm] 7.89 (t, J=5.9 Hz, 1H), 7.82-7.79 (m, 2H), 7.75-7.66 (m, 2H), 6.68 (s, 1H), 3.10-3.00 (m, 2H), 2.85-2.81 (m, 2H), 2.79 (s, 6H), 2.44 (s, 3H).

Step 6: 4-bromo-N-(2-(2-methyl-1H-imidazol-4-yl)ethyl)-benzenesulfonamide

To a solution of 4-(2-(4-bromophenylsulfonamido)ethyl)-N,N,2-trimethyl-1H-imidazole-1-sulfonamide (540 mg, 1.20 mmol) in dioxane (10 mL) was added conc. HCl (3 mL). The reaction was stirred at 45° C. for 88 h then concentrated. The residue was neutralized with $NaHCO_3$ solid (4 g) and stirred for 1 h then filtered. The filtrate was concentrated and purified by column chromatography (silica gel, 6% methanol/ethyl acetate) to give 4-bromo-N-(2-(2-methyl-1H-imidazol-4-yl)ethyl)benzenesulfonamide (400 mg, 97%) as a clear oil. $^1$H NMR (400 MHz, DMSO-$d_6$) δ [ppm] 11.38 (br s, 1H), 7.84-7.76 (m, 3H), 7.73-7.65 (m, 2H), 6.58 (br s, 1H), 2.93 (br s, 2H), 2.53-2.50 (m, 2H), 2.16 (s, 3H).

Step 7: 4-(6-fluoro-1H-indol-3-yl)-N-(2-(2-methyl-1H-imidazol-4-yl)ethyl)benzenesulfonamide A red suspension of tert-butyl 6-fluoro-3-(4,4,5,5-tetramethyl-1,3,2-dioxaborolan-2-yl)-1H-indole-1-carboxylate (472 mg, 0.784 mmol), 4-bromo-N-(2-(2-methyl-1H-imidazol-4-yl)ethyl)benzenesulfonamide (200 mg, 0.52 mmol), $PdCl_2(dppf)$ (38.3 mg, 0.052 mmol) and $K_3PO_4$ (222 mg, 1.05 mmol) in dioxane (8 mL) and $H_2O$ (3 mL) was stirred at 80° C. under a $N_2$ atmosphere for 16 h. The resulting black suspension was diluted with water (10 mL) and extracted with ethyl acetate (20 mL×2). The combined organic layers were washed with brine (10 mL) then dried over anhydrous $Na_2SO_4$, filtered and concentrated. The crude product was purified by column chromatography (silica gel, 15% methanol/ethyl acetate) and further purified by prep-HPLC to give 4-(6-fluoro-1H-indol-3-yl)-N-(2-(2-methyl-1H-imidazol-4-yl)ethyl)benzenesulfonamide (35 mg, 17%) as an off-white solid. $^1$H NMR (400 MHz, DMSO-$d_6$) δ [ppm] 11.67 (br s, 1H), 7.98-7.85 (m, 4H), 7.81 (d, J=8.3 Hz, 2H), 7.68 (br s, 1H), 7.26 (d, J=8.0 Hz, 1H), 7.05-6.94 (m, 1H), 6.63 (s, 1H), 2.96 (br s, 2H), 2.56 (t, J=7.5 Hz, 2H), 2.18 (s, 3H); LC-MS: m/z 399.0 $(M+H)^+$.

Example 162: 3-(2-ethyl-4-(6-fluoro-1H-indol-3-yl)phenylsulfonamido)-propanamide

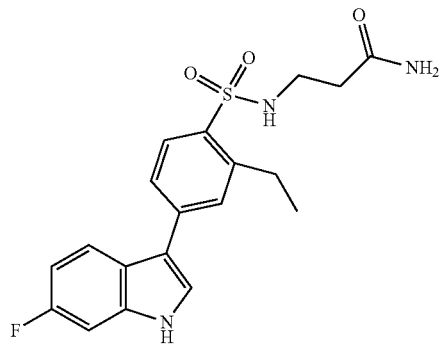 [SMILES: CCc1cc(-c2c[nH]c3cc(F)ccc23)ccc1S(=O)(=O)NCCC(N)=O]

Step 1: 4-bromo-2-ethylbenzene-1-sulfonyl chloride

A 100 ml round bottom flask was purged with N₂ and charged with 1-bromo-3-ethylbenzene (5.00 g, 27.0 mmol) and chloroform (50 ml). The reaction was cooled in an ice bath then chlorosulfonic acid (18.9 g, 162 mmol) was added drop-wise and stirred at 30° C. for 15 h. The light yellow solution was carefully poured into ice-water (100 ml) and extracted with dichloromethane (3×15 ml). The combined organic layers were washed with brine (10 ml) then dried over Na₂SO₄, filtered and concentrated to give the title compound (7.5 g, 98.0%) as light yellow oil.

Step 2: 3-(4-bromo-2-ethylphenylsulfonamido)propanamide

To a clear solution of 4-bromo-2-ethylbenzene-1-sulfonyl chloride (600 mg, 2.12 mmol) in dichloromethane (10 ml) and H₂O (1 ml) was added NaHCO₃ (533 mg, 6.35 mmol), triethylamine (856 mg, 8.46 mmol) and 3-aminopropanamide (280 mg, 3.17 mmol). The reaction was stirred at ambient temperature for 4 h then concentrated and purified by column chromatography (silica gel, dichloromethane/methanol=20/1) to afford the title compound (660 mg, 93%).

Step 3: tert-butyl 3-(4-(N-(3-amino-3-oxopropyl)sulfamoyl)-3-ethylphenyl)-6-fluoro-1H-indole-1-carboxylate To a suspension of 3-(4-bromo-2-ethylphenylsulfonamido)propanamide (480 mg, 1.43 mmol), tert-butyl 6-fluoro-3-(4,4,5,5-tetramethyl-1,3,2-dioxaborolan-2-yl)-1H-indole-1-carboxylate (517 mg, 1.43 mmol) and Cs₂CO₃ (933 mg, 2.0 mmol) in dioxane (9 ml) and H₂O (3 ml) was added PdCl₂(dppf) (105 mg, 0.143 mmol). The reaction was stirred at 80° C. under N₂ for 6 h then filtered and concentrated to give the title compound (1.3 g, 93%).

Step 4: 3-(2-ethyl-4-(6-fluoro-1H-indol-3-yl)phenyl-sulfonamido)-propanamide To a solution of 3-(2-ethyl-4-(6-fluoro-1H-indol-3-yl)phenylsulfonamido)-propanamide (1.3 g, 2.7 mmol) in dichloromethane (10 ml) was added trifluoroacetic acid (5 ml). The reaction was stirred at 30° C. for 1 h then concentrated. The residue was diluted with ethyl acetate (20 ml) and H₂O (15 ml) then neutralized to pH 7 with NaHCO₃. The layers were separated and the aqueous phase was back-extracted with ethyl acetate (20 ml×3) and the combined organic layers were washed with brine (15 ml) then dried over anhydrous Na₂SO₄, filtered and concentrated. The crude residue was purified by column chromatography (silica gel, methanol/dichloromethane=0-20%) then further purified by prep-HPLC to afford the title compound (40 mg, 4%) as a white solid. ¹H NMR (400 MHz, MeOD) δ [ppm] 7.95 (d, J=8.3 Hz, 1H), 7.86 (dd, J=5.3, 8.8 Hz, 1H), 7.73 (d, J=1.8 Hz, 1H), 7.68-7.62 (m, 2H), 7.15 (dd, J=2.4, 9.7 Hz, 1H), 6.94 (dt, J=2.4, 9.2 Hz, 1H), 3.22-3.07 (m, 4H), 2.44 (t, J=6.9 Hz, 2H), 1.37 (t, J=7.4 Hz, 3H); LCMS: m/z 412.0 (M+Na)⁺.

Example 163: 3-((4-(6-fluoro-1H-indol-3-yl)-2-isopropylphenyl)-sulfonamido)propanamide

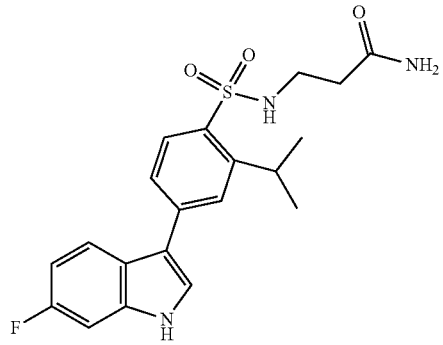 [SMILES: CC(C)c1cc(-c2c[nH]c3cc(F)ccc23)ccc1S(=O)(=O)NCCC(N)=O]

Following the general methods as outlined in Example 162, starting from 1-bromo-3-isopropylbenzene, the title compound was obtained as a white solid. ¹H NMR (400 MHz, MeOD) δ [ppm] 7.95 (d, J=8.3 Hz, 1H), 7.84-7.79 (m, 2H), 7.64-7.59 (m, 2H), 7.15 (dd, J=2.4, 9.7 Hz, 1H), 6.94 (dt, J=2.5, 9.2 Hz, 1H), 3.90 (quin, J=6.7 Hz, 1H), 3.19 (t, J=7.0 Hz, 2H), 2.44 (t, J=6.9 Hz, 2H), 1.36 (d, J=6.8 Hz, 6H); LCMS: m/z 426 (M+Na)⁺.

Example 164: 3-((4-(6-fluoro-1H-indol-3-yl)-2-isobutylphenyl)-sulfonamido)propanamide

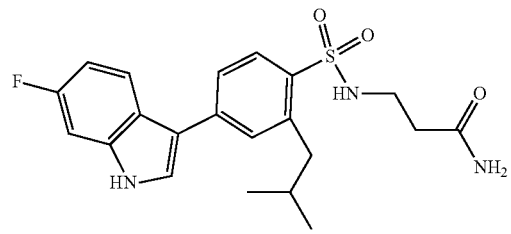 [SMILES: CC(C)Cc1cc(-c2c[nH]c3cc(F)ccc23)ccc1S(=O)(=O)NCCC(N)=O]

Following the general methods as outlined in Example 162, starting from 1-bromo-3-isobutylbenzene, the title compound was isolated as a pale yellow solid. ¹H NMR (400 MHz, MeOD) δ [ppm] 7.98 (d, J=8.3 Hz, 1H), 7.86 (dd, J=5.0, 8.8 Hz, 1H), 7.69 (s, 2H), 7.64 (s, 1H), 7.17 (dd, J=2.3, 9.8 Hz, 1H), 6.96 (dt, J=2.5, 9.2 Hz, 1H), 3.17 (t, J=7.0 Hz, 2H), 2.97 (d, J=7.0 Hz, 2H), 2.44 (t, J=6.9 Hz, 2H), 2.25-2.13 (m, 1H), 1.04 (d, J=6.5 Hz, 6H); LC-MS: m/z 440.0 (M+Na)⁺.

Example 165: 3-((4-(6-fluoro-1H-indol-3-yl)-2-(methoxymethyl)phenyl)-sulfonamido)propanamide

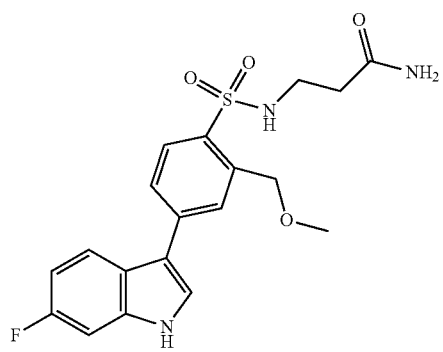 [SMILES: COCc1cc(-c2c[nH]c3cc(F)ccc23)ccc1S(=O)(=O)NCCC(N)=O]

Step 1: 5-bromo-2-nitrobenzaldehyde

To a clear solution of conc. nitric acid (25 mL) and conc. sulfuric acid (120 mL) was added 3-bromobenzaldehyde (20 g, 108.1 mmol) at 0° C. The reaction was stirred at 20° C. under a $N_2$ atmosphere for 1 h then cold water (250 mL) was added dropwise. The mixture was extracted with ethyl acetate (50 mL×3) and the combined organic layers were dried over $Na_2SO_4$, filtered and concentrated. The crude residue was purified by column chromatography ($SiO_2$, petroleum ether/ethyl acetate=1/1 to ethyl acetate/methanol=10/1) to give 5-bromo-2-nitrobenzaldehyde (21 g, 85%) as a yellow oil. $^1$H NMR (400 MHz, DMSO-$d_6$) δ [ppm] 10.21 (s, 1H), 8.11 (s, 2H), 8.06-8.01 (m, 1H).

Step 2: (5-bromo-2-nitrophenyl)methanol

To a yellow solution of 5-bromo-2-nitrobenzaldehyde (21 g, 91 mmol) in methanol (150 mL) was added $NaBH_4$ (4.14 g, 110 mmol) at 0° C. The reaction was stirred at 20° C. under a $N_2$ atmosphere for 1 h then concentrated to remove methanol. Ice-$H_2O$ (50 mL) was carefully added and the mixture was extracted with ethyl acetate (50 mL×3). The combined organic layers were dried over $Na_2SO_4$, filtered and concentrated then purified by column chromatography ($SiO_2$, petroleum ether/ethyl acetate=1/1 to ethyl acetate/methanol=10/1) to give (5-bromo-2-nitrophenyl)methanol (18 g, 85%) as a yellow solid. $^1$H NMR (400 MHz, CDCl$_3$) δ [ppm] 8.03-7.96 (m, 2H), 7.60 (dd, J=2.1, 8.7 Hz, 1H), 5.01 (s, 2H).

Step 3: 4-bromo-2-(methoxymethyl)-1-nitrobenzene

To a yellow solution of (5-bromo-2-nitrophenyl)methanol (10.0 g, 43.1 mmol) in anhydrous THF (100 mL) was added MeI (32.6 g, 230 mmol) and $Ag_2O$ (20 g, 86 mmol). The yellow suspension was stirred at 35° C. in a sealed tube for 48 h then filtered and concentrated. The crude residue was purified by column chromatography ($SiO_2$, petroleum ether/ethyl acetate=20/1 to 10/1) to give 4-bromo-2-(methoxymethyl)-1-nitrobenzene (9 g, 85%) as a yellow solid.

Step 4: 4-bromo-2-(methoxymethyl)aniline

To a yellow solution of 4-bromo-2-(methoxymethyl)-1-nitrobenzene (9.0 g, 37 mmol) in ethyl acetate/$H_2O$ (100 mL/20 mL) was added Fe (10.2 g, 183 mmol) and $NH_4Cl$ (9.78 g, 183 mmol) at 20° C. The reaction was stirred at 20° C. under a $N_2$ atmosphere for 18 h then filtered. The filtrate was extracted with ethyl acetate (50 mL×3) and the combined organic layers were dried over $Na_2SO_4$, filtered and concentrated. The crude residue was purified by column chromatography ($SiO_2$, petroleum ether/ethyl acetate=10/1 to 3/1) to give 4-bromo-2-(methoxymethyl)aniline (3 g, 38%) as a yellow gum.

Step 5: 4-bromo-2-(methoxymethyl)benzene-1-sulfonyl chloride

To a cooled (ice bath) solution of 4-bromo-2-(methoxymethyl)aniline (3.0 g, 14 mmol) in MeCN (150 mL) was added HOAc (15 mL) and conc. HCl (15 mL) then a solution of $NaNO_2$ (1.15 g, 16.7 mmol) in water (3 mL) was added drop-wise. The reaction was stirred for 20 min then sparged with $SO_2$ for 15 min while the temperature was maintained at 5° C. A solution of $CuCl_2$ (1.96 g, 14.6 mmol) in water (5 mL) was added in one portion and the mixture was stirred at 20° C. for 16 h then diluted with water (20 mL) and concentrated to remove MeCN. The mixture was extracted with ethyl acetate (30 mL×3) and the combined organic layers were washed with water (20 mL) and brine (20 mL) then dried over anhydrous $Na_2SO_4$, filtered, and concentrated. The crude residue was purified by column chromatography ($SiO_2$, petroleum ether) to give 4-bromo-2-(methoxymethyl)benzene-1-sulfonyl chloride (2 g, 48%) as a yellow gum. $^1$H NMR (400 MHz, CDCl$_3$) δ [ppm] 8.06 (d, J=1.0 Hz, 1H), 7.92 (d, J=8.5 Hz, 1H), 7.64 (dd, J=2.0, 8.5 Hz, 1H), 4.93 (s, 2H), 3.56 (s, 3H).

Step 6: 3-(4-bromo-2-(methoxymethyl)phenylsulfonamido)propanamide

To a yellow solution of 4-bromo-2-(methoxymethyl)benzene-1-sulfonyl chloride (2.0 g, 6.7 mmol) and 3-aminopropanamide HCl salt (1.04 g, 8.35 mmol) in anhydrous dichloromethane (50 mL) was added pyridine (3.17 g, 40.1 mmol) at 25° C. The yellow suspension was stirred for 36 h then washed with $H_2O$ (10 mL) and brine (10 mL). The organic phase was dried over anhydrous $Na_2SO_4$ then filtered and concentrated to give crude 3-(4-bromo-2-(methoxymethyl)phenylsulfonamido)propanamide (400 mg, 17%) as a yellow gum.

Step 7: tert-butyl 3-(4-(N-(3-amino-3-oxopropyl)sulfamoyl)-3-(methoxymethyl)phenyl)-6-fluoro-1H-indole-1-carboxylate A yellow solution of tert-butyl 6-fluoro-3-(4,4,5,5-tetramethyl-1,3,2-dioxaborolan-2-yl)-1H-indole-1-carboxylate (412 mg, 1.14 mmol), 3-(4-bromo-2-(methoxymethyl)phenylsulfonamido)propanamide (400 mg, 1.14 mmol), $PdCl_2$(dppf) (83 mg, 0.11 mmol) and $Cs_2CO_3$ (743 mg, 2.28 mmol) in dioxane (8 mL) and $H_2O$ (2 mL) was stirred at 85° C. under a $N_2$ atmosphere for 14 h. The resulting black solution was diluted with ethyl acetate (5 mL) and the organic layer was washed with brine (5 mL) then dried over anhydrous $Na_2SO_4$, filtered and concentrated to give crude tert-butyl 3-(4-(N-(3-amino-3-oxopropyl)sulfamoyl)-3-(methoxymethyl)phenyl)-6-fluoro-1H-indole-1-carboxylate (576 mg, 100%) as a red gum.

Step 8: 3-((4-(6-fluoro-1H-indol-3-yl)-2-(methoxymethyl)-phenyl)sulfonamido)propanamide A yellow solution of tert-butyl 3-(4-(N-(3-amino-3-oxopropyl)sulfamoyl)-3-(methoxymethyl)phenyl)-6-fluoro-1H-indole-1-carboxylate (576 mg, 1.14 mmol) in MeNH$_2$/EtOH (30% w/w, 10 mL) was stirred at 20° C. in a sealed tube for 18 h. The reaction was concentrated and purified by the prep-HPLC to give 3-(4-(6-fluoro-1H-indol-3-yl)-2-(methoxymethyl)phenylsulfonamido)propanamide (30 mg, 7%) as a brown solid. $^1$H NMR (400 MHz, DMSO-$d_6$) δ

[ppm] 11.67 (br s, 1H), 7.97 (s, 1H), 7.93-7.85 (m, 3H), 7.82-7.77 (m, 1H), 7.49 (t, J=5.9 Hz, 1H), 7.35 (br s, 1H), 7.27 (dd, J=2.4, 9.9 Hz, 1H), 7.03 (dt, J=2.4, 9.2 Hz, 1H), 6.87 (br s, 1H), 4.84 (s, 2H), 3.44 (s, 3H), 2.97 (q, J=7.0 Hz, 2H), 2.25 (t, J=7.3 Hz, 2H); LC-MS: m/z 427.9 (M+Na)$^+$.

Example 166: 3-((4-(6-fluoro-1H-indol-3-yl)-2-isopropoxyphenyl)-sulfonamido)propanamide

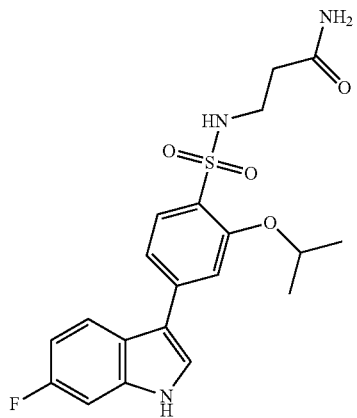 [SMILES: CC(C)Oc1cc(-c2c[nH]c3cc(F)ccc23)ccc1S(=O)(=O)NCCC(N)=O]

Step 1: 4-bromo-2-isopropoxy-1-nitrobenzene

A yellow suspension of 4-bromo-2-fluoro-1-nitrobenzene (3.0 g, 14 mmol) and $Cs_2CO_3$ (8.9 g, 27 mmol) in i-PrOH (30 mL) was stirred at 80° C. for 3 h. The resulting suspension was filtered and the filtrate was concentrated to give crude 4-bromo-2-isopropoxy-1-nitrobenzene (3.5 g, 99%) as yellow oil.

Step 2: 4-bromo-2-isopropoxyaniline

To a solution of 4-bromo-2-isopropoxyaniline (3.5 g, 14 mmol) in $EtOAc/H_2O$ (50 ml/20 mL) was added Fe (3.8 g, 67 mmol) and $NH_4Cl$ (3.6 g, 67 mmol) at 20° C. The reaction was stirred under a $N_2$ atmosphere for 64 h then the solids were filtered off and rinsed with EtOAc. The layers were separated and the organic layer was washed with brine (50 mL) then dried over anhydrous $Na_2SO_4$, filtered and concentrated. The crude residue was purified by column chromatography (silica gel, 5% EtOAc in PE) to give 4-bromo-2-isopropoxyaniline (3 g, 97%) as yellow oil.

Step 3: 4-bromo-2-isopropoxybenzene-1-sulfonyl chloride

To a solution of 4-bromo-2-isopropoxyaniline (3.0 g, 13 mmol) in MeCN (120 mL) at 0° C. was added HOAc (12 mL) and HCl (12 mL) followed by dropwise addition of $NaNO_2$ (1.03 g, 15.0 mmol) in water (1.9 mL). The reaction was stirred for 20 minutes then sparged with $SO_2$ for 15 minutes then a solution of $CuCl_2$ (1.84 g, 13.7 mmol) in water (3 mL) was added quickly. The reaction was stirred at room temperature for 16 h then diluted with water (100 mL) and extracted with ethyl acetate (200 mL). The organic layers was washed with brine (200 mL×3) then dried over anhydrous $Na_2SO_4$, filtered, and concentrated. The crude product was purified by column chromatography to give 4-bromo-2-isopropoxybenzene-1-sulfonyl chloride (1.7 g, 42%) as a white solid.

Step 4: 3-(4-bromo-2-isopropoxyphenylsulfonamido)propanamide

A yellow suspension of 3-aminopropanamide HCl salt (238 mg, 1.59 mmol) and 4-bromo-2-isopropoxybenzene-1-sulfonyl chloride (500 mg, 1.59 mmol) in pyridine (15 mL) was stirred at 25° C. for 16 h then concentrated and purified by column chromatography to give 3-(4-bromo-2-isopropoxyphenylsulfonamido)propanamide (550 mg, 94%) as yellow oil.

Step 5: tert-butyl 3-(4-(N-(3-amino-3-oxopropyl) sulfamoyl)-3-isopropoxyphenyl)-6-fluoro-1H-indole-1-carboxylate A suspension of 3-(4-bromo-2-isopropoxyphenylsulfonamido)-propanamide (550 mg, 1.51 mmol), tert-butyl 6-fluoro-3-(4,4,5,5-tetramethyl-1,3,2-dioxaborolan-2-yl)-1H-indole-1-carboxylate (544 mg, 1.51 mmol), $PdCl_2(dppf)$ (110 mg, 0.151 mmol) and $K_3PO_4$ (639 mg, 3.01 mmol) in dioxane (8 mL) and $H_2O$ (2 mL) was stirred at 80° C. under a $N_2$ atmosphere for 2 h. The resulting mixture was diluted with water (15 mL) and extracted with EtOAc (20 mL×3). The combined organic layers were washed with brine (15 mL) then dried over anhydrous $Na_2SO_4$, filtered and concentrated. The crude residue was purified by column chromatography (silica gel, 80-100% EtOAc in PE) to give tert-butyl 3-(4-(N-(3-amino-3-oxopropyl)sulfamoyl)-3-isopropoxyphenyl)-6-fluoro-1H-indole-1-carboxylate (500 mg, 64%) as yellow oil.

Step 6: 3-(4-(6-fluoro-1H-indol-3-yl)-2-isopropoxyphenyl-sulfonamido)propanamide A solution of tert-butyl 3-(4-(N-(3-amino-3-oxopropyl) sulfamoyl)-3-isopropoxyphenyl)-6-fluoro-1H-indole-1-carboxylate (500 mg, 0.962 mmol) in TFA (5 mL) and DCM (5 mL) was stirred at 20° C. for 1 h then concentrated. The residue was neutralized with $NaHCO_3$ (sat) then extracted with EtOAc (100 mL×2). The combined organic layers were washed with brine (50 mL) then dried over anhydrous $Na_2SO_4$, filtered and concentrated. The residue was triturated with $EtOAc/H_2O$ (15 mL/10 mL) then filtered and rinsed with EtOAc. The resulting solid was triturated with $MeOH/CH_3CN$ (20 mL/15 mL) then filtered to give 3-(4-(6-fluoro-1H-indol-3-yl)-2-isopropoxyphenylsulfonamido) propanamide (125 mg, 31%) as an off-white solid. $^1$H NMR (400 MHz, DMSO-d$_6$) δ [ppm] 11.65 (br s, 1H), 8.01-7.84 (m, 2H), 7.75 (d, J=8.0 Hz, 1H), 7.45-7.33 (m, 3H), 7.26 (dd, J=2.3, 9.8 Hz, 1H), 7.00 (dt, J=2.3, 9.3 Hz, 1H), 6.90 (br s, 1H), 6.62 (t, J=6.1 Hz, 1H), 4.99 (td, J=5.7, 11.9 Hz, 1H), 2.98 (q, J=6.6 Hz, 2H), 2.28 (t, J=6.9 Hz, 2H), 1.39 (d, J=5.8 Hz, 6H); LCMS: m/z, 441.9 (M+Na)+.

Example 167: 3-((4-(6-fluoro-1H-indol-3-yl)-2-(hydroxymethyl)-phenyl)sulfonamido)propanamide

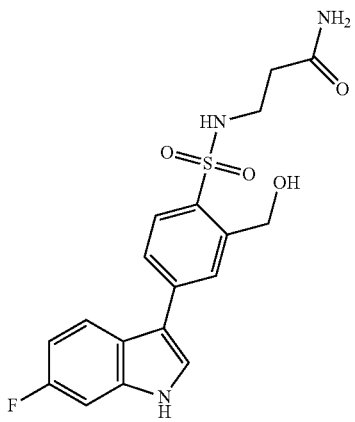 [SMILES: NC(=O)CCNS(=O)(=O)c1ccc(-c2c[nH]c3cc(F)ccc23)cc1CO]

Step 1: 5-bromo-2-nitrobenzyl acetate

To a clear solution of (5-bromo-2-nitrophenyl)methanol (2.5 g, 11 mmol) and DMAP (132 mg, 1.08 mmol) in DCM (40 mL) was added Ac$_2$O (1.1 g, 11 mmol) at 0° C. The reaction was warmed and stirred at 20° C. under a N$_2$ atmosphere for 1 h. The crude reaction was concentrated then diluted with H$_2$O (50 mL) and extracted EtOAc (50 mL×3). The combined organic layers were dried over Na$_2$SO$_4$, filtered and purified by column chromatography to give 5-bromo-2-nitrobenzyl acetate (2.8 g, 95%) as a yellow solid.

Step 2: 2-amino-5-bromobenzyl acetate

To a solution of 5-bromo-2-nitrobenzyl acetate (2.8 g, 10 mmol) in EtOAc/H$_2$O (50 ml/20 mL) was added Fe (2.85 g, 51.1 mmol) and NH$_4$Cl (2.73 g, 51.1 mmol) at 20° C. The reaction was stirred under N$_2$ atmosphere for 18 h. The suspension was filtered and the filtrate was extracted EtOAc (50 mL×3). The combined organic layers were dried over Na$_2$SO$_4$, filtered and concentrated then purified by column chromatography to give 2-amino-5-bromobenzyl acetate (1.6 g, 64%) as a yellow gum. $^1$H NMR (400 MHz, CDCl$_3$) δ [ppm] 7.31 (d, J=2.3 Hz, 1H), 7.24 (dd, J=2.3, 8.5 Hz, 1H), 6.58 (d, J=8.5 Hz, 1H), 5.03 (s, 2H), 4.12 (br s, 2H), 2.09 (s, 3H).

Step 3: 5-bromo-2-(chlorosulfonyl)benzyl acetate

To a clear solution of 2-amino-5-bromobenzyl acetate (1.6 g, 6.6 mmol) in MeCN (80 mL) at 0° C. was added HOAc (8 mL) and HCl (8 mL, 12 N) then a solution of NaNO$_2$ (0.68 g, 9.8 mmol) in water (3 mL) was added dropwise. The reaction was stirred for 20 minutes then sparged with SO$_2$ for 15 minutes while keeping the temperature below 5° C. A solution of CuCl$_2$ (1.1 g, 7.9 mmol) in water (5 mL) was added in one portion and the mixture was stirred at room temperature for 16 h. The reaction was diluted with water (20 mL) and concentrated then extracted with ethyl acetate (30 mL×3). The combined organic layers were washed with water (20 mL) and brine (20 mL) then dried over anhydrous Na$_2$SO$_4$, filtered, and concentrated. The crude residue was purified by column chromatography to give 5-bromo-2-(chlorosulfonyl)benzyl acetate (1 g, 47%) as a yellow gum. $^1$H NMR (400 MHz, CDCl$_3$) δ [ppm] 7.97 (d, J=8.5 Hz, 1H), 7.82 (d, J=2.0 Hz, 1H), 7.74-7.65 (m, 1H), 5.60 (s, 2H), 4.00 (s, 1H), 2.23 (s, 3H).

Step 4: 2-(N-(3-amino-3-oxopropyl)sulfamoyl)-5-bromobenzyl acetate

To a solution of crude 4-bromo-2-(methoxymethyl)benzene-1-sulfonyl chloride (500 mg, 1.53 mmol) and 3-aminopropanamide HCl salt (228 mg, 1.83 mmol) in H$_2$O/acetone (2 ml/10 mL) was added NaHCO$_3$ (0.64 g, 7.6 mmol) at 25° C. The reaction was stirred for 3 h then concentrated to remove acetone and extracted with EtOAc (20 mL×2). The combined organic layers were washed with H$_2$O (10 mL) and brine (10 mL) then dried over Na$_2$SO$_4$, filtered and concentrated to give crude 2-(N-(3-amino-3-oxopropyl)sulfamoyl)-5-bromobenzyl acetate (500 mg, 86%) as a yellow gum.

Step 5: tert-butyl 3-(4-(N-(3-amino-3-oxopropyl)sulfamoyl)-3-(methoxymethyl)phenyl)-6-fluoro-1H-indole-1-carboxylate A solution of tert-butyl 6-fluoro-3-(4,4,5,5-tetramethyl-1,3,2-dioxaborolan-2-yl)-1H-indole-1-carboxylate (477 mg, 1.32 mmol), 2-(N-(3-amino-3-oxopropyl)sulfamoyl)-5-bromobenzyl acetate (500 mg, 1.32 mmol), PdCl$_2$(dppf) (97 mg, 0.13 mmol) and Cs$_2$CO$_3$ (860 mg, 2.64 mmol) in dioxane (8 mL) and H$_2$O (2 mL) was stirred at 85° C. under a N$_2$ atmosphere for 14 h. The reaction was diluted with EtOAc (50 mL) and water (15 mL) and the layers were separated. The organic layer was washed with brine (20 mL) then dried over anhydrous Na$_2$SO$_4$, filtered and concentrated to give crude tert-butyl 3-(4-(N-(3-amino-3-oxopropyl)sulfamoyl)-3-(methoxymethyl)phenyl)-6-fluoro-1H-indole-1-carboxylate (649 mg, 100%) as a red gum.

Step 6: 3-(4-(6-fluoro-1H-indol-3-yl)-2-(hydroxymethyl)-phenylsulfonamido)propanamide A solution of crude tert-butyl 3-(4-(N-(3-amino-3-oxopropyl)sulfamoyl)-3-(methoxymethyl)phenyl)-6-fluoro-1H-indole-1-carboxylate (649 mg, 1.32 mmol) in MeNH$_2$/EtOH (30% w/w, 10 mL) was stirred at 45° C. in a sealed tube for 2 h. The reaction was concentrated and purified by prep HPLC to give 3-(4-(6-fluoro-1H-indol-3-yl)-2-(hydroxymethyl)phenylsulfonamido)propanamide (220 mg, 43%) as a brown solid. $^1$H NMR (400 MHz, DMSO-d$_6$) δ [ppm] 11.65 (brs, 1H), 8.13 (s, 1H), 7.95 (dd, J=5.3, 8.8 Hz, 1H), 7.88 (d, J=2.5 Hz, 1H), 7.85-7.80 (m, 1H), 7.77-7.72 (m, 1H), 7.55 (brs, 1H), 7.36 (br s, 1H), 7.27 (dd, J=2.4, 9.9 Hz, 1H), 7.03 (dt, J=2.4, 9.2 Hz, 1H), 6.87 (br, 1H), 5.53 (t, J=5.8 Hz, 1H), 4.93 (d, J=5.5 Hz, 2H), 2.95 (br, 2H), 2.26 (t, J=7.4 Hz, 2H); LC-MS: m/z 413.9 (M+Na)⁺.

Example 168: 3-((4-(6-fluoro-1H-indol-3-yl)-2-(trifluoromethyl)phenyl)-sulfonamido)propanamide

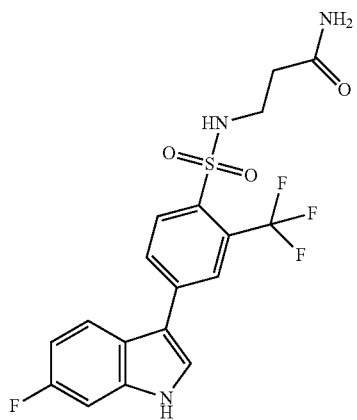 [SMILES: NC(=O)CCNS(=O)(=O)c1ccc(-c2c[nH]c3cc(F)ccc23)cc1C(F)(F)F]

Step 1:
4-bromo-2-(trifluoromethyl)benzene-1-sulfonyl chloride

To a solution of 4-bromo-2-(trifluoromethyl)aniline (3.0 g, 12.5 mmol) in MeCN (120 mL) at 0° C. was added HOAc (12 mL) and HCl (12 mL) followed by dropwise addition of a solution of NaNO₂ (1.03 g, 15.0 mmol) in water (1.9 mL). The reaction was stirred for 20 minutes then sparged with SO₂ over 15 minutes. A solution of CuCl₂ (1.76 g, 13.1 mmol) in water (3 mL) was added and the reaction was stirred at 20° C. for 16 h. The crude reaction was diluted with water (20 mL) and concentrated to remove MeCN then extracted with ethyl acetate (30 mL×3). The combined organic layers were washed with ammonium chloride (sat) (20 mL), water (20 mL) and brine (20 mL) then dried over anhydrous Na₂SO₄, filtered, and concentrated. The crude product was purified by column chromatography to give 4-bromo-2-(trifluoromethyl)benzene-1-sulfonyl chloride (2.1 g, 52%) as a clear oil.

Step 2: 3-(4-bromo-2-(trifluoromethyl)phenylsulfonamido)propanamide

To a solution of 3-aminopropanamide HCl salt (327 mg, 3.71 mmol) in dichloromethane/water (12 mL/3 mL) was added NaHCO₃ (390 mg, 4.64 mmol), Et₃N (626 mg, 0.862 mL, 6.18 mmol) and 4-bromo-2-(trifluoromethyl)benzene-1-sulfonyl chloride (1.0 g, 3.1 mmol). The reaction was stirred at 19° C. for 16 h then extracted with DCM (10 mL×3). The combined organic layers were washed with water (10 mL) and brine (10 mL) then dried over anhydrous Na₂SO₄, filtered, and concentrated to give crude 3-(4-bromo-2-(trifluoromethyl)phenylsulfonamido)propanamide (236 mg, 20%) as a yellow solid.

Step 3: tert-butyl 3-(4-(N-(3-amino-3-oxopropyl)sulfamoyl)-3-(trifluoromethyl)phenyl)-6-fluoro-1H-indole-1-carboxylate A mixture of 3-(4-bromo-2-(trifluoromethyl)phenylsulfonamido)-propanamide (236 mg, 0.771 mmol), tert-butyl 6-fluoro-3-(4,4,5,5-tetramethyl-1,3,2-dioxaborolan-2-yl)-1H-indole-1-carboxylate (278 mg, 0.771 mmol), PdCl₂(dppf)CH₂Cl₂ (58 mg, 0.08 mmol), and K₃PO₄ (491 mg, 2.31 mmol) in 1,4-dioxane (8 mL) and water (2 mL) was sparged with nitrogen for 1 minute. The reaction was stirred at 80° C. for 16 h. The crude reaction was diluted with water (5 mL) then extracted with EtOAc (15 mL×3). The combined organic layers were washed with water (15 mL) and brine (15 mL) then dried over anhydrous Na₂SO₄, filtered, and concentrated. The crude residue was purified by column chromatography to give tert-butyl 3-(4-(N-(3-amino-3-oxopropyl)sulfamoyl)-3-(trifluoromethyl) phenyl)-6-fluoro-1H-indole-1-carboxylate (360 mg, 88%) as a black solid.

Step 4: 3-(4-(6-fluoro-1H-indol-3-yl)-2-(trifluoromethyl)-phenylsulfonamido)propanamide To a cooled (ice bath) solution of tert-butyl 3-(4-(N-(3-amino-3-oxopropyl)sulfamoyl)-3-(trifluoromethyl)phenyl)-6-fluoro-1H-indole-1-carboxylate (360 mg, 0.680 mmol) in DCM (8 mL) was slowly added TFA (4 mL). The reaction was stirred at 19° C. for 2 h then quenched with water (5 mL) and concentrated. The residue was diluted with DCM (10 mL) and the pH adjusted to 8 with NaHCO₃ (sat) (20 mL). The mixture was extracted with DCM (15 mL×3) and the combined organic layers were washed with water (15 mL) and brine (15 mL) then dried over anhydrous Na₂SO₄, filtered, and concentrated. The crude residue was purified by prep-HPLC to give 3-(4-(6-fluoro-1H-indol-3-yl)-2-(trifluoromethyl)phenylsulfonamido)propanamide (40 mg, 14%) as a white solid. ¹H NMR (400 MHz, DMSO-d₆) δ [ppm] (br s, 1H), 8.20-8.09 (m, 3H), 7.93 (dd, J=5.3, 8.8 Hz, 1H), 7.85 (br s, 1H), 7.62-7.55 (m, 1H), 7.36 (br s, 1H), 7.28 (dd, J=2.4, 9.7 Hz, 1H), 7.05 (dt, J=2.4, 9.2 Hz, 1H), 6.87 (br s, 1H), 3.10-3.06 (m, 2H), 2.30 (t, J=7.4 Hz, 2H); ¹⁹F NMR (376 MHz, MeOD) δ [ppm]−59.100, −122.860; LC-MS: m/z 452.1 (M+Na)⁺.

Example 169: N-(3-((cis)-3,4-dihydroxypyrrolidin-1-yl)-3-oxopropyl)-4-(6-fluoro-1H-indol-3-yl)benzenesulfonamide

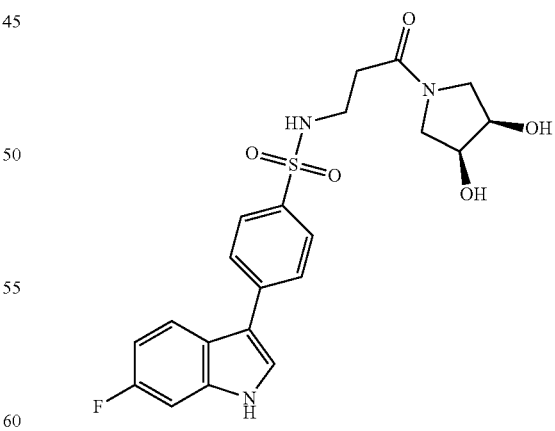

Step 1: ethyl 3-(4-(6-fluoro-1H-indol-3-yl)phenylsulfonamido)propanoate

A suspension of tert-butyl 6-fluoro-3-(4,4,5,5-tetramethyl-1,3,2-dioxaborolan-2-yl)-1H-indole-1-carboxylate (4.0 g, 8.9 mmol), ethyl 3-((4-bromophenylsulfonamido)propanoate (2.9 g, 8.9 mmol), Pd(dppf)Cl$_2$ (648 mg, 0.886 mmol) and K$_3$PO$_4$ (4.7 g, 22 mmol) in dioxane (120 mL) and water (30 mL) was stirred under a N$_2$ atmosphere at 100° C. for 16 h. The suspension was concentrated then purified by column chromatography (silica gel, 0-50% petroleum/ethyl acetate) to afford the title compound (2.7 g, 77%) as an off-white solid.

Step 2: 3-(4-(6-fluoro-1H-indol-3-yl)phenylsulfonamido)propanoic acid

A solution of ethyl 3-(4-(6-fluoro-1H-indol-3-yl)phenylsulfonamido)propanoate (2660 mg, 6.1 mmol), LiOH—H$_2$O (772 mg, 18.4 mmol) in H$_2$O (30 ml) and THF (30 mL) was stirred at 20° C. for 1 h. The reaction was concentrated and diluted with ethyl acetate (30 mL) and water (15 mL). The mixture was neutralizing with diluted hydrochloric acid then extracted with ethyl acetate (30 mL×2). The combined organic layers were dried over anhydrous Na$_2$SO$_4$, filtered and concentrated to afford the title compound (2.0 g, 90%) as a red solid.

Step 3: N-(3-((cis)-3,4-dihydroxypyrrolidin-1-yl)-3-oxopropyl)-4-(6-fluoro-1H-indol-3-yl)benzenesulfonamide A solution of 3-(4-(6-fluoro-1H-indol-3-yl)phenylsulfonamido)propanoic acid (110 mg, 0.28 mmol), (3R, 4S)-pyrrolidine-3,4-diol (39.4 mg, 0.28 mmol), HATU (161 mg, 0.423 mmol) and DIPEA (146 mg, 1.13 mmol) in DMF (3 mL) was a stirred at 20° C. for 1 h. The reaction was diluted with ethyl acetate (20 mL) and water (10 mL) then extracted with ethyl acetate (20 mL×2). The combined organic layers were dried over Na$_2$SO$_4$, filtered and concentrated. The crude product purified by prep-HPLC to give the title compound (82 mg, 65%) as a white solid. $^1$H NMR (400 MHz, DMSO-d$_6$) δ [ppm] 11.64 (br s, 1H), 7.96-7.88 (m, 4H), 7.84-7.79 (m, 2H), 7.54 (br s, 1H), 7.26 (dd, J=2.5, 9.8 Hz, 1H), 7.00 (dt, J=2.4, 9.2 Hz, 1H), 4.96 (d, J=5.3 Hz, 1H), 4.88 (d, J=4.5 Hz, 1H), 4.05-3.91 (m, 2H), 3.48 (dd, J=6.0, 10.0 Hz, 1H), 3.33-3.30 (m, 1H), 3.21-3.11 (m, 2H), 2.97 (t, J=7.0 Hz, 2H), 2.37 (dt, J=2.4, 7.1 Hz, 2H); LCMS: m/z 448.0 (M+H)$^+$.

Example 170: (+)-N-(3-((3R,4R)-3,4-dihydroxypyrrolidin-1-yl)-3-oxopropyl)-4-(6-fluoro-1H-indol-3-yl)benzenesulfonamide

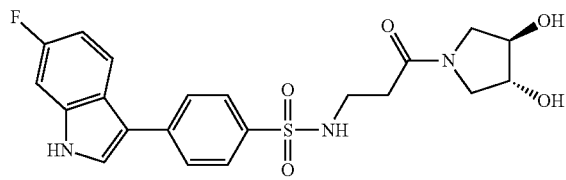 [SMILES: O=C(CCNS(=O)(=O)c1ccc(-c2c[nH]c3cc(F)ccc23)cc1)N1C[C@@H](O)[C@H](O)C1]

Step 1: tert-butyl 6-oxa-3-azabicyclo[3.1.0]hexane-3-carboxylate

To a clear solution of tert-butyl 2,5-dihydro-1H-pyrrole-1-carboxylate (1.50 g, 8.86 mmol) in dichloromethane (20 mL) was added m-CPBA (1.84 g, 10.6 mmol). The reaction was stirred at 25° C. for 16 h. The resulting white suspension was quenched with Na$_2$SO$_3$ (sat) (30 mL) and stirred for 30 min then extracted with dichloromethane (30 mL×2). The combined organic layers were washed with brine (20 mL) then dried over Na$_2$SO$_4$, filtered and concentrated. The crude residue was purified by column chromatography (silica gel, 50% ethyl acetate/petroleum ether) to give tert-butyl 6-oxa-3-azabicyclo[3.1.0]hexane-3-carboxylate (1.0 g, 61%) as a clear oil. $^1$H NMR (400 MHz, CDCl$_3$) δ [ppm] 3.88-3.70 (m, 2H), 3.67 (dd, J=1.0, 4.0 Hz, 2H), 3.38-3.26 (m, 2H), 1.44 (s, 9H).

Step 2: (3R,4R)-tert-butyl 3,4-dihydroxypyrrolidine-1-carboxylate

To a clear solution of 6-oxa-3-azabicyclo[3.1.0]hexane (430 mg, 2.16 mmol) in dioxane (4 mL) was added 10% H$_2$SO$_4$ (4 mL). The reaction was stirred at 100° C. for 6 h then cooled to room temperature. The mixture was neutralized to pH 8-9 with NaHCO$_3$ (sat) then Boc$_2$O (432 mg, 1.98 mmol) was added and the yellow suspension was stirred at 20° C. for 1 h. The mixture was extracted with ethyl acetate (30 mL×2) and the combined organic layers were washed with brine (20 mL) then dried over anhydrous Na$_2$SO$_4$, filtered and concentrated. The resulting solid was washed with petroleum ether (15 mL) and dried to give (3R,4R)-tert-butyl 3,4-dihydroxypyrrolidine-1-carboxylate (400 mg, 91%) as an off-white solid. $^1$H NMR (400 MHz, DMSO-d$_6$) δ [ppm] 5.06 (d, J=3.0 Hz, 2H), 3.86 (d, J=3.5 Hz, 2H), 3.37 (d, J=3.8 Hz, 1H), 3.31 (d, J=4.0 Hz, 1H), 3.11 (dd, J=2.9, 11.4 Hz, 2H), 1.39 (s, 9H).

Step 3: (3R,4R)-pyrrolidine-3,4-diol

A clear solution of (3R,4R)-tert-butyl 3,4-dihydroxypyrrolidine-1-carboxylate (400 mg, 1.97 mmol) in HCl/ethyl acetate (20 mL) was stirred at 20° C. for 1 h. The reaction was concentrated to give the HCl salt of (3R, 4R)-pyrrolidine-3,4-diol (400 mg, 99%) as a yellow solid. $^1$H NMR (400 MHz, DMSO-d$_6$) δ [ppm] 9.46 (br s, 2H), 5.61 (br s, 2H), 4.07 (d, J=3.3 Hz, 2H), 3.30-3.18 (m, 2H), 3.01 (td, J=4.6, 11.8 Hz, 2H).

Step 4: (+)-N-(3-(3,4-dihydroxypyrrolidin-1-yl)-3-oxopropyl)-4-(6-fluoro-1H-indol-3-yl)benzenesulfonamide A yellow solution of 3-(4-(6-fluoro-1H-indol-3-yl)phenylsulfonamido)-propanoic acid (457 mg, 1.26 mmol), pyrrolidine-3,4-diol (176 mg, 1.26 mmol), HATU (719 mg, 1.89 mmol) and DIPEA (489 mg, 3.78 mmol) in anhydrous DMF (10 mL) was stirred at 20° C. for 1 h. The reaction was concentrated to remove DMF then diluted with water (15 mL) and extracted with ethyl acetate (20 mL×3). The combined organic layers were washed with brine (15 mL) then dried over anhydrous Na$_2$SO$_4$, filtered and concentrated. The crude residue was purified by column chromatography (silica gel, 5% methanol/ethyl acetate) to give the racemic product (300 mg) as an off-white solid. The enantiomers were separation by prep-chiral SFC to provide (+)-N-(3-(3,4-dihydroxypyrrolidin-1-yl)-3-oxopropyl)-4-(6-fluoro-1H-indol-3-yl) benzenesulfonamide as the first eluting peak (42 mg, 7%) as an off-white solid. $^1$H NMR (400 MHz, DMSO-d$_6$) δ [ppm] 11.64 (br s, 1H), 7.97-7.87 (m, 4H), 7.86-7.79 (m, 2H), 7.55 (t, J=5.6 Hz, 1H), 7.26 (dd, J=2.3, 9.8 Hz, 1H), 7.00 (dt, J=2.4, 9.2 Hz, 1H), 5.17 (d, J=3.5 Hz, 1H), 5.10 (d, J=3.5 Hz, 1H), 3.99-3.83 (m, 2H), 3.53 (dd, J=4.0, 10.8 Hz, 1H), 3.35-3.31 (m, 1H), 3.29-3.16

(m, 2H), 3.03-2.92 (m, 2H), 2.40 (dt, J=2.4, 7.2 Hz, 2H); LC-MS: m/z 448.0 (M+H); $[\alpha]^{20}_D$+4.67° (c=1.5 mg/mL, methanol).

Example 171: (−)-N-(3-((3S,4S)-3,4-dihydroxypyrrolidin-1-yl)-3-oxopropyl)-4-(6-fluoro-1H-indol-3-yl)benzenesulfonamide

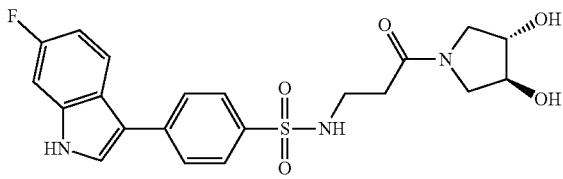 [SMILES: O=C(CCNS(=O)(=O)c1ccc(-c2c[nH]c3cc(F)ccc23)cc1)N1C[C@H](O)[C@@H](O)C1]

The title compound was obtained as the second eluting peak from the chiral separation described in Example 170 (55 mg, 9.7% yield) as an off-white solid. $^1$H NMR (400 MHz, DMSO-d$_6$) δ [ppm] 11.65 (br s, 1H), 7.97-7.88 (m, 4H), 7.85-7.79 (m, 2H), 7.55 (t, J=5.9 Hz, 1H), 7.26 (dd, J=2.4, 9.9 Hz, 1H), 7.00 (dt, J=2.5, 9.3 Hz, 1H), 5.17 (d, J=3.5 Hz, 1H), 5.09 (d, J=3.5 Hz, 1H), 3.97-3.84 (m, 2H), 3.53 (dd, J=4.0, 10.8 Hz, 1H), 3.32 (d, J=4.0 Hz, 1H), 3.27-3.17 (m, 2H), 3.02-2.93 (m, 2H), 2.40 (dt, J=2.5, 7.2 Hz, 2H); LC-MS: m/z 448.0 (M+H)$^+$; $[\alpha]^{20}_D$−2.78° (c=1.8 mg/mL, methanol).

Example 172: (−)-N-(3-((3S,4R)-3-amino-4-fluoropyrrolidin-1-yl)-3-oxopropyl)-4-(6-fluoro-1H-indol-3-yl)benzenesulfonamide

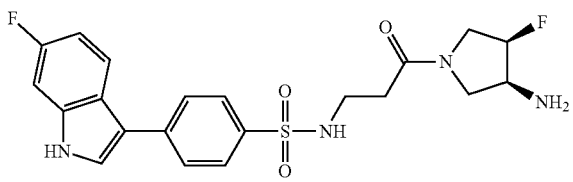 [SMILES: N[C@H]1CN(C(=O)CCNS(=O)(=O)c2ccc(-c3c[nH]c4cc(F)ccc34)cc2)C[C@H]1F]

Step 1: tert-butyl ((3S,4R)-4-fluoro-1-(3-(4-(6-fluoro-1H-indol-3-yl)phenylsulfonamido)propanoyl)pyrrolidin-3-yl)carbamate A yellow solution of 3-((4-(6-fluoro-1H-indol-3-yl)phenyl)sulfonamido)-propanoic acid (200 mg, 0.552 mmol), tert-butyl ((3S,4R)-4-fluoropyrrolidin-3-yl)carbamate (113 mg, 0.552 mmol), HATU (315 mg, 0.828 mmol) and DIPEA (214 mg, 1.66 mmol) in anhydrous DMF (5 mL) was stirred at 20° C. for 1 h. The reaction was diluted with water (15 mL) and extracted with ethyl acetate (20 mL×3). The combined organic layers were washed with brine (15 mL) then concentrated and purified by column chromatography (silica gel, 60% ethyl acetate/petroleum ether) to give crude tert-butyl ((3S, 4R)-4-fluoro-1-(3-(4-(6-fluoro-1H-indol-3-yl)phenylsulfonamido)propanoyl)pyrrolidin-3-yl)carbamate (260 mg, 86%) as an off-white solid.

Step 2: (−)-N-(3-((3S,4R)-3-amino-4-fluoropyrrolidin-1-yl)-3-oxopropyl)-4-(6-fluoro-1H-indol-3-yl)benzenesulfonamide A clear solution of tert-butyl ((3S,4R)-4-fluoro-1-(3-(4-(6-fluoro-1H-indol-3-yl)phenylsulfonamido)propanoyl)pyrrolidin-3-yl)carbamate (260 mg, 0.474 mmol) in 4M HCl/ethyl acetate (20 mL) was stirred at 20° C. for 1 h. The reaction was concentrated then diluted with water (10 mL) and washed with ethyl acetate (20 mL). The aqueous layer was neutralized with NaHCO$_3$ (sat) (10 mL) and extracted with ethyl acetate (20 mL×3). The combined organic layers were washed with brine (10 mL) then dried over anhydrous Na$_2$SO$_4$, filtered and concentrated. The crude residue was purified by prep-chiral SFC to give (−)-N-(3-((3S,4R)-3-amino-4-fluoropyrrolidin-1-yl)-3-oxopropyl)-4-(6-fluoro-1H-indol-3-yl) benzene sulfonamide as the first eluting peak (19 mg, 9%) as an off-white solid. $^1$H NMR (400 MHz, MeOD) δ [ppm] 7.92-7.82 (m, 5H), 7.65 (s, 1H), 7.16 (dd, J=2.3, 9.8 Hz, 1H), 6.94 (dt, J=2.4, 9.2 Hz, 1H), 5.07 (t, J=3.6 Hz, 1H), 4.94 (t, J=3.5 Hz, 1H), 4.35-4.20 (m, 1H), 3.30-3.06 (m, 5H), 2.73 (t, J=10.7 Hz, 1H), 2.50-2.43 (m, 2H); LC-MS: m/z 448.9 (M+H)$^+$; $[\alpha]^{20}_D$−10° (c=1.3 mg/mL, methanol).

Example 173: (+)-N-(3-((3S,4R)-3-amino-4-fluoropyrrolidin-1-yl)-3-oxopropyl)-4-(6-fluoro-1H-indol-3-yl)benzenesulfonamide

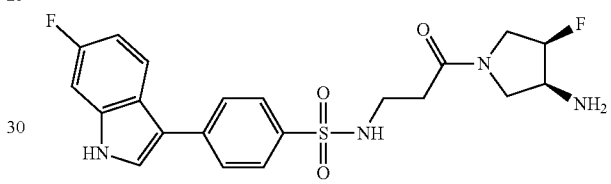

The title compound was obtained as the second eluting peak from the chiral separation described in Example 172 (14 mg, 7%) as an off-white solid. $^1$H NMR (400 MHz, MeOD) δ [ppm]7.92-7.84 (m, 5H), 7.65 (s, 1H), 7.16 (dd, J=2.3, 9.8 Hz, 1H), 6.94 (dt, J=2.5, 9.2 Hz, 1H), 5.08 (t, J=3.8 Hz, 1H), 4.95-4.93 (m, 1H), 4.36-4.21 (m, 1H), 3.30-3.06 (m, 5H), 2.74 (t, J=10.7 Hz, 1H), 2.50-2.43 (m, 2H); LC-MS: m/z 448.9 (M+H)$^+$; $[\alpha]^{20}_D$+7.5° (c=1.2 mg/mL, methanol).

Example 174: (+)-N-(3-((3R,4R)-3-amino-4-fluoropyrrolidin-1-yl)-3-oxopropyl)-4-(6-fluoro-1H-indol-3-yl)benzenesulfonamide

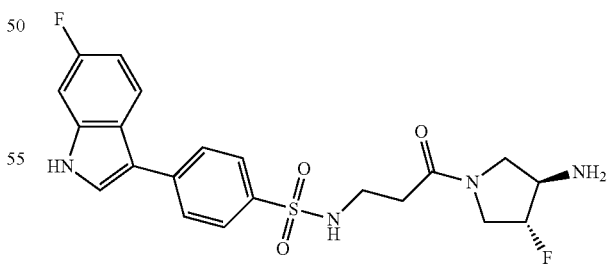

Step 1: tert-butyl ((3R,4R)-4-fluoro-1-(3-(4-(6-fluoro-1H-indol-3-yl)phenylsulfonamido)propanoyl)pyrrolidin-3-yl)carbamate A solution of 3-(4-(6-fluoro-1H-indol-3-yl)phenylsulfonamido)propanoic acid (200 mg, 0.552 mmol), tert-butyl ((3R,4R)-4-fluoropyrrolidin-3-yl)carbamate (113 mg, 0.552 mmol), HATU (315 mg, 0.828 mmol) and DIPEA (214 mg, 1.66 mmol) in anhydrous DMF (5 mL) was stirred at 20° C. for 1 h. The reaction was diluted with water (15 mL) and extracted with ethyl acetate (20 mL×3). The combined organic layers were washed with brine (15 mL) then dried over anhydrous $Na_2SO_4$, filtered and concentrated. The crude residue was purified by column chromatography (silica gel, 70% ethyl acetate/petroleum ether) to give tert-butyl ((3R,4R)-4-fluoro-1-(3-(4-(6-fluoro-1H-indol-3-yl)phenyl-sulfonamido)propanoyl)pyrrolidin-3-yl)carbamate (250 mg, 83%) as a clear oil.

Step 2: (+)-N-(3-((3R,4R)-3-amino-4-fluoropyrrolidin-1-yl)-3-oxopropyl)-4-(6-fluoro-1H-indol-3-yl)benzenesulfonamide A clear solution of tert-butyl ((3R,4R)-4-fluoro-1-(3-(4-(6-fluoro-1H-indol-3-yl)phenyl sulfonamido)propanoyl)pyrrolidin-3-yl)carbamate (250 mg, 0.456 mmol) in 4M HCl/ethyl acetate (20 mL) was stirred at 20° C. for 1 h. The reaction was concentrated then diluted with $NaHCO_3$ (sat) (10 mL) and extracted with ethyl acetate (20 mL×3). The combined organic layers were washed with brine (10 mL) then dried over anhydrous $Na_2SO_4$, filtered and concentrated. The crude residue was purified by prep-HPLC then prep-chiral SFC to give (+)-N-(3-((3R, 4R)-3-amino-4-fluoropyrrolidin-1-yl)-3-oxopropyl)-4-(6-fluoro-1H-indol-3-yl)benzenesulfonamide (31 mg, 15%) as an off-white solid. $^1$H NMR (400 MHz, DMSO-$d_6$) δ [ppm] 11.64 (br s, 1H), 7.99-7.87 (m, 4H), 7.85-7.78 (m, 2H), 7.57 (br s, 1H), 7.26 (dd, J=2.4, 9.9 Hz, 1H), 7.00 (dt, J=2.4, 9.2 Hz, 1H), 5.14-4.70 (m, 1H), 3.86-3.48 (m, 4H), 3.24 (d, J=9.8 Hz, 1H), 2.99 (t, J=7.2 Hz, 2H), 2.49-2.37 (m, 2H); LC-MS: m/z 449.0 (M+H)$^+$; $[α]^{20}_D$+3.3° (c=1.2 mg/mL, methanol).

Example 175: 3-((2-(2,2-difluoroethyl)-4-(6-fluoro-1H-indol-3-yl)-phenyl)sulfonamido)propanamide

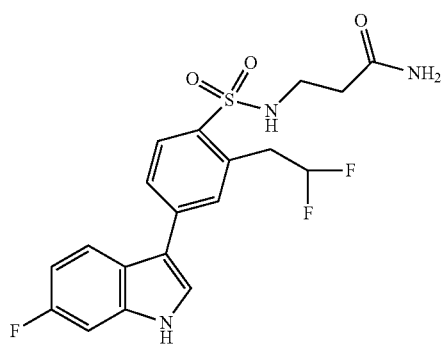 [SMILES: NC(=O)CCNS(=O)(=O)c1ccc(-c2c[nH]c3cc(F)ccc23)cc1CC(F)F]

Step 1: 1-bromo-3-(2,2-difluoroethyl)benzene

A solution of 4-iodototoluene (1.7 g, 7.7 mmol), m-CPBA (12 g, 57 mmol) and Py-HF (38 g, 382 mmol) in DCM (80 mL) was stirred at 10° C. for 30 min then a solution of 3-bromostyrene (7 g, 38 mmol) in DCM (20 mL) was added. The reaction was stirred for 2 h then quenched with $Na_2SO_3$ (30 mL) and filtered. The organic layer was separated and washed with $NaHCO_3$ (sat) (30 mL) and $H_2O$ (30 mL) then dried over $Na_2SO_4$, filtered and concentrated. The crude residue was purified by column chromatography to give 1-bromo-3-(2,2-difluoroethyl)benzene (2.8 g, 33%) as yellow gum. $^1$H NMR (400 MHz, CDCl$_3$) δ [ppm] 7.48-7.39 (m, 1H), 7.25-7.16 (m, 1H), 6.09-5.75 (m, 1H), 3.12 (dt, J=4.5, 17.2 Hz, 2H).

Step 2: 4-bromo-2-(2,2-difluoroethyl)benzene-1-sulfonyl chloride

To a cooled (ice bath) solution of 1-bromo-3-(2,2-difluoroethyl)benzene (2.5 g, 5.7 mmol) in chloroform (50 mL) was added chlorosulfonic acid (10.5 g, 90.5 mmol). The reaction was stirred at 10° C. for 16 h then quenched with ice-water (50 mL) and extracted with DCM (50 mL×2). The combined organic layers were concentrated to give crude 4-bromo-2-(2,2-difluoroethyl)benzene-1-sulfonyl chloride (0.7 g, 39%) as yellow solid, which was used directly in the next step.

Step 3: 3-(4-bromo-2-(2,2-difluoroethyl)phenylsulfonamido)propanamide

To a solution of crude 4-bromo-2-(2,2-difluoroethyl)benzene-1-sulfonyl chloride (700 mg, 2.2 mmol) and 3-aminopropanamide HCl salt (273 mg, 2.19 mmol) in $H_2O$/acetone (2 mL/10 mL) was added $Na_2CO_3$ (0.18 g, 2.2 mmol). The reaction was stirred at 15° C. for 1 hour then concentrated to remove acetone. The aqueous solution was extracted with EtOAc (20 ml×2) and the combined organic layers were washed with $H_2O$ (10 mL) and brine (10 mL) then dried over $Na_2SO_4$, filtered and concentrated to give 3-(4-bromo-2-(2,2-difluoroethyl) phenylsulfonamido) propanamide (400 mg, 49%) as a yellow solid, which was used in the next step without further purification.

Step 4: tert-butyl 3-(4-(N-(3-amino-3-oxopropyl)sulfamoyl)-3-(2,2-difluoroethyl)phenyl)-6-fluoro-1H-indole-1-carboxylate A suspension of 3-(4-bromo-2-(2,2-difluoroethyl)phenyl-sulfonamido)propanamide (400 mg, 1.1 mmol), tert-butyl 6-fluoro-3-(4,4,5,5-tetramethyl-1,3,2-dioxaborolan-2-yl)-1H-indole-1-carboxylate (452 mg, 1.25 mmol), PdCl$_2$(dppf)CH$_2$Cl$_2$ (92 mg, 0.13 mmol), and K$_3$PO$_4$ (531 mg, 2.5 mmol) in 1,4-dioxane (8 mL) and water (2 mL) was sparged with N$_2$ for 1 minute. The reaction was stirred at 80° C. for 1 hour then diluted with EtOAc (50 mL). The mixture was washed with $H_2O$ (10 mL×2) and dried over $Na_2SO_4$, filtered and concentrated to give crude tert-butyl 3-(4-(N-(3-amino-3-oxopropyl)sulfamoyl)-3-(2,2-difluoroethyl)phenyl)-6-fluoro-1H-indole-1-carboxylate (200 mg, 30%) as a yellow solid, which was used the next step without further purification.

Step 5: 3-(2-(2,2-difluoroethyl)-4-(6-fluoro-1H-indol-3-yl)-phenylsulfonamido)propanamide A solution of crude tert-butyl 3-(4-(N-(3-amino-3-oxopropyl)sulfamoyl)-3-(2,2-difluoroethyl)phenyl)-6-fluoro-1H-indole-1-carboxylate (200 mg, 0.381 mmol) in MeNH$_2$/EtOH (30% w/w, 10 mL) was stirred at 45° C. in a sealed tube for 2 hours then concentrated and purified by prep HPLC to give 3-(2-(2,2-difluoroethyl)-4-(6-fluoro-1H-indol-3-yl)phenylsulfonamido)propanamide (30 mg, 19%) as a brown solid. $^1$H NMR (400 MHz, DMSO-$d_6$) δ [ppm] 11.70 (br s, 1H), 7.85-7.81 (m, 2H), 7.93-7.81 (m, 2H), 7.66-7.53 (m, 2H), 7.36 (br s, 1H), 7.31-7.21 (m, 1H), 7.02

(dt, J=2.4, 9.2 Hz, 1H), 6.88 (br s, 1H), 6.49-6.14 (m, 1H), 3.67 (dt, J=4.5, 16.7 Hz, 2H), 2.99 (t, J=7.3 Hz, 2H), 2.27 (t, J=7.3 Hz, 2H); LC-MS: m/z 426.0 (M+H)+.

Example 176: 4-(6-fluoro-1H-indol-3-yl)-2-(hydroxymethyl)benzenesulfonamide

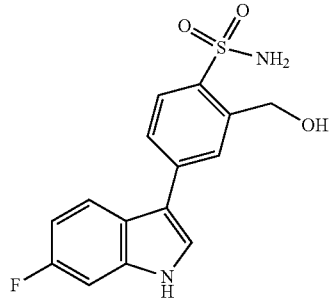 [SMILES: NS(=O)(=O)c1ccc(-c2c[nH]c3cc(F)ccc23)cc1CO]

Step 1: tert-butyl 3-(3-(acetoxymethyl)-4-(N-(tert-butyl)sulfamoyl)phenyl)-6-fluoro-1H-indole-1-carboxylate To a suspension of 5-bromo-2-(N-(tert-butyl)sulfamoyl) benzyl acetate (300 mg, 0.824 mmol) and tert-butyl 6-fluoro-3-(4,4,5,5-tetramethyl-1,3,2-dioxaborolan-2-yl)-1H-indole-1-carboxylate (350 mg, 0.91 mmol) in dioxane/water (8 ml/3 ml) was added Pd(dppf)Cl$_2$ (60 mg, 0.0824 mmol) and K$_3$PO$_4$ (350 mg, 1.65 mmol). The reaction was stirred at 80° C. for 2 h then concentrated and purified by column chromatography to give tert-butyl 3-(3-(acetoxymethyl)-4-(N-(tert-butyl)sulfamoyl)phenyl)-6-fluoro-1H-indole-1-carboxylate (300 mg, 70%) as a yellow solid.

Step 2: 5-(6-fluoro-1H-indol-3-yl)-2-sulfamoylbenzyl acetate

To a solution of tert-butyl 3-(3-(acetoxymethyl)-4-(N-(tert-butyl)sulfamoyl)-phenyl)-6-fluoro-1H-indole-1-carboxylate (300 mg, 0.58 mmol) in DCM (20 mL) was added TFA (5 mL). The reaction was stirred at 20° C. for 20 h then concentrated, diluted with water (100 mL) and extracted with EA (100 mL×2). The combined organic layer were washed with brine (100 mL) then dried over anhydrous Na$_2$SO$_4$, filtered and concentrated to give 5-(6-fluoro-1H-indol-3-yl)-2-sulfamoylbenzyl acetate as a yellow solid, which was used directly in the next step without further purification.

Step 3: 4-(6-fluoro-1H-indol-3-yl)-2-(hydroxymethyl)benzenesulfonamide

To a solution of 5-(6-fluoro-1H-indol-3-yl)-2-sulfamoyl-benzyl acetate (200 mg, 0.55 mmol) in MeOH (20 ml) was added 3N NaOH (5 ml). The reaction was stirred at 50° C. for 16 h then poured into water (100 ml) and extracted with EA (100 ml×2). The combined organic layers were washed with brine (100 ml) then dried over anhydrous Na$_2$SO$_4$, filtered and concentrated. The crude residue was purified by prep-HPLC to give 4-(6-fluoro-1H-indol-3-yl)-2-(hydroxymethyl) benzenesulfonamide (64 mg, 36%) as a white solid. $^1$H NMR (400 MHz, MeOD) δ [ppm] 8.03-7.99 (m, 2H), 7.91 (dd, J=5.3, 8.8 Hz, 1H), 7.74-7.70 (m, 1H), 7.64 (s, 1H), 7.15 (dd, J=2.4, 9.7 Hz, 1H), 6.93 (d, J=2.3 Hz, 1H), 5.10 (s, 2H); LC-MS: m/z 342.7 (M+Na)+.

Example 177: 2-(aminomethyl)-4-(6-fluoro-1H-indol-3-yl)benzenesulfonamide

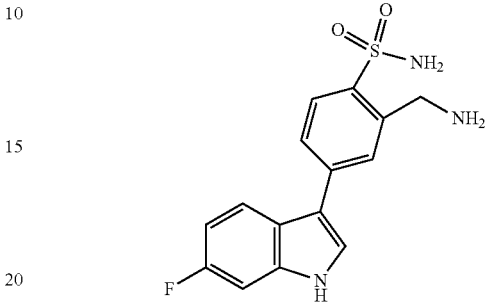

Step 1: 2-(aminomethyl)-N-(tert-butyl)-4-chlorobenzenesulfonamide

To a yellow solution of N-(tert-butyl)-4-chloro-2-cyanobenzenesulfonamide (500 mg, 1.83 mmol) in THF (5 mL) was added LAH (313 mg, 8.25 mmol) in portions at 0° C. The reaction mixture was stirred at 20° C. for 2 h. The reaction mixture was quenched with ice water (20 mL) and extracted with EtOAc (100 mL×2). The combined organic layers were washed with brine (100 mL), dried over anhydrous Na$_2$SO$_4$ and concentrated under reduced pressure to give 2-(aminomethyl)-N-(tert-butyl)-4-chlorobenzenesulfonamide (200 mg, 39%) as a yellow solid. $^1$H NMR (400MHz, DMSO-d6) δ=7.86 (d, J=8.3 Hz, 1H), 7.76 (d, J=2.0 Hz, 1H), 7.52-7.48 (m, 1H), 5.44-4.70 (m, 2H), 4.11 (s, 2H), 1.10 (s, 9H).

Step 2: 2-(aminomethyl)-N-(tert-butyl)-4-(6-fluoro-1H-indol-3-yl)-benzenesulfonamide A black solution of tert-butyl 6-fluoro-3-(4,4,5,5-tetramethyl-1,3,2-dioxaborolan-2-yl)-1H-indole-1-carboxylate (287 mg, 0.795 mmol), 2-(aminomethyl)-N-(tert-butyl)-4-chlorobenzenesulfonamide (200 mg, 0.723 mmol), Pd$_2$(dba)$_3$ (66 mg, 0.072 mmol), P(Cy)$_3$ (61 mg, 0.022 mmol) and K$_3$PO$_4$ (307 mg, 1.45 mmol) in dioxane (8 mL) and H$_2$O (3 mL) was stirred at 100° C. under a N$_2$ atmosphere for 18 h. The reaction mixture was concentrated and purified by column chromatography to give 2-(aminomethyl)-N-(tert-butyl)-4-(6-fluoro-1H-indol-3-yl)benzenesulfonamide (220 mg, 64%) as a yellow solid.

Step 3: 2-(aminomethyl)-4-(6-fluoro-1H-indol-3-yl) benzenesulfonamide

A yellow solution of 2-(aminomethyl)-N-(tert-butyl)-4-(6-fluoro-1H-indol-3-yl)benzenesulfonamide (220 mg, 0.586) in TFA (20 mL) was stirred at 80° C. for 4 h. The reaction mixture was concentrated, poured into a saturated NaHCO$_3$ solution (20 mL) and extracted with EtOAc (20 mL×2). The combined organic layers were washed with brine (50 mL), dried over anhydrous Na$_2$SO$_4$ and concentrated. The crude residue was purified by prep-HPLC (0.1% NH$_3$.H$_2$O as additive) to give 2-(aminomethyl)-4-(6-fluoro- 1H-indol-3-yl)benzenesulfonamide (29 mg, 20%) as a white solid. $^1$H NMR (400 MHz, DMSO-d6) b=11.71-11.42 (m, 1H), 8.02-7.80 (m, 4H), 7.73 (d, J=8.0 Hz, 1H), 7.30-7.21 (m, 1H), 7.04-6.94 (m, 1H), 4.16 (s, 2H); LCMS: m/z 320.0 [M+H]$^+$ (ESI).

Example 178: (5-(6-fluoro-1H-indol-3-yl)-2-(methylsulfonyl)phenyl)methanamine

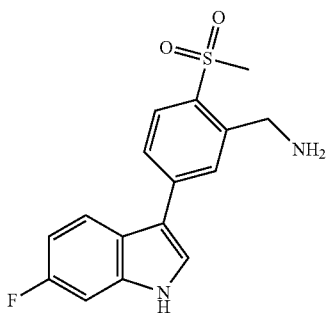 [SMILES: CS(=O)(=O)c1ccc(-c2c[nH]c3cc(F)ccc23)cc1CN]

Step 1: 5-bromo-2-(methylsulfonyl)benzyl methanesulfonate

To a yellow solution of (5-bromo-2-(methylsulfonyl)phenyl)methanol (500 mg, 1.89 mmol) in dry DCM (6 mL) was added TEA (0.52 mL, 3.8 mmol) and MsCl (0.19 mL, 2.45 mmol) at 0° C. The cold bath was removed and the reaction was stirred at 15° C. for 4 h. The reaction was quenched with water (3 mL) and extracted with DCM (10 mL×2). The organic layer was dried over Na$_2$SO$_4$, filtered and concentrated to afford crude 5-bromo-2-(methylsulfonyl)benzyl methanesulfonate (660 mg, 100%) as a gray solid, which was directly used the next step.

Step 2: (5-bromo-2-(methylsulfonyl)phenyl)methanamine

A light yellow solution of 5-bromo-2-(methylsulfonyl) benzyl methanesulfonate (300 mg, 0.874 mmol) in saturated NH$_3$ (g)/MeOH (10 mL) was stirred at 80° C. in a sealed tube for 1 h. The reaction mixture was concentrated to obtain crude (5-bromo-2-(methylsulfonyl)phenyl)methanamine (260 mg, 100%) as a light yellow solid, which was directly used for the next step.

Step 3: tert-butyl 3-(3-(aminomethyl)-4-(methylsulfonyl)phenyl)-6-fluoro-1H-indole-1-carboxylate A light red suspension of (5-bromo-2-(methylsulfonyl) phenyl)methanamine (231 mg, 0.874 mmol), tert-butyl 6-fluoro-3-(4,4,5,5-tetramethyl-1,3,2-dioxaborolan-2-yl)-1H-indole-1-carboxylate (316 mg, 0.874 mmol), K$_3$PO$_4$ (557 mg, 2.62 mmol) and Pd(dppf)Cl$_2$ (64.0 mg, 0.0874 mmol) in 1,4-dioxane (8 mL) was stirred at 80° C. for 14 h under N$_2$. The black suspension was filtered, concentrated and purified by column chromatography to give crude tert-butyl 3-(3-(aminomethyl)-4-(methylsulfonyl) phenyl)-6-fluoro-1H-indole-1-carboxylate (350 mg, 96%) as light yellow oil.

Step 4: (5-(6-fluoro-1H-indol-3-yl)-2-(methylsulfonyl)phenyl)methanamine

A light yellow solution of tert-butyl 3-(3-(aminomethyl)-4-(methylsulfonyl)-phenyl)-6-fluoro-1H-indole-1-carboxylate (350 mg, 0.64 mmol) in MeNH$_2$/EtOH (30%, 10 mL) was stirred in a sealed tube at 60° C. for 2 h. The brown solution was concentrated then purified by prep. HPLC to give (5-(6-fluoro-H-indol-3-yl)-2-(methylsulfonyl)phenyl) methanamine (114.79 mg, 51% yield) as a brown solid. $^1$H NMR (400MHz, DMSO-d6) b=11.84 (br. s., 1H), 8.56 (br. s., 2H), 8.13 (s, 2H), 8.04-8.01 (m, 1H), 7.97 (s, 2H), 7.30-7.25 (m, 1H), 7.05-6.97 (m, 1H), 4.47 (br. s., 2H), 3.33 (s, 3H); LCMS: m/z 318.7 [M+H]$^+$ (ESI).

Example 179: 2-(5-(6-fluoro-1H-indol-3-yl)-2-(methylsulfonyl)phenyl)ethanol

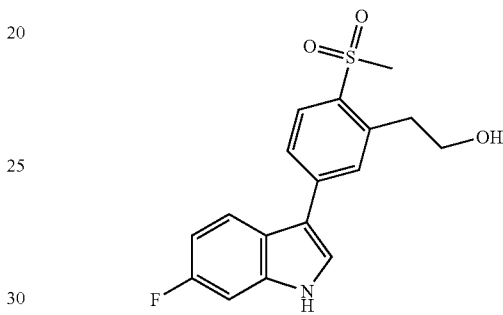

Step 1: 4-bromo-2-(chloromethyl)-1-(methylsulfonyl)benzene

To a colorless suspension of (5-bromo-2-(methylsulfonyl) phenyl)methanol (900 mg, 3.39 mmol) in DCM (10 mL) was added TEA (0.94 mL, 6.8 mmol) at 0° C. then MsCl (0.342 mL, 4.41 mmol) was slowly added. The reaction was stirred in the ice bath for 4 h then quenched with H$_2$O (5 mL) and extracted with DCM (10 mL×2). The combined organic layers were dried over Na$_2$SO$_4$, filtered and concentrated to afford crude 4-bromo-2-(chloromethyl)-1-(methylsulfonyl) benzene (880 mg, 91%) as a gray solid, which was directly used for the next step. $^1$H NMR (400MHz, CHLOROFORM-d) δ=7.94 (s, 1H), 7.80-7.76 (m, 1H), 7.72-7.66 (m, 1H), 5.09 (s, 2H), 3.22 (s, 3H).

Step 2: 2-(5-bromo-2-(methylsulfonyl)phenyl)acetonitrile

To a yellow solution of 4-bromo-2-(chloromethyl)-1-(methylsulfonyl)benzene (880 mg, 3.10 mmol) in MeCN (15 mL) was added 18-crown-6 (82 mg, 0.31 mmol) and KCN (310 mg, 4.76 mmol). The reaction was stirred at 30° C. for 15 h then diluted with DCM (50 mL). The mixture was washed with water (10 mL×4), dried over Na$_2$SO$_4$, filtered and concentrated. The crude residue was purified by column chromatography to give 2-(5-bromo-2-(methylsulfonyl)phenyl)acetonitrile (260 mg, 31%) as a white solid. $^1$H NMR (400MHz, CHLOROFORM-d) δ=7.98-7.92 (m, 1H), 7.84-7.80 (m, 1H), 7.77-7.71 (m, 1H), 4.29 (s, 2H), 3.16 (s, 3H).

Step 3: tert-butyl 3-(3-(cyanomethyl)-4-(methylsulfonyl)phenyl)-6-fluoro-1H-indole-1-carboxylate To a light yellow suspension of 2-(5-bromo-2-(methylsulfonyl)phenyl)-acetonitrile (190 mg, 0.693 mmol), tert-butyl 6-fluoro-3-(4,4,5,5-tetramethyl-1,3,2-dioxaborolan-2-yl)-1Hindole-1-carboxylate (250 mg, 0.693 mmol), $K_3PO_4$ (294 mg, 1.39 mmol) in dioxane (10 mL) was added $Pd(dppf)Cl_2$ (51 mg, 0.07 mmol). The reaction was stirred at 80° C. for 2 h then filtered and concentrated. The crude residue was purified by column chromatography to give tert-butyl 3-(3-(cyanomethyl)-4-(methylsulfonyl)phenyl)-6-fluoro-1H-indole-1-carboxylate (210 mg, 71%) as a light yellow solid. $^1$H NMR (400MHz, CHLOROFORM-d) δ=8.17 (d, J=8.0 Hz, 1H), 8.04-7.94 (m, 1H), 7.91-7.79 (m, 3H), 7.75-7.69 (m, 1H), 7.16-7.07 (m, 1H), 4.40 (s, 2H), 3.22 (s, 3H), 1.72 (s, 9H).

Step 4: 2-(5-(6-fluoro-1H-indol-3-yl)-2-(methylsulfonyl)phenyl)acetic acid

To a suspension of tert-butyl 3-(3-(cyanomethyl)-4-(methylsulfonyl)-phenyl)-6-fluoro-1H-indole-1-carboxylate (140 mg, 0.511 mmol) in MeOH (2 mL) was added aq.

NaOH (20% w/w in $H_2O$, 6 mL). The suspension was stirred at 100° C. for 5 h. The reaction was cooled in an ice bath and the pH was adjusted to 1.0 with conc. HCl. The resulting solid was filtered, washed with $H_2O$ (10 mL) and dried to give 2-(5-(6-fluoro-1H-indol-3-yl)-2-(methylsulfonyl)phenyl)acetic acid (120 mg, 68%) as a yellow gum.

Step 5: 2-(5-(6-fluoro-1H-indol-3-yl)-2-(methylsulfonyl)phenyl)ethanol

To a yellow solution of 2-(5-(6-fluoro-1H-indol-3-yl)-2-(methylsulfonyl)phenyl)acetic acid (120 mg, 0.345 mmol) in THF (3 mL) was added $BH_3$.DMS (0.21 mL, 2.1 mmol) at 0° C. The solution was stirred at ice bath for 4 h then slowly quenched with $NH_4Cl$ (sat) (2 mL) and $H_2O$ (5 mL). The mixture was extracted with EtOAc (10 mL×3) and the combined organic layers were washed with brine, then dried over $Na_2SO_4$, filtered, concentrated. The crude residue was purified by column chromatography to give 2-(5-(6-fluoro-1H-indol-3-yl)-2-(methylsulfonyl)phenyl) ethanol (46 mg, 40%) as a white solid. $^1$H NMR (400MHz, DMSO-d6) δ=11.73-11.63 (m, 1H), 7.98-7.89 (m, 3H), 7.85-7.81 (m, 1H), 7.79-7.74 (m, 1H), 7.30-7.23 (m, 1H), 7.05-6.97 (m, 1H), 4.90-4.83 (m, 1H), 3.82-3.74 (m, 2H), 3.26 (s, 3H), 3.25-3.20 (m, 2H); LCMS: m/z 355.9 [M+Na]$^+$[ESI].

I. Biology Examples

II.1. Assay for TDO2 enzymatic activity determination

The compounds of formula I, its subformulae, and enantiomers, salts and solvates thereof, are useful to inhibit the enzymatic activity of human TDO2.

To measure the TDO2 activity, the procedure described in Dolusic et al. J. Med. Chem.; 2011, 54, 5320-533 was adapted: the reaction mixture contained (final concentrations) potassium phosphate buffer (50 mM, pH 7.5), ascorbic acid (0.25 M), methylene blue (0.125 μM), catalase (40 units/mL, from bovine liver, Sigma), and human recombinant TDO2 enzyme (prepared as described in Dolusic et al. J. Med. Chem.; 2011, 54, 5320-5334; 0.9 μg) without or with the compounds of the present invention at the indicated concentrations (total volume 112.5 μL). The reaction was initiated by the addition of 37.5 μL of L-Trp (final concentration 1 mM) at room temperature. The reaction was conducted at room temperature during one hour and stopped by the addition of 30 μL of 30% (w/v) trichloroacetic acid.

To convert N-formylkynurenine into kynurenine, the reaction mixture was incubated at 65° C. for 30 min. Then 150 μL of the reaction mixture was mixed with 120 μL of 2.5% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of the compounds of the present invention. Data were fitted using the Prism™ software (GraphPad Software, Inc.) using standard parameters.

The TDO2 biological activity of representative Compounds in this assay is summarized in the following Table 1:

TABLE 1

| Example | $IC_{50}$ (nM) |
|---|---|
| 1 | 1500 |
| 2 | 1100 |
| 3 | 2100 |
| 4 | 2100 |
| 5 | 4700 |
| 6 | 1000 |
| 7 | 4400 |
| 8 | 890 |
| 9 | 1800 |
| 10 | 2400 |
| 18 | 1100 |
| 21 | 740 |
| 26 | 730 |
| 32 | 730 |
| 34 | 520 |
| 35 | 420 |
| 36 | 770 |
| 40 | 930 |
| 50 | 960 |
| 58 | 530 |
| 76 | 470 |
| 77 | 170 |
| 79 | 120 |
| 80 | 900 |
| 84 | 1900 |
| 86 | 1300 |
| 87 | 930 |
| 88 | 940 |
| 90 | 2000 |
| 93 | 550 |
| 94 | 840 |
| 95 | 1300 |
| 96 | 1000 |
| 97 | 820 |
| 98 | 910 |
| 99 | 1100 |
| 101 | 840 |
| 120 | 120 |

In one embodiment, compounds having an $IC_{50}$<2000 nM, preferably compound having an $IC_{50}$<1000 nM are selected. In still other embodiments, compounds having $IC_{50}$ values higher than these thresholds are selected in view of factors other than the present assay.

II.2. Cellular Assay for TDO2 Activity determination

II.2.a A172 cells

The compounds of formula I inhibit the activity of human TDO2 in cells that constitutively express TDO2, such as A172 cells. A172 is a cell line derived from human brain glioblastoma cells. The cells are available from the American Type Culture Collection (ATCC®) as CRL-1620™.

The assay (adapted from Pilotte L et al., Proc Natl Acad Sci USA, 2012, 109(7), 2497-502) was performed in 96-well flat bottom plates seeded with human glioblastoma A172 cells, naturally expressing hTDO2 (prepared as described in Tilman et al., Mol Cancer, 2007, 17(6), 80), at a concentration of 1.25×10$^4$ cells/well in a final volume of 200 μL. To determine TDO, the cells were incubated overnight at 37° C. at 5% $CO_2$ in IMDM (Invitrogen) supplemented with 2% FBS and 2% penicillin/streptomycin in the presence of the compounds of the present invention, at different concentrations.

The plates were then centrifuged 5 min at 1000 rpm, and 100 µL of the supernatant were collected in a conical plate, 30 µL of TCA 30% were added and a further centrifuged at 3000×g for 10 minutes. 100 µL of the supernatant were collected in a flat bottomed plate and 100 µL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of the compounds of the present invention. Data were fitted using the Prism™ software (GraphPad Software, Inc.) using standard parameters.

The biological activity of representative compounds in human brain glioblastoma cells as determined in the above-referenced assay is summarized in the following Table 2:

TABLE 2

| Example | hTDO2 A172 IC$_{50}$ (nM) |
|---|---|
| 1 | 84 |
| 2 | 150 |
| 3 | 110 |
| 4 | 130 |
| 5 | 250 |
| 6 | 82 |
| 7 | 340 |
| 8 | 95 |
| 9 | 240 |
| 10 | 83 |
| 11 | 320 |
| 12 | 140 |
| 13 | 210 |
| 14 | 190 |
| 15 | 220 |
| 16 | 180 |
| 17 | 200 |
| 18 | 190 |
| 19 | 1000 |
| 20 | 250 |
| 21 | 120 |
| 22 | 600 |
| 23 | 630 |
| 24 | 510 |
| 25 | 1400 |
| 26 | 110 |
| 27 | 160 |
| 28 | 220 |
| 29 | 190 |
| 30 | 3900 |
| 31 | 740 |
| 32 | 170 |
| 33 | 910 |
| 34 | 290 |
| 35 | 330 |
| 36 | 430 |
| 37 | 3700 |
| 38 | 2500 |
| 39 | 2900 |
| 40 | 170 |
| 41 | 990 |
| 42 | 260 |
| 43 | 410 |
| 44 | 430 |
| 45 | 230 |
| 46 | 220 |
| 47 | 9600 |
| 48 | 440 |
| 49 | 210 |
| 50 | 110 |
| 51 | 630 |
| 52 | 1700 |
| 53 | 210 |
| 54 | 250 |
| 55 | 210 |
| 56 | 670 |
| 57 | 7100 |
| 58 | 130 |
| 59 | 360 |
| 60 | 9100 |
| 61 | 4300 |
| 62 | 3500 |
| 63 | 170 |
| 64 | 270 |
| 65 | 160 |
| 66 | 84 |
| 67 | 180 |
| 68 | 140 |
| 69 | 330 |
| 70 | 580 |
| 71 | 450 |
| 72 | 300 |
| 73 | 150 |
| 74 | 96 |
| 75 | 380 |
| 76 | 833 |
| 77 | 55 |
| 78 | 18000 |
| 79 | 94 |
| 80 | 170 |
| 81 | 230 |
| 82 | 250 |
| 83 | 110 |
| 84 | 260 |
| 85 | 390 |
| 86 | 260 |
| 87 | 170 |
| 88 | 95 |
| 89 | 200 |
| 90 | 130 |
| 91 | 1800 |
| 92 | 560 |
| 93 | 200 |
| 94 | 300 |
| 95 | 140 |
| 96 | 160 |
| 97 | 100 |
| 98 | 250 |
| 99 | 300 |
| 100 | 100 |
| 101 | 93 |
| 102 | 260 |
| 103 | 260 |
| 104 | 240 |
| 105 | 220 |
| 106 | 270 |
| 107 | 160 |
| 108 | 170 |
| 109 | 1000 |
| 110 | 180 |
| 111 | 146 |
| 112 | 116 |
| 113 | 90500 |
| 114 | 91000 |
| 115 | 133 |
| 116 | 92000 |
| 117 | 109 |
| 118 | 89 |
| 119 | 123 |
| 120 | 120 |
| 121 | 156 |
| 122 | 86000 |
| 123 | 138 |
| 124 | 93500 |
| 125 | 97 |
| 126 | 145 |
| 127 | 85500 |
| 128 | 93500 |
| 129 | 92000 |

TABLE 2-continued

| Example | hTDO2 A172 IC$_{50}$ (nM) |
|---|---|
| 130 | 96 |
| 131 | 90000 |
| 132 | 83000 |
| 133 | 169 |
| 134 | 125 |
| 135 | 161 |
| 136 | 271 |
| 137 | 7510 |
| 138 | 3160 |
| 139 | 120 |
| 140 | 541 |
| 141 | 295 |
| 142 | 247 |
| 143 | 550 |
| 144 | 174 |
| 145 | 3610 |
| 146 | 380 |
| 147 | 441 |
| 148 | 570 |
| 149 | 443 |
| 150 | 365 |
| 151 | 439 |
| 152 | 1320 |
| 153 | 1038 |
| 154 | 360 |
| 155 | 186 |
| 156 | 150 |
| 157 | 66 |
| 158 | 283 |
| 159 | 220 |
| 160 | 171 |
| 161 | 220 |
| 162 | 405 |
| 163 | 2220 |
| 164 | 5930 |
| 165 | 341 |
| 166 | 4060 |
| 167 | 41 |
| 168 | 270 |
| 169 | 511 |
| 170 | 1210 |
| 171 | 1740 |
| 172 | 957 |
| 173 | 919 |
| 174 | 383 |
| 175 | 449 |
| 176 | 55 |
| 177 | 700 |
| 178 | 411 |
| 179 | 79 |

In one embodiment, compounds having an IC$_{50}$<1000 nM are selected. In another embodiment, compounds having an IC$_{50}$<300 nM are selected. In still other embodiments, compounds having IC$_{50}$ values higher than these thresholds are selected in view of factors other than the present assay.

II.3. Pharmacodynamic assay for TDO2 in vivo activity determination: increase of blood tryptophan levels in mice The compounds of the present invention increase the amount of Tryptophan in mouse blood. Briefly, female BALB/c mice (7-8 weeks old) were treated with either a suspension of one of the compounds of the present invention in 0.5% hydroxypropyl methyl cellulose (HPMC) K4M (4000 mPa·s (cPs), Methocell™, Dow chemical)/0.25% Tween® 20 (Sigma Aldrich) at different doses (30, 60 and 100 mg/kg), or with a vehicle control (0.5% HPMC K4M/0.25% Tween 20), by the oral route by gavage (dosing volume 5 mL/kg, 10 mice per group). After two hours, blood was harvested, plasma was prepared and the amount of Tryptophan present was determined by LC-MS-MS (HPLC column Unison UK-Phenyl, 75×4.6, 3 μm, flow rate 0.8 mL/min, 8 minutes gradient from 95% water+0.1% formic acid/5% Acetonitrile+0.1% formic acid to 5% water+0.1% formic acid/95% Acetonitrile+0.1% formic acid, retention time 2.4 min; API4000 MS-MS system from AB Sciex, ESI+ mode, parent ion 205.1, daughter ion 146.1).

The compound of Example 18 increased circulating Tryptophan by 67% at 30 mg/kg (p<0.0001), by 81% at 60 mg/kg (p<0.0001) and by 74% at 100 mg/kg (p<0.0001) compared to vehicle-treated controls, as evidenced in Table 3 below.

TABLE 3

| | Tryptophan concentration in plasma: | | | |
|---|---|---|---|---|
| | Dose of the compound of Example 16 | | | |
| | Vehicle | 30 mg/kg | 60 mg/kg | 100 mg/kg |
| Trp in plasma (average ± standard error of the mean, ng/mL) | 19500 ± 700 | 32700 ± 1500 | 35300 ± 1300 | 34000 ± 1300 |

All documents cited in this specification are incorporated herein by reference. U.S. Provisional Patent Application No. 62/309,530, filed Mar. 17, 2016, PCT/IB2016/051509, Filed Mar. 18, 2016, and U.S. Provisional Patent Application No. 62/203,032, filed Aug. 10, 2015 are hereby incorporated by reference. While the invention has been described with reference to particular embodiments, it will be appreciated that modifications can be made without departing from the spirit of the invention. Such modifications are intended to fall within the scope of the appended claims.

The invention claimed is:
1. A compound selected from:
6-Fluoro-3-(4-methanesulfonyl-phenyl)-1H-indole,
N-(2-aminoethyl)-4-(6-fluoro-1H-indol-3-yl)benzamide,
(4-(6-fluoro-1H-indol-3-yl)phenyl)(piperazin-1-yl)methanone,
6-fluoro-3-(4-(piperazin-1-ylsulfonyl)phenyl)-1H-indole,
4-((4-(6-fluoro-1H-indol-3-yl)phenyl)sulfonyl)morpholine,
4-(6-fluoro-1H-indol-3-yl)benzenesulfonamide,
6-fluoro-3-(3-(piperazin-1-ylsulfonyl)phenyl)-1H-indole,
N-(2-aminoethyl)-4-(6-fluoro-1H-indol-3-yl)benzenesulfonamide,
N-(2-aminoethyl)-3-(6-fluoro-1H-indol-3-yl)benzenesulfonamide,
3-(6-fluoro-1H-indol-3-yl)benzenesulfonamide,
3-(4-(((cis)-3,5-dimethylpiperazin-1-yl)sulfonyl)phenyl)-6-fluoro-1H-indole,
(4-((4-(6-fluoro-1H-indol-3-yl)phenyl)sulfonyl)piperazin-2-yl)methanol,
(1-((4-(6-fluoro-1H-indol-3-yl)phenyl)sulfonyl)piperazin-2-yl)methanol,
(1-((4-(6-fluoro-1H-indol-3-yl)phenyl)sulfonyl)piperazin-2-yl)methanol,
3-(4-(((3S,5S)-3,5-dimethylpiperazin-1-yl)sulfonyl)phenyl)-6-fluoro-1H-indole,
N-(2-(4-(6-fluoro-1H-indol-3-yl)phenylsulfonamido)ethyl)acetamide,
(R)-(4-((4-(6-fluoro-1H-indol-3-yl)phenyl)sulfonyl)piperazin-2-yl)methanol,
(S)-(4-((4-(6-fluoro-1H-indol-3-yl)phenyl)sulfonyl)piperazin-2-yl)methanol,
6-fluoro-3-(4-((4-(methylsulfonyl)piperazin-1-yl)sulfonyl)phenyl)-1H-indole,
3-(4-(piperazin-1-ylsulfonyl)phenyl)-1H-indole,
4-(6-fluoro-1H-indol-3-yl)-N-(2-(methylsulfonamido)ethyl)benzenesulfonamide,

6-fluoro-3-(2-fluoro-4-(piperazin-1-ylsulfonyl)phenyl)-1H-indole,
3-(4-chloro-3-(piperazin-1-ylsulfonyl)phenyl)-6-fluoro-1H-indole,
6-fluoro-3-(4-(piperazin-1-ylsulfonyl)-3-(trifluoromethyl)phenyl)-1H-indole,
6-fluoro-3-(2-methyl-4-(piperazin-1-ylsulfonyl)phenyl)-1H-indole,
3-(4-(6-fluoro-1H-indo-3-yl)phenylsulfonamido)propanamide,
3-(4-(6-fluoro-1H-indol-3-yl)-N-methylphenylsulfonamido)-propanamide,
6-fluoro-3-(3-fluoro-4-(piperazin-1-ylsulfonyl)phenyl)-1H-indole,
6-fluoro-3-(3-methoxy-4-(piperazin-1-ylsulfonyl)phenyl)-1H-indole,
N-(2-aminoethyl)-3-(6-fluoro-1H-indol-3-yl)-5-methyl-benzene-sulfonamide,
6-fluoro-3-(3-(methylsulfonyl)phenyl)-1H-indole,
5-(6-Fluoro-1H-indol-3-yl)-2-(piperazine-1-sulfonyl)-benzonitrile,
N-(2-Amino-ethyl)-5-(6-fluoro-1H-indol-3-yl)-2-methyl-benzenesulfonamide,
6-fluoro-3-(3-methyl-4-(piperazin-1-ylsulfonyl)phenyl)-1H-indole,
5-(6-fluoro-1H-indol-3-yl)-2-(piperazin-1-ylsulfonyl)phenol,
N-(2-aminoethyl)-2-chloro-5-(6-fluoro-1H-indol-3-yl)-benzenesulfonamide,
2-(6-fluoro-1H-indol-3-yl)-5-(piperazin-1-ylsulfonyl)benzonitrile,
N-(2-aminoethyl)-3-chloro-5-(6-fluoro-1H-indol-3-yl)-benzenesulfonamide,
N-(2-aminoethyl)-5-(6-fluoro-1H-indol-3-yl)-2-hydroxy-benzenesulfonamide,
4-((4-(6-fluoro-1H-indol-3-yl)phenyl)sulfonyl)piperazin-2-one,
5-(6-fluoro-1H-indol-3-yl)-2-(piperazin-1-ylsulfonyl)benzamide,
4-((4-(6-fluoro-1H-indol-3-yl)phenyl)sulfonyl)-1-methylpiperazin-2-one,
N-(2-aminoethyl)-2-fluoro-5-(6-fluoro-1H-indol-3-yl)-benzenesulfonamide,
N-(2-aminoethyl)-3-fluoro-5-(6-fluoro-1H-indol-3-yl)-benzenesulfonamide,
3-(3-chloro-4-(piperazin-1-ylsulfonyl)phenyl)-6-fluoro-1H-indole,
4-(6-fluoro-1H-indol-3-yl)-N-(tetrahydro-pyran-4-yl)-benzenesulfonamide,
6-fluoro-N,N-dimethyl-3-(4-(piperazin-1-ylsulfonyl)phenyl)-1H-indole-1-carboxamide,
4-(6-fluoro-1H-indol-3-yl)-N-(2-(5-oxo-4,5-dihydro-1,3,4-oxadiazol-2-yl)-ethyl)benzenesulfonamide,
3-(4-(6-fluoro-1H-indol-3-yl)phenylsulfonamido)-N,N-dimethylpropanamide,
3-(4-(6-fluoro-1H-indol-3-yl)phenylsulfonamido)-N-methylpropanamide,
1-(6-fluoro-3-(4-(piperazin-1-ylsulfonyl)phenyl)-1H-indol-1-yl)propan-1-one,
1-(6-fluoro-3-(4-(piperazin-1-ylsulfonyl)phenyl)-1H-indol-1-yl)-3-methyl-butan-1-one,
4-(4-(6-fluoro-1H-indol-3-yl)phenylsulfonamido)butanamide,
4-(4-(6-fluoro-1H-indol-3-yl)-N-methylphenylsulfonamido)-butanamide,
(R)-4-(6-fluoro-1H-indol-3-yl)-N-(tetrahydrofuran-3-yl)benzenesulfon-amide,
N-(2-aminoethyl)-5-(6-fluoro-1H-indol-3-yl)-2-methyl-benzenesulfon-amide,
5-(6-fluoro-1H-indol-3-yl)-N-methyl-2-(piperazin-1-ylsulfonyl)-benzamide,
(cis)-1((4-(6-fluoro-1H-indol-3-yl)phenyl)sulfonyl)pyrrolidine-3,4-diol,
4-(6-fluoro-1H-indol-3-yl)-N-(2-(3-methyl-1,2,4-oxadiazol-5-yl)ethyl)-benzenesulfonamide,
6-fluoro-N-methyl-3-(4-(piperazin-1-ylsulfonyl)phenyl)-1H-indole-1-carboxamide,
N-(2-aminoethyl)-3-(6-fluoro-1H-indol-3-yl)-5-methoxybenzenesulfon-amide,
N-(2-aminoethyl)-4-fluoro-3-(6-fluoro-1H-indol-3-yl)benzene-sulfonamide,
(1-((4-(6-fluoro-1H-indol-3-yl)phenyl)sulfonyl)azetidin-3-yl)methanol,
(S)-4-(6-fluoro-1H-indol-3-yl)-N-(tetrahydrofuran-3-yl)benzenesulfon-amide,
1((4-(6-fluoro-1H-indol-3-yl)phenyl)sulfonyl)azetidin-3-ol,
(3S,4S)1-[4-(6-Fluoro-1H-indol-3-yl)-benzenesulfonyl]-pyrrolidine-3,4-diol,
1((4-(6-fluoro-1H-indol-3-yl)phenyl)sulfonyl)azetidine-3-carboxamide,
N-(azetidin-3-yl)-4-(6-fluoro-1H-indol-3-yl)benzenesulfonamide,
N-(2-aminoethyl)-3-(6-fluoro-1H-indol-3-yl)-5-hydroxy-benzenesulfon-amide,
1-(6-fluoro-3-(4-(piperazin-1-ylsulfonyl)phenyl)-1H-indol-1-yl)ethanone,
3-(3,5-dimethyl-4-(piperazin-1-ylsulfonyl)phenyl)-6-fluoro-1H-indole,
N-(2-(1H-1,2,3-triazol-4-yl)ethyl)-4-(6-fluoro-1H-indol-3-yl) benzenesulfonamide,
N-(2-(1H-imidazol-2-yl)ethyl)-4-(6-fluoro-1H-indol-3-yl)-benzenesulfonamide,
(3R,4R)-1-((4-(6-fluoro-1H-indol-3-yl)phenyl)sulfonyl)pyrrolidine-3,4-diol,
3-(3,5-difluoro-4-(piperazin-1-ylsulfonyl)phenyl)-6-fluoro-1H-indole,
3-(3,5-dichloro-4-(piperazin-1-ylsulfonyl)phenyl)-6-fluoro-1H-indole,
(R)-1-((4-(6-fluoro-1H-indol-3-yl)phenyl)sulfonyl)pyrrolidin-3-ol,
6-fluoro-3-(4-(piperazin-1-ylsulfonyl)phenyl)-1H-indole-1-carboxamide,
(S)-1((4-(6-fluoro-1H-indol-3-yl)phenyl)sulfonyl)pyrrolidin-3-ol,
(3S,4S)-4-fluoro-1-{[4-(6-fluoro-1H-indol-3-yl)phenyl]sulfonyl}-pyrrolidin-3-amine,
(+)-cis-4-fluoro-1-{[4-(6-fluoro-1H-indol-3-yl)phenyl]sulfonyl}-pyrrolidin-3-amine,
(3R,4R)-4-fluoro-1-{[4-(6-fluoro-1H-indol-3-yl)phenyl]sulfonyl}-pyrrolidin-3-amine,
(−)-(cis)-4-fluoro-1-((4-(6-fluoro-1H-indol-3-yl)phenyl)sulfonyl)-pyrrolidin-3-amine,
2-[(1-{[4-(6-fluoro-1H-indol-3-yl)phenyl]sulfonyl}piperidin-4-yl)oxy]-acetamide, 4-(6-fluoro-1H-indol-3-yl)-N-[1-(4-methyl-4H-1,2,4-triazol-3-yl)ethyl]-benzenesulfonamide,
4-(6-fluoro-1H-indol-3-yl)-N-[(4-methyl-5-oxomorpholin-2-yl-methyl]benzenesulfonamide,
N-(1,1-dioxidotetrahydrothiophen-3-yl)-4-(6-fluoro-1H-indol-3-yl)-benzenesulfonamide,
4-(6-fluoro-1H-indol-3-yl)-N-[2-(methylsulfonyl)ethyl]benzenesulfon-amide, 4-(6-fluoro-1H-indol-3-yl)-N-((5-methyl-1,3,4-oxadiazol-2-yl)methyl)-benzenesulfonamide,
1((4-(6-fluoro-1H-indol-3-yl)phenyl)sulfonyl)-1,4-diazepan-5-one,
4-(6-fluoro-1H-indol-3-yl)-N-(1-methyl-1H-pyrazol-5-yl)-benzenesulfonamide,
4-(6-fluoro-1H-indol-3-yl)-N-[(4-methyl-4H-1,2,4-triazol-3-yl)methyl]-benzenesulfonamide,
(−)-(R)-4-(6-fluoro-1H-indol-3-yl)-N-(2-hydroxypropyl)benzenesulfon-amide,
(+)-(S)-4-(6-fluoro-1H-indol-3-yl)-N-(2-hydroxypropyl)benzenesulfon-amide,
(cis)-3-(4-(6-fluoro-1H-indol-3-yl)phenylsulfonamido)cyclobutane-carboxamide,
4-(6-fluoro-1H-indol-3-yl)-N- [(2R)-1-hydroxypropan-2-yl]benzene-sulfonamide,
(Trans)-3-(4-(6-fluoro-1H-indol-3-yl)phenylsulfonamido)cyclobutane-carboxamide,
4-(6-fluoro-1H-indol-3-yl)-N-methyl-N-(2-sulfamoylethyl)-benzenesulfonamide,
4-(6-fluoro-1H-indol-3-yl)-N-[2-(1H-1,2,4-triazol-1-yl)ethyl]benzene-sulfonamide,
4-(6-fluoro-1H-indol-3-yl)-N-methyl-N-[2-(methylsulfamoyl)ethyl]benzenesulfonamide,
(−)-(6-fluoro-1H-indol-3-yl)-N-[(2S)-1-hydroxypropan-2-yl]-benzenesulfonamide,
4-(6-fluoro-1H-indol-3-yl)-N-(3-oxo-3-(piperazin-1-yl)propyl) benzenesulfonamide,
4-(6-fluoro-1H-indol-3-yl)-N-(3-(4-methylpiperazin-1-yl)-3-oxopropyl) benzenesulfonamide,
(−)-(S)-3-(4-(6-fluoro-1H-indol-3-yl)phenylsulfonamido)-N-(tetrahydro-furan-3-yl)propanamide,
(−)-N-(3-((3S,4S)-3-amino-4-fluoropyrrolidin-1-yl)-3-oxopropyl)-4-(6-fluoro-1H-indol-3-yl)benzenesulfonamide,
4-(6-fluoro-1H-indol-3-yl)-N-(3-morpholino-3-oxopropyl)-benzenesulfonamide,
(+)-(R)-3-(4-(6-fluoro-1H-indol-3-yl)phenylsulfonamido)-N-(tetrahydro-furan-3-yl)propanamide,
N-(2-(4-(6-fluoro-1H-indol-3-yl)phenylsulfonamido)ethyl)-morpholine-4-carboxamide,
N-(2-(4-(6-fluoro-1H-indol-3-yl)phenylsulfonamido)ethyl)piperazine-1-carboxamide,
N-(2-(4-(6-fluoro-1H-indol-3-yl)phenylsulfonamido)ethyl)-4-methyl-piperazine-1-carboxamide,
4-(6-fluoro-1H-indol-3-yl)-N-((2S,3R)-3-hydroxybutan-2-yl)-N-(2-hydroxyethyl)benzenesulfonamide,
(S)-(4-((4-(6-fluoro-1H-indol-3-yl)phenyl)sulfonyl)morpholin-3-yl)methanol,
1((4-(6-fluoro-1H-indol-3-yl)phenyl)sulfonyl)-3-(1-methyl-1H-pyrazol-5-yl)pyrrolidin-3-ol,
4-(6-fluoro-1H-indol-3-yl)-N-(2-hydroxyethyl)-N-((1-methyl-1H-pyrazol-4-yl)methyl)benzenesulfonamide,
(R)-(4-((4-(6-fluoro-1H-indol-3-yl)phenyl)sulfonyl)morpholin-3-yl)methanol,
S)-1-((4-(6-fluoro-1H-indol-3-yl)phenyl)sulfonyl)-3-methylpyrrolidin-3-ol,
4-(6-fluoro-1H-indol-3-yl)-N-(2-hydroxyethyl)-N-(3-hydroxypropyl)benzenesulfonamide,
4-((4-(6-fluoro-1H-indol-3-yl)phenyl)sulfonyl)-1,4-oxazepan-6-ol,
1((4-(6-fluoro-1H-indol-3-yl)phenyl)sulfonyl)-3-(pyrimidin-4-yl)pyrrolidin-3-ol,
1((4-(6-fluoro-1H-indol-3-yl)phenyl)sulfonyl)-3-(pyrimidin-5-yl)pyrrolidin-3-ol,
4-(6-fluoro-1H-indol-3-yl)-N-(2-hydroxy-2-(pyridazin-3-yl)ethyl)-N-methylbenzenesulfonamide,
1((4-(6-fluoro-1H-indol-3-yl)phenyl)sulfonyl)-3-((2-methyl-1H-imidazol-1-yl)methyl)piperidin-3-ol,
((2S,4S)-4-fluoro-1((4-(6-fluoro-1H-indol-3-yl)phenyl)sulfonyl)pyrrolidin-2-yl)methanol,
1((4-(6-fluoro-1H-indol-3-yl)phenyl)sulfonyl)pyrrolidin-3-ol,
((2R,4R)-4-fluoro-1-((4-(6-fluoro-1H-indol-3-yl)phenyl)sulfonyl)pyrrolidin-2-yl)methanol,
((2R,4S)-4-fluoro-1((4-(6-fluoro-1H-indol-3-yl)phenyl)sulfonyl)pyrrolidin-2-yl)methanol,
1-((1-((4-(6-fluoro-1H-indol-3-yl)phenyl)sulfonyl)-3-hydroxypyrrolidin-3-yl)methyl)pyrrolidin-2-one,
(3S,4R)-1-((4-(6-fluoro-1H-indol-3-yl)phenyl)sulfonyl)piperidine-3,4-diol,
(2R,3R,4S,5S)-5-fluoro-1-((4-(6-fluoro-1H-indol-3-yl)phenyl)sulfonyl)-2-(hydroxymethyl)piperidine-3,4-diol,
(3R,4R)-1-((4-(6-fluoro-1H-indol-3-yl)phenyl)sulfonyl)piperidine-3,4-diol,
1((4-(6-fluoro-1H-indol-3-yl)phenyl)sulfonyl)-3-((2-methyl-1H-imidazol-1-yl)methyl)pyrrolidin-3-ol,
1-((1-((4-(6-fluoro-1H-indol-3-yl)phenyl)sulfonyl)-3-hydroxypiperidin-3-yl)methyl)pyrrolidin-2-one,
4-(6-fluoro-1H-indol-3-yl)-N-(2-hydroxy-2-(1H-imidazol-2-yl)ethyl)-N-methylbenzenesulfonamide,
(2S,3S,4S)-1-((4-(6-fluoro-1H-indol-3-yl)phenyl)sulfonyl)-2-(hydroxymethyl)pyrrolidine-3,4-diol,
4-(6-fluoro-1H-indol-3-yl)-N-(2-hydroxy-2-(pyrazin-2-yl)ethyl)-N-methylbenzenesulfonamide,
3-chloro-4-(6-fluoro-1H-indol-3-yl)benzenesulfonamide,
3,5-dichloro-4-(6-fluoro-1H-indol-3-yl)benzenesulfonamide,
2-(5-(6-fluoro-1H-indol-3-yl)-2-sulfamoylphenyl)-N,N-dimethylacetamide,
4-(6-fluoro-1H-indol-3-yl)-2-(2-hydroxyethyl)benzenesulfonamide,
4-(6-fluoro-1H-indol-3-yl)-2-(2-(methylamino)ethyl)benzenesulfonamide,
2-(2-(dimethylamino)ethyl)-4-(6-fluoro-1H-indol-3-yl)benzenesulfonamide,
4-(6-fluoro-1H-indol-3-yl)-2-(2,2,2-trifluoroethyl)benzenesulfonamide,
2-(5-(6-fluoro-1H-indol-3-yl)-2-sulfamoylphenyl)-N-methylacetamide,
2-(5-(6-fluoro-1H-indol-3-yl)-2-sulfamoylphenyl)acetamide,
4-((4-(6-fluoro-1H-indol-3-yl)phenyl)sulfonyl)-1-methylpiperazine-2,6-dione,
(R)-1-(2,3-dihydroxypropyl)-4-((4-(6-fluoro-1H-indol-3-yl)phenyl)sulfonyl)piperazin-2-one,
(S)-1-(2,3-dihydroxypropyl)-4-((4-(6-fluoro-1H-indol-3-yl)phenyl)sulfonyl)piperazin-2-one,
1-(2-aminoethyl)-4-((4-(6-fluoro-1H-indol-3-yl)phenyl)sulfonyl)piperazin-2-one,
1-(2-(dimethylamino)ethyl)-4-((4-(6-fluoro-1H-indol-3-yl)phenyl)sulfonyl)piperazin-2-one,
4-((4-(6-fluoro-1H-indol-3-yl)phenyl)sulfonyl)-1-(2-(methylamino)ethyl)piperazin-2-one,
4-((4-(6-fluoro-1H-indol-3-yl)phenyl)sulfonyl)-1-(2-hydroxyethyl)piperazin-2-one,
1-(3-aminopropyl)-4-((4-(6-fluoro-1H-indol-3-yl)phenyl)sulfonyl)piperazin-2-one,
4-((4-(6-fluoro-1H-indol-3-yl)phenyl)sulfonyl)-1-(3-(methylamino)propyl)piperazin-2-one,
1-(3-(dimethylamino)propyl)-4-((4-(6-fluoro-1H-indol-3-yl)phenyl)sulfonyl)piperazine-2-one, 4-(6-fluoro-1H-indol-3-yl)-N-((3-methyl-1,2,4-oxadiazol-5-yl)methyl)benzenesulfonamide,
N((1,2,4-oxadiazol-3-yl)methyl)-4-(6-fluoro-1H-indol-3-yl) benzenesulfonamide,
4-(6-fluoro-1H-indol-3-yl)-N-(2-hydroxyethyl)benzenesulfonamide,
3-chloro-4-(6-fluoro-1H-indol-3-yl)-N-(2-hydroxyethyl) benzenesulfonamide,
(−)-4-(6-fluoro-1H-indol-3-yl)-N-(2-(methylsulfinyl)ethyl)benzenesulfonamide,
(+)-4-(6-fluoro-1H-indol-3-yl)-N-(2-(methylsulfinyl)ethyl)benzenesulfonamide,
4-(6-fluoro-1H-indol-3-yl)-N-(2-(2-methyl-1H-imidazol-4-yl)ethyl)benzenesulfonamide,
3-(2-ethyl-4-(6-fluoro-1H-indol-3-yl)phenylsulfonamido)propanamide,
3-((4-(6-fluoro-1H-indol-3-yl)-2-isopropylphenyl)sulfonamido)propanamide,
3-((4-(6-fluoro-1H-indol-3-yl)-2-isobutylphenyl)sulfonamido)propanamide,
3-((4-(6-fluoro-1H-indol-3-yl)-2-(methoxymethyl)phenyl)sulfonamido)propanamide,
3-((4-(6-fluoro-1H-indol-3-yl)-2-isopropoxyphenyl)sulfonamido)propanamide,
3-((4-(6-fluoro-1H-indol-3-yl)-2-(hydroxymethyl)phenyl)sulfonamido)propanamide,
3-((4-(6-fluoro-1H-indol-3-yl)-2-(trifluoromethyl)phenyl)sulfonamido)propanamide,
N-(3-((cis)-3,4-dihydroxypyrrolidin-1-yl)-3-oxopropyl)-4-(6-fluoro-1H-indol-3-yl)benzenesulfonamide,
(+)-N-(3-((3R,4R)-3,4-dihydroxypyrrolidin-1-yl)-3-oxopropyl)-4-(6-fluoro-1H-indol-3-yl)benzenesulfonamide,
(−)-N-(3-((3S,4S)-3,4-dihydroxypyrrolidin-1-yl)-3-oxopropyl)-4-(6-fluoro-1H-indol-3-yl)benzenesulfonamide,
(−)-N-(3-((3S,4R)-3-amino-4-fluoropyrrolidin-1-yl)-3-oxopropyl)-4-(6-fluoro-1H-indol-3-yl)benzenesulfonamide,
(+)-N-(3-((3S,4R)-3-amino-4-fluoropyrrolidin-1-yl)-3-oxopropyl)-4-(6-fluoro-1H-indol-3-yl)benzenesulfonamide,
(+)-N-(3-((3R,4R)-3-amino-4-fluoropyrrolidin-1-yl)-3-oxopropyl)-4-(6-fluoro-1H-indol-3-yl)benzenesulfonamide,
3-((2-(2,2-difluoroethyl)-4-(6-fluoro-1H-indol-3-yl)phenyl)sulfonamido)propanamide,
4-(6-fluoro-1H-indol-3-yl)-2-(hydroxymethyl)benzenesulfonamide,
2-(aminomethyl)-4-(6-fluoro-1H-indol-3-yl)benzenesulfonamide,
(5-(6-fluoro-1H-indol-3-yl)-2-(methylsulfonyl)phenyl)methanamine, or
2-(5-(6-fluoro-1H-indol-3-yl)-2-(methylsulfonyl)phenyl)ethanol.

2. A pharmaceutical composition comprising a compound according to claim 1 or a pharmaceutically acceptable enantiomer, salt, solvate thereof, and at least one pharmaceutically acceptable carrier, diluent, excipient and/or adjuvant.

3. A compound of Formula Ia:

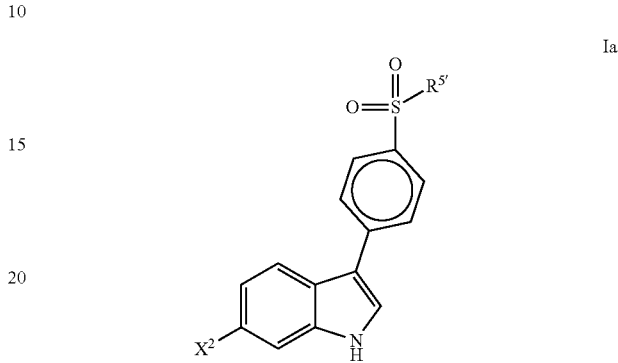

or a pharmaceutically acceptable enantiomer, salt or solvate thereof, wherein:
$X^2$ is H, halogen, OH, $OR^7$; or C1-C4 alkyl;
$R^{5'}$ is a heterocycle or C1-C2alkyl-heterocycle, the heterocycle being optionally substituted with up to three substituents which are independently halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, or alkyl, the alkyl group being optionally substituted by one or more groups selected from halogen, hydroxyl, amino or COOH; wherein $R^9$ and $R^{10}$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

4. The compound according to claim 3, wherein $X^2$ is F.

5. The compound according to claim 3, wherein $R^5$ is the heterocycle or C1-C2 alkyl-heterocycle, the heterocycle is a 5 or 6-membered ring having a one, two or three heteroatoms selected from N and O.

6. The compound according to claim 3, wherein the compound is in free base form.

7. A pharmaceutical composition comprising a compound according to claim 3 and at least one pharmaceutically acceptable carrier, diluent, excipient and/or adjuvant.

* * * * *